United States Patent
Bae et al.

(10) Patent No.: US 7,965,032 B2
(45) Date of Patent: Jun. 21, 2011

(54) ANTHRACENE DERIVATIVE AND ORGANIC ELECTRONIC DEVICE USING THE SAME

(75) Inventors: Jae-Soon Bae, Daejeon Metropolitan (KR); Dae-Woong Lee, Daejeon Metropolitan (KR); Dong-Hoon Lee, Seoul (KR); Jun-Gi Jang, Daejeon Metropolitan (KR); Sang-Young Jeon, Daejeon Metropolitan (KR); Ji-Eun Kim, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 695 days.

(21) Appl. No.: 11/714,167

(22) Filed: Mar. 6, 2007

(65) Prior Publication Data
US 2007/0205412 A1 Sep. 6, 2007

(30) Foreign Application Priority Data
Mar. 6, 2006 (KR) .................. 10-2006-0021119

(51) Int. Cl.
*C09K 11/06* (2006.01)
*H01L 51/54* (2006.01)

(52) U.S. Cl. ........ 313/504; 313/506; 428/690; 428/917; 257/40; 257/E51.05

(58) Field of Classification Search .................. None
See application file for complete search history.

(56) References Cited

U.S. PATENT DOCUMENTS

| | | | | |
|---|---|---|---|---|
| 4,719,049 A * | 1/1988 | Bair | ............... | 562/112 |
| 5,635,308 A * | 6/1997 | Inoue et al. | ............... | 428/696 |
| 6,465,115 B2 * | 10/2002 | Shi et al. | ............... | 428/690 |
| 2002/0038867 A1 * | 4/2002 | Kobori et al. | ............... | 257/40 |
| 2005/0064233 A1 * | 3/2005 | Matsuura et al. | ............... | 428/690 |
| 2006/0121309 A1 * | 6/2006 | D'Andrade | ............... | 428/690 |

FOREIGN PATENT DOCUMENTS

| | | |
|---|---|---|
| JP | 2003-115624 | 4/2003 |
| JP | 2004-231563 | 8/2004 |
| JP | 2005-008559 | 1/2005 |
| JP | 2005-120296 | 5/2005 |
| JP | 2005-285466 | 10/2005 |
| KR | 10-2005-0058465 | 6/2005 |
| KR | 10-2005-0100708 | 10/2005 |

OTHER PUBLICATIONS

House et al., Journal of Organic Chemistry, (1973), vol. 38, No. 6, pp. 1167-1173.*
Ishida et al., JP2003-261472, Machine Assisted Translation.*
Ishida et al., JP2003-282268, Machine Assisted Translation.*
Ikeda et al., JP2004-231563, Machine Assisted Translation.*
Badone et al., Journal of Organic Chemistry, (1997), vol. 62, pp. 7170-7173.*
PCT International Search Report for Int'l Appl. No. PCT/KR2007/001082 mailed Jun. 13, 2007.

* cited by examiner

*Primary Examiner* — Angela Ortiz
*Assistant Examiner* — Brett A Crouse
(74) *Attorney, Agent, or Firm* — McKenna Long & Aldridge LLP

(57) ABSTRACT

The present invention provides a novel anthracene derivative and an organic electronic device using the same. The organic electronic device according to the present invention shows excellent characteristics in efficiency, drive voltage, and life time.

9 Claims, 3 Drawing Sheets

ANTHRACENE DERIVATIVE AND ORGANIC ELECTRONIC DEVICE USING THE SAME

BACKGROUND OF THE INVENTION

This application claims priority benefits from Korean Patent Application No. 10-2006-0021119, filed on Mar. 6, 2006, the entire contents of which are fully incorporated herein by reference.

1. Field of the Invention

The present invention relates to a novel anthracene derivative having a heteroaryl group bonded to anthracene, and to an organic electronic device using the same.

2. Discussion of the Related Art

SUMMARY OF THE INVENTION

The term, organic electronic device, as used in the present specification refers to a electronic device using an organic semiconductor material, which requires hole and/or electron exchange between an electrode and an organic semiconductor material. The organic electronic device can be largely classified into two types according to its operational principle as follows. One type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electronic device having a configuration in which holes and/or electrons are injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) drum and an organic transistor, which all require an electron/hole injecting material, an electron/hole extracting material, an electron/hole transporting material, or a light emitting material for driving the device. Hereinafter, the organic light emitting device will be mainly and specifically described, but in the above-mentioned organic electronic devices, the electron/hole injecting material, the electron/hole extracting material, the electron/hole transporting material or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast, and high-speed response.

The materials used for the organic material layer of the organic light emitting device can be classified into a light emitting material and a charge-transporting material, for example, a hole injecting material, a hole transporting material, an electron transporting material, and an electron injecting material, according to their functions. The light emitting materials can be divided into a blue, green or red light emitting material and a yellow or orange light emitting material required for giving more natural color, according to a light emitting color. Further, a host/dopant system can be used as the light emitting material for the purpose of enhancing the color purity and the light emitting efficiency through energy transfer. It is based on the principle that if a small amount of a dopant having a smaller energy band gap and a higher light emitting efficiency than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material, and an electron injecting material should be essentially composed of a stable and efficient material. However, the development of a stable and efficient organic material layer material for the organic light emitting device has not yet been fully realized. Accordingly, the development of new materials is continuously desired.

Disclosure

Technical Problem

The present inventors have synthesized an anthracene derivative having a novel structure, and then have found that the novel anthracene derivative can exhibit effects of increased efficiency, lower voltage, and higher stability of a device when it is used to form an organic material layer of the organic electronic device.

Technical Solution

Therefore, it is an object of the present invention to provide a novel anthracene derivative and an organic electronic device using the same.

Advantageous Effects

The novel anthracene compound according to the present invention can be used as a material for an organic material layer of an organic electronic device including an organic light emitting device by the introduction of various aryl groups, heteroaryl groups, arylamino groups, or the like to the anthracene compound. The organic electronic device including an organic light emitting device, which uses the anthracene compound according to the present invention as a material for an organic material layer, shows excellent characteristics in efficiency, drive voltage, life time, or the like.

BEST MODE

Figure 1:
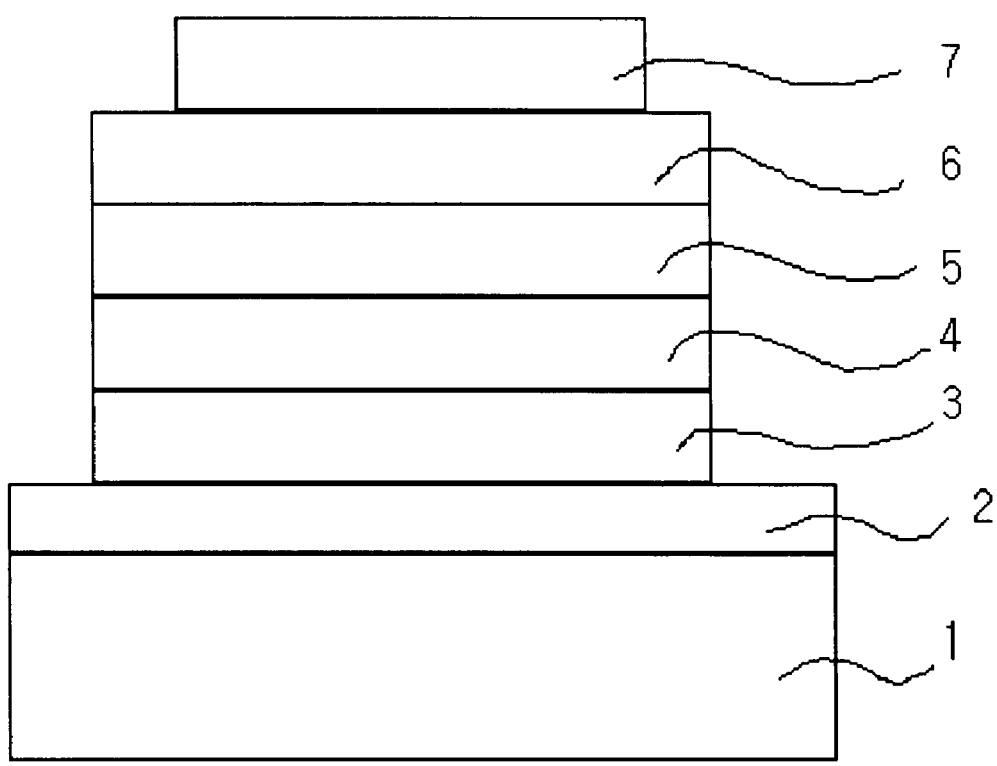
FIG. 1 illustrates one example of the organic light emitting device according to the present invention.
Figure 2:
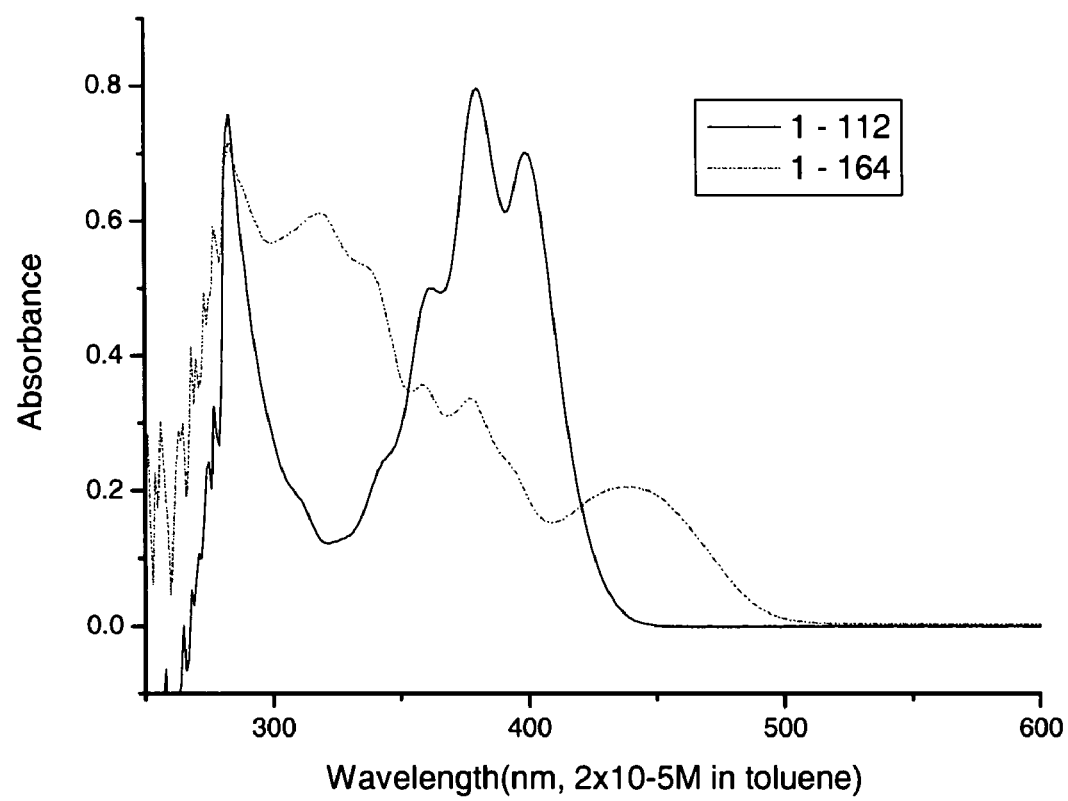
FIG. 2 illustrates the UV data of the compound according to the present invention synthesized in Preparative Examples 9 and 10.
Figure 3:
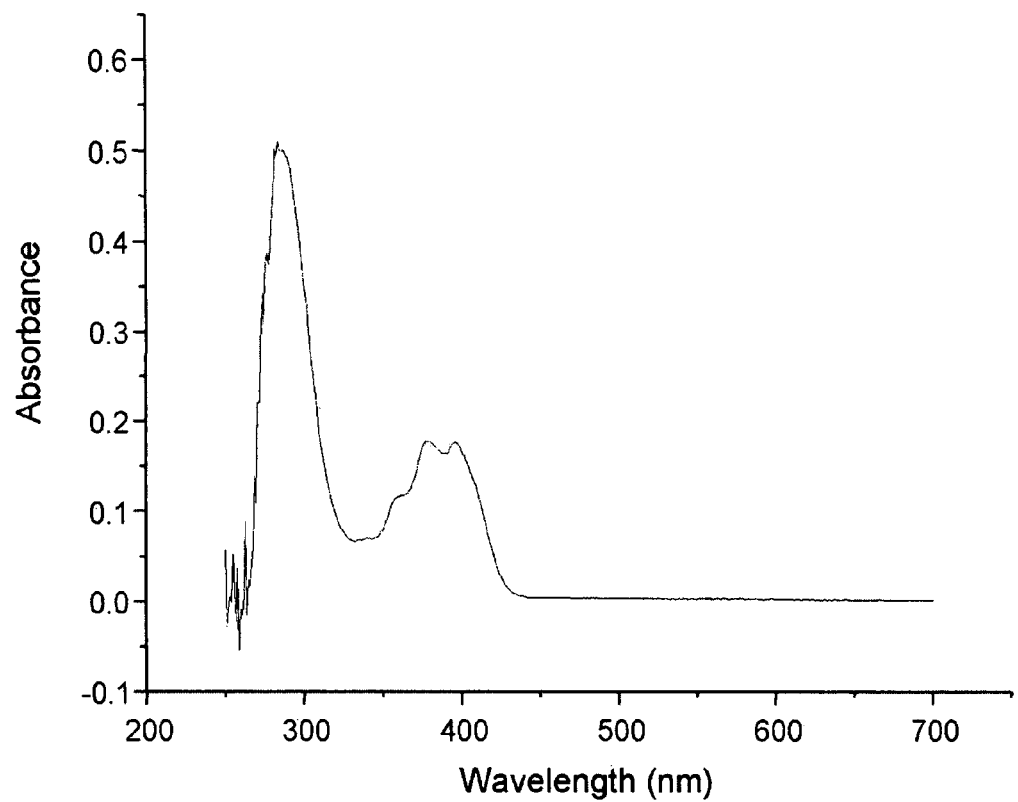
FIG. 3 illustrates the UV data of the compound according to the present invention synthesized in Preparative Example 11.

The present invention provides a compound represented by the following formula 1:

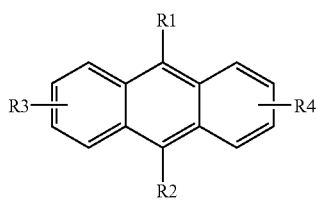

[Formula 1]

wherein R1 and R2 may be the same or different from each other, and are each independently selected from the group consisting of a $C_6$ to $C_{40}$ aryl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_5$ to $C_{40}$ heteroaryl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; and a $C_6$ to $C_{40}$ amino group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group, at least one of R3 and R4 is a group of the following formula 2:

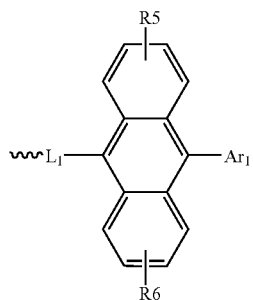

[Formula 2]

wherein R5 and R6 may be the same or different from each other, and are each independently selected from the group consisting of hydrogen; a $C_1$ to $C_{40}$ alkyl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_3$ to $C_{40}$ cycloalkyl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_3$ to $C_{40}$ alkenyl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_3$ to $C_{40}$ alkoxy group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_3$ to $C_{40}$ an amino group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_6$ to $C_{40}$ aryl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; and a $C_5$ to $C_{40}$ heteroaryl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group, or are bonded with an adjacent group to form an aliphatic, aromatic, heteroaliphatic, or heteroaromatic fused ring, or to form a spiro bond, L1 is a direct bond; or is selected from the group consisting of a $C_2$ to $C_{40}$ alkenylene group which is unsubstituted or substituted with at least one selected from the group consisting of a $C_6$ to $C_{40}$ aryl group and a $C_5$ to $C_{40}$ heteroaryl group; a $C_6$ to $C_{40}$ arylene group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; $C_5$ to $C_{40}$ heteroarylene group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; and a $C_6$ to $C_{40}$ arylamino group which is unsubstituted or substituted with at least one selected from the group consisting of a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group, Ar1 is selected from the group consisting of a $C_2$ to $C_{40}$ alkenyl group which is unsubstituted or substituted with at least one selected from the group consisting of a $C_1$ to $C_{40}$ alkyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, a $C_5$ to $C_{40}$ heteroaryl group, and a $C_6$ to $C_{40}$ arylamino group; a $C_6$ to $C_{40}$ aryl group which is unsubstituted or substituted with at least one selected from the group consisting of a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, a $C_5$ to $C_{40}$ heteroaryl group, a substituted $C_2$ to $C_{40}$ alkenylene group, and a $C_6$ to $C_{40}$ arylamino group; a $C_5$ to $C_{40}$ heteroaryl group which is unsubstituted or substituted with at least one selected from the group consisting of a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, a $C_5$ to $C_{40}$ heteroaryl group, and a $C_6$ to $C_{40}$ arylamino group; and a $C_6$ to $C_{40}$ arylamino group which is unsubstituted or substituted with at least one selected from the group consisting of a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, a $C_5$ to $C_{40}$ heteroaryl group, and a $C_6$ to $C_{40}$ arylamino group, and a group of R3 or R4, which is not a group of the formula 2, is selected from the group consisting of hydrogen; a $C_1$ to $C_{40}$ alkyl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_3$ to $C_{40}$ cycloalkyl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_6$ to $C_{40}$ aryl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; a $C_5$ to $C_{40}$ heteroaryl group which is unsubstituted or substituted with at least one selected from the group consisting of a halogen, an amino group, a nitrile group, a nitro group, a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group; and a $C_6$ to $C_{40}$ arylamino group which is unsubstituted or substituted with at least one selected from the group consisting of a $C_1$ to $C_{40}$ alkyl group, a $C_2$ to $C_{40}$ alkenyl group, a $C_1$ to $C_{40}$ alkoxy group, a $C_3$ to $C_{40}$ cycloalkyl group, a $C_3$ to $C_{40}$ heterocycloalkyl group, a $C_6$ to $C_{40}$ aryl group, and a $C_5$ to $C_{40}$ heteroaryl group.

In one embodiment of the present invention, R1 and R2 of the formula 1 can be the same aryl groups. This aryl group is preferably a phenyl group, a biphenyl group or a naphthyl group, which can be substituted or unsubstituted.

In another embodiment of the present invention, R1 and R2 of the formula 1 can be the same heteroaryl groups. This heteroaryl group is preferably a pyridyl group, a bipyridyl group, a quinoline group, or an isoquinoline group, which can be substituted or unsubstituted.

In another embodiment of the present invention, R1 and R2 of the formula 1 can be the same amino groups substituted with a $C_6$ to $C_{40}$ aryl group or a $C_5$ to $C_{40}$ heteroaryl group.

In another embodiment of the present invention, R1 and R2 of the formula 1 can be specifically selected from the group consisting of the following structural formulae.

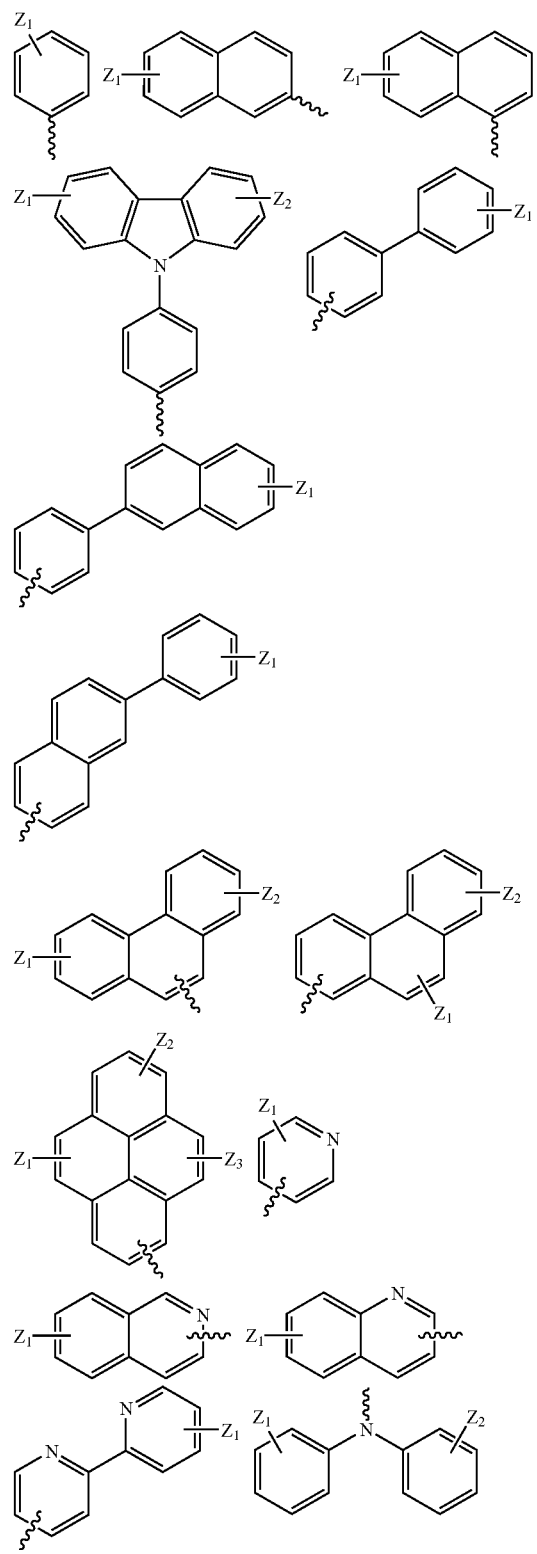

wherein $Z_1$ to $Z_3$ may be the same or different from each other, and can be each independently selected from the groups as defined for R5 and R6 of the formula 2.

In another embodiment of the present invention, one of R5 and R6 of the formula 2 can be a hydrogen atom, or both of R5 and R6 may be hydrogen atoms.

In another embodiment of the present invention, if Ar1 of the formula 2 is an aryl group, this can be selected from the group consisting of the following structural formulae.

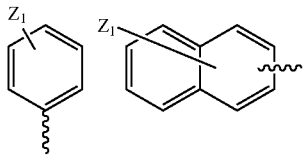
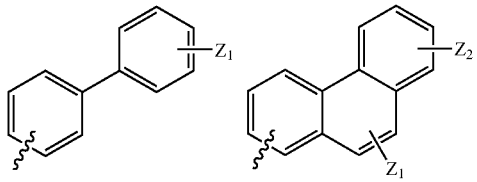
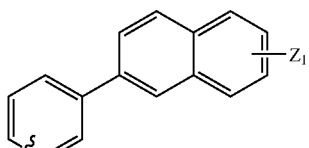
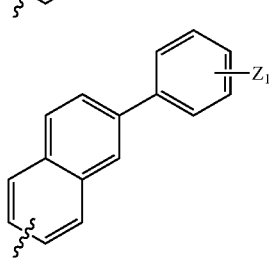
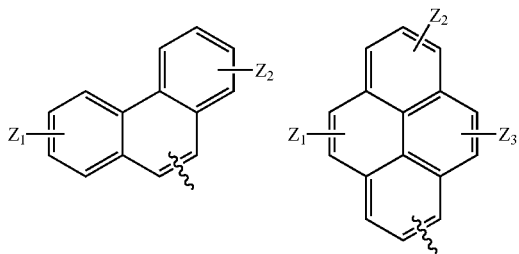
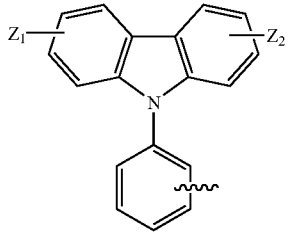
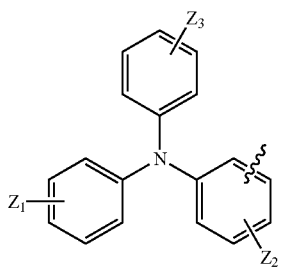

wherein $Z_1$ to $Z_3$ may be the same or different from each other, and can be each independently selected from the groups as defined for R5 and R6 of the formula 2.

In another embodiment of the present invention, if Ar1 of the formula 2 is a heteroaryl group, this can be selected from the group consisting of the following structural formulae.

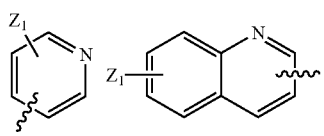
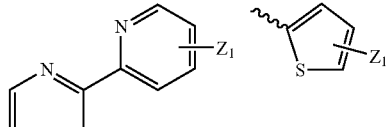
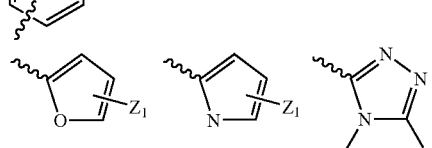
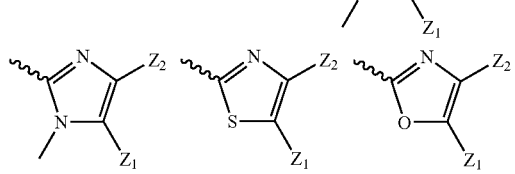

wherein $Z_1$ and $Z_2$ may be the same or different from each other, and can be each independently selected from the groups as defined for R5 and R6 of the formula 2.

In another embodiment of the present invention, if Ar1 of the formula 2 is an arylamino group, this can be selected from the group consisting of the following structural formulae.

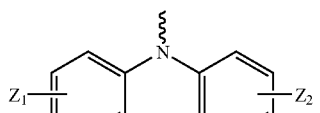
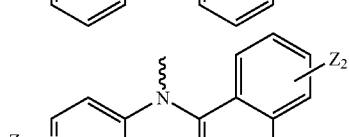
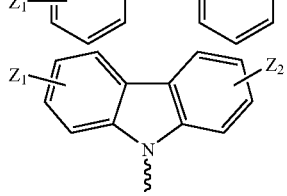

wherein $Z_1$ and $Z_2$ may be the same or different from each other, and can be each independently selected from the groups as defined for R5 and R6 of the formula 2.

In the above description, the alkyl group is preferably a alkyl group having 1 to 40 carbon atoms, which does not give steric hindrance. Specific examples thereof include, but not limited thereto, a methyl group, an ethyl group, a propyl group, an isopropyl group, a butyl group, a t-butyl group, a pentyl group, a hexyl group, and a heptyl group.

The cycloalkyl group is preferably a cycloalkyl group having 3 to 40 carbon atoms, which does not give steric hindrance. More preferable specific examples thereof include a cyclopentyl group and a cyclohexyl group.

The alkenyl group is preferably an alkenyl group having 2 to 40 carbon atoms, and specifically it is one substituted with an aryl group such as a stilbenyl group and a styrenyl group.

The alkoxy group is preferably an alkoxy group having 1 to 40 carbon atoms.

Examples of the aryl group include a phenyl group, a naphthyl group, an anthracenyl group, a biphenyl group, a pyrenyl group, a perylene group, and a derivative thereof.

Examples of the arylamine group include a phenylamine group, a naphthylamine group, a biphenylamine group, an anthracenylamine group, a 3-methyl-phenylamine group, a 4-methyl-naphthylamine group, a 2-methyl-biphenylamine group, a 9-methyl-anthracenylamine group, a diphenylamine group, a phenylnaphthylamine group, a ditolylamine group, a phenyltolylamine group, a carbazole group, and a triphenylamine group.

Examples of the heterocyclic group include a pyridyl group, a bipyridyl group, a triazine group, an acridyl group, a thiophene group, a puran group, an imidazole group, an oxazole group, a thiazole group, a triazole group, a quinolidyl group, and an isoquinoline group.

Examples of the halogen include a fluorine, a chlorine, a bromine, and a iodine.

If the $C_2$ to $C_{40}$ alkenylene group is substituted, the substituent is at least one selected from the group consisting of a substituted or unsubstituted $C_1$ to $C_{40}$ alkyl group, a substituted or unsubstituted $C_2$ to $C_{40}$ alkenyl group, a substituted or unsubstituted $C_2$ to $C_{40}$ alkynyl group, a substituted or unsubstituted $C_1$ to $C_{40}$ alkoxy group, a substituted or unsubstituted $C_6$ to $C_{40}$ aryl group, and a substituted or unsubstituted $C_3$ to $C_{40}$ heteroaryl group.

Preferable specific examples of the compound of the formula 1 include the followings, but not limited thereto.

[Formula 1-1]

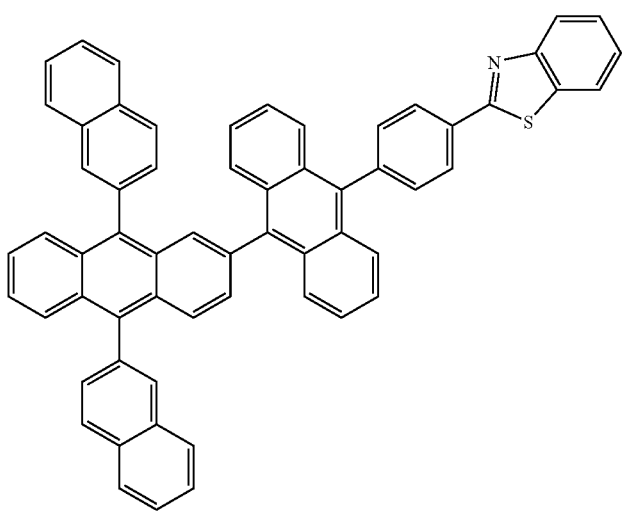

[Formula 1-2]

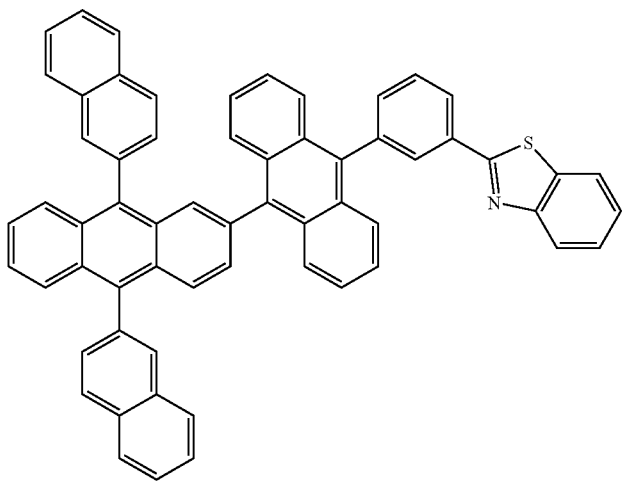

[Formula 1-3]
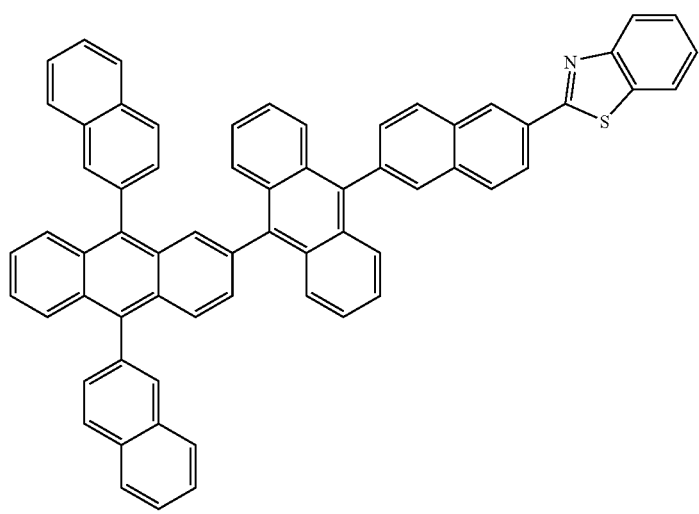
[Formula 1-4]
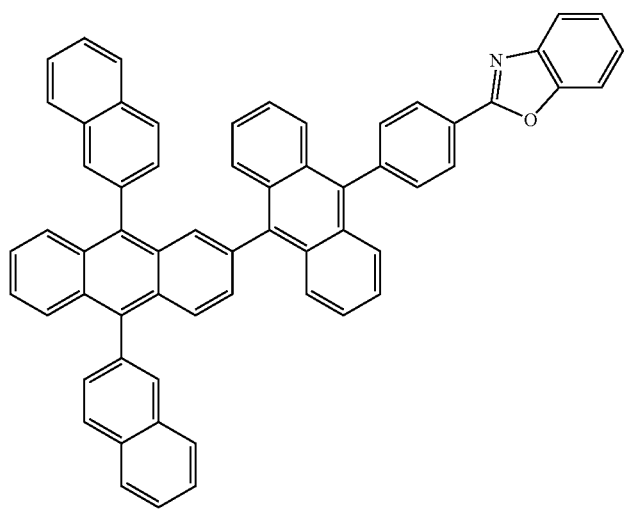
[Formula 1-5]
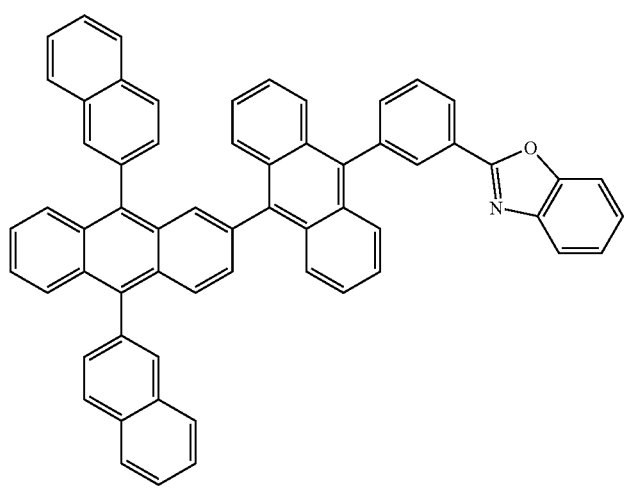

[Formula 1-6]
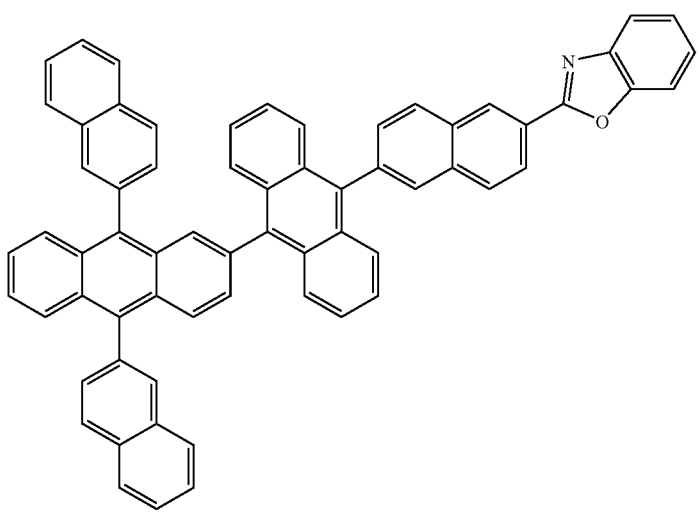
[Formula 1-7]
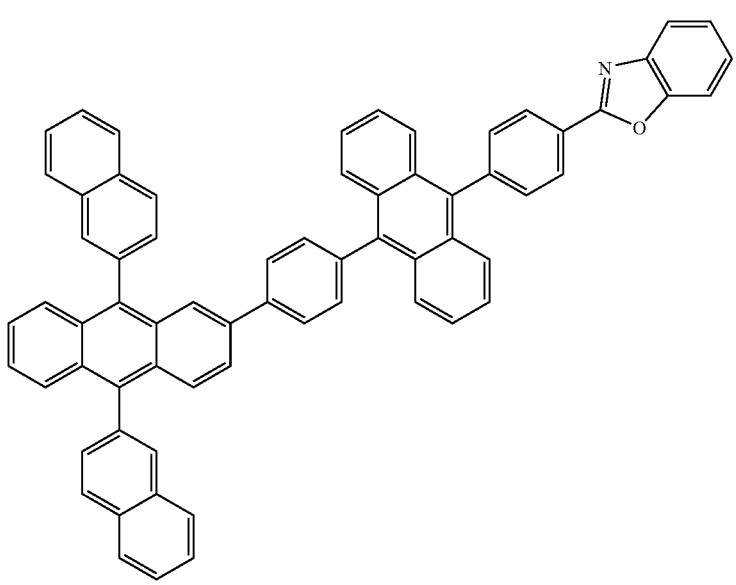
[Formula 1-8]
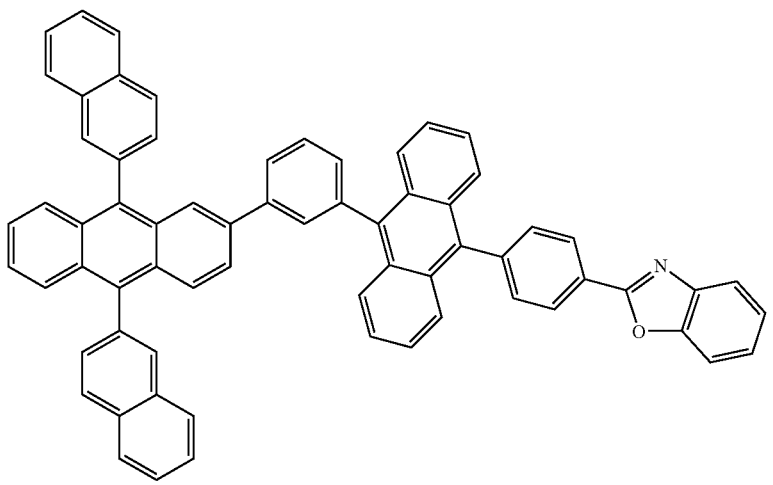

[Formula 1-9]
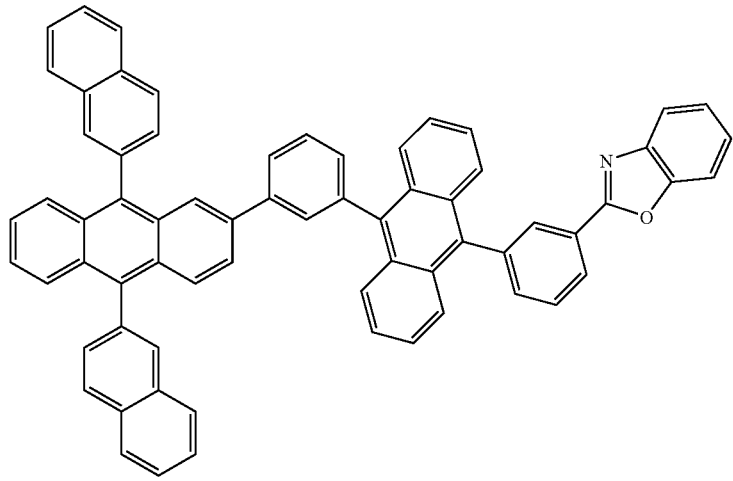
[Formula 1-10]
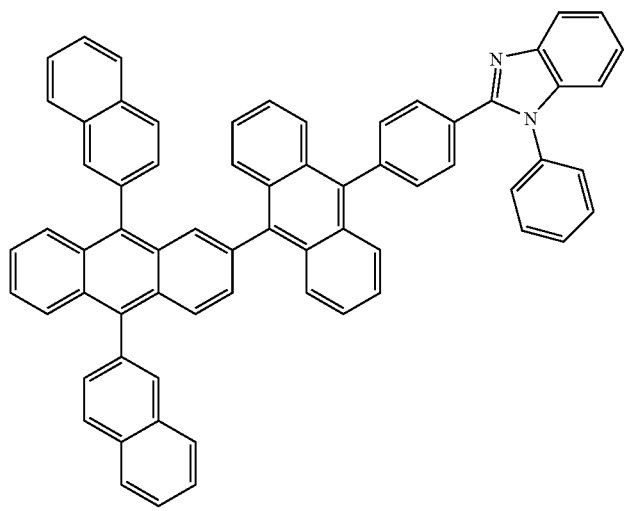
[Formula 1-11]
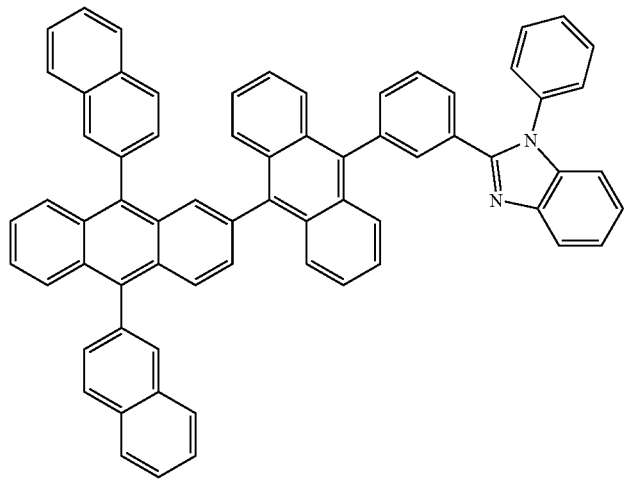

-continued
[Formula 1-12]
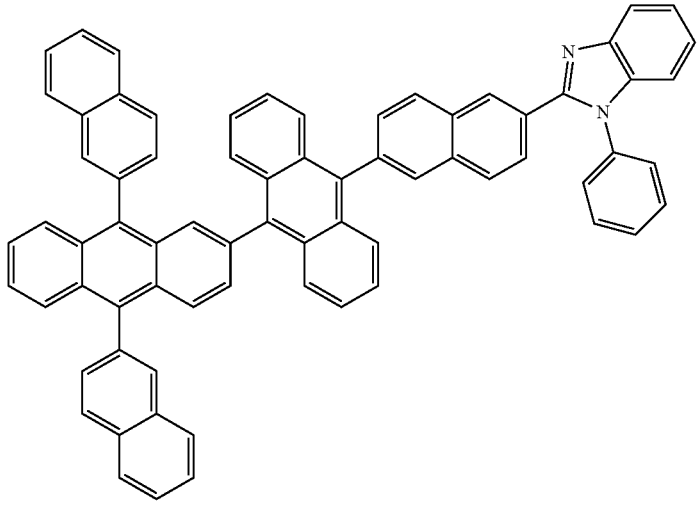
[Formula 1-13]
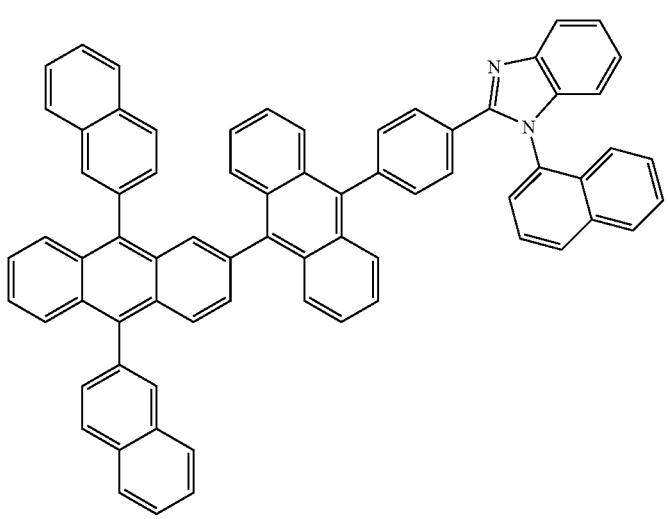
[Formula 1-14]
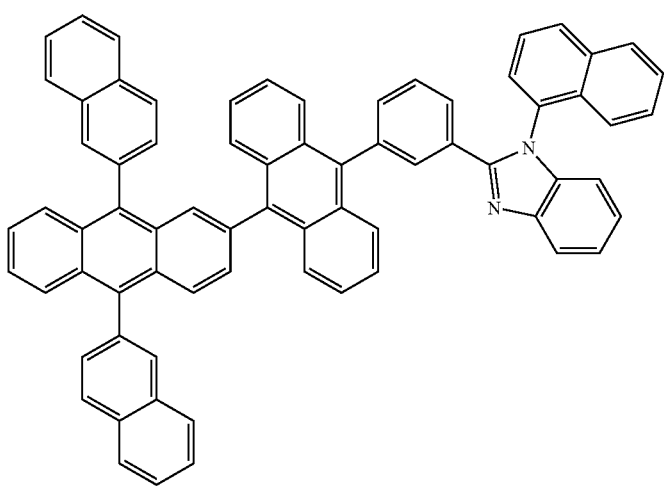

[Formula 1-15]
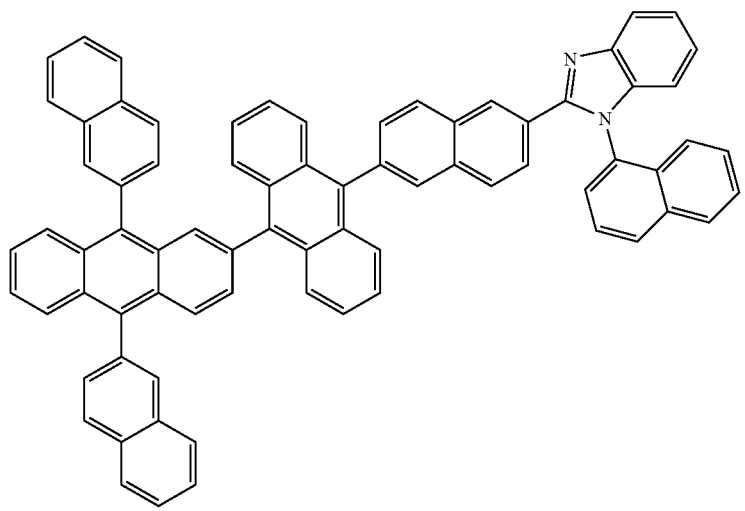
[Formula 1-16]
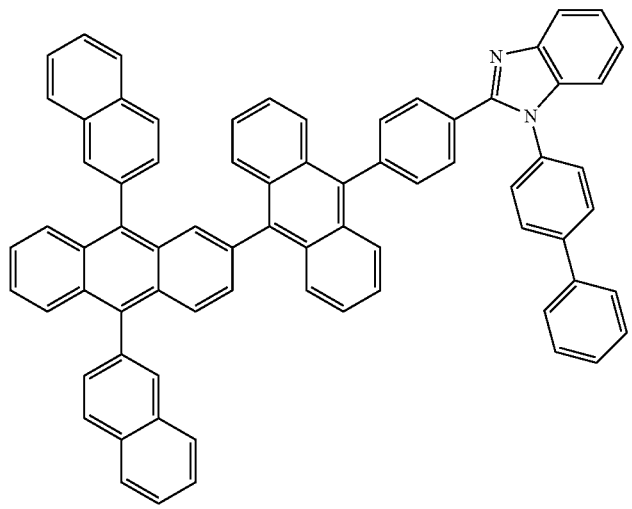
[Formula 1-17]
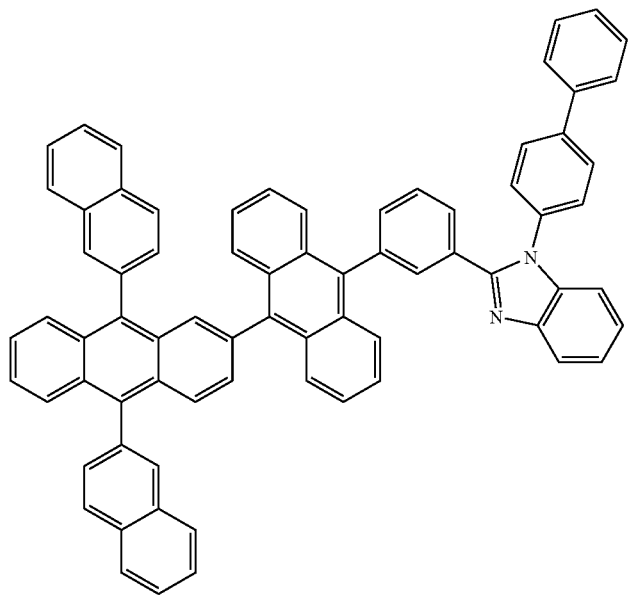

[Formula 1-18]
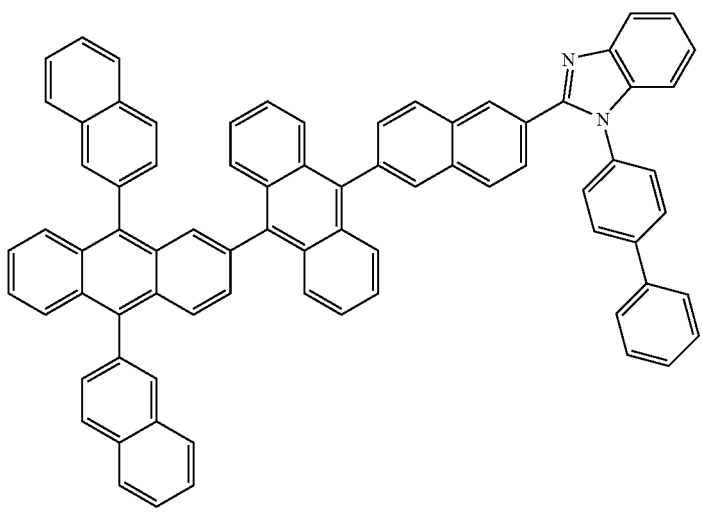
[Formula 1-19]
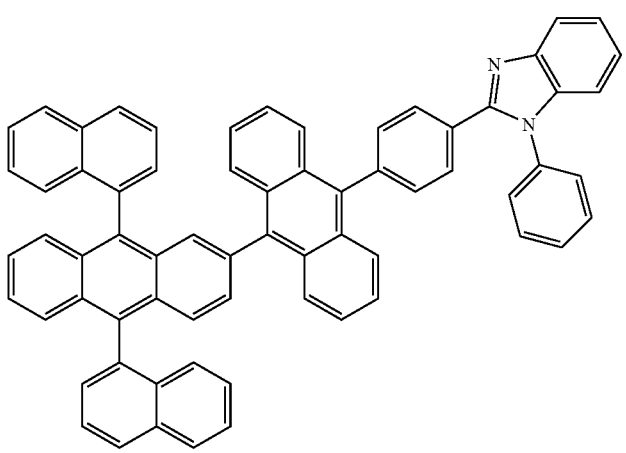
[Formula 1-20]
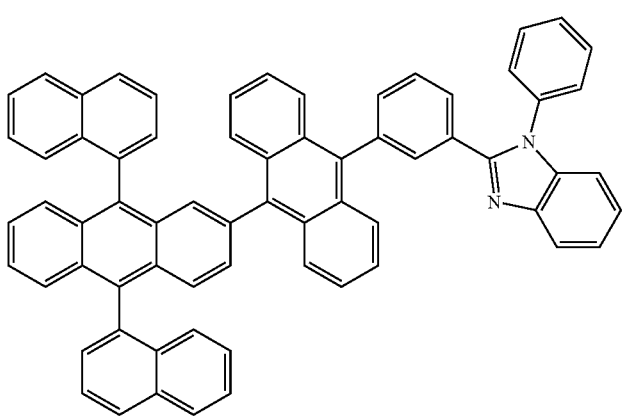

[Formula 1-21]
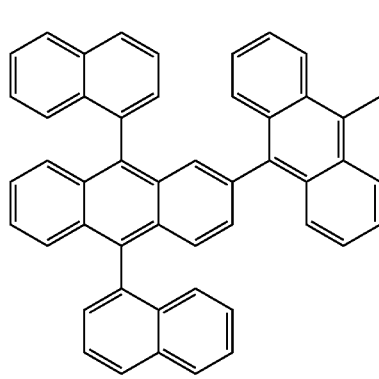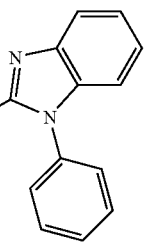
[Formula 1-22]
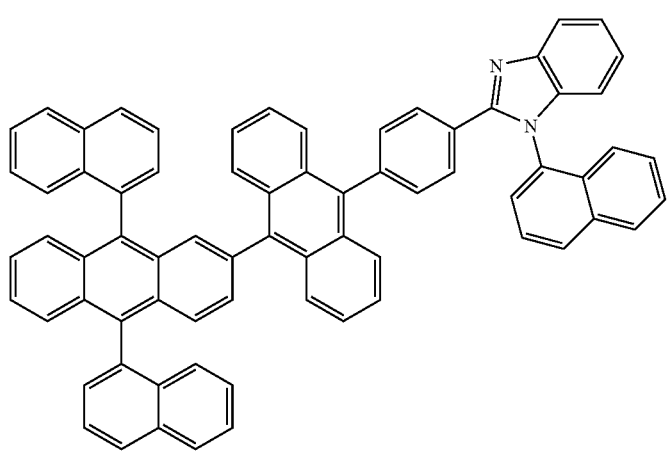
[Formula 1-23]
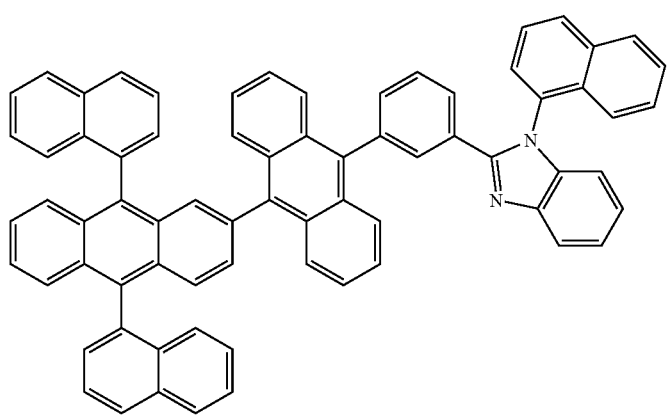

[Formula 1-24]
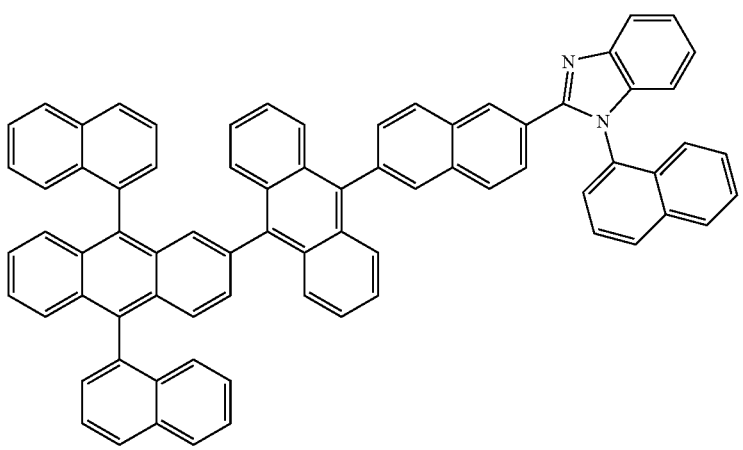
[Formula 1-25]
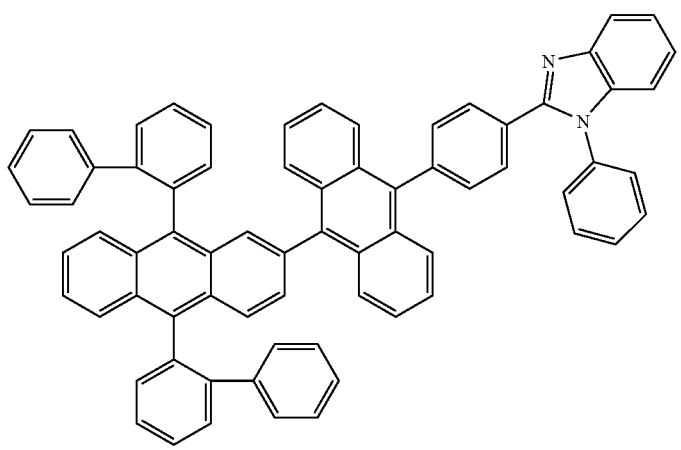
[Formula 1-26]
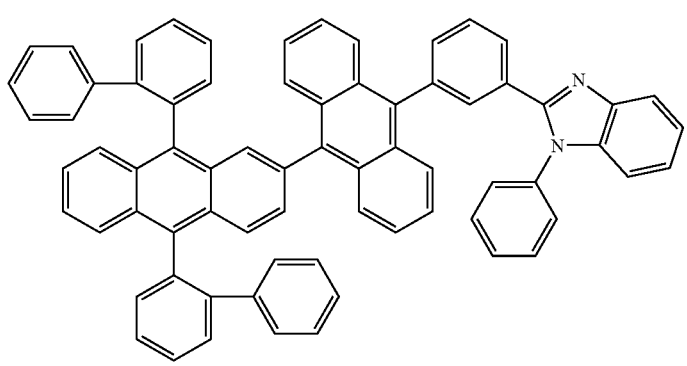

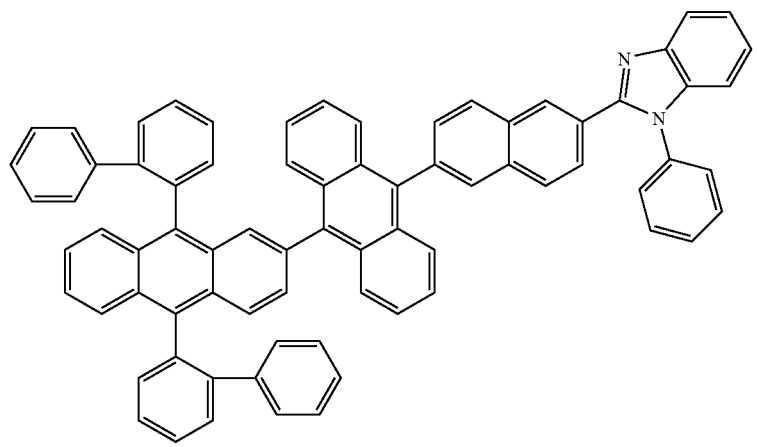
[Formula 1-27]
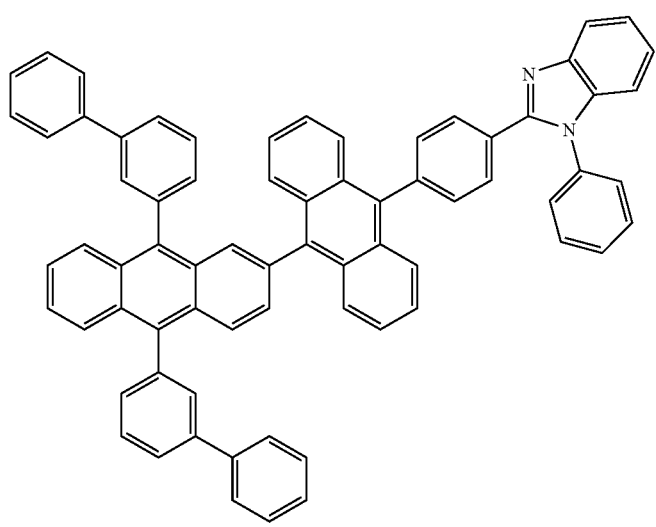
[Formula 1-28]
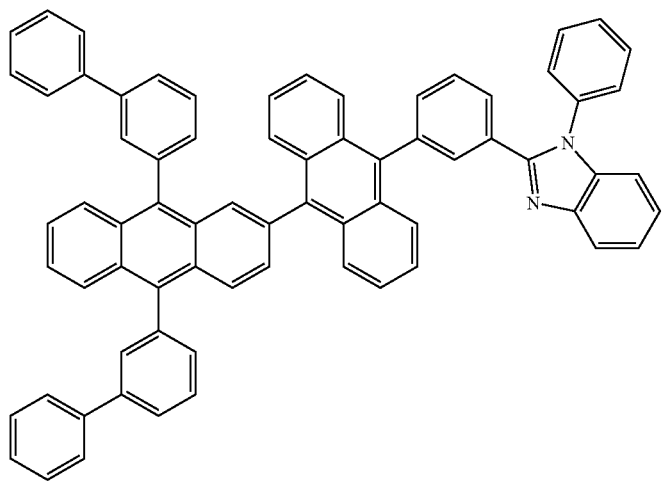
[Formula 1-29]

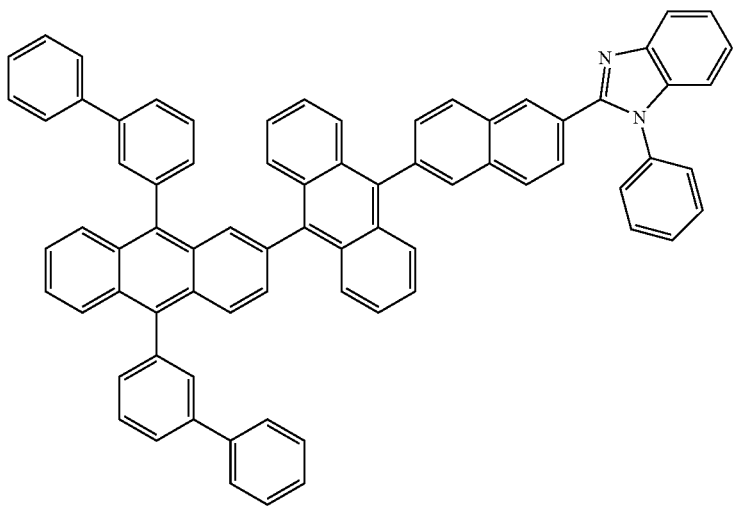
[Formula 1-30]
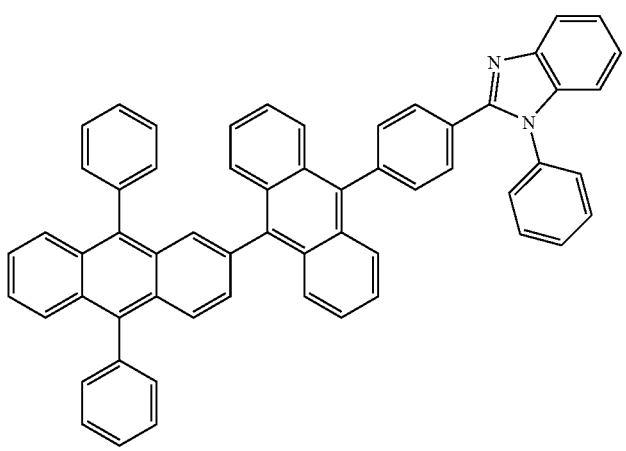
[Formula 1-31]
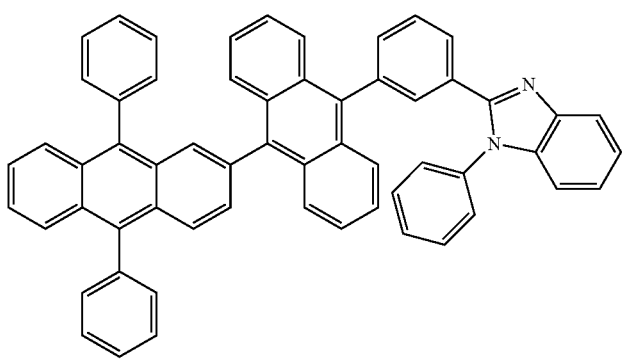
[Formula 1-32]

-continued
[Formula 1-33]
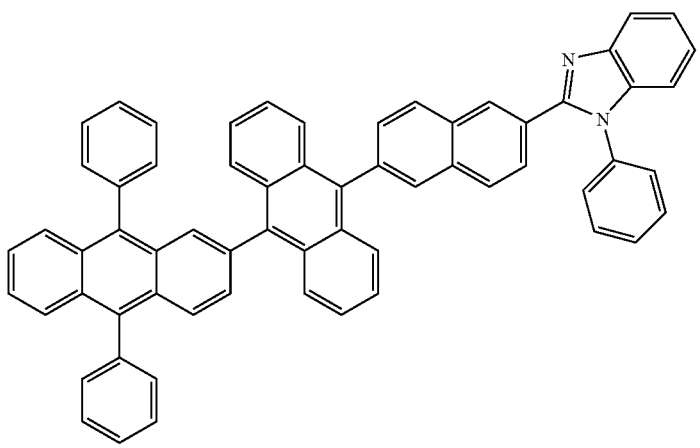
[Formula 1-34]
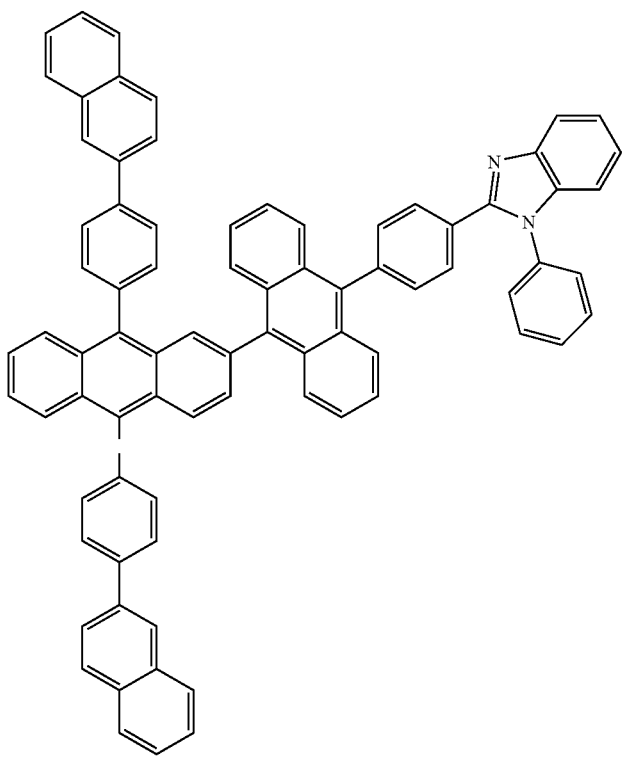
[Formula 1-35]
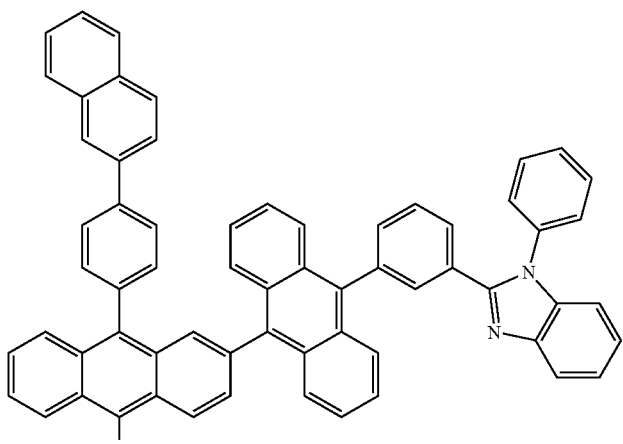

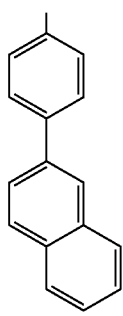
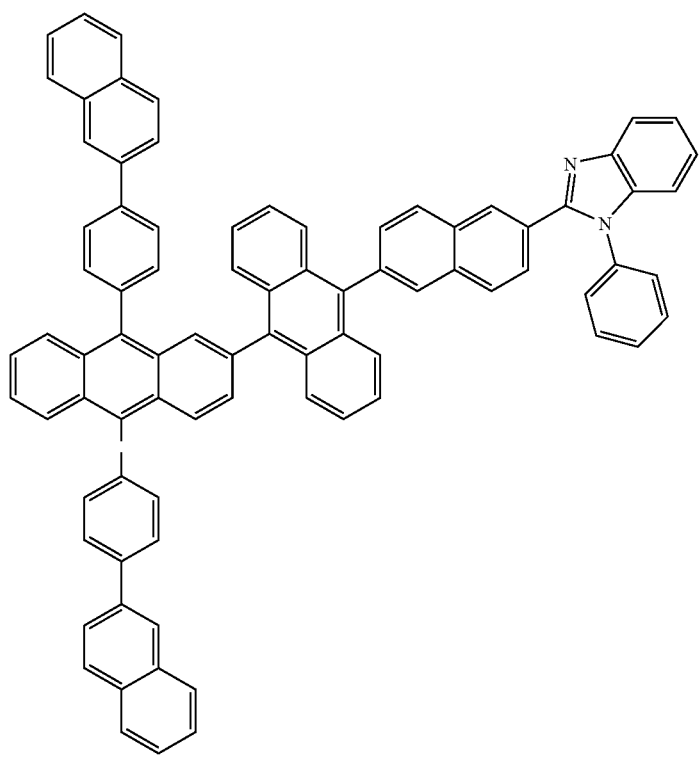
[Formula 1-36]
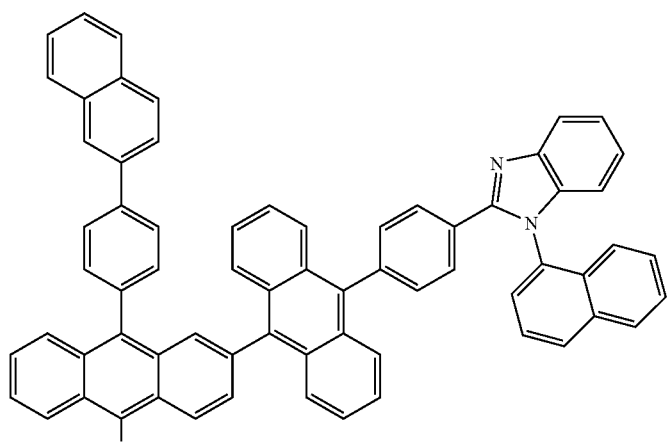
[Formula 1-37]

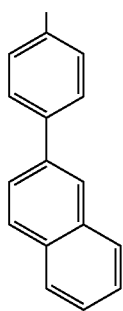
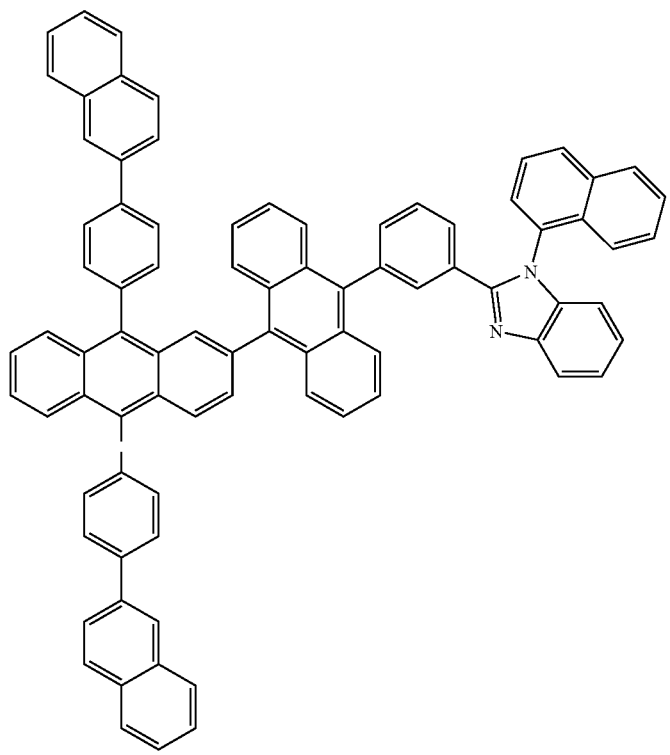
[Formula 1-38]
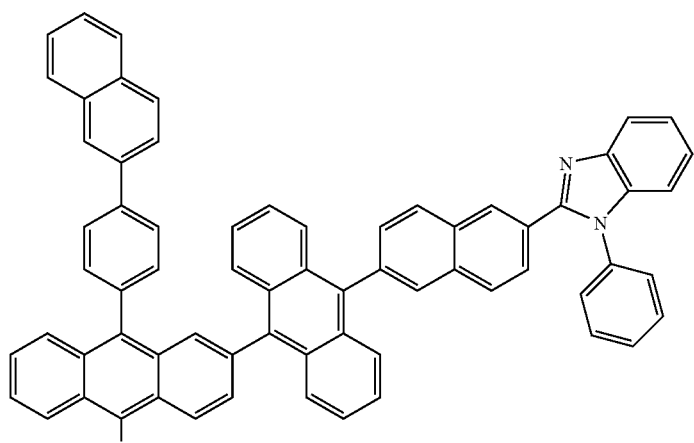
[Formula 1-39]

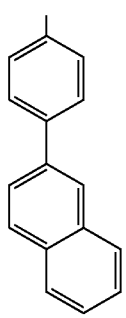
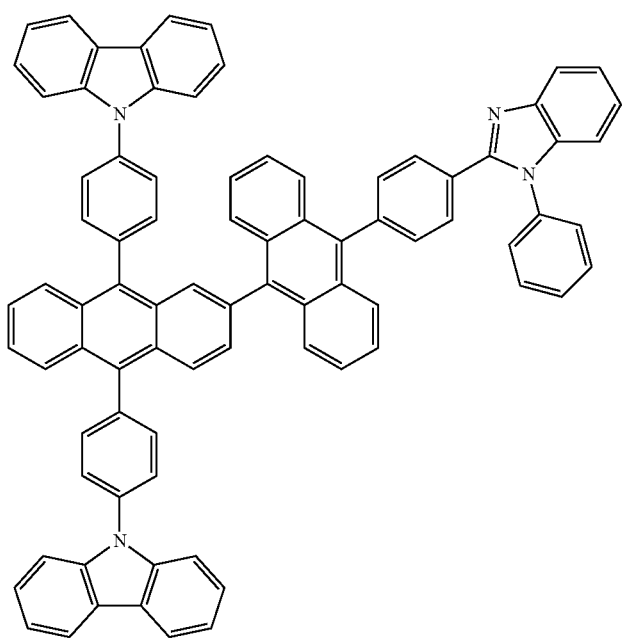
[Formula 1-40]
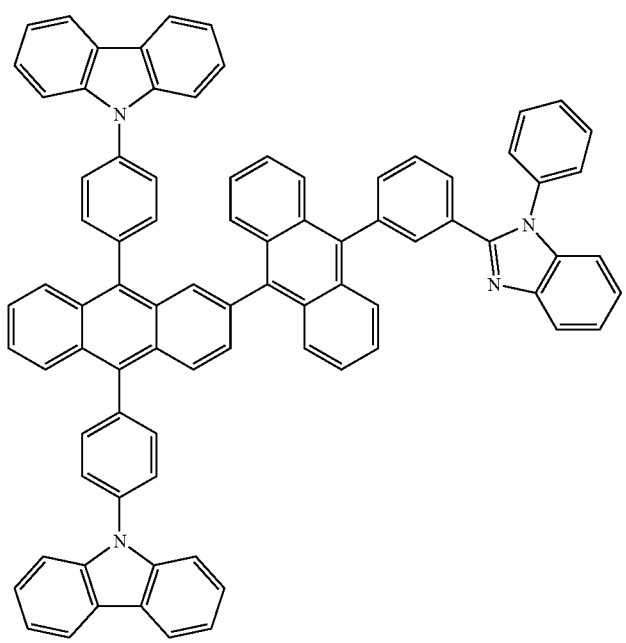
[Formula 1-41]

-continued
[Formula 1-42]
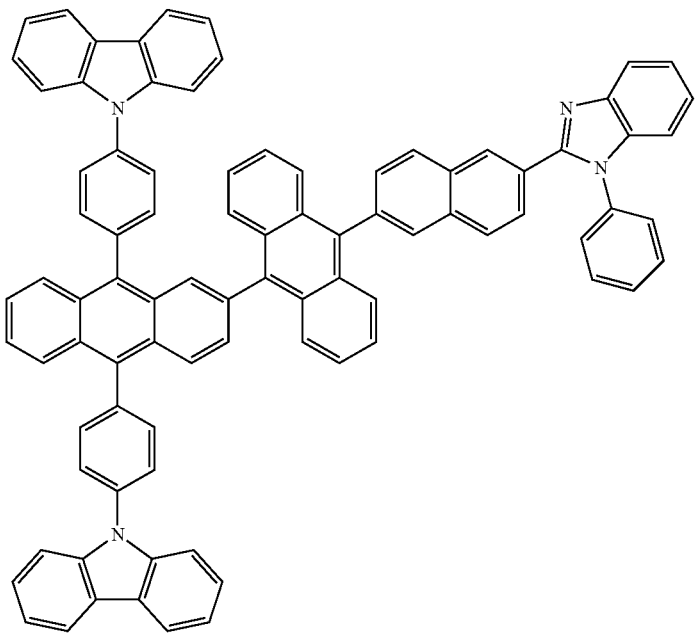
[Formula 1-43]
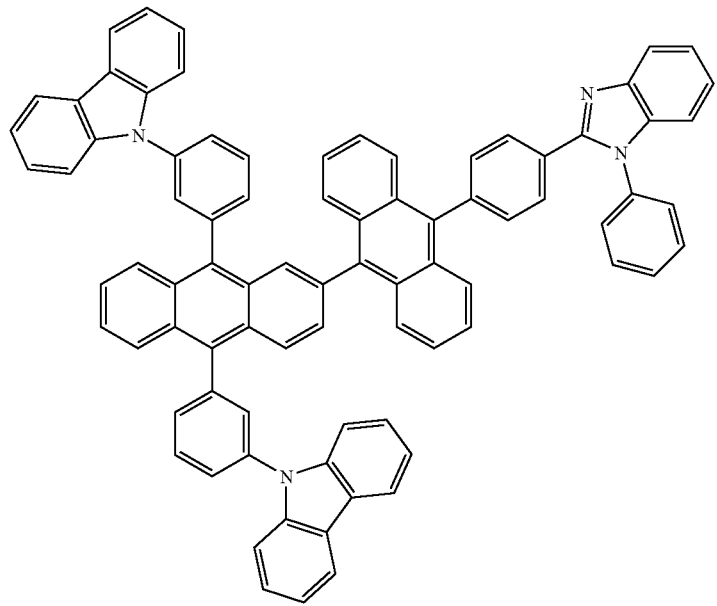

[Formula 1-44]
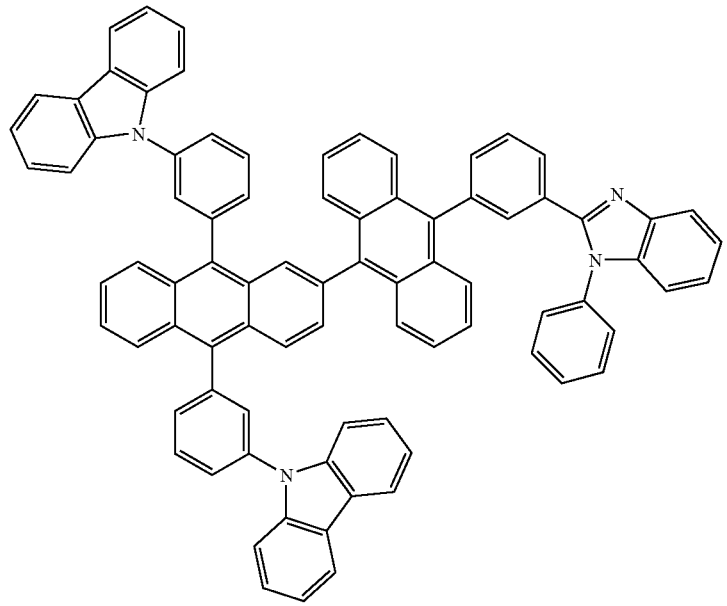
[Formula 1-45]
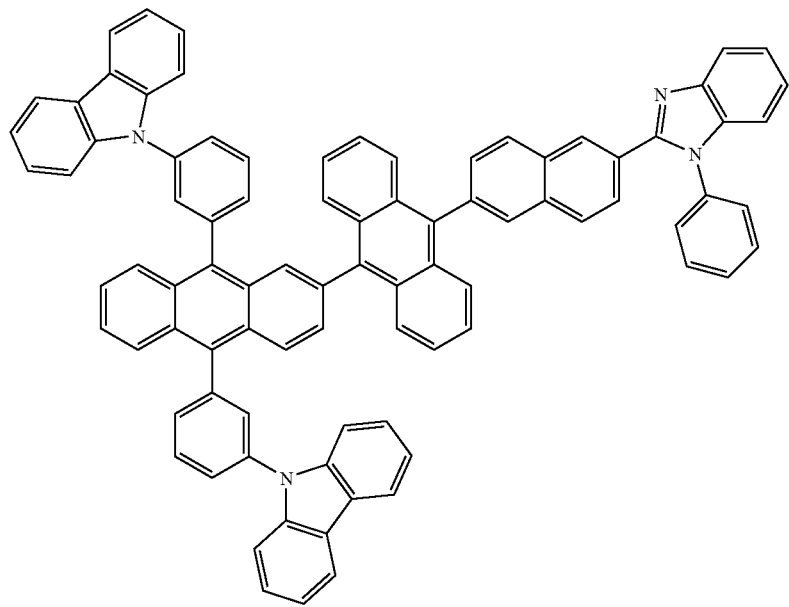

[Formula 1-46]
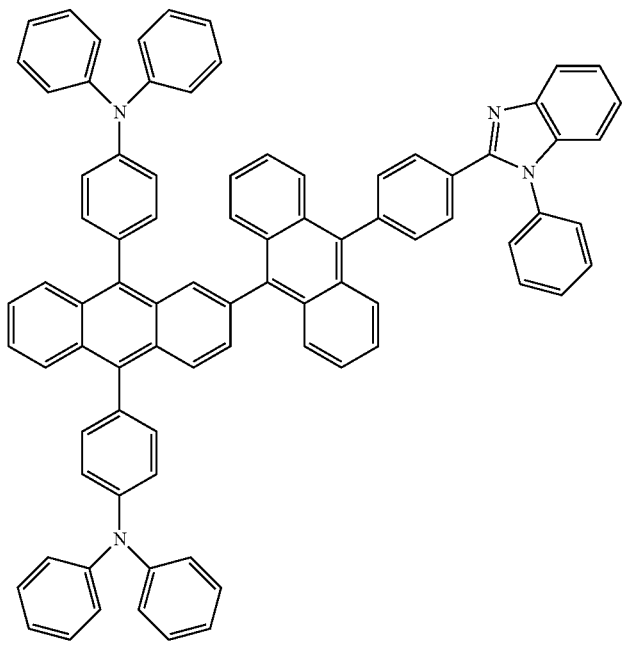
[Formula 1-47]
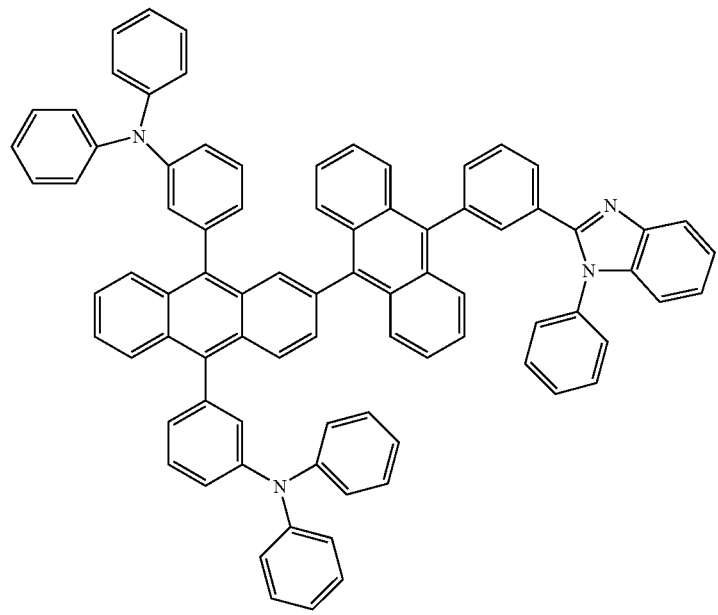

[Formula 1-48]
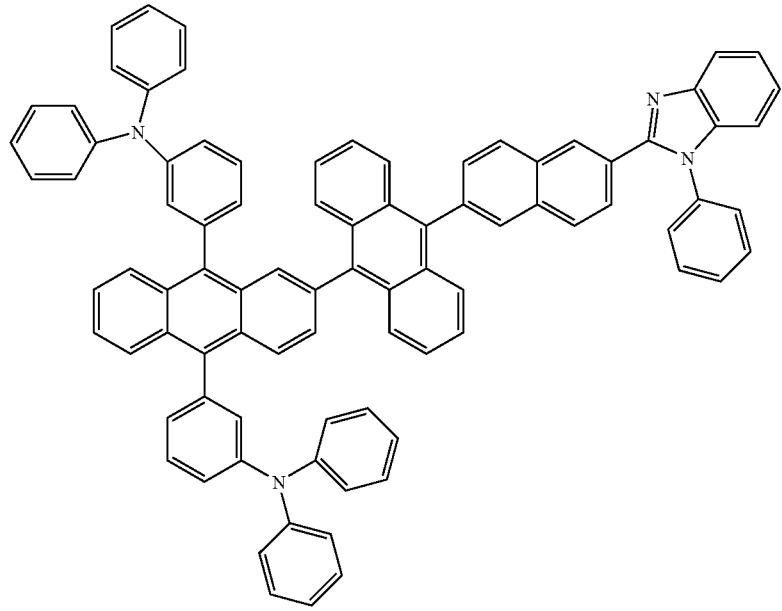
[Formula 1-49]
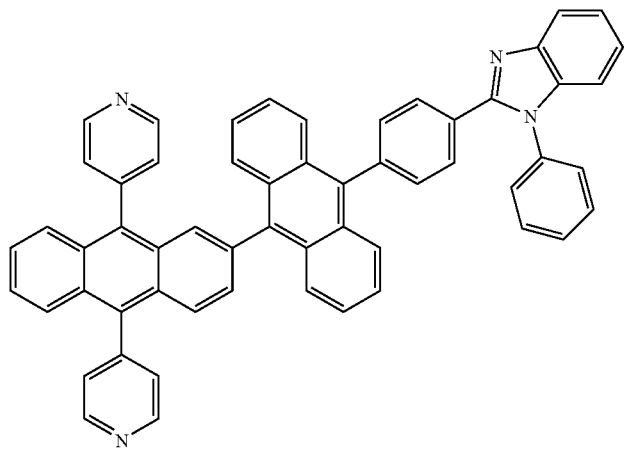
[Formula 1-50]
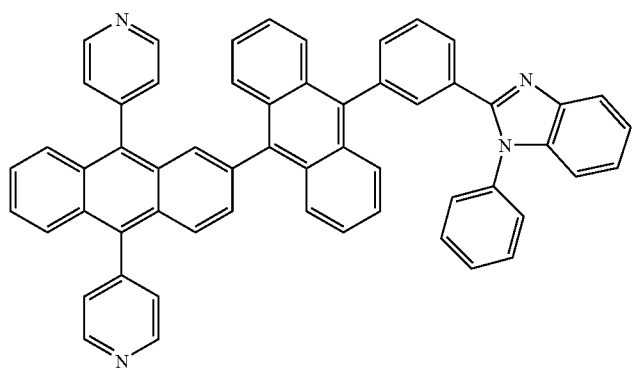

[Formula 1-51]
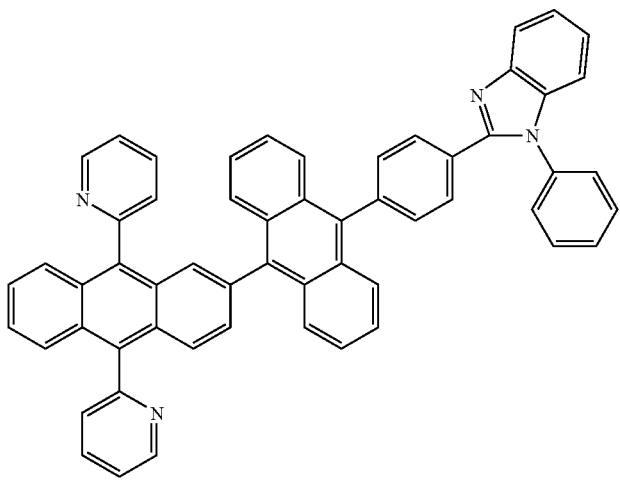
[Formula 1-52]
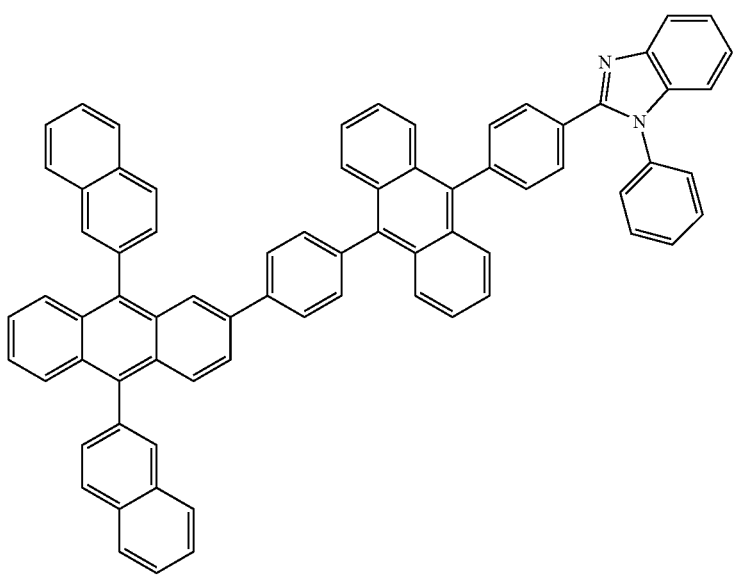
[Formula 1-53]
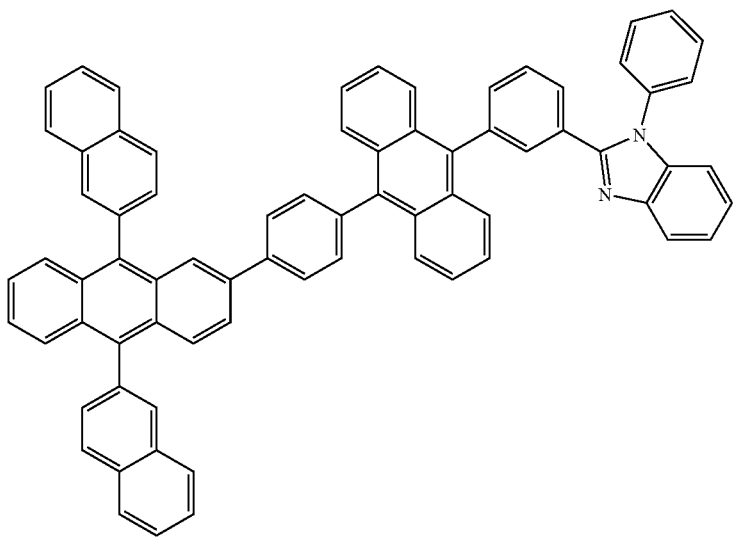

[Formula 1-54]
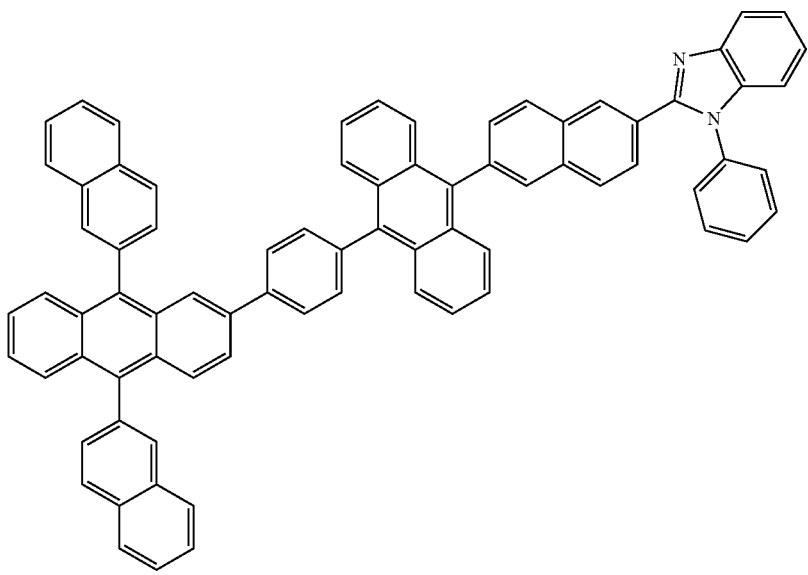
[Formula 1-55]
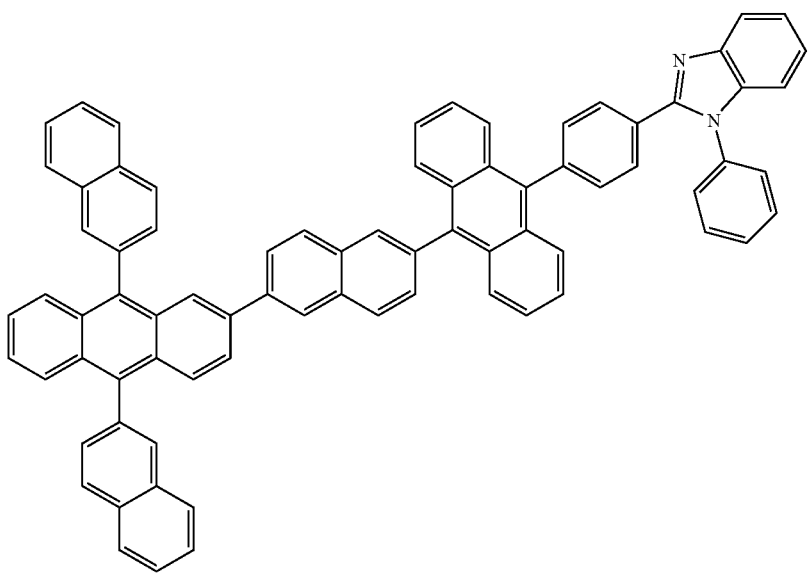
[Formula 1-56]
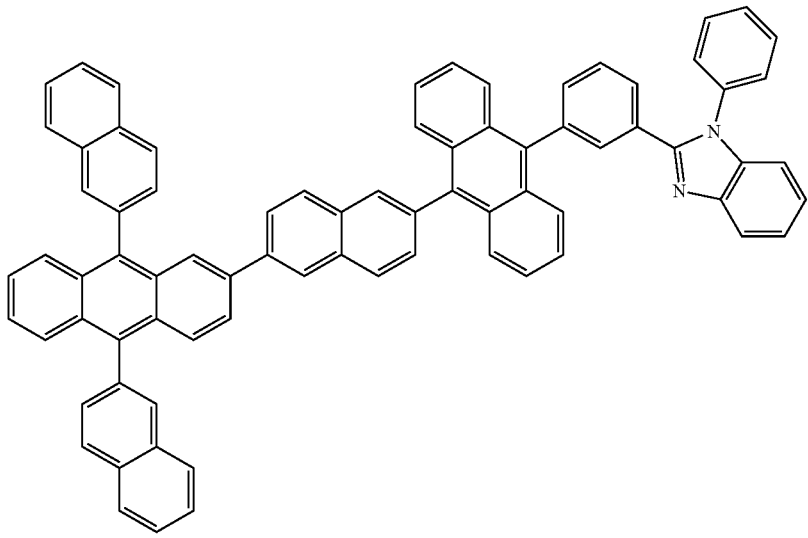

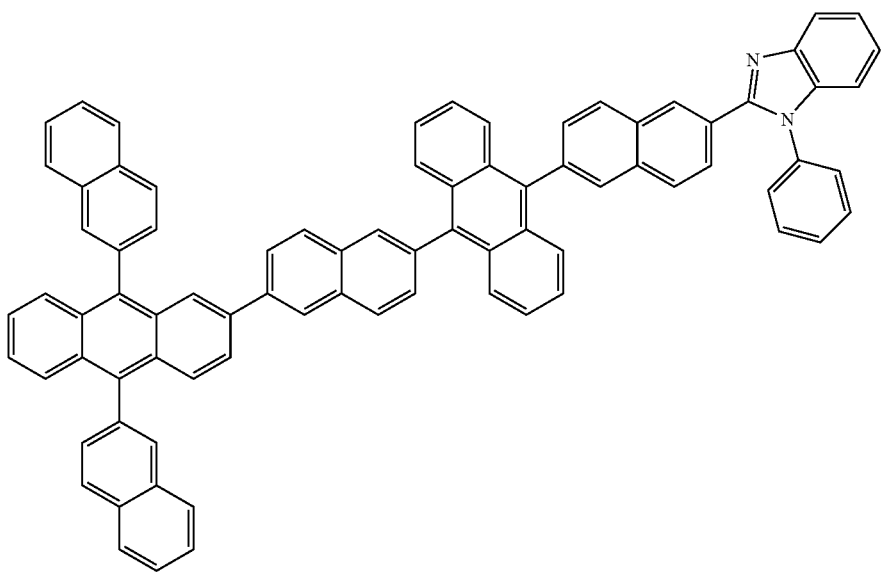
[Formula 1-57]
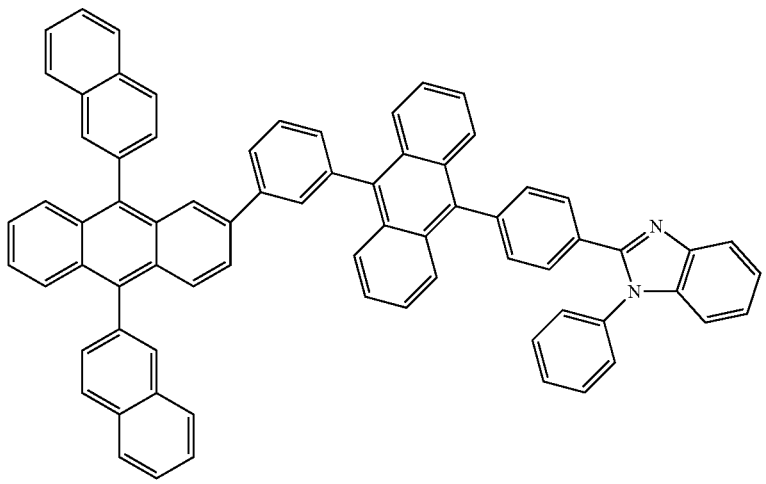
[Formula 1-58]
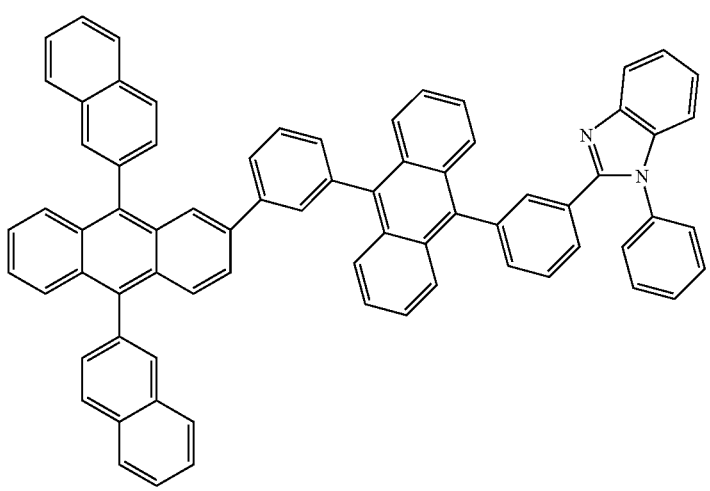
[Formula 1-59]

[Formula 1-60]
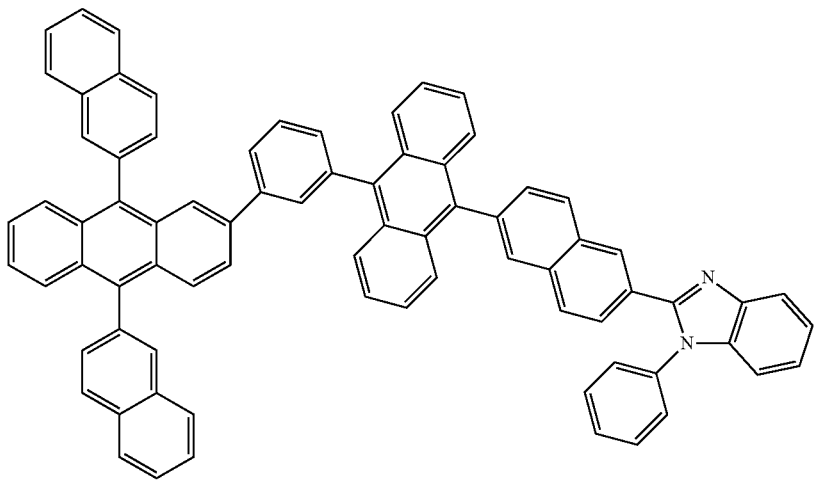
[Formula 1-61]
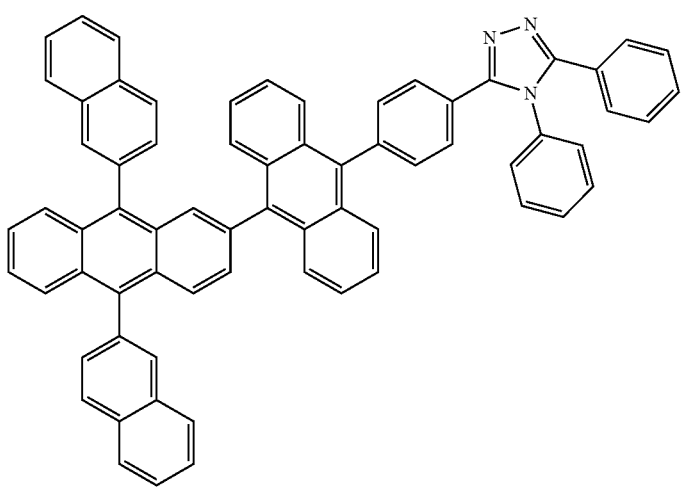
[Formula 1-62]
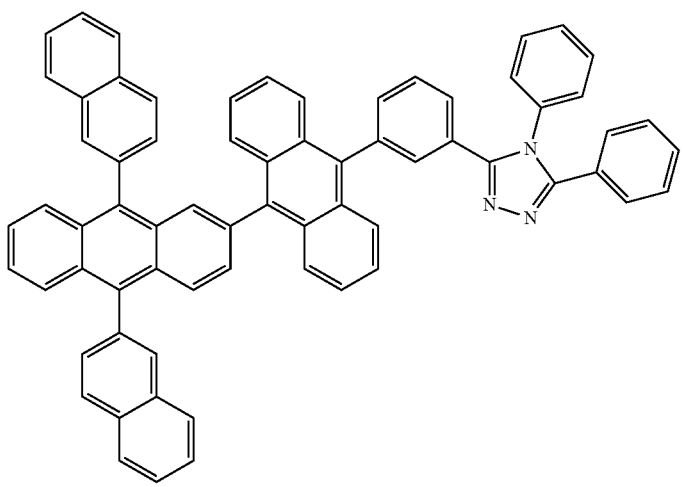

[Formula 1-63]
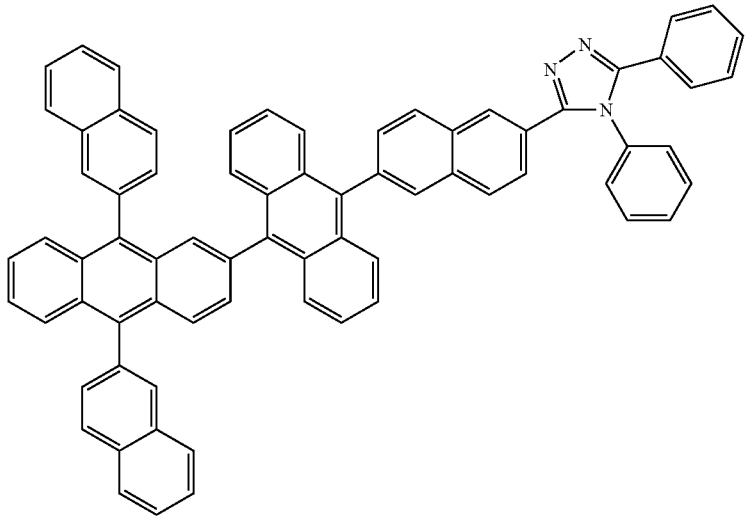
[Formula 1-64]
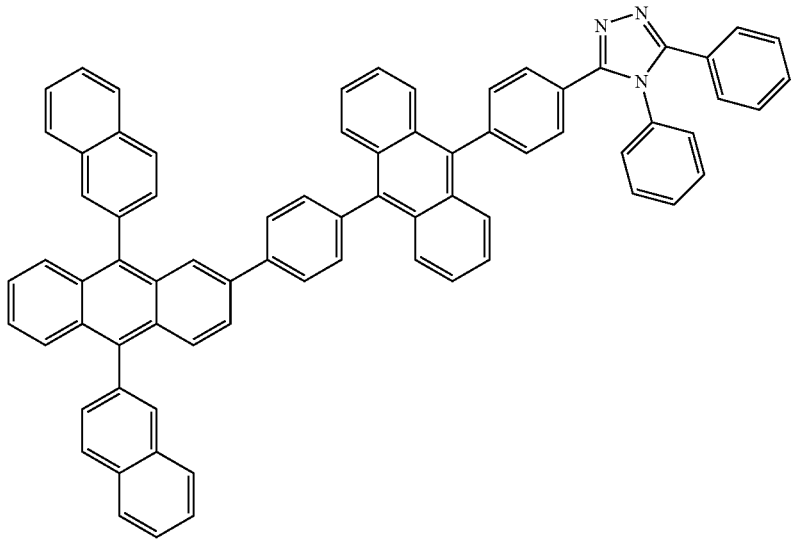
[Formula 1-65]
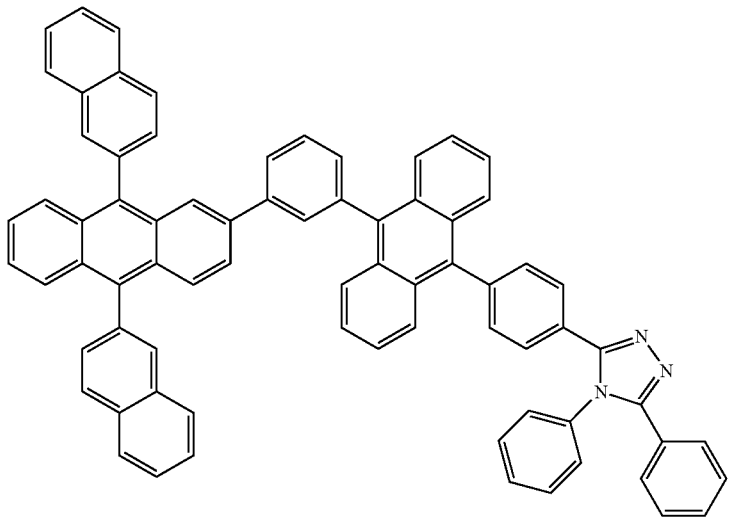

[Formula 1-66]
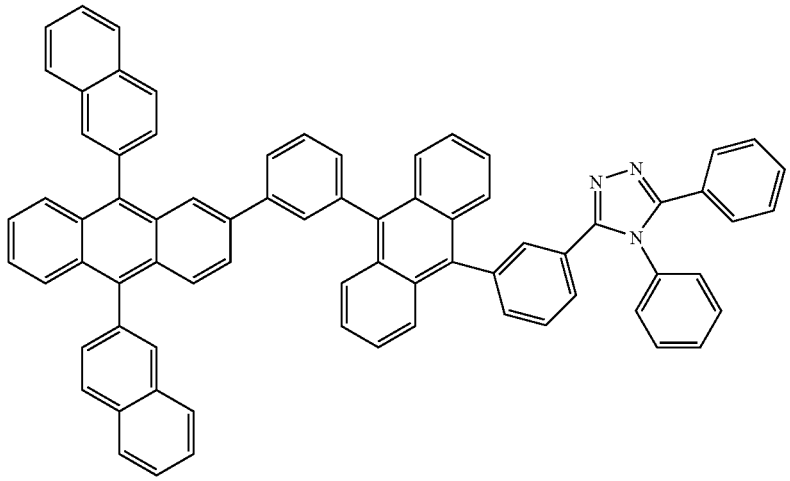
[Formula 1-67]
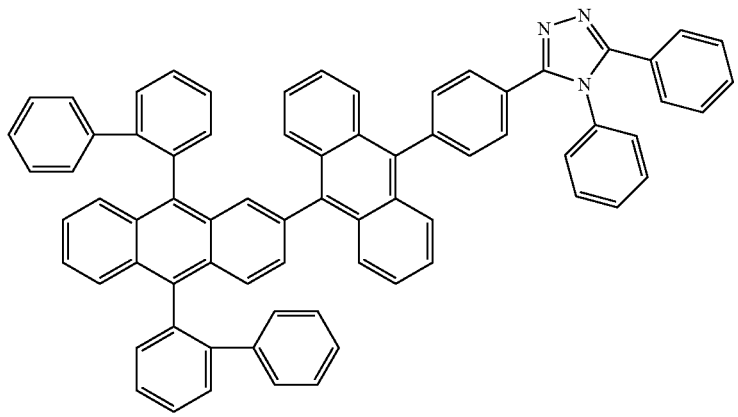
[Formula 1-68]
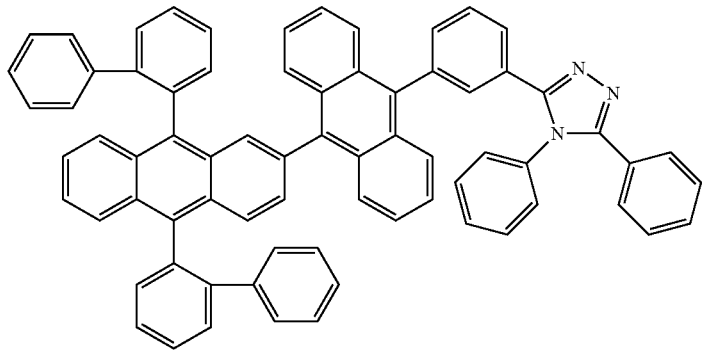
[Formula 1-69]
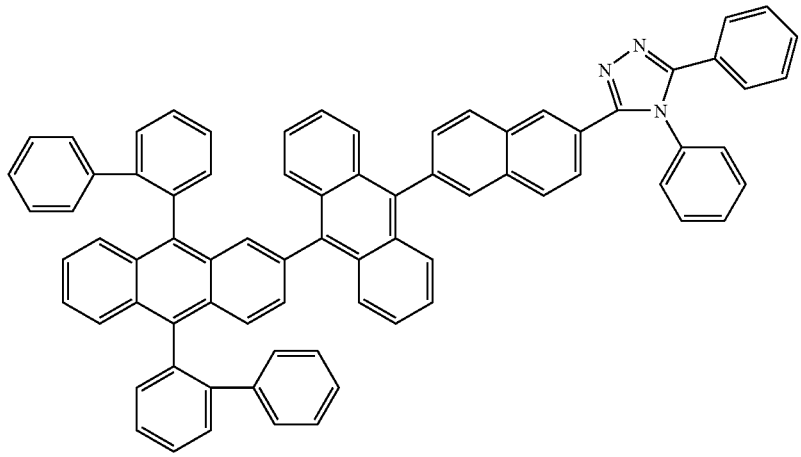

[Formula 1-70]
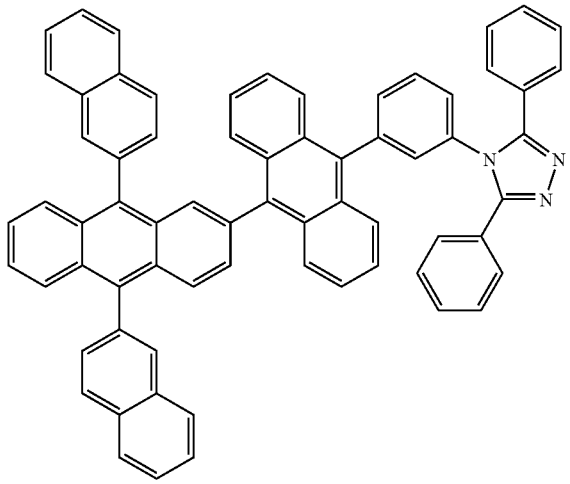
[Formula 1-71]
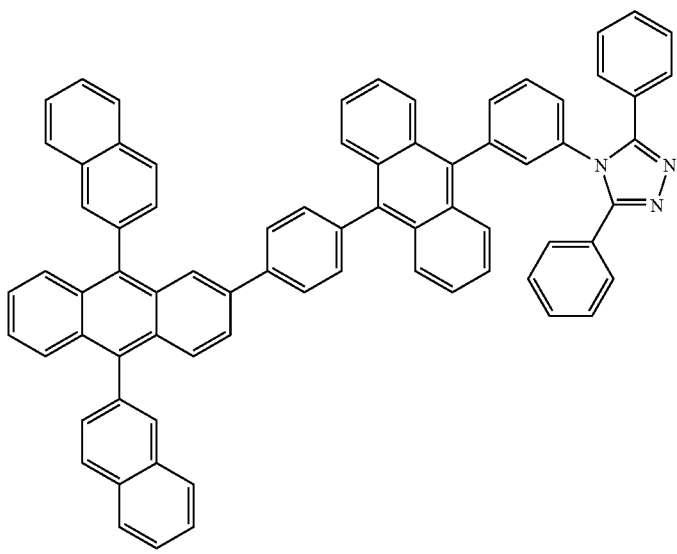
[Formula 1-72]
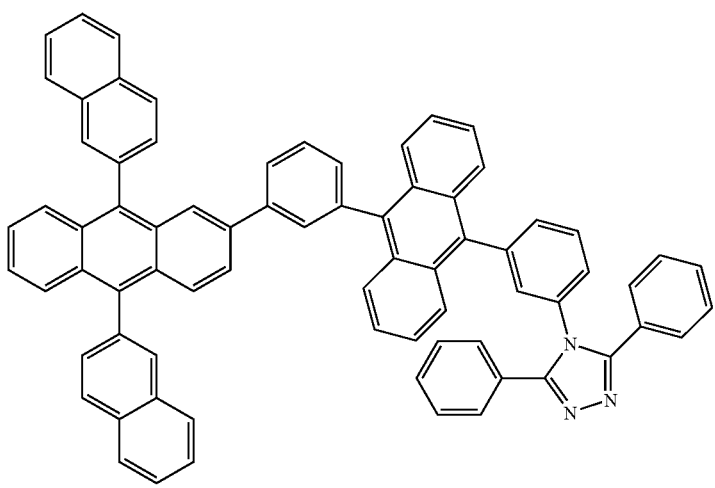

[Formula 1-73]
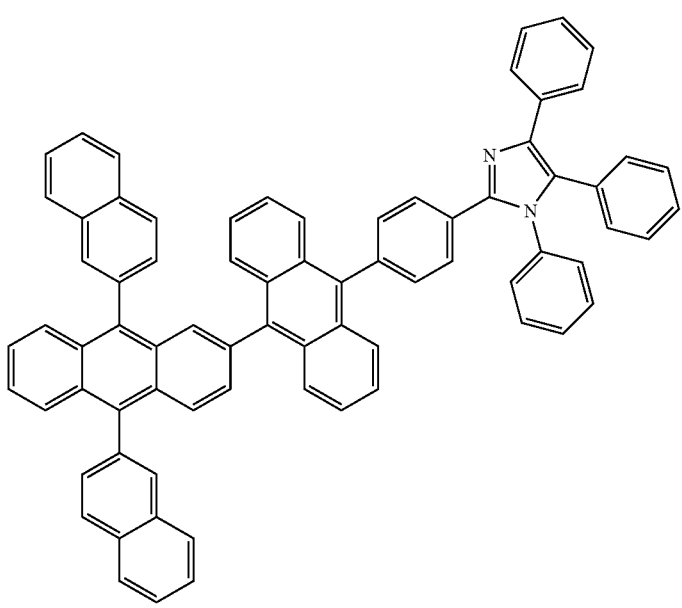
[Formula 1-74]
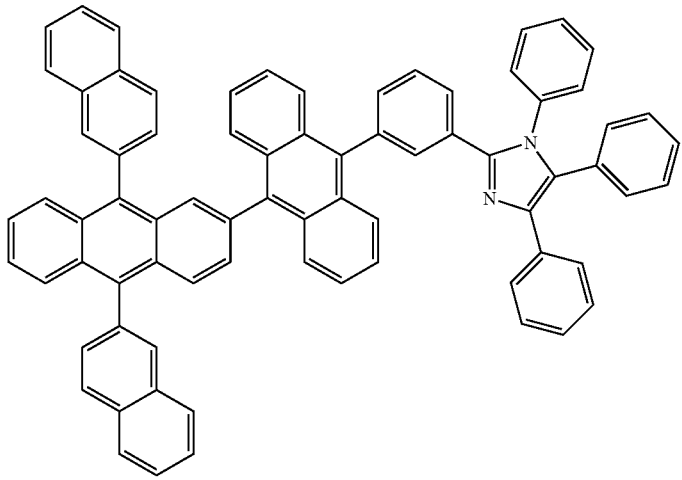
[Formula 1-75]
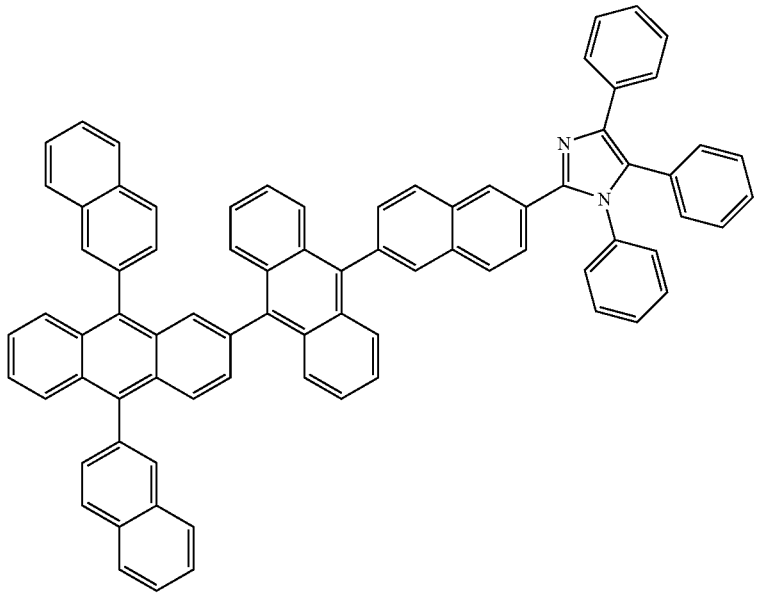

[Formula 1-76]
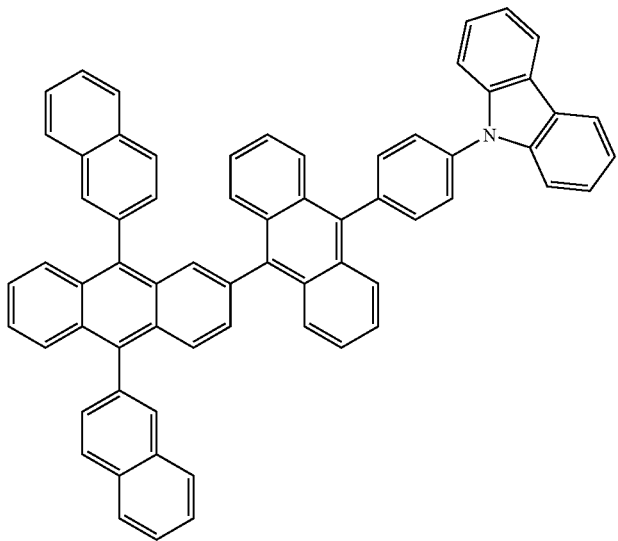
[Formula 1-77]
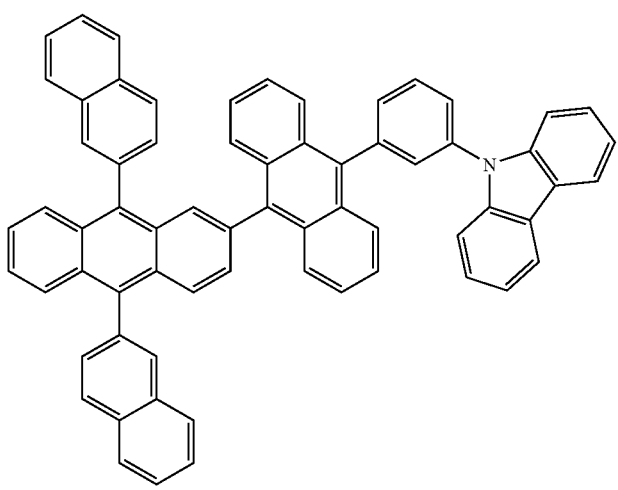
[Formula 1-78]
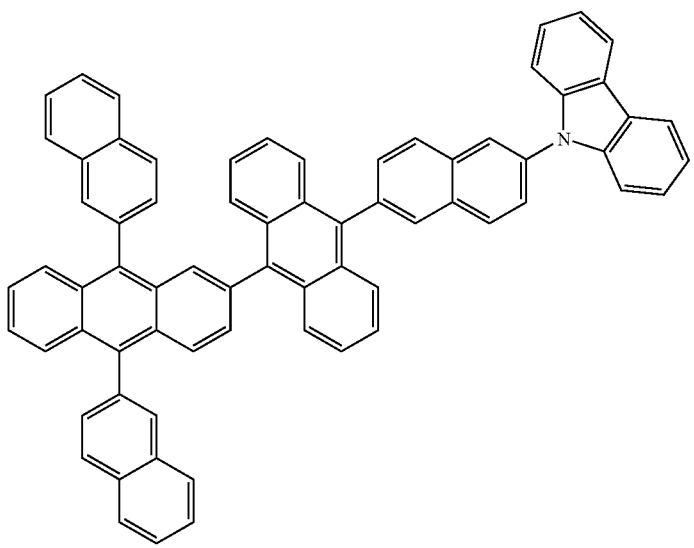

[Formula 1-79]
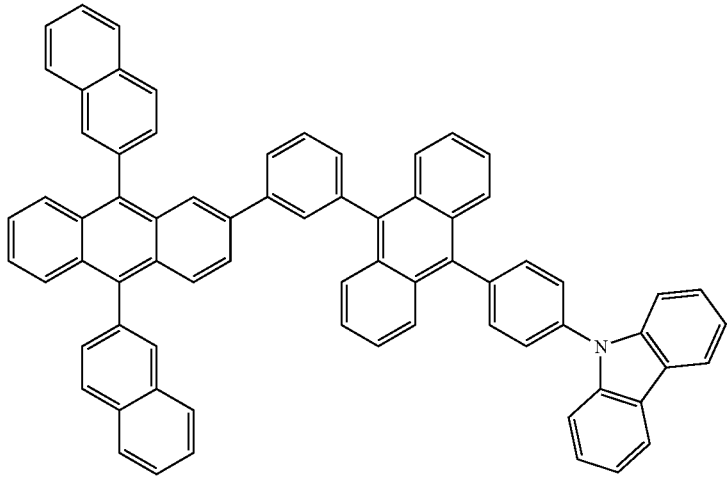
[Formula 1-80]
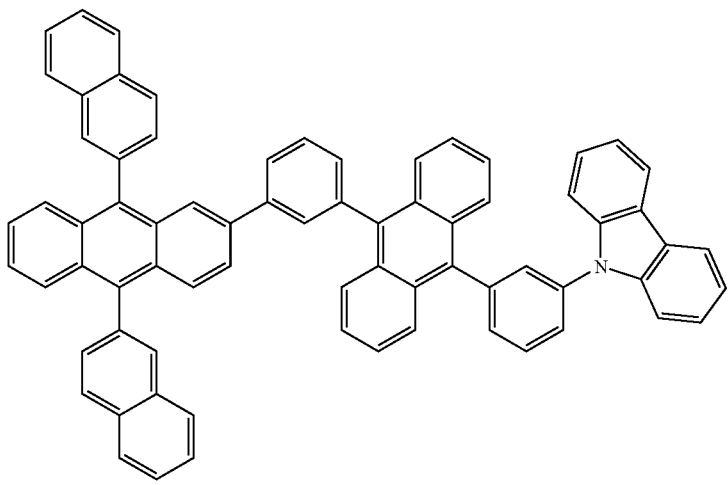
[Formula 1-81]
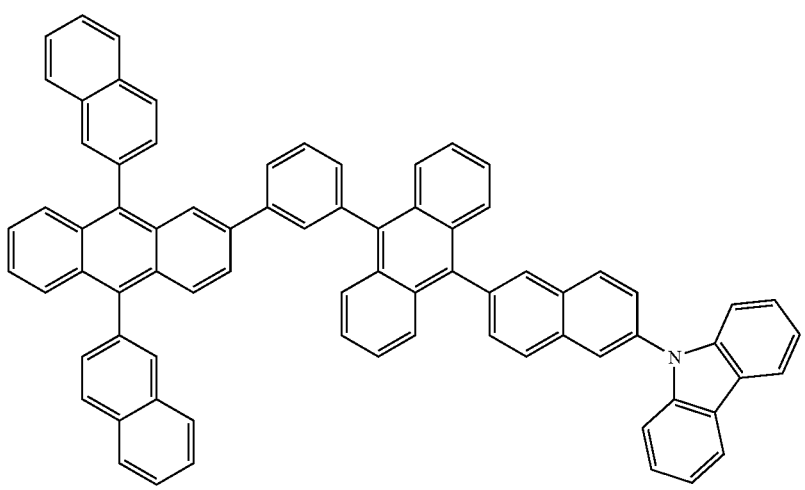

[Formula 1-82]
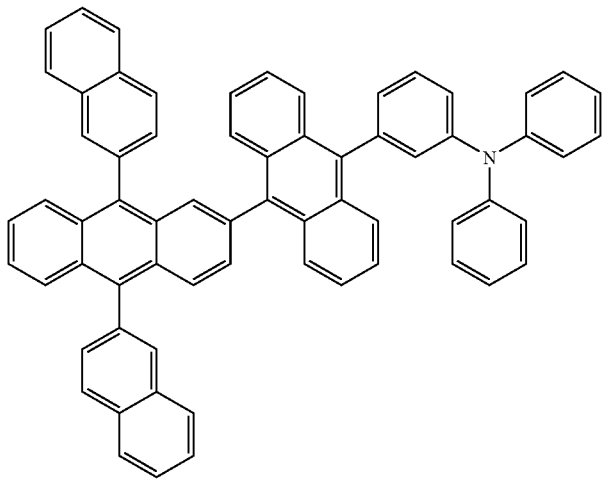
[Formula 1-83]
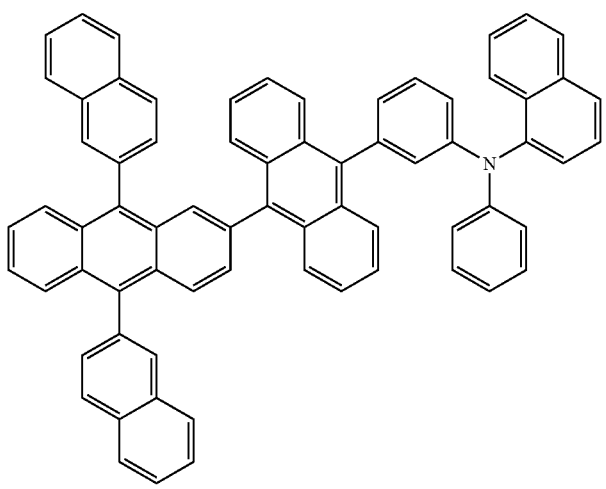
[Formula 1-84]
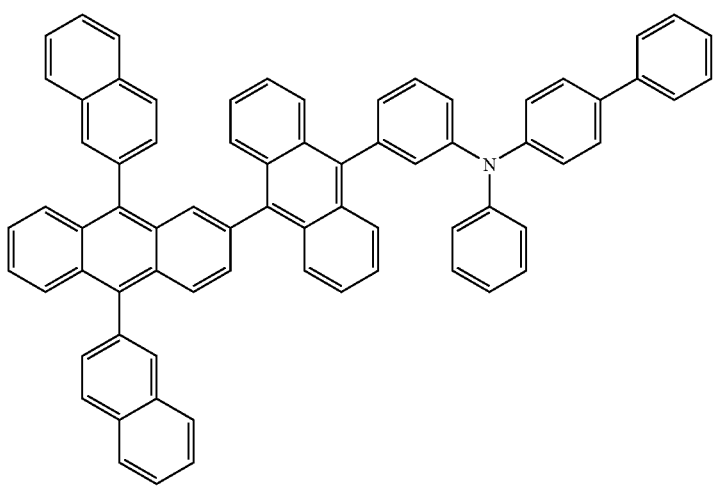

[Formula 1-85]
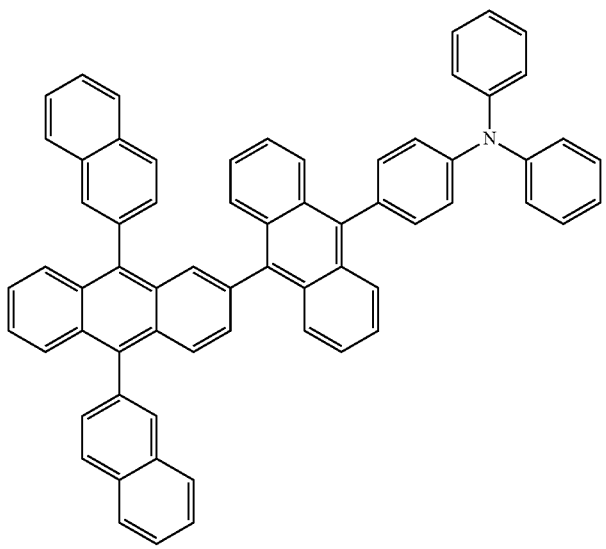
[Formula 1-86]
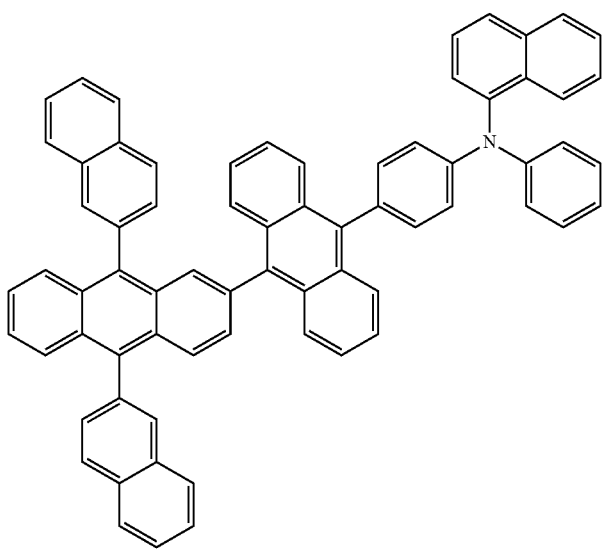
[Formula 1-87]
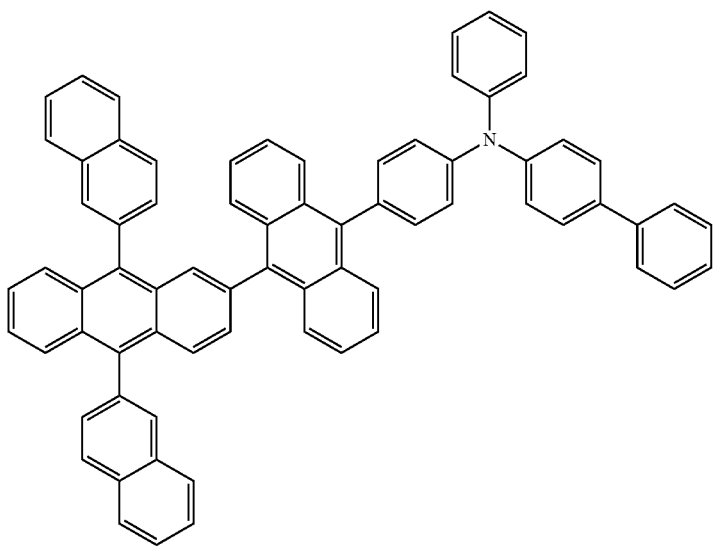

[Formula 1-88]
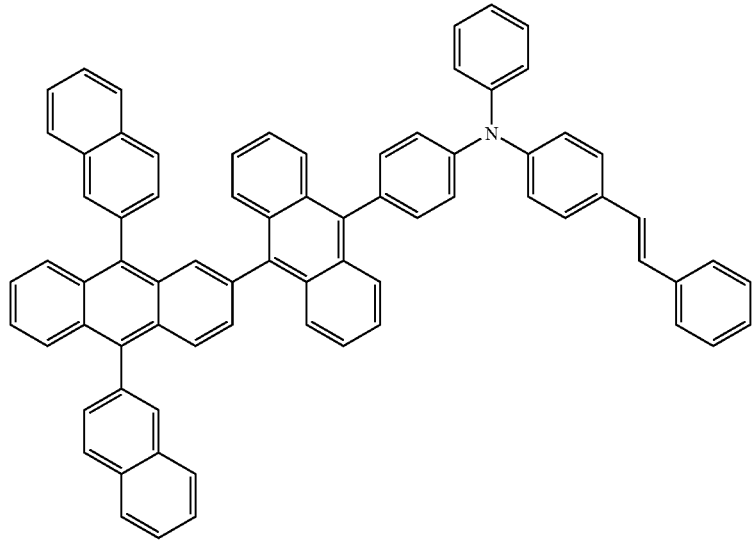
[Formula 1-89]
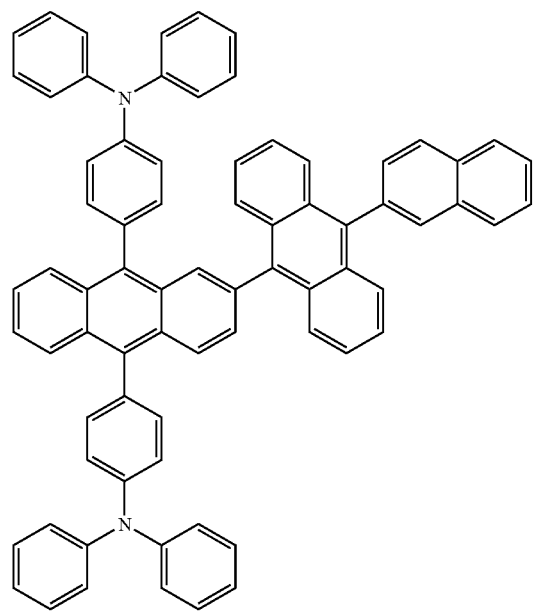
[Formula 1-90]
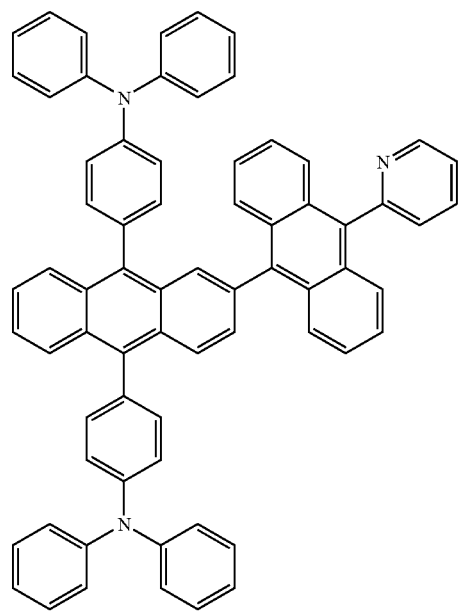

[Formula 1-91]
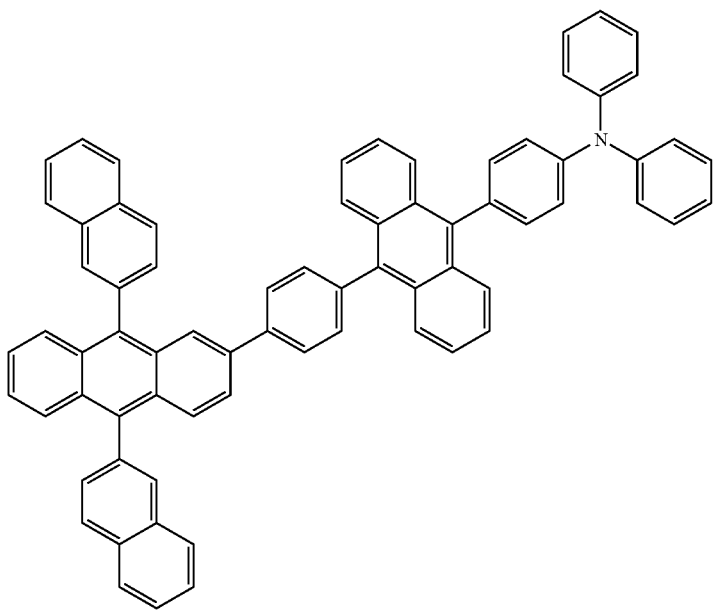
[Formula 1-92]
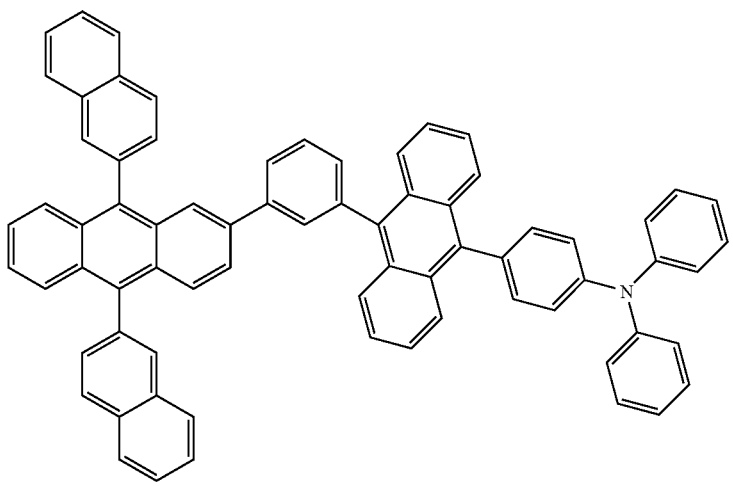
[Formula 1-93]
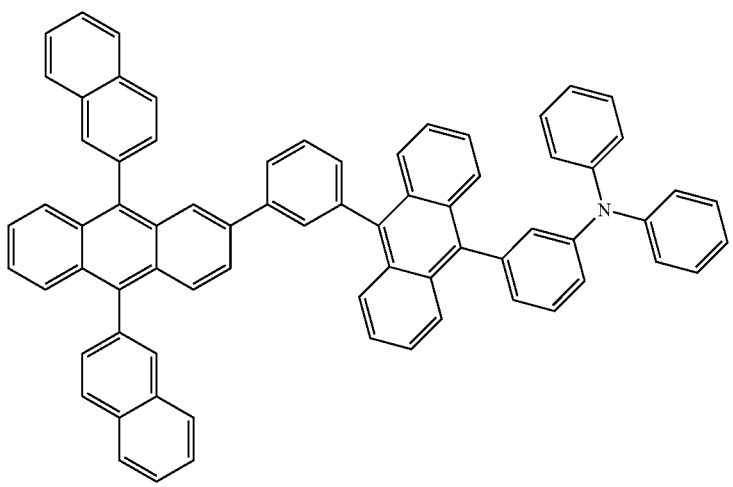

[Formula 1-94]
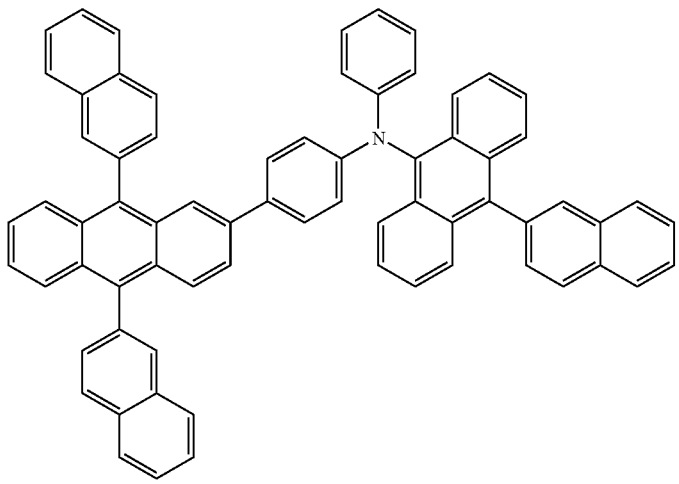
[Formula 1-95]
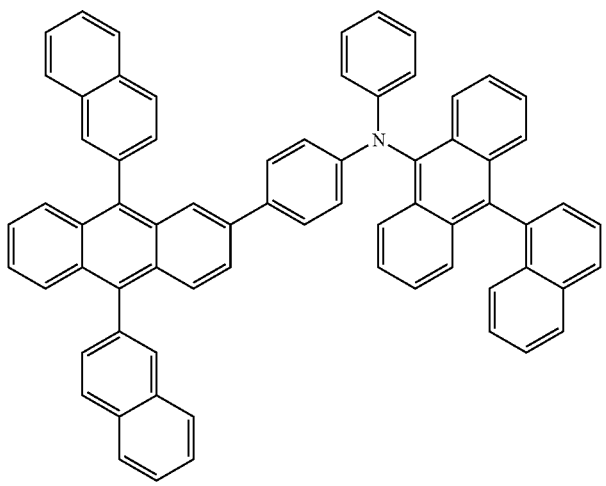
[Formula 1-96]
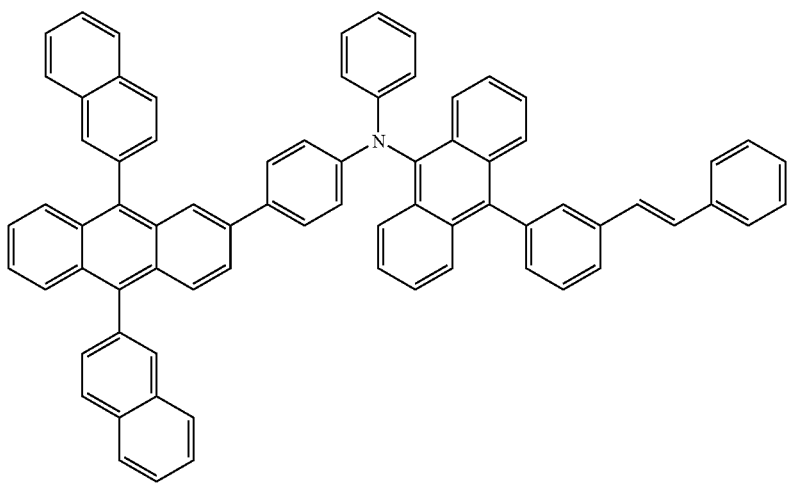

-continued
[Formula 1-97]
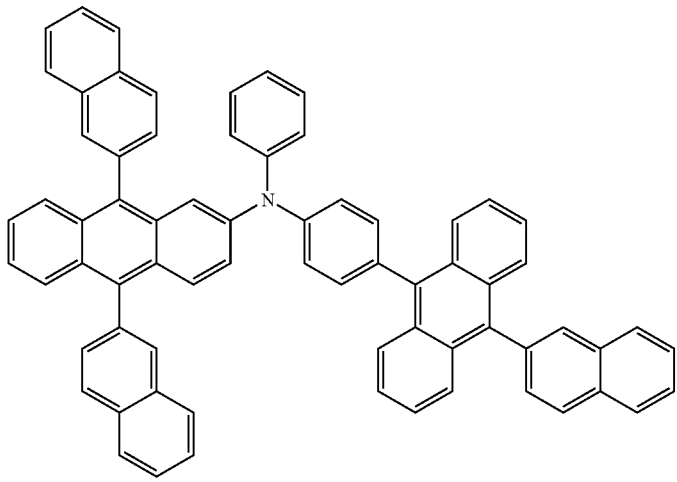
[Formula 1-98]
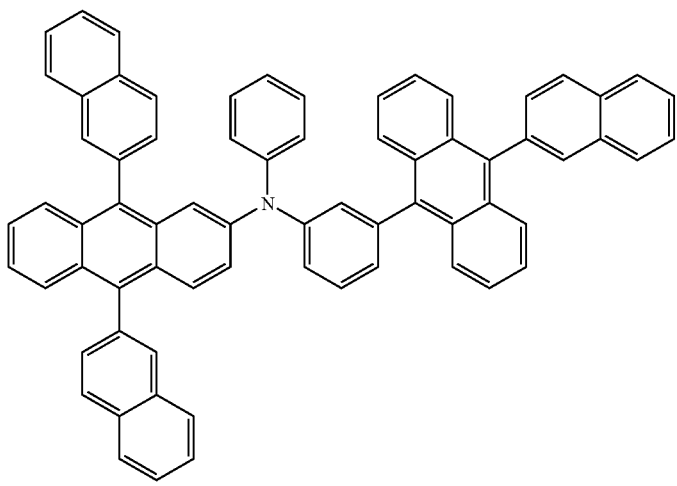
[Formula 1-99]
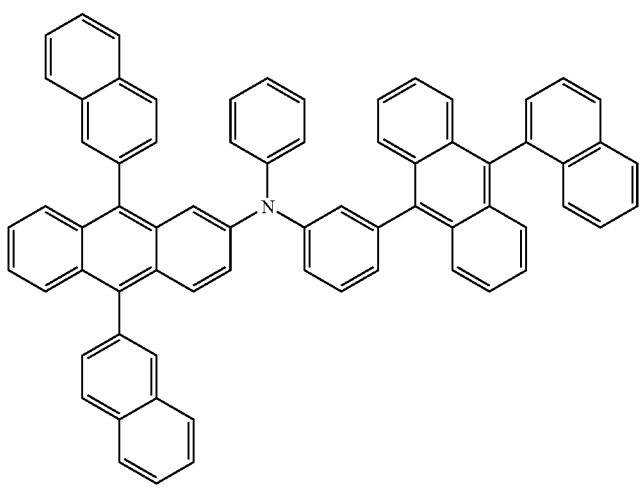

-continued
[Formula 1-100]
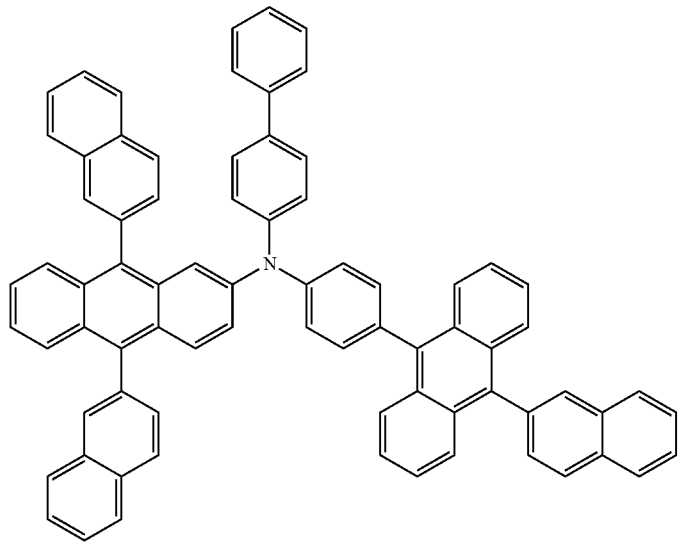
[Formula 1-101]
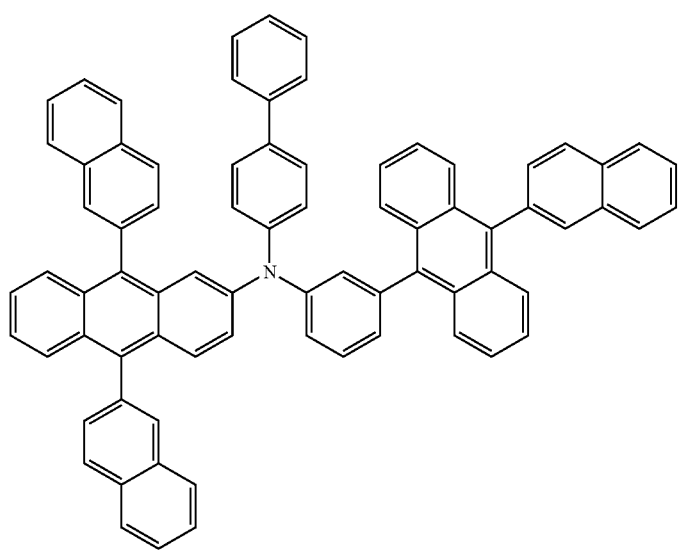
[Formula 1-102]
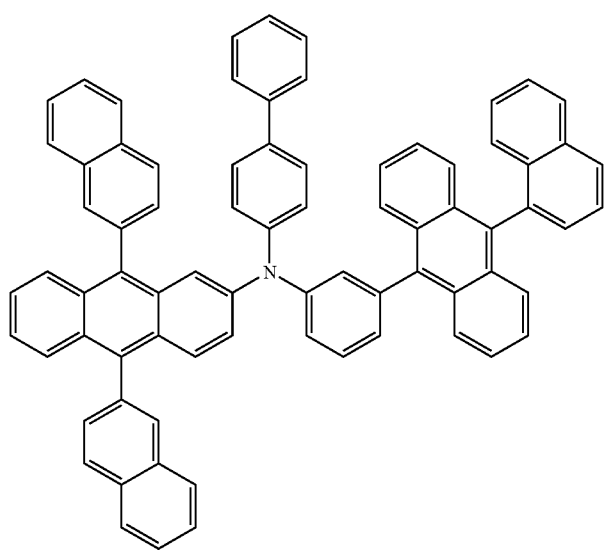

[Formula 1-103]
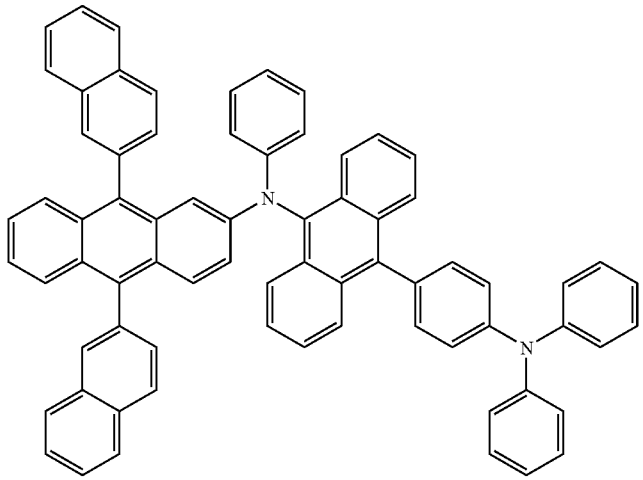
[Formula 1-104]
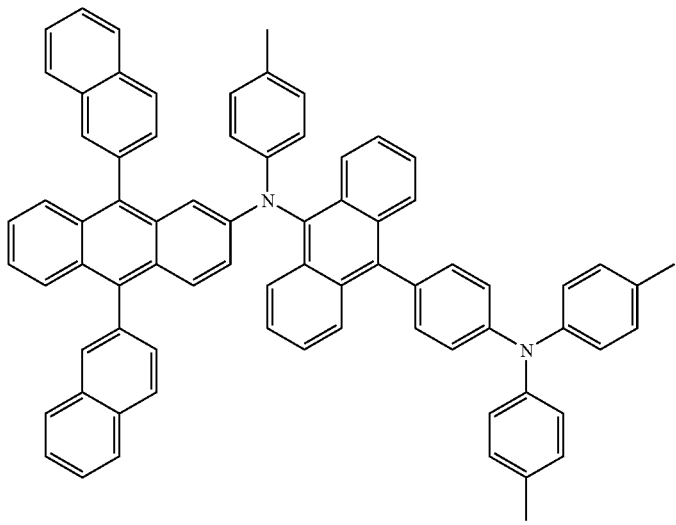
[Formula 1-105]
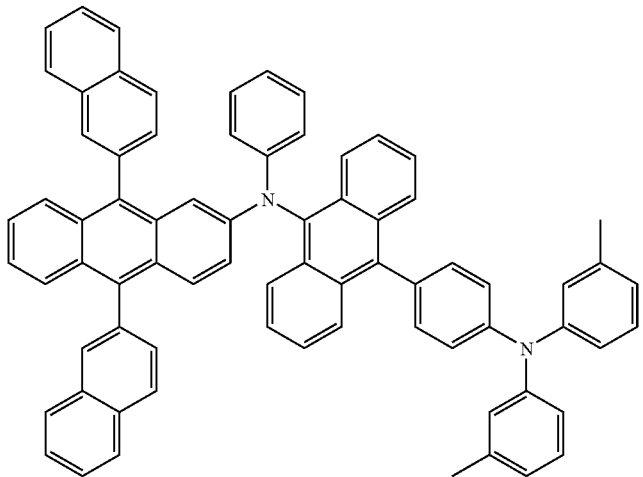

[Formula 1-106]
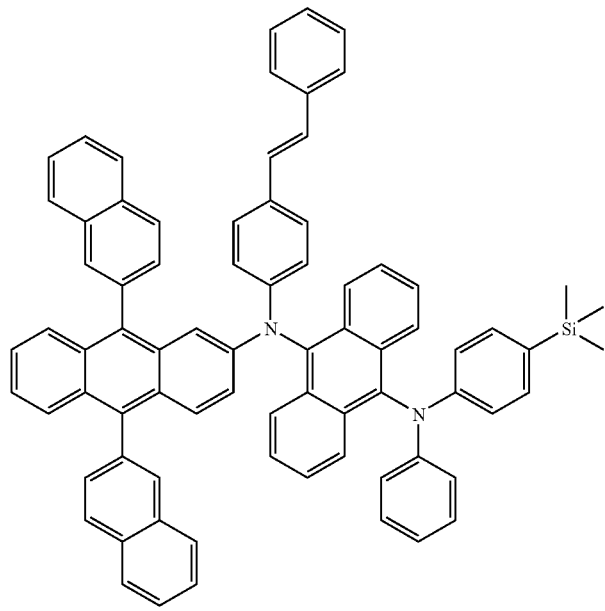
[Formula 1-107]
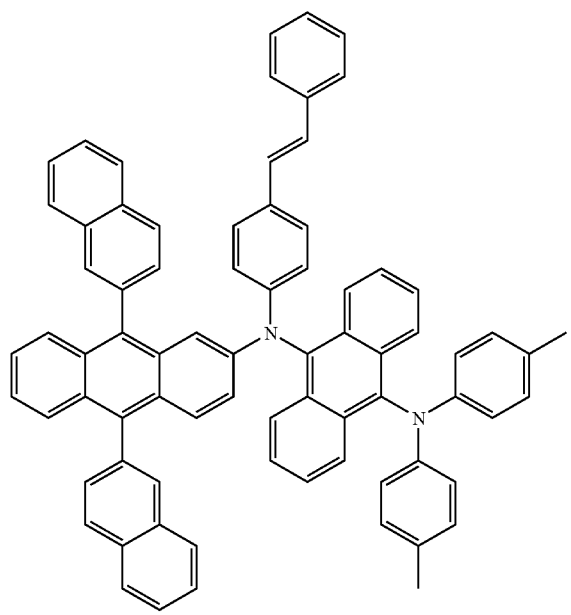

[Formula 1-108]
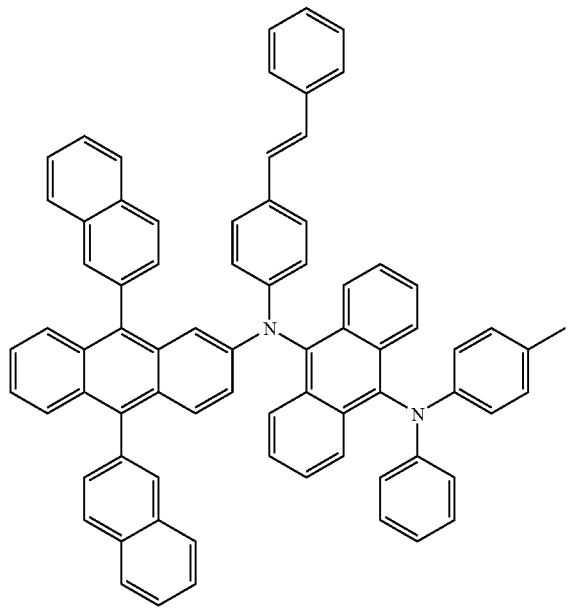
[Formula 1-109]
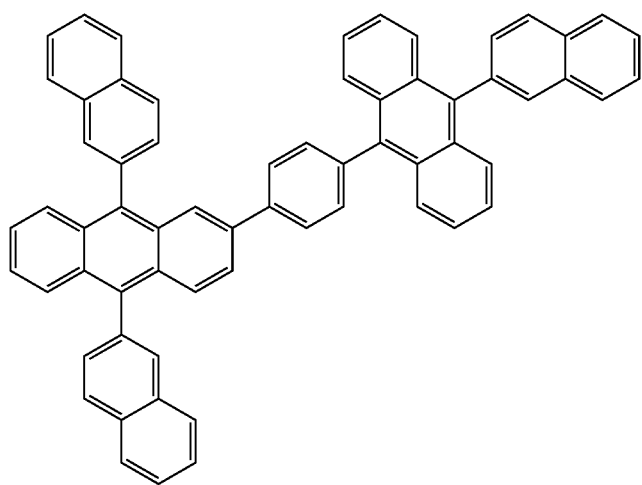
[Formula 1-110]
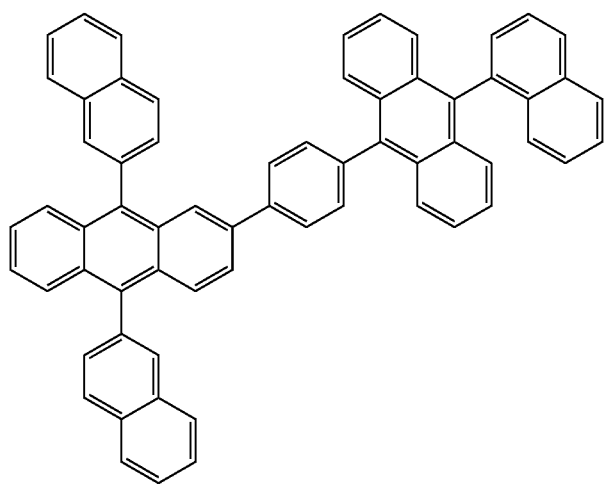

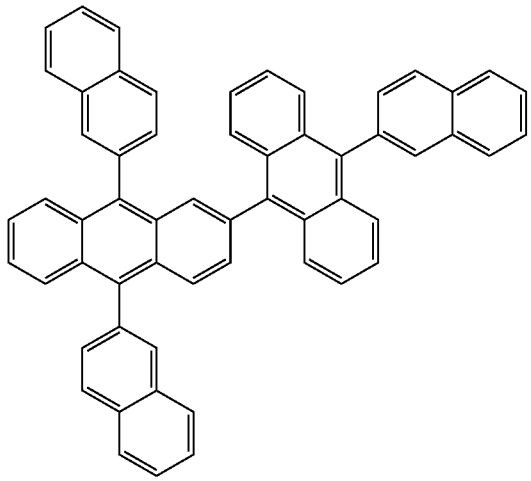
[Formula 1-112]
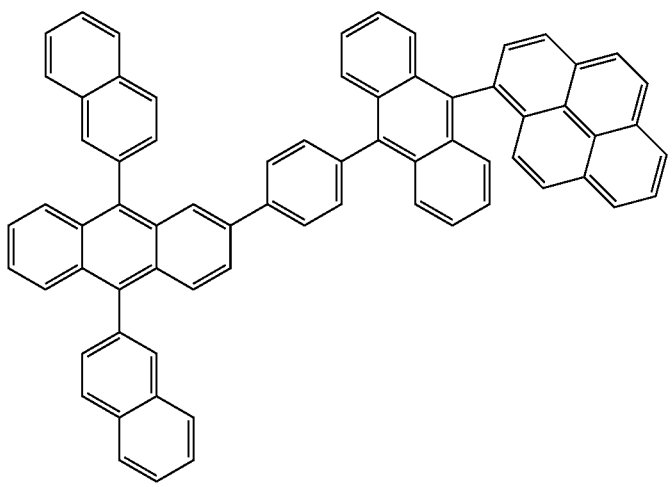
[Formula 1-113]
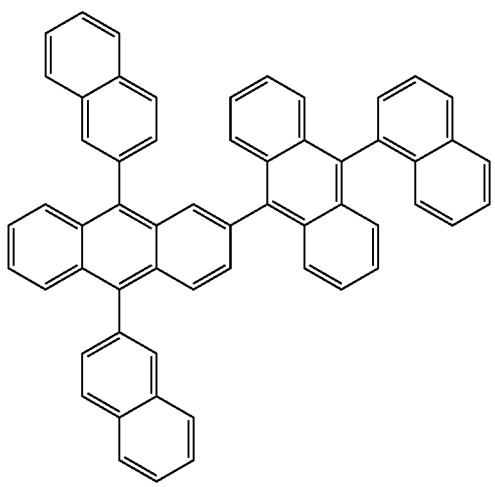
[Formula 1-114]

[Formula 1-115]
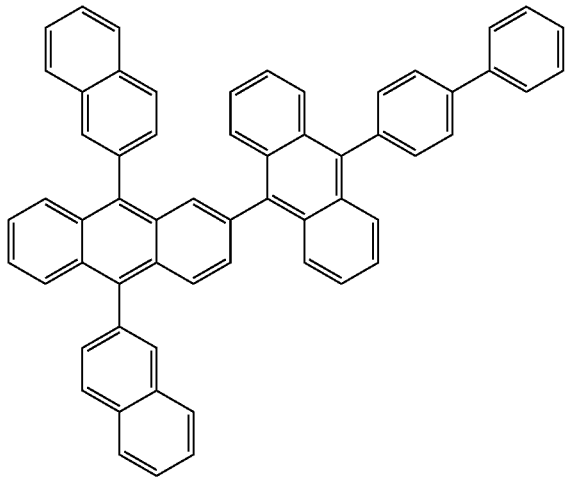
[Formula 1-116]
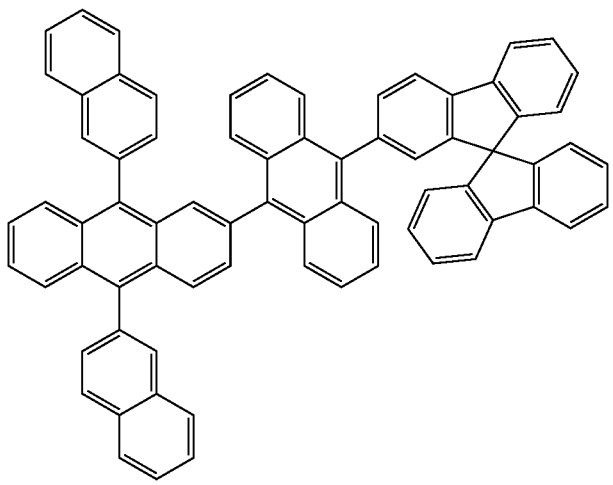
[Formula 1-117]
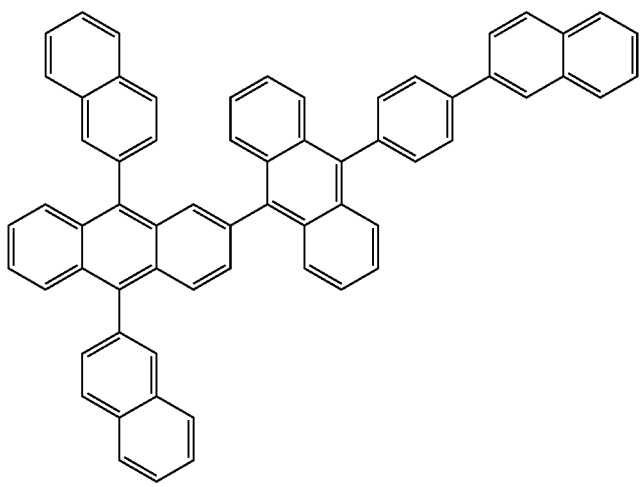

[Formula 1-118]
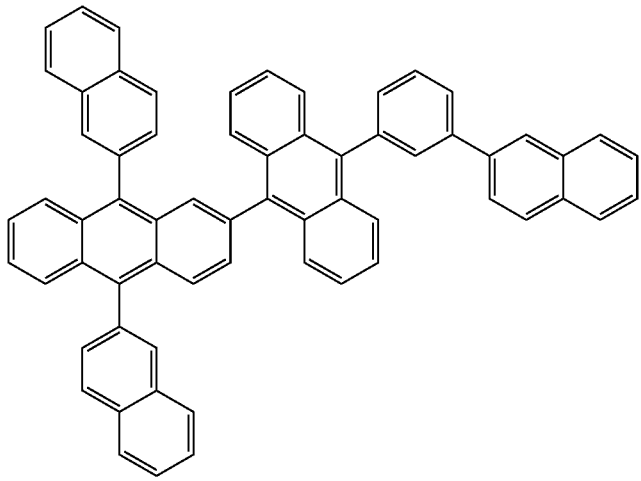
[Formula 1-119]
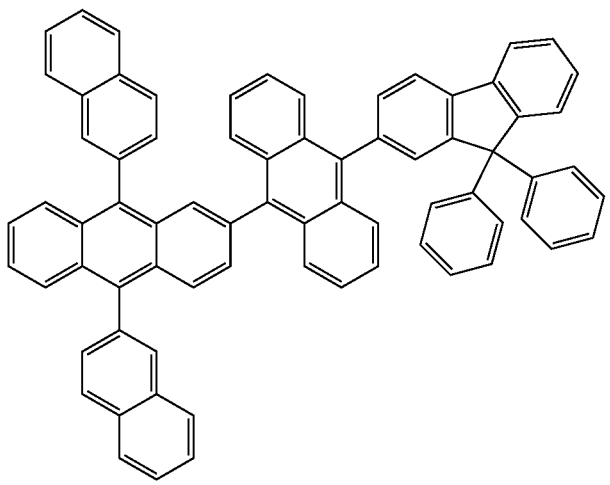
[Formula 1-120]
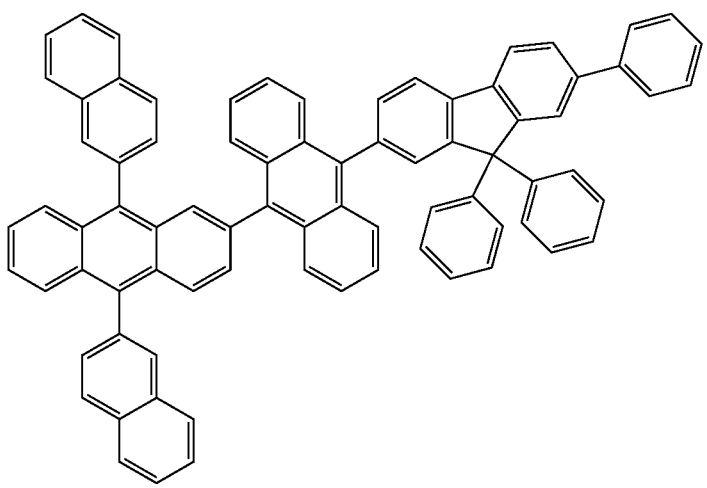

[Formula 1-121]
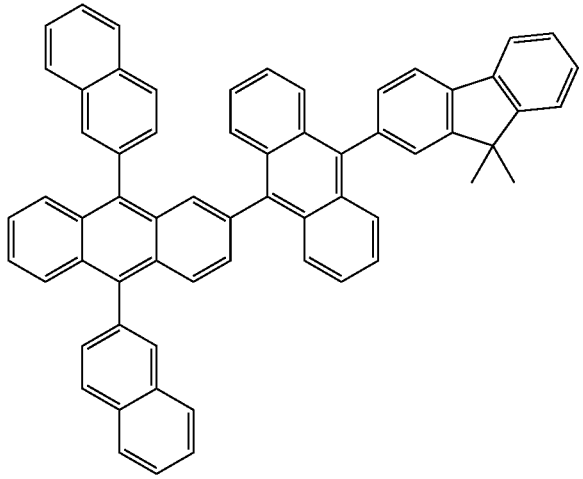
[Formula 1-122]
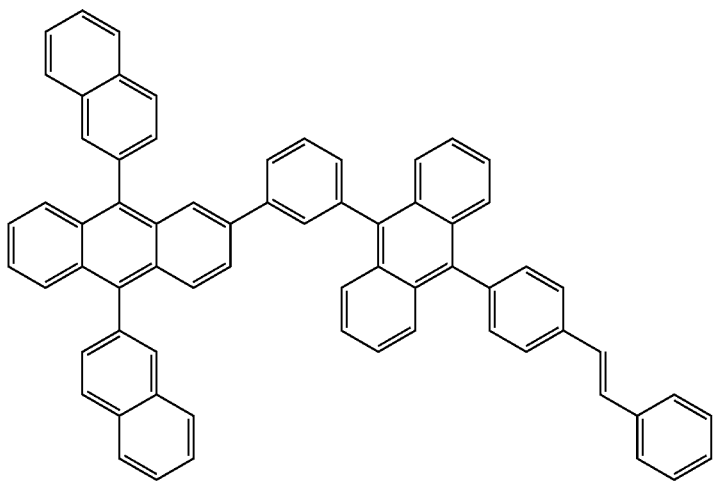
[Formula 1-123]
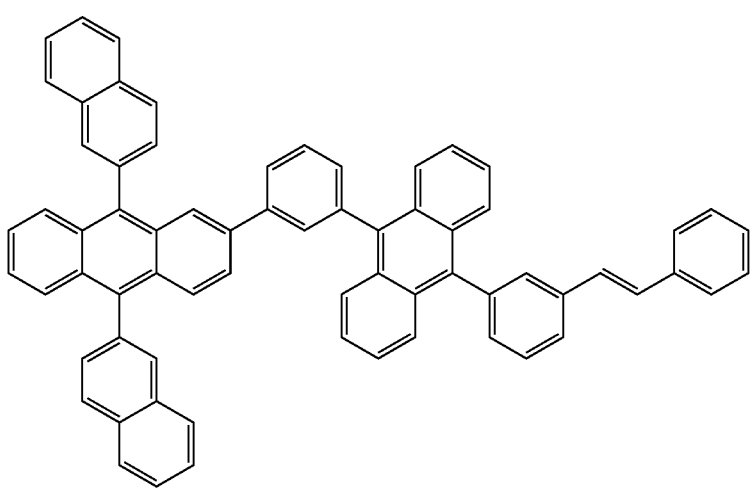

[Formula 1-124]
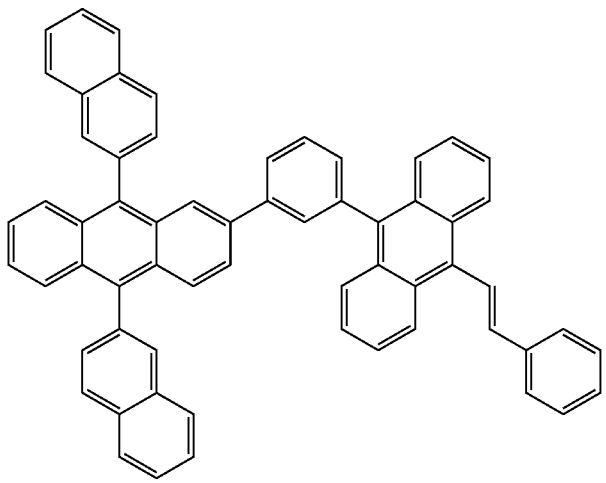
[Formula 1-125]
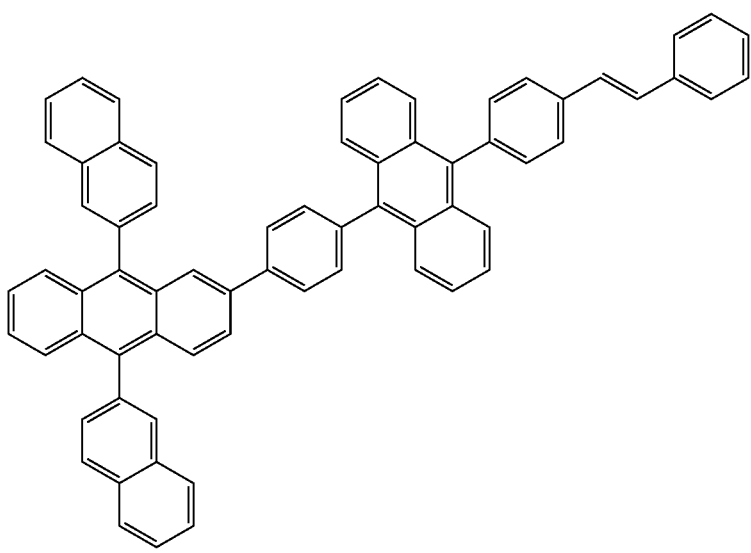
[Formula 1-126]
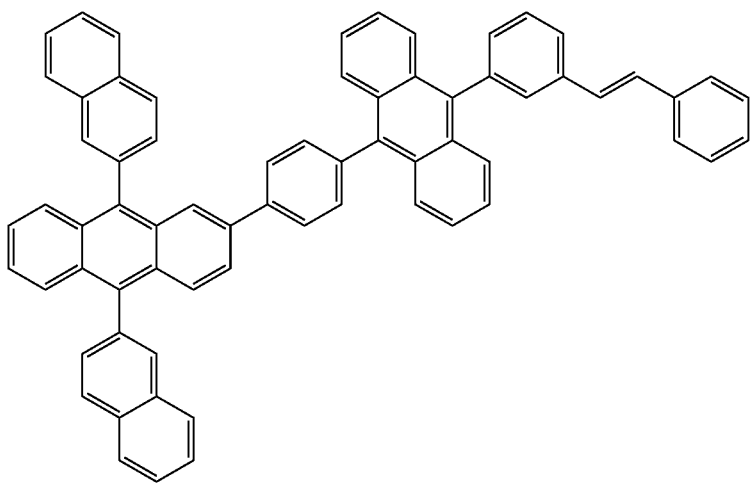

[Formula 1-127]
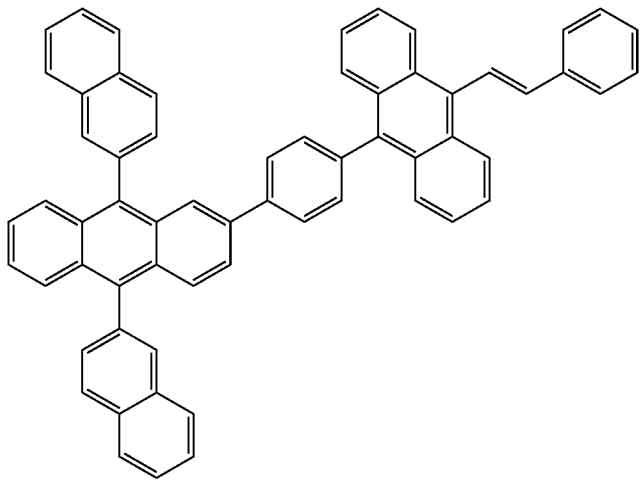
[Formula 1-128]
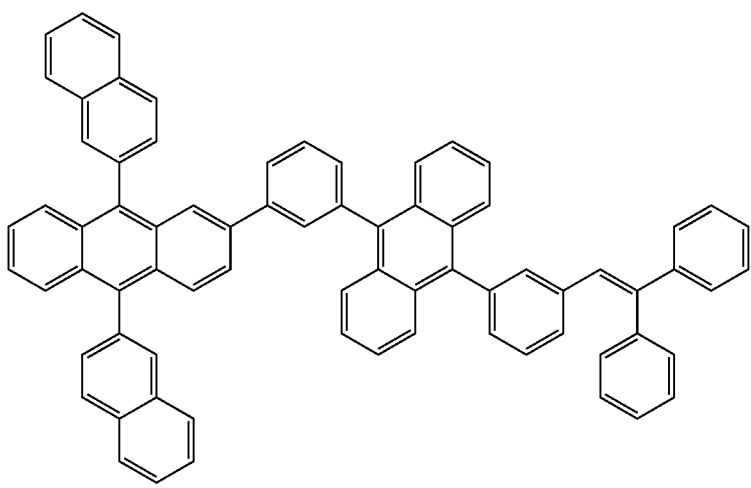
[Formula 1-129]
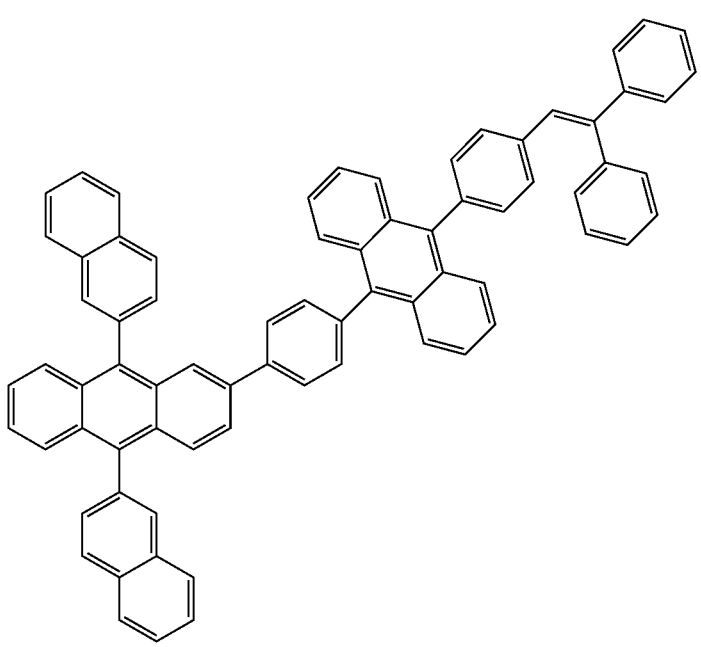

[Formula 1-130]
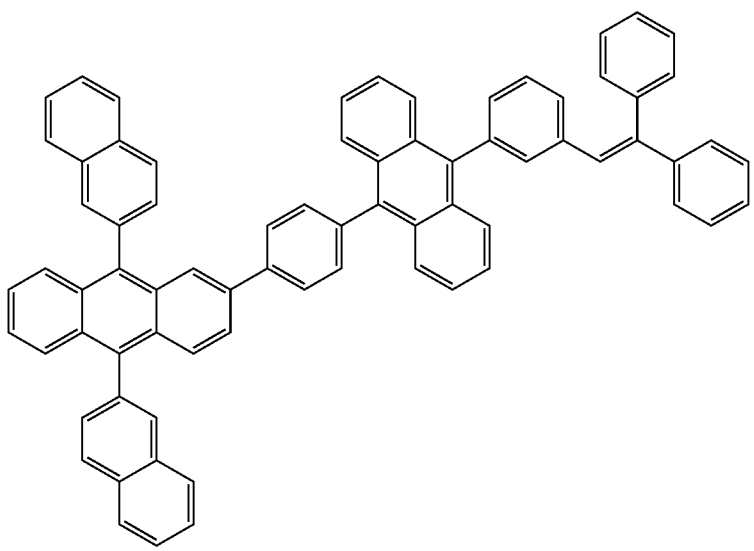
[Formula 1-131]
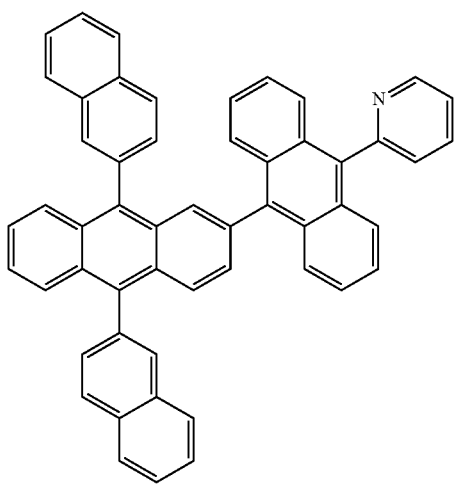
[Formula 1-132]
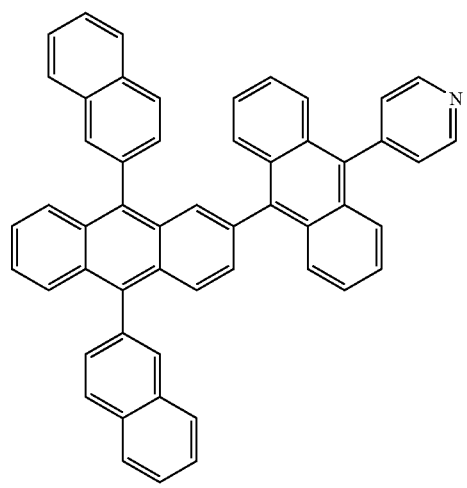
[Formula 1-133]
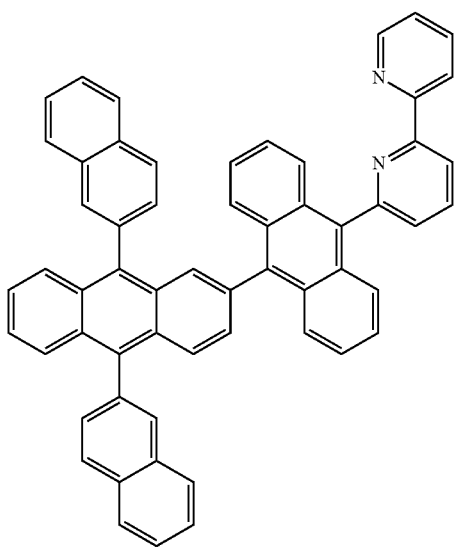
[Formula 1-134]
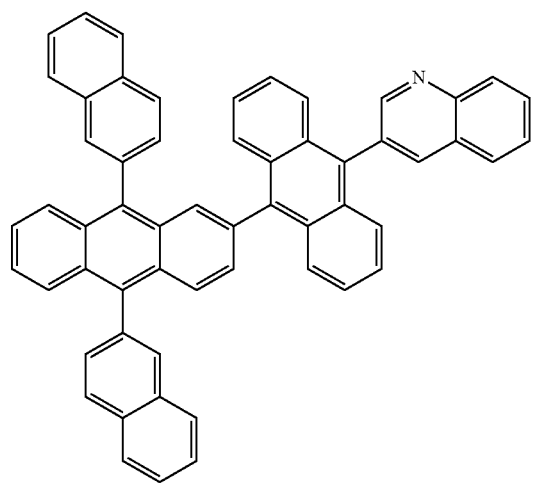

[Formula 1-135]
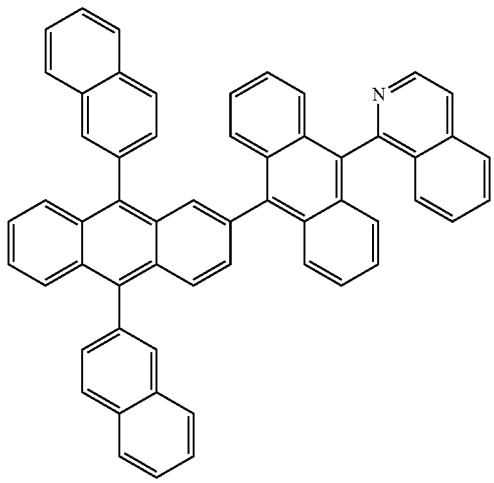
[Formula 1-136]
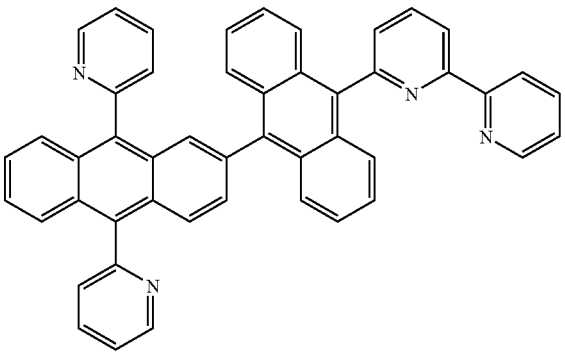
[Formula 1-137]
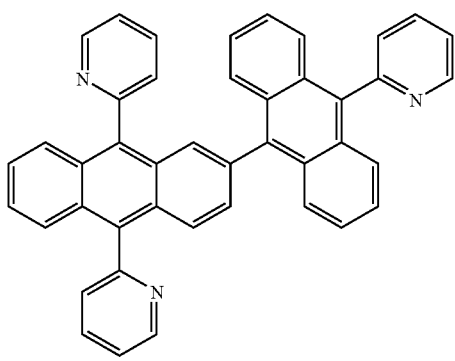
[Formula 1-138]
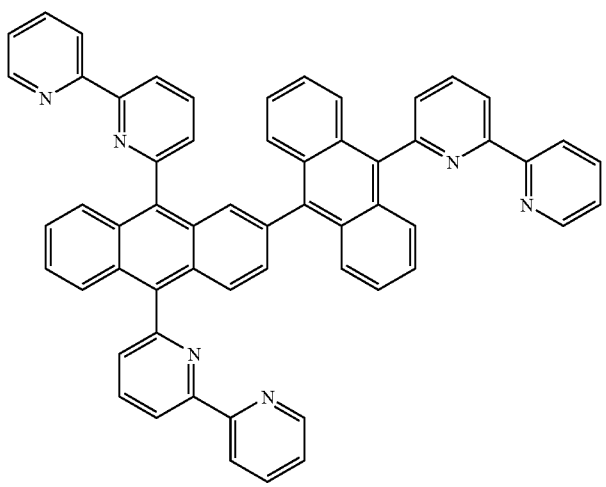

[Formula 1-139]
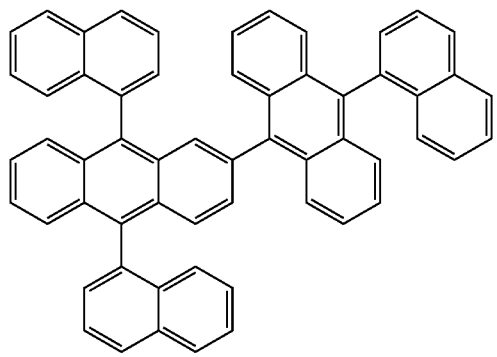
[Formula 1-140]
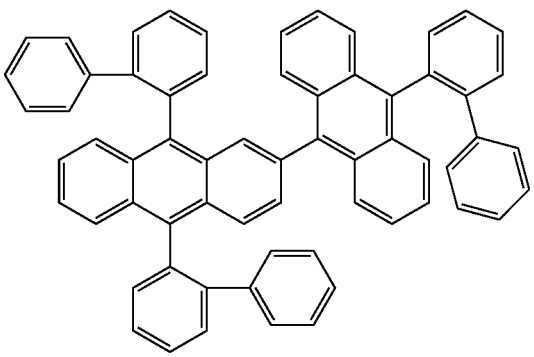
[Formula 1-141]
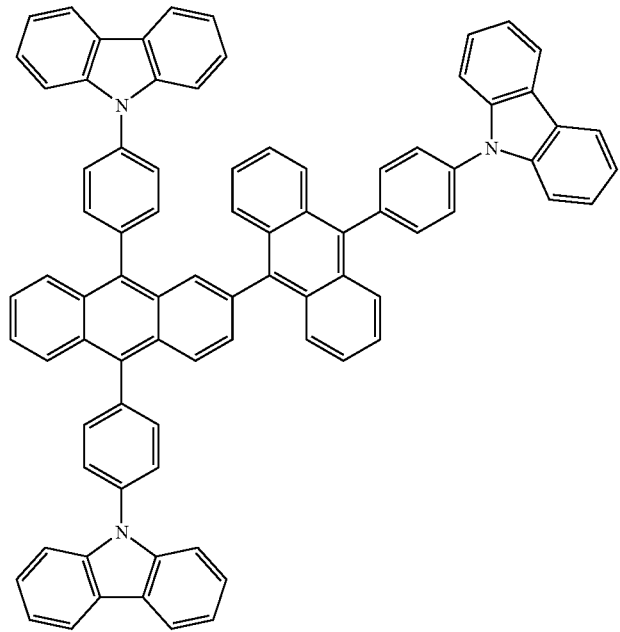
[Formula 1-142]
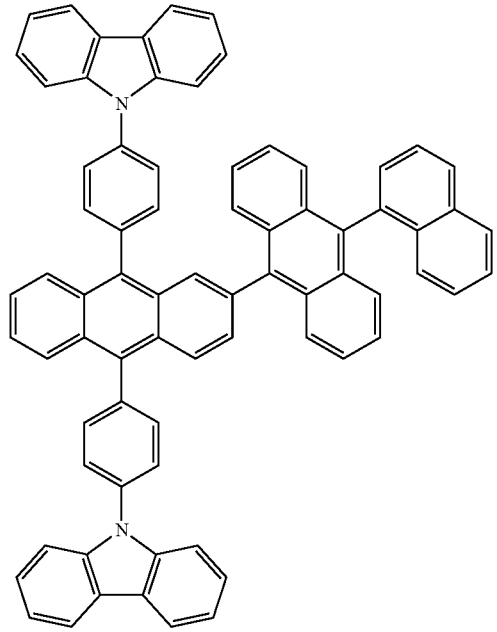

[Formula 1-143]
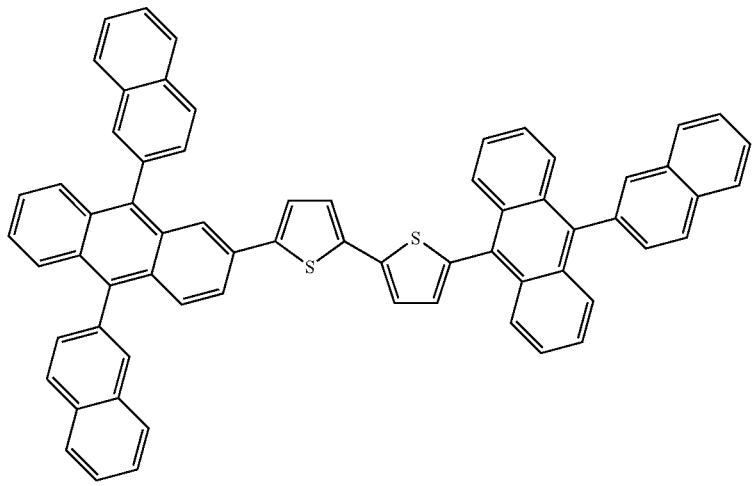
[Formula 1-144]
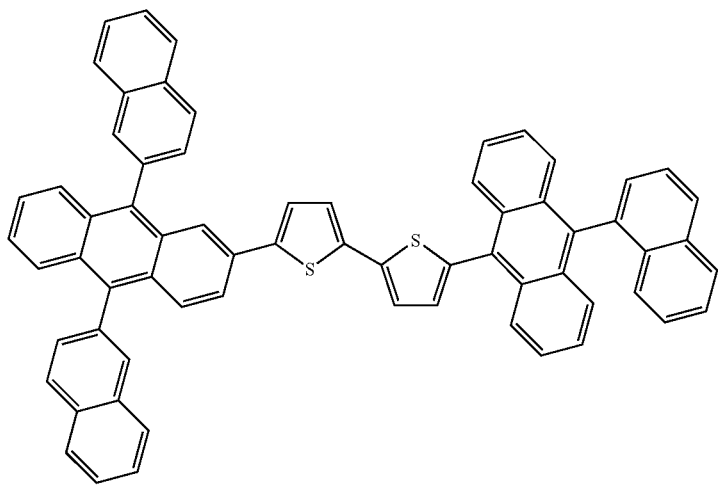
[Formula 1-145]
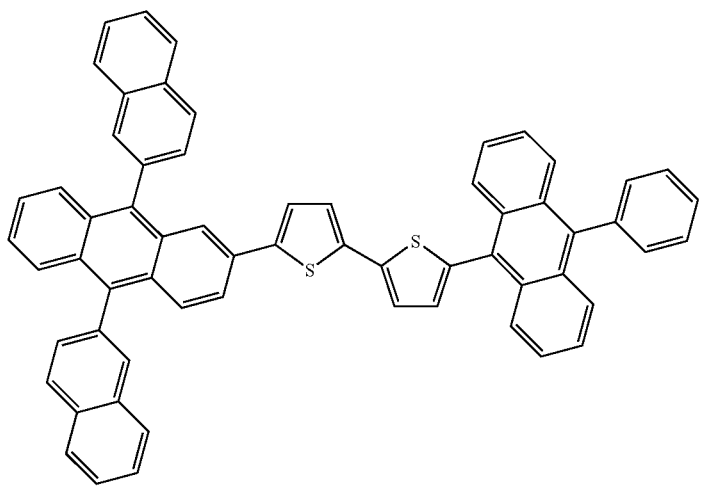

[Formula 1-146]
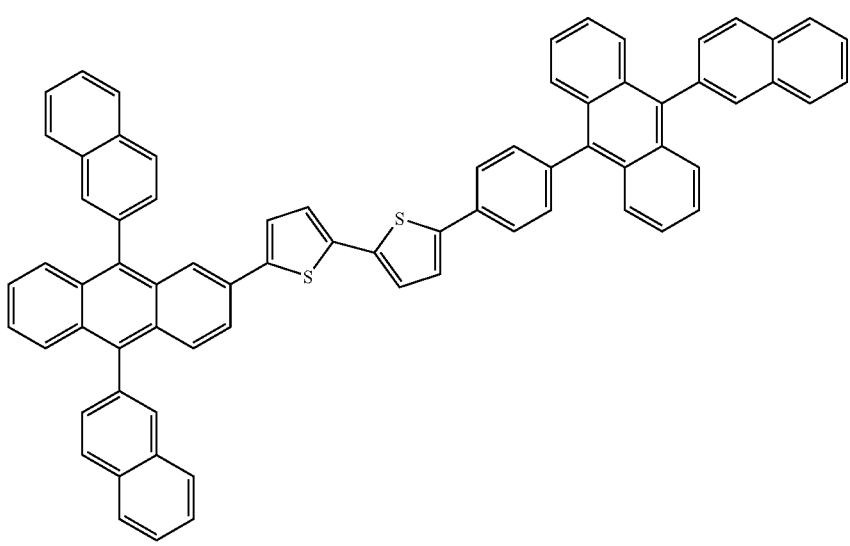
[Formula 1-147]
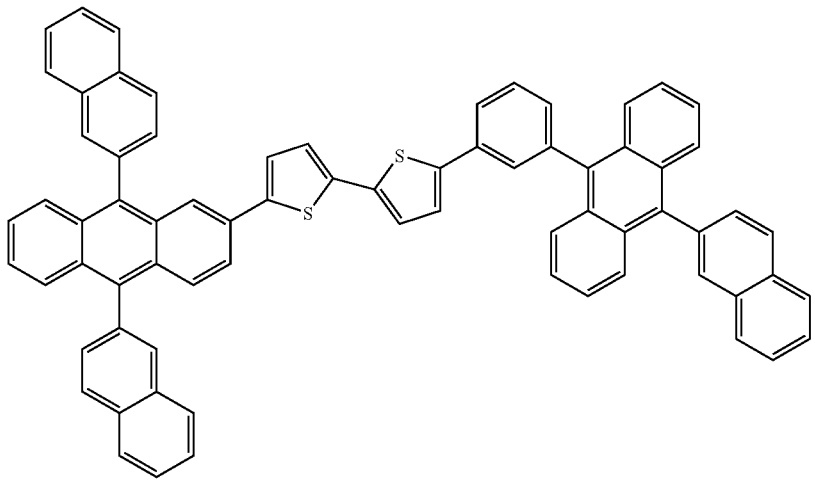
[Formula 1-148]
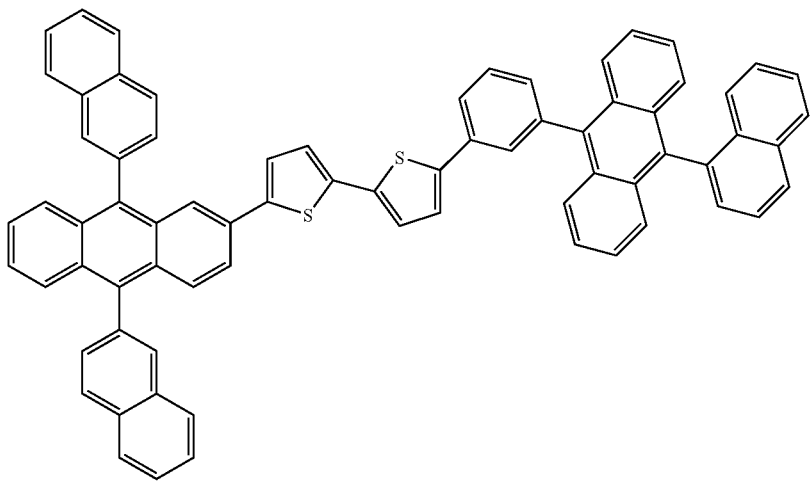

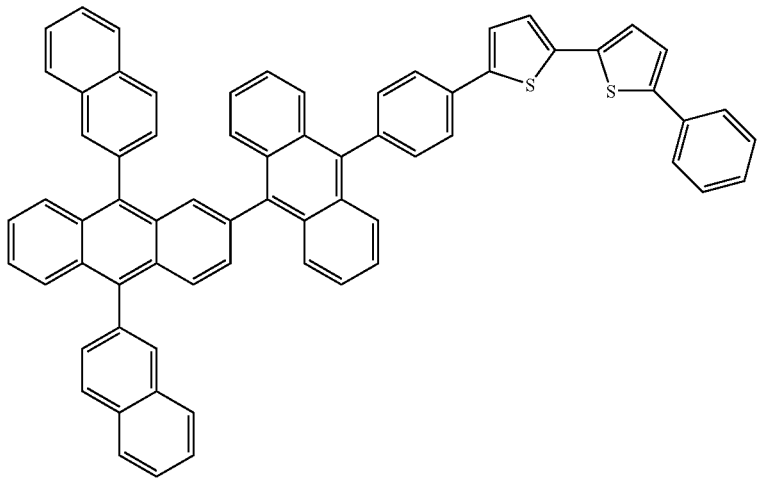
[Formula 1-149]
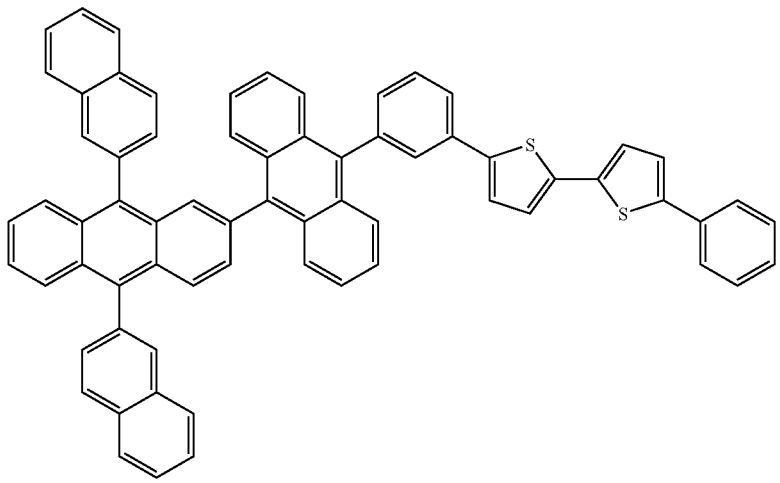
[Formula 1-150]
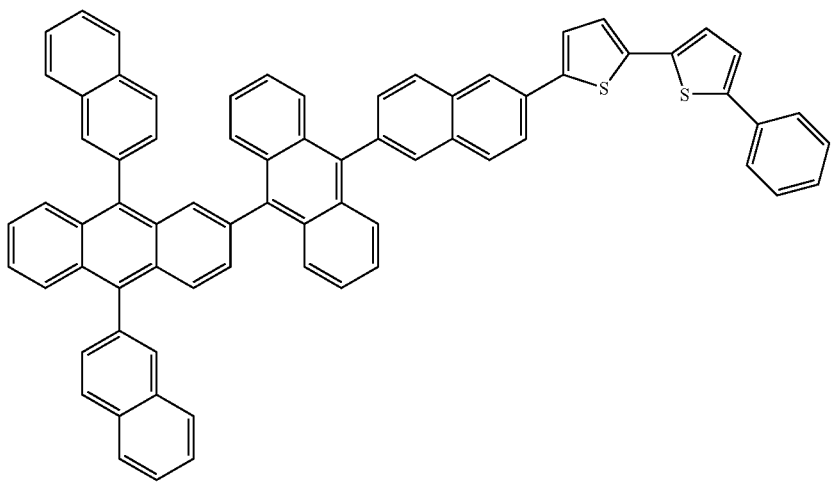
[Formula 1-151]

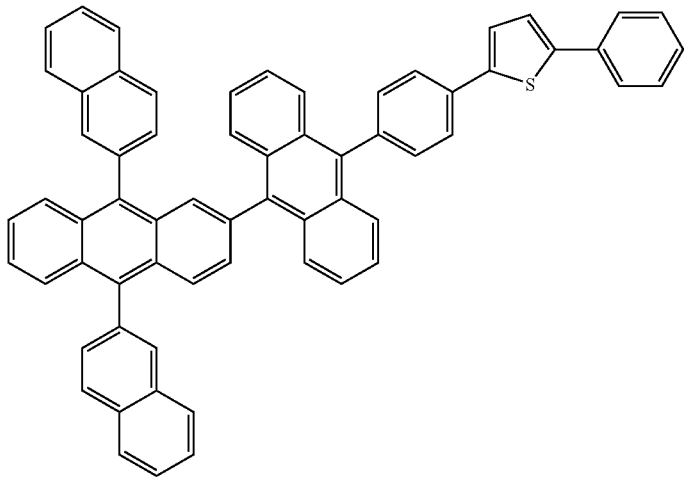
[Formula 1-152]
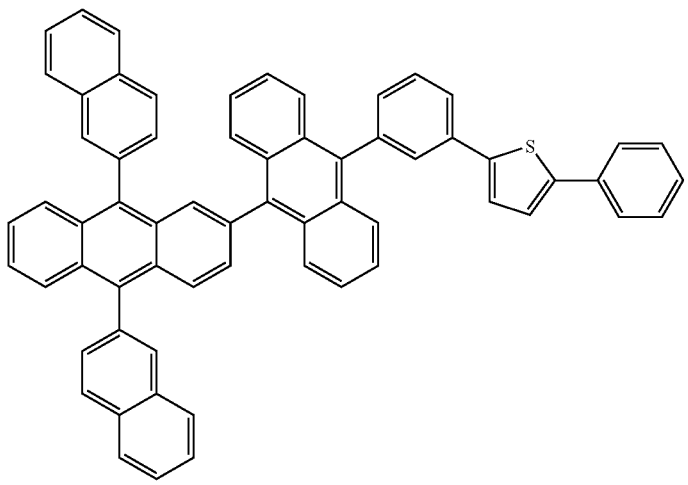
[Formula 1-153]
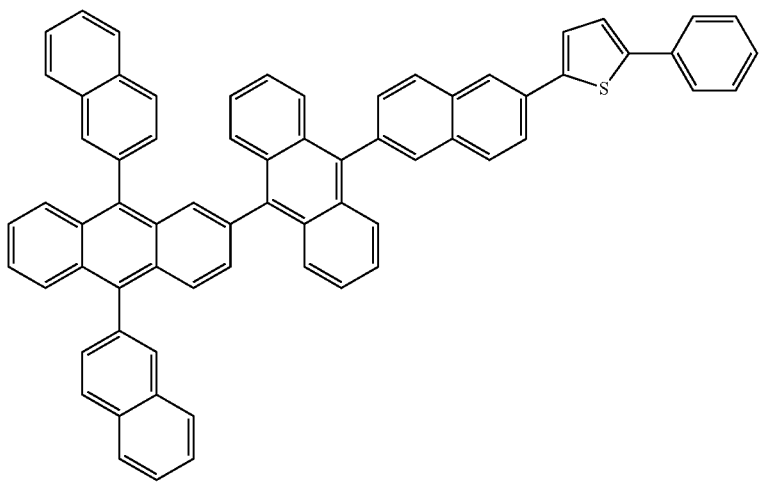
[Formula 1-154]

[Formula 1-155]
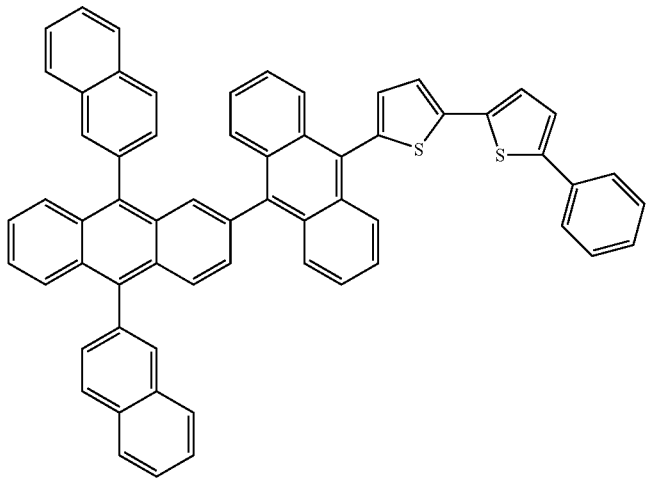
[Formula 1-156]
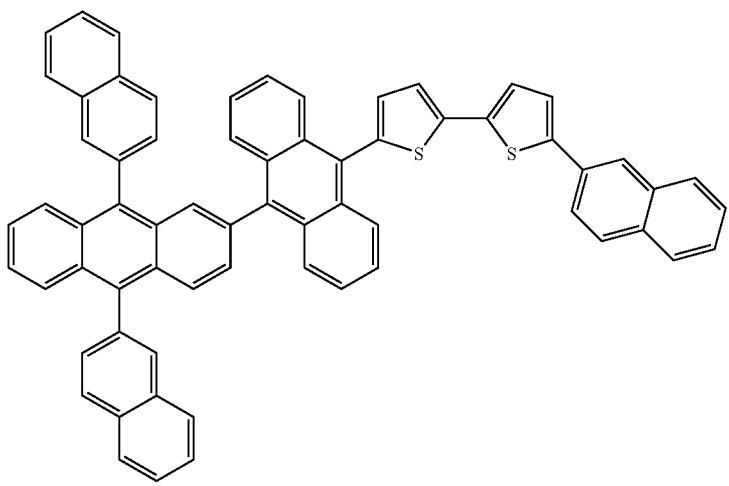
[Formula 1-157]
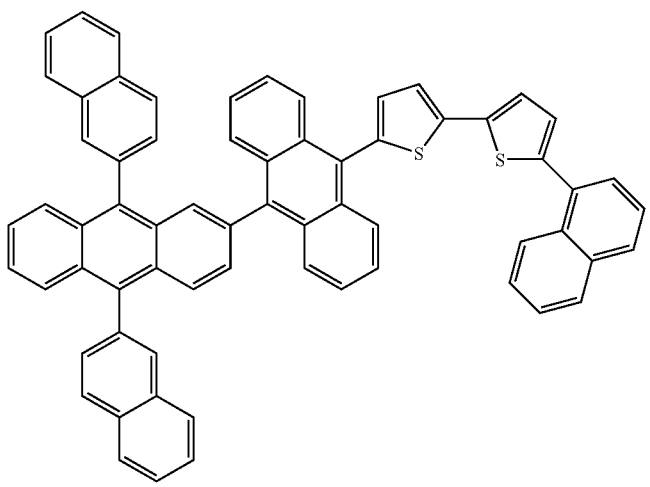

[Formula 1-158]
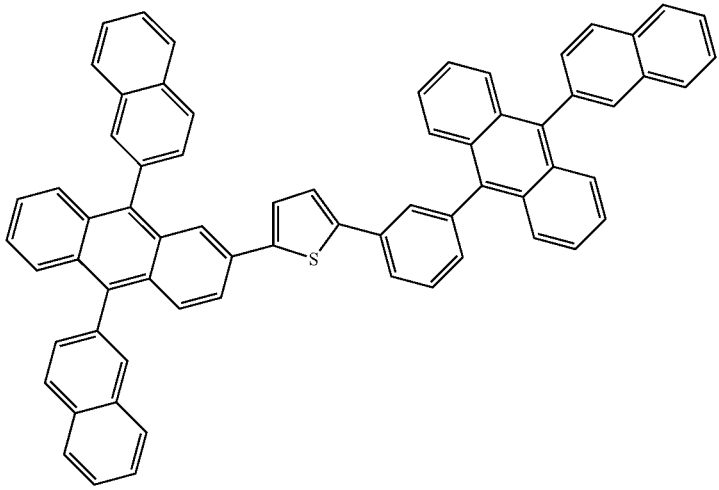
[Formula 1-159]
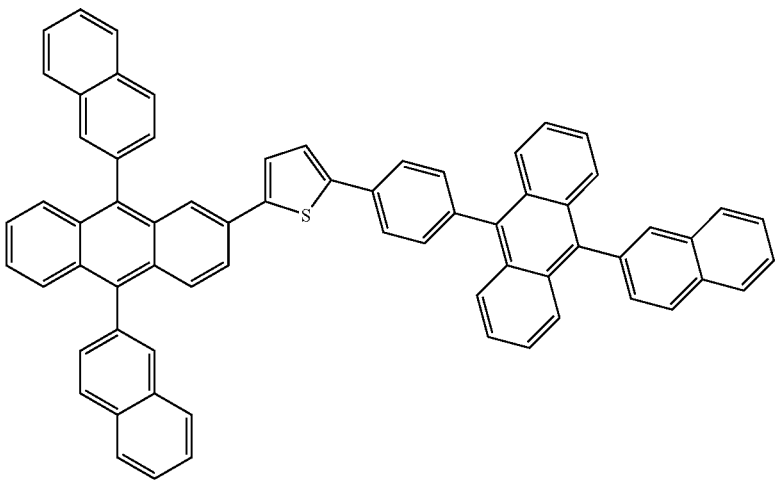
[Formula 1-160]
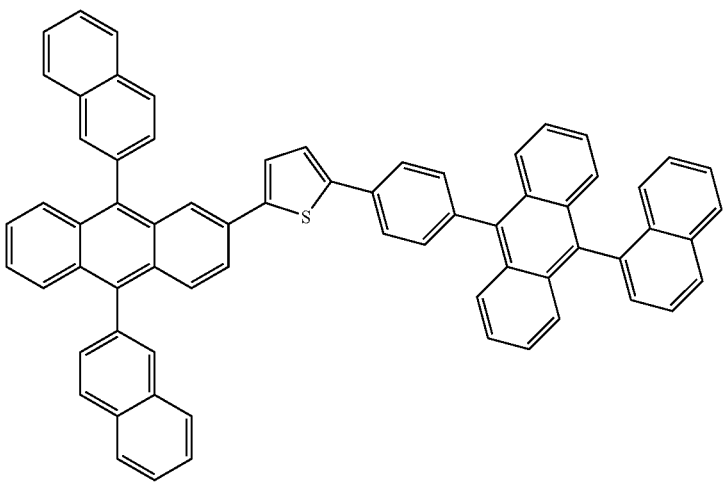

[Formula 1-161]
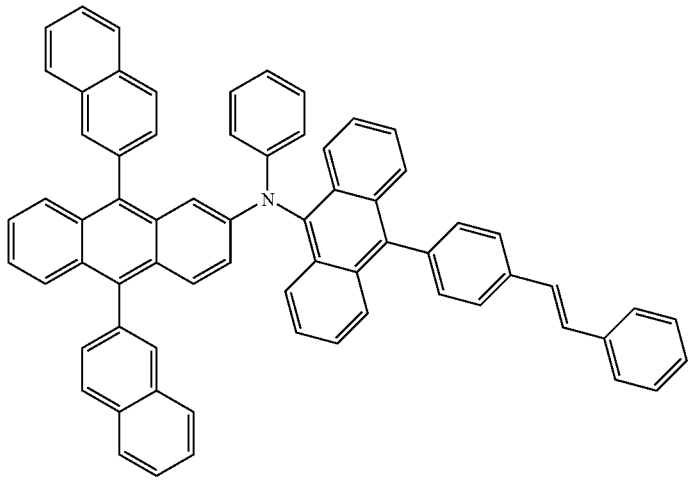
[Formula 1-162]
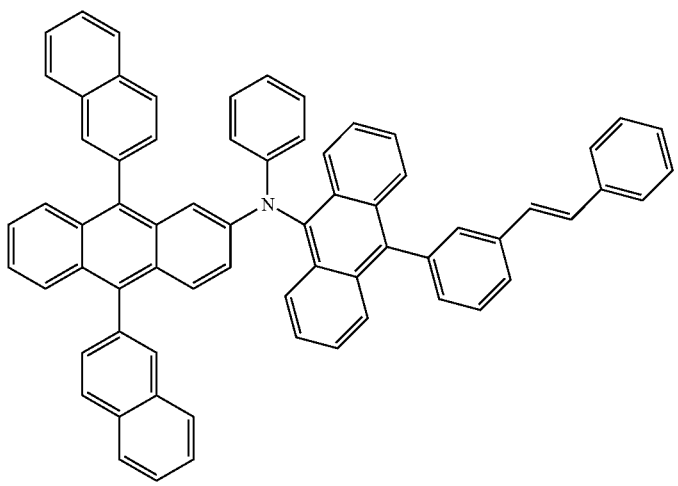
[Formula 1-163]
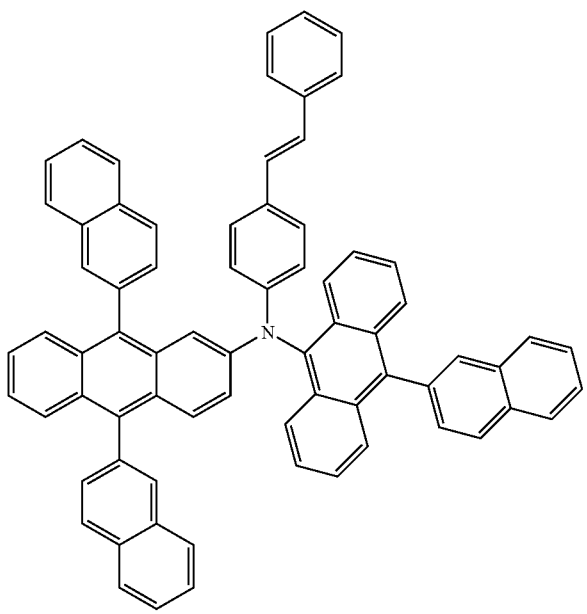

[Formula 1-164]
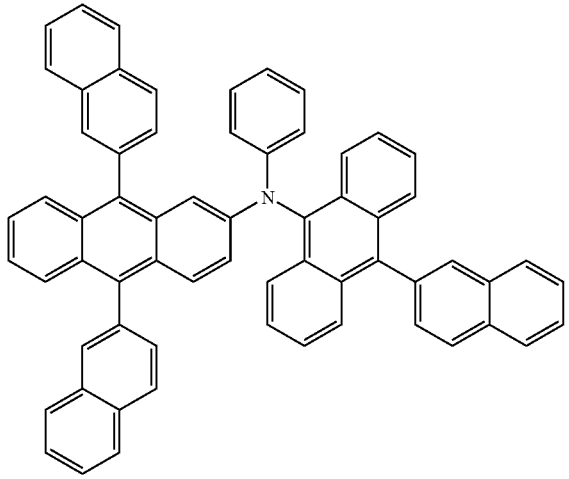
[Formula 1-165]
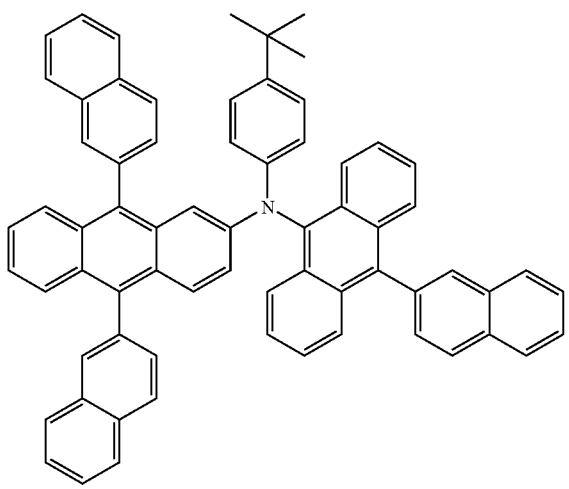
[Formula 1-166]
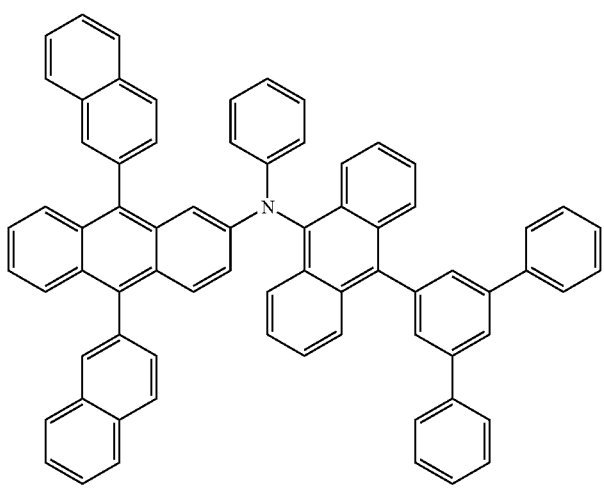

[Formula 1-167]
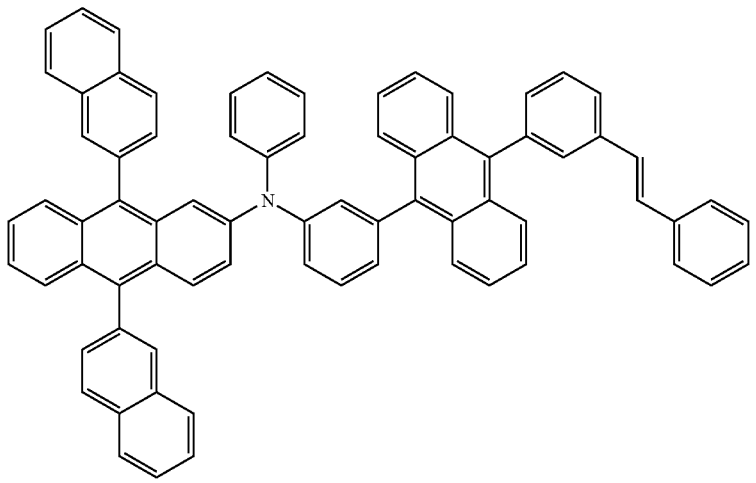
[Formula 1-168]
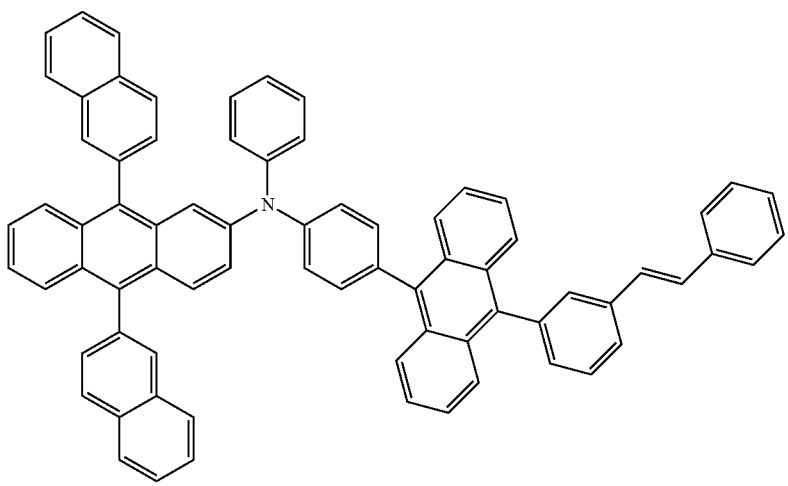
[Formula 1-169]
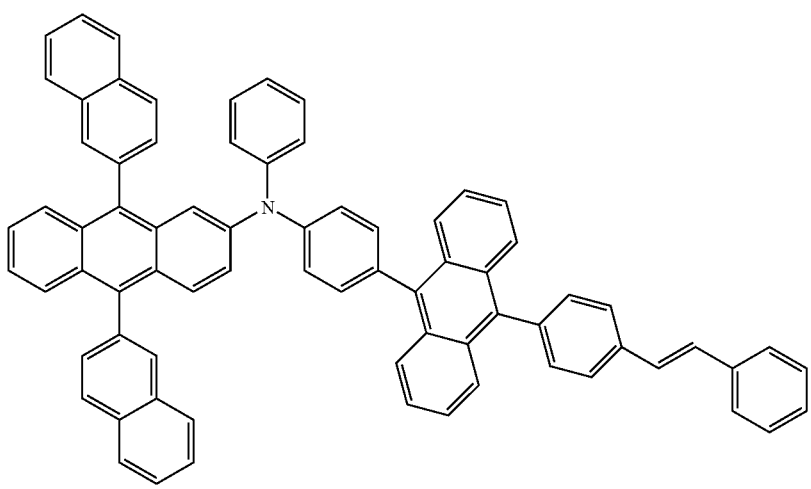

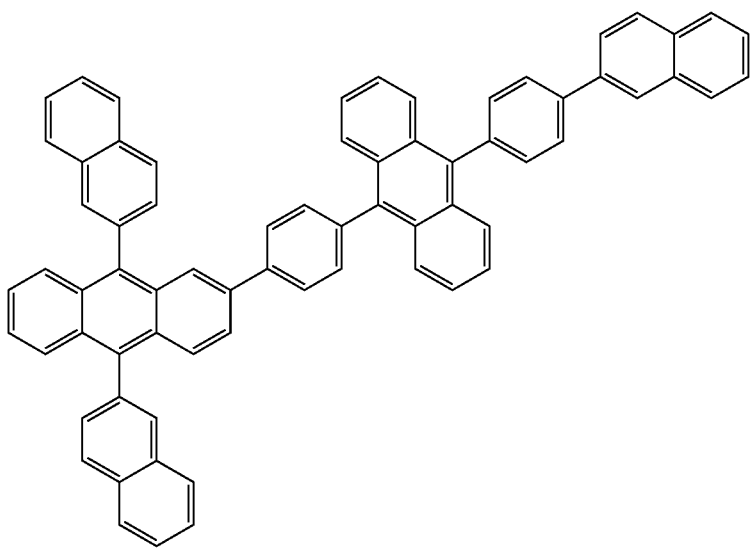
[Formula 1-170]
[Formula 1-171]
[Formula 1-172]

[Formula 1-173]
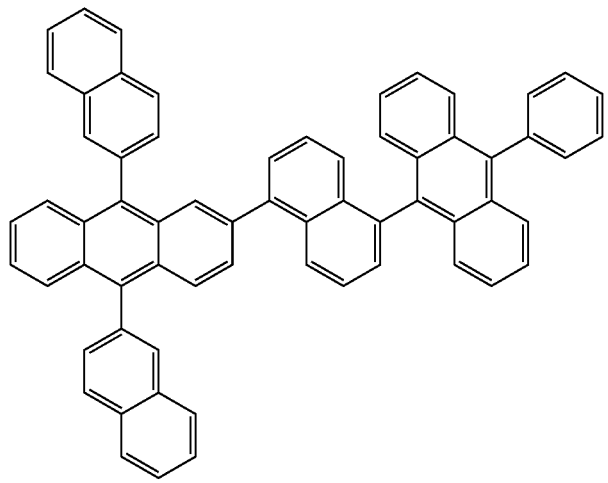
[Formula 1-174]
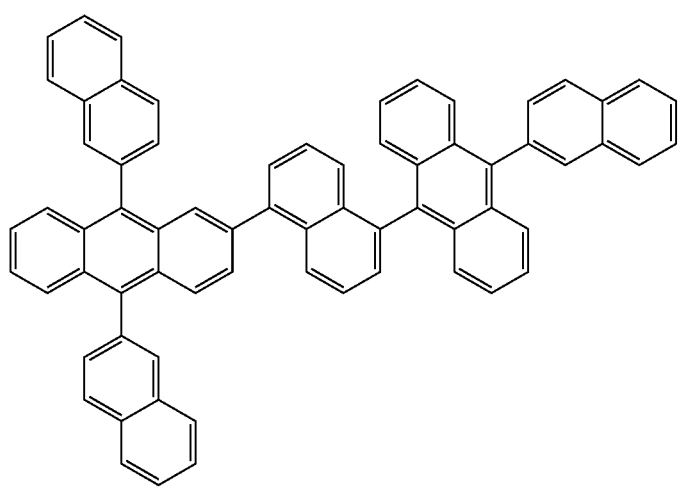
[Formula 1-175]
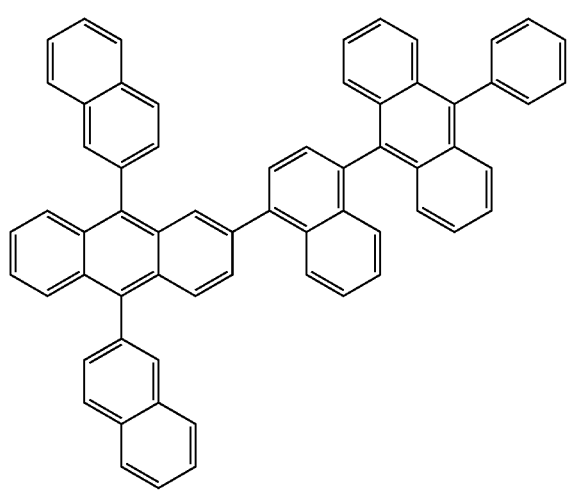

[Formula 1-176]
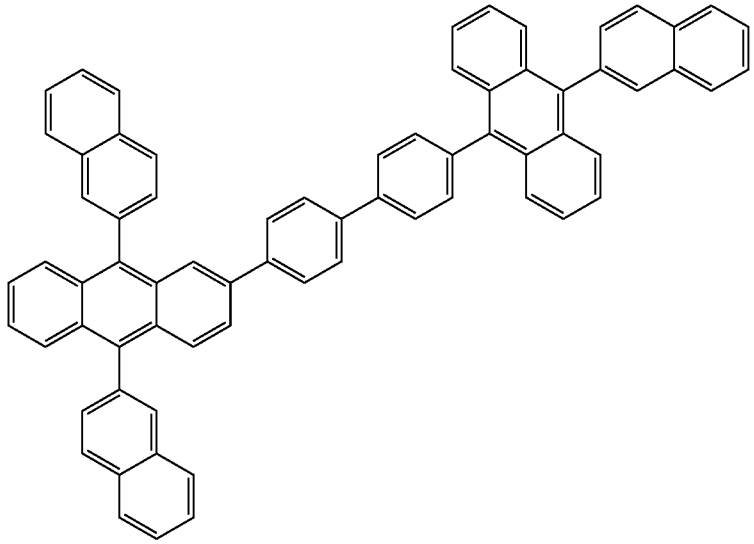
[Formula 1-177]
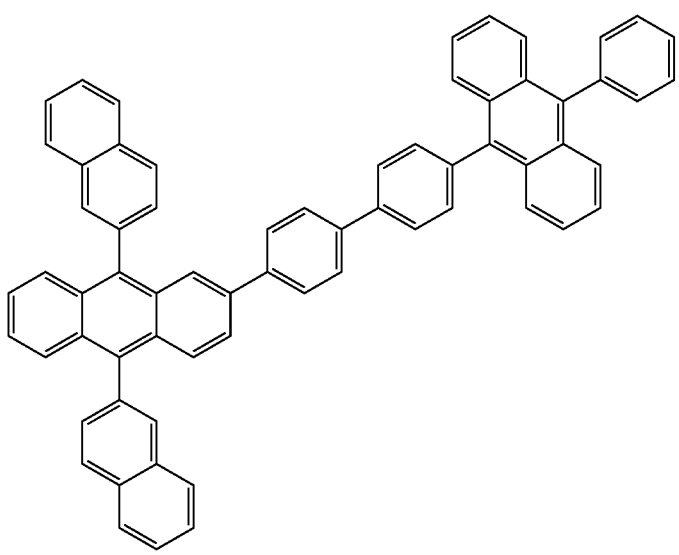
[Formula 1-178]
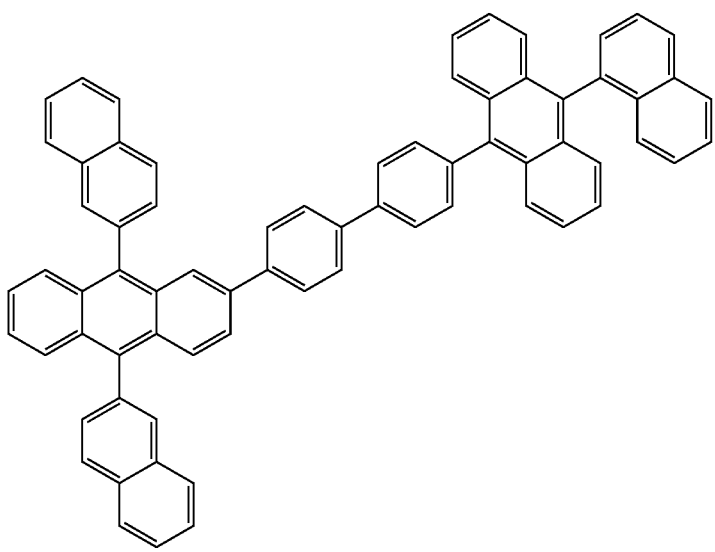

[Formula 1-179]
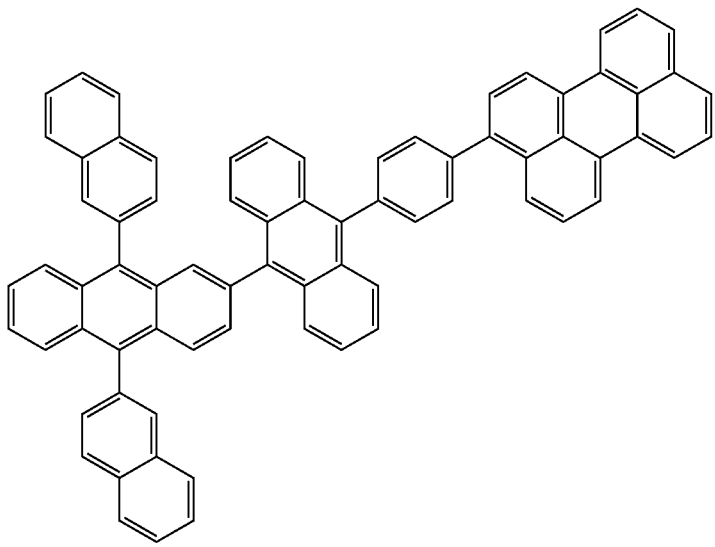
[Formula 1-180]
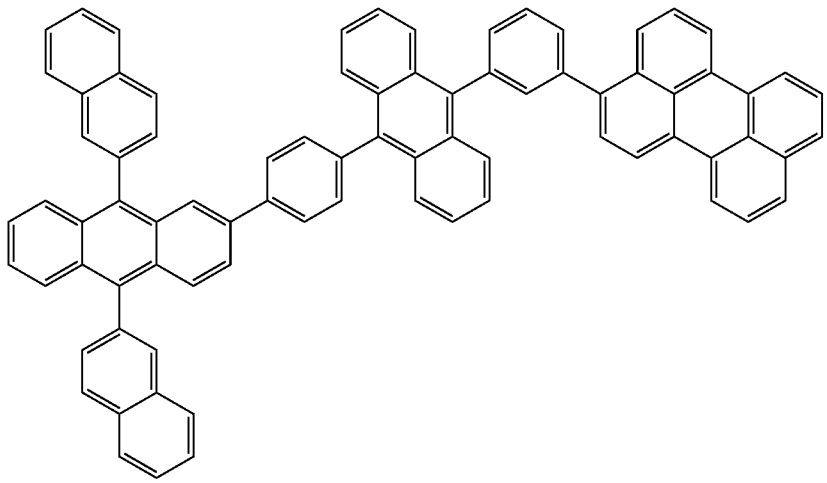
[Formula 1-181]
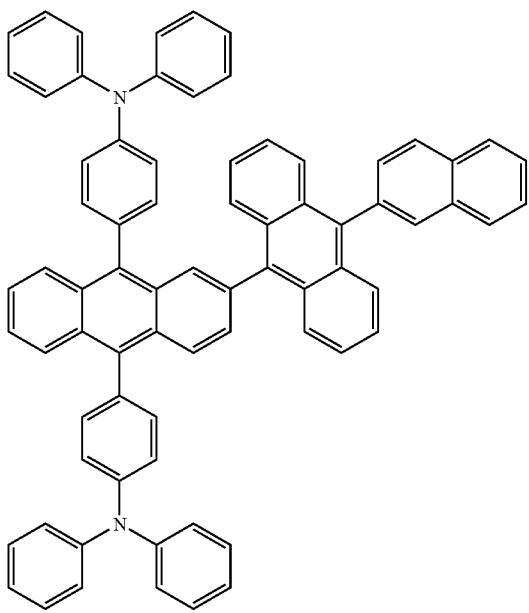
[Formula 1-182]
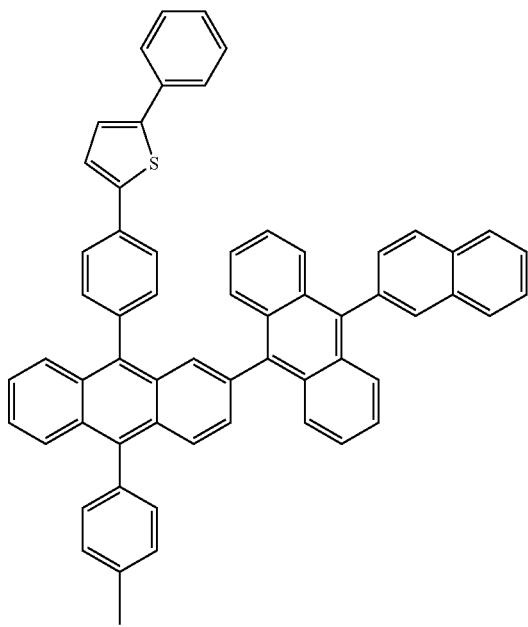

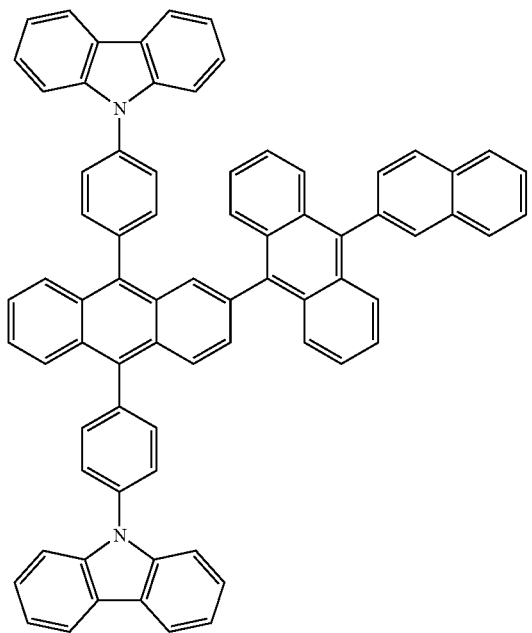
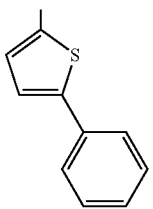
[Formula 1-183]
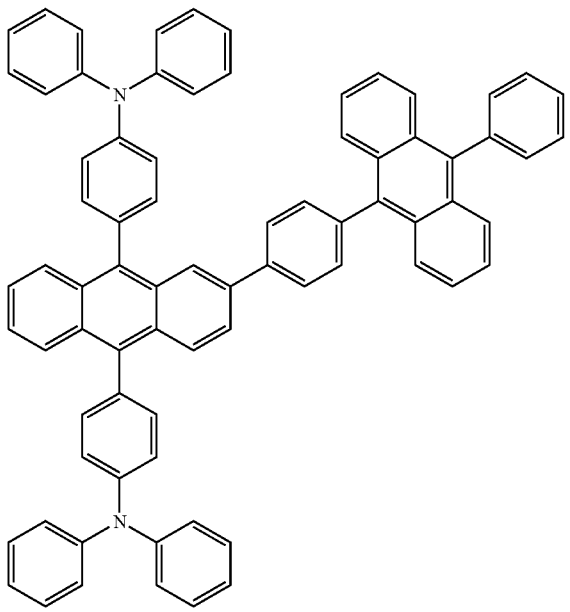
[Formula 1-184]

[Formula 1-185]
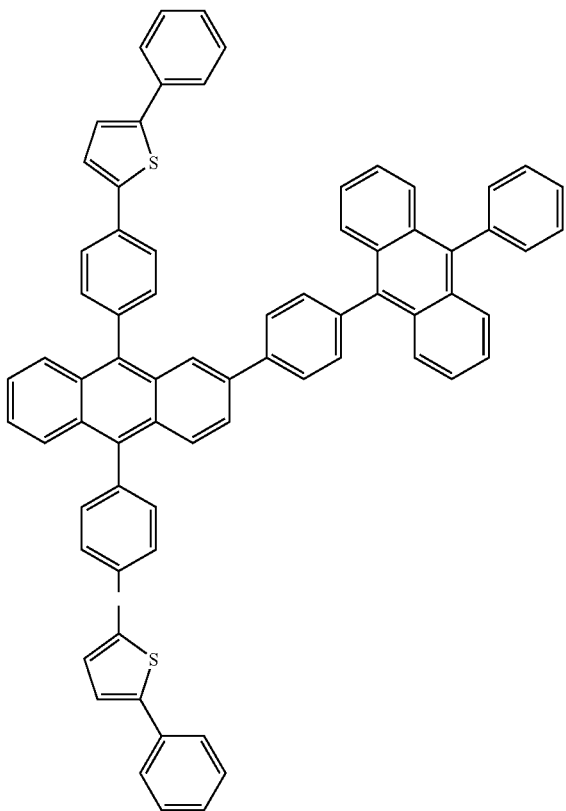
[Formula 1-186]
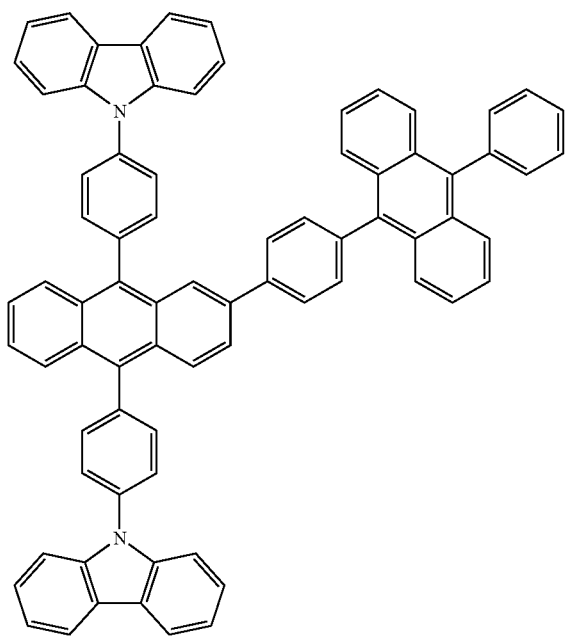

[Formula 1-187]
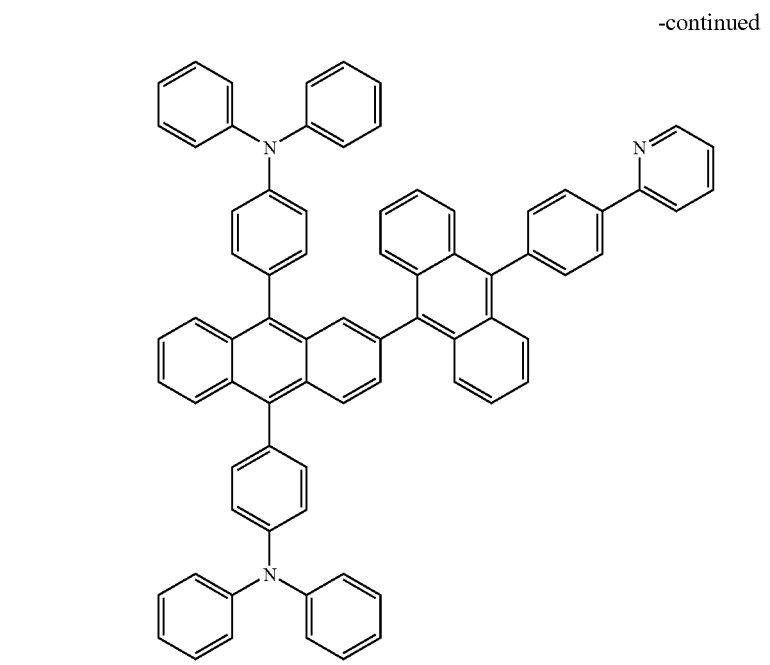
[Formula 1-188]
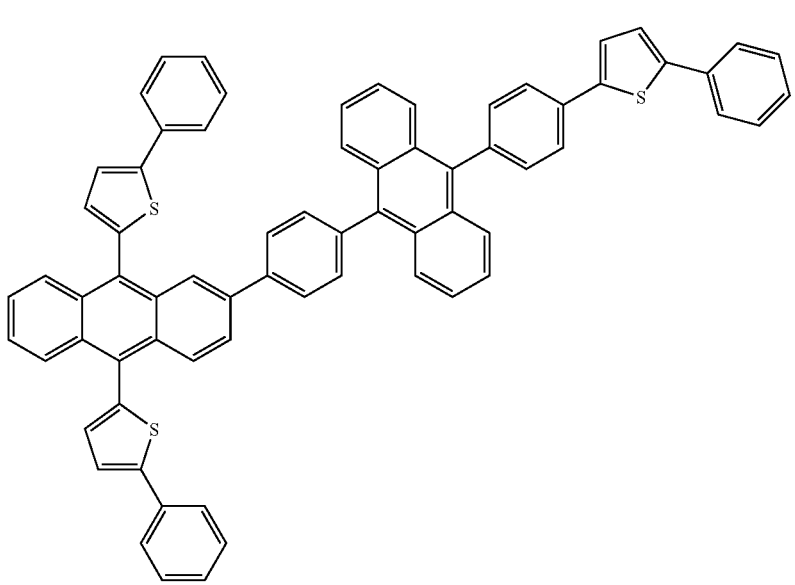
[Formula 1-189]
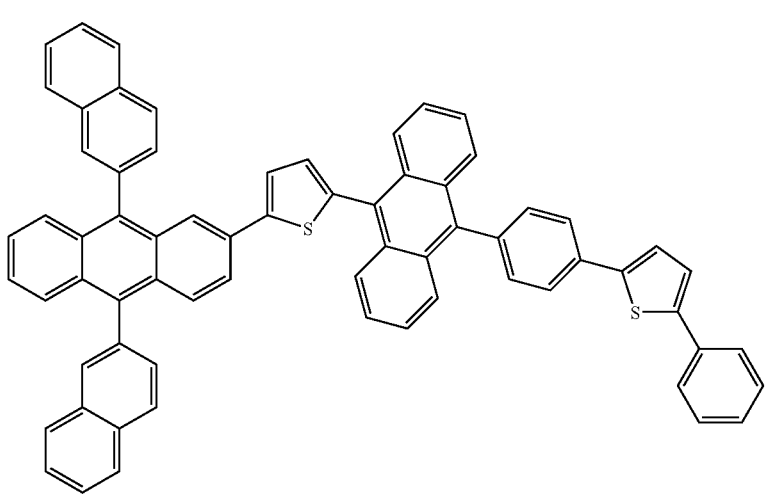

[Formula 1-190]
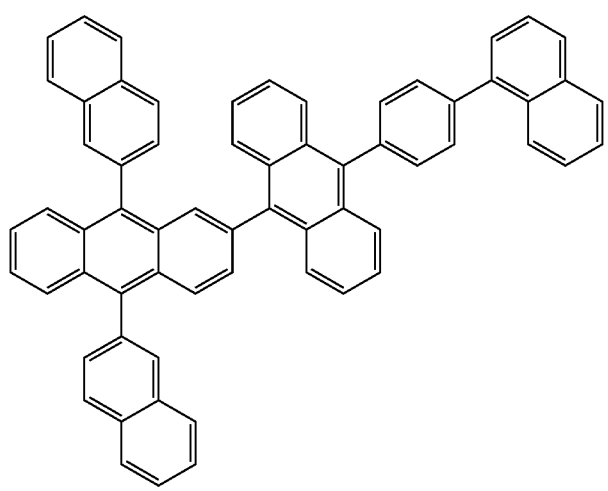
[Formula 1-191]
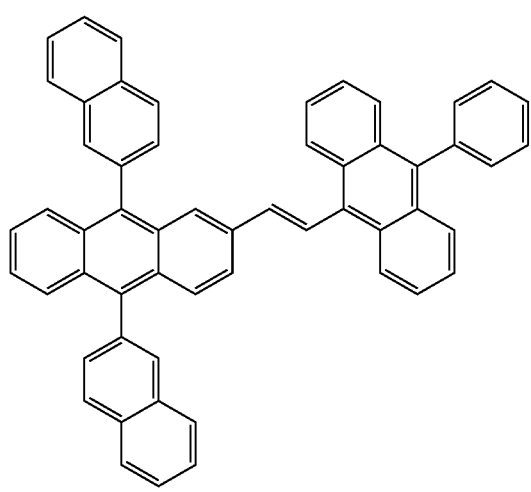
[Formula 1-192]
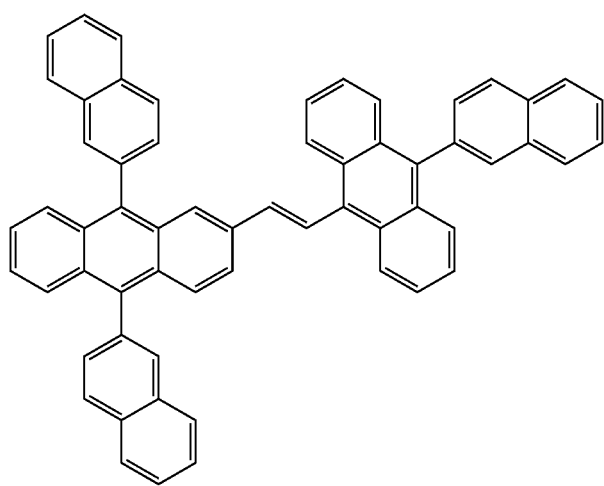

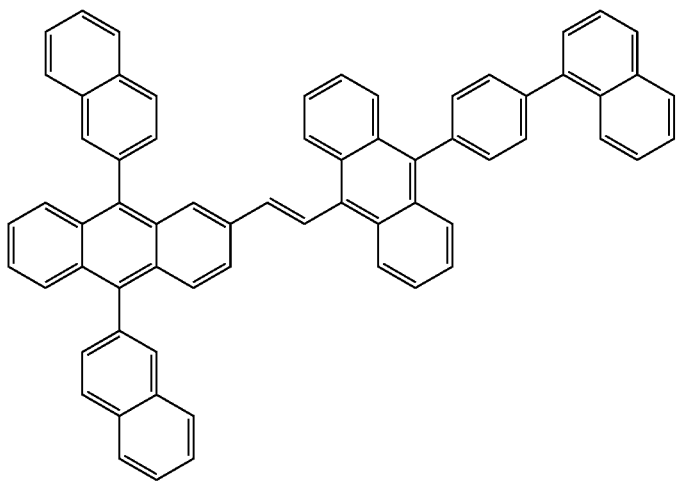
[Formula 1-193]
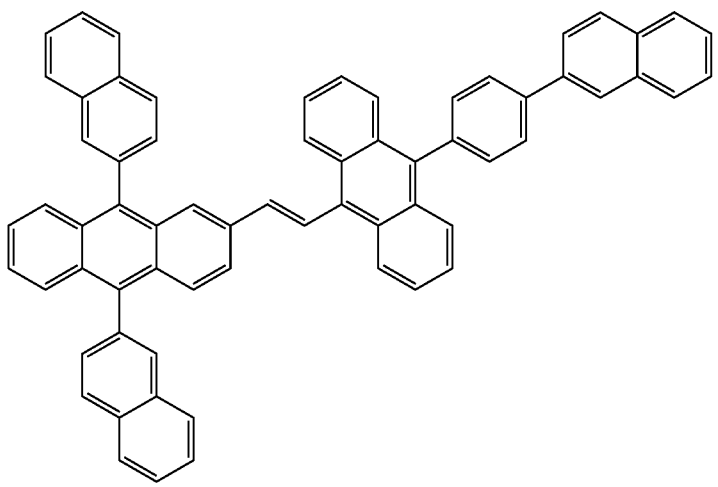
[Formula 1-194]
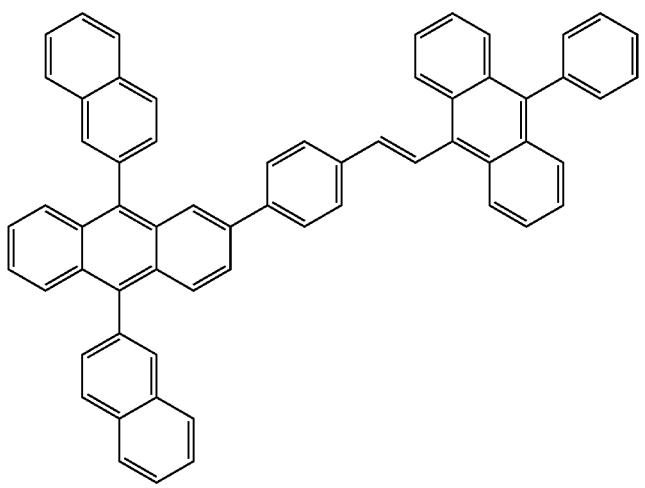
[Formula 1-195]

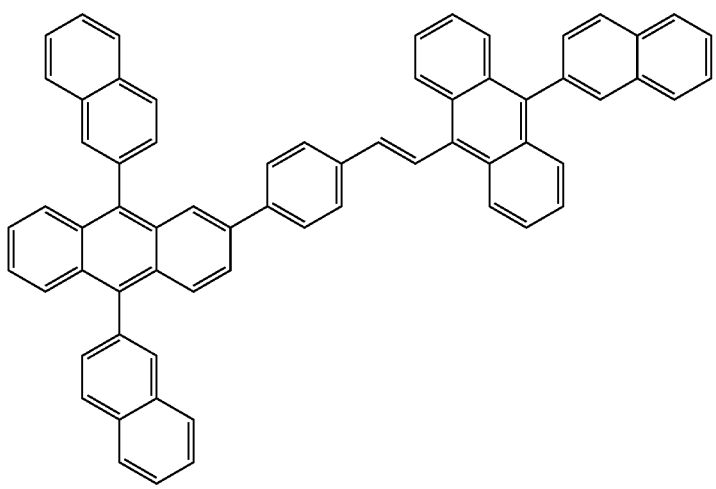
[Formula 1-196]
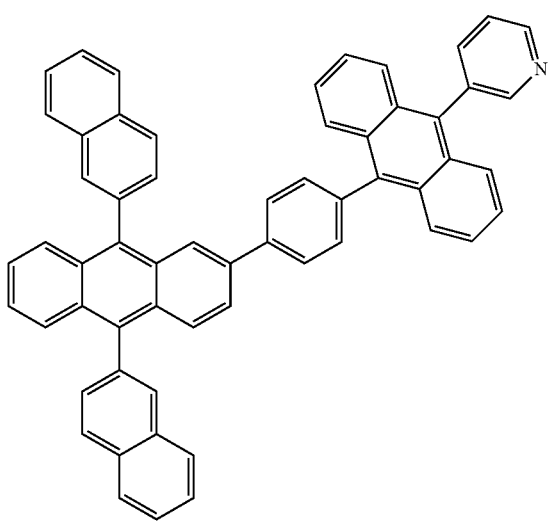
[Formula 1-197]
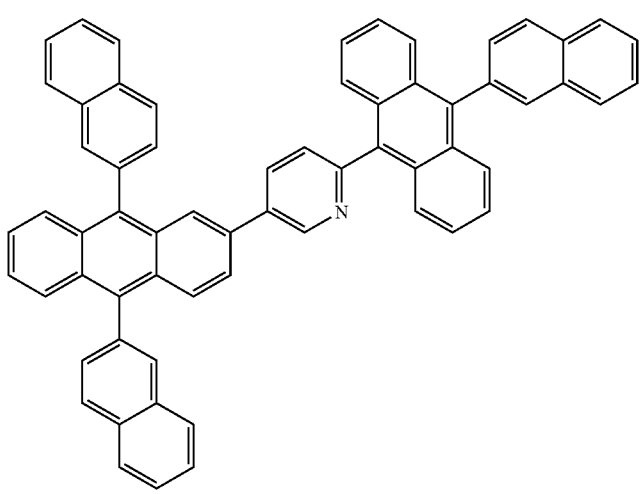
[Formula 1-198]

-continued
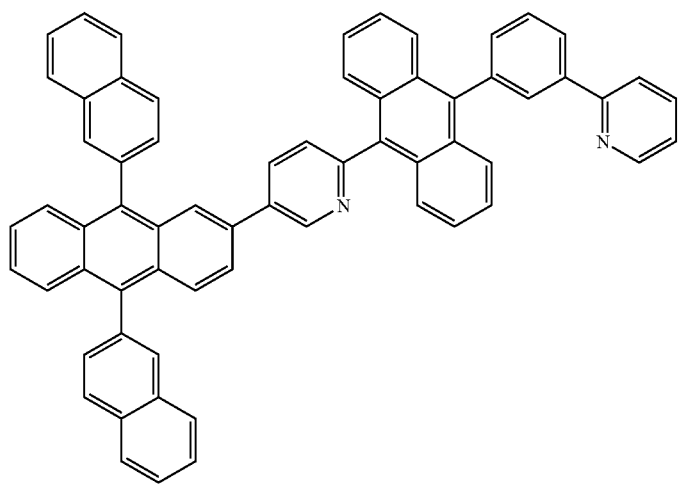
[Formula 1-199]
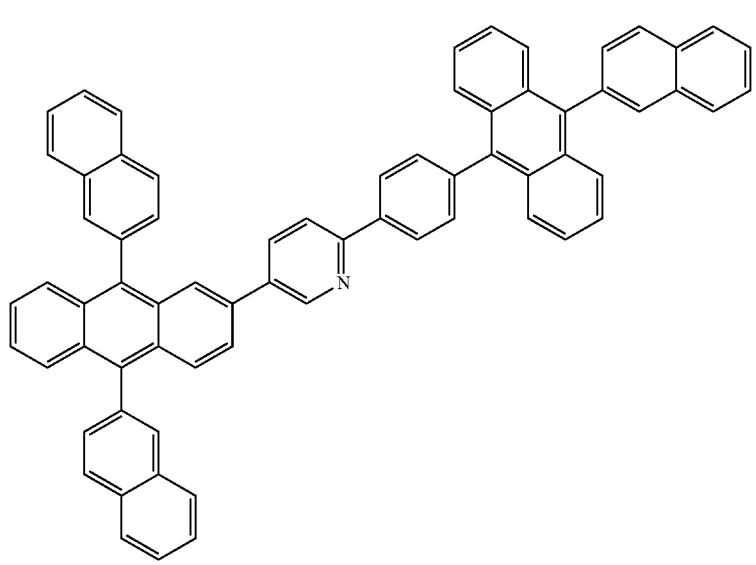
[Formula 1-200]
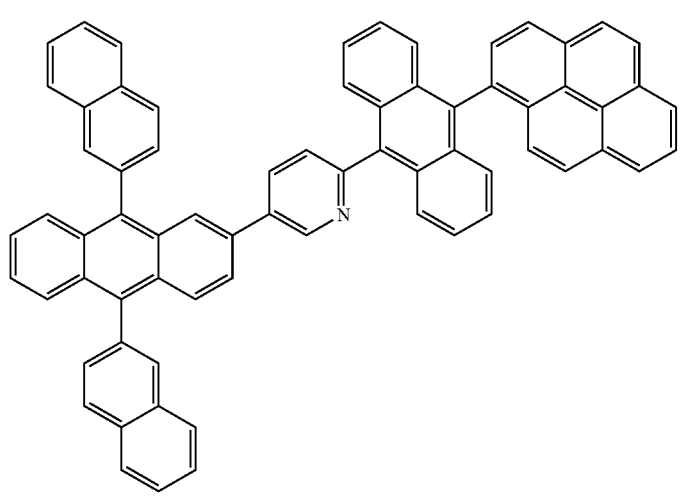
[Formula 1-201]

[Formula 1-202]
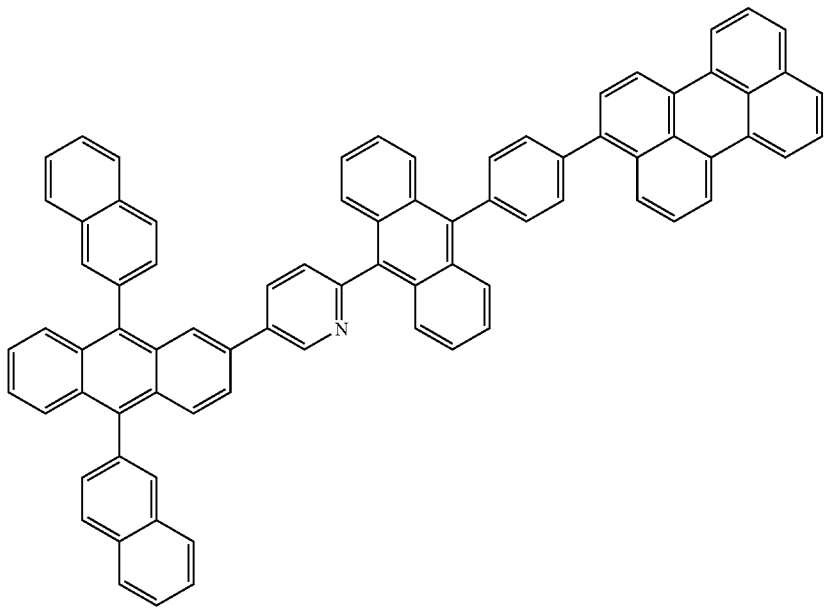
[Formula 1-203]
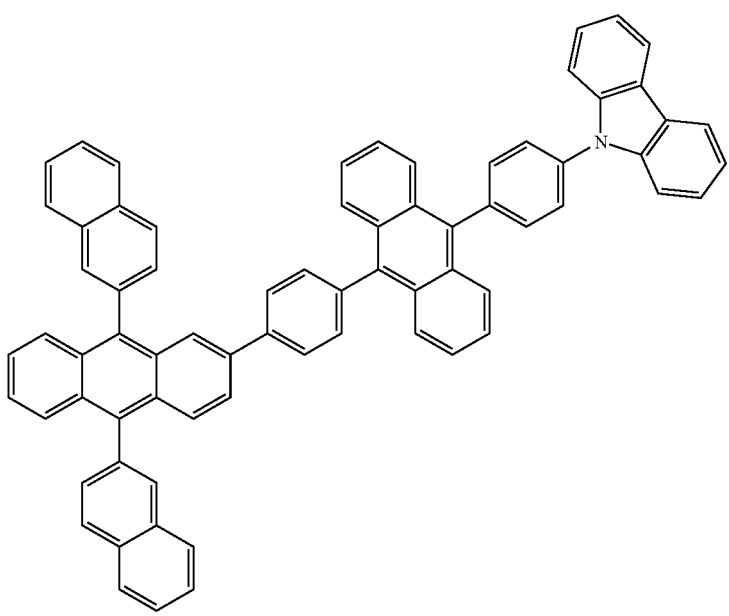
[Formula 1-204]
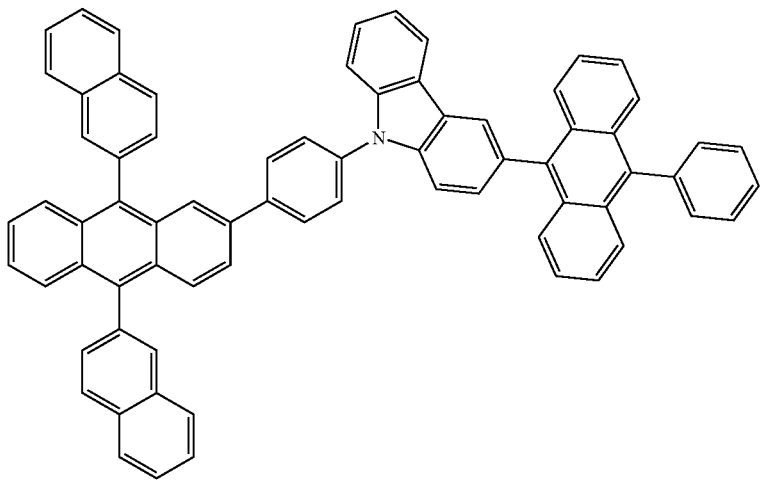

[Formula 1-205]
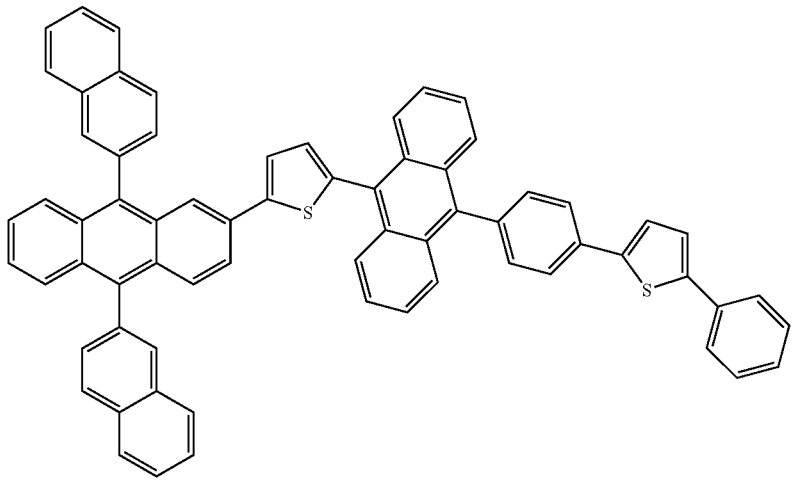
[Formula 1-206]
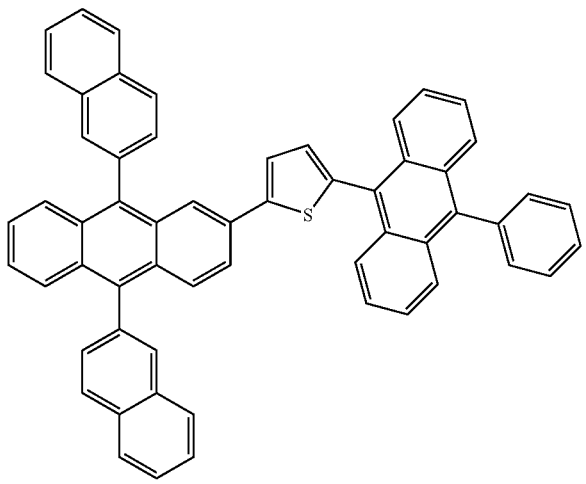
[Formula 1-207]
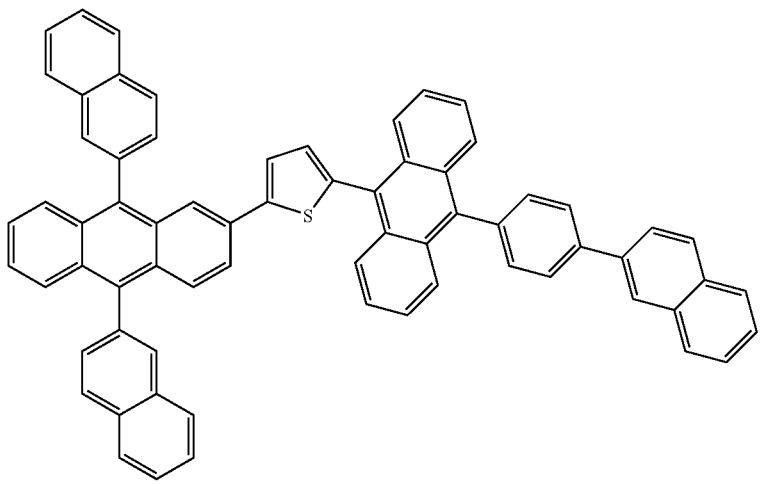

[Formula 1-208]
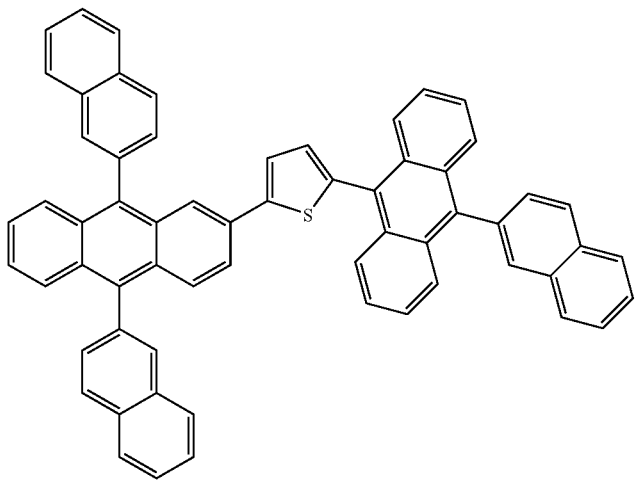
[Formula 1-209]
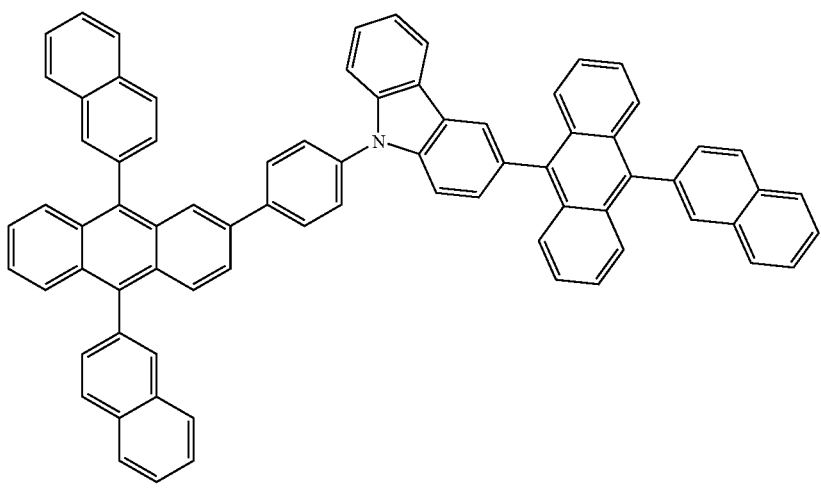
[Formula 1-210]
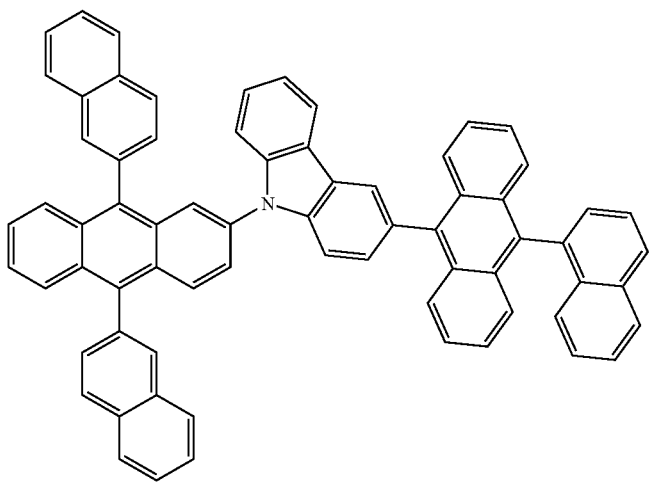

[Formula 1-211]
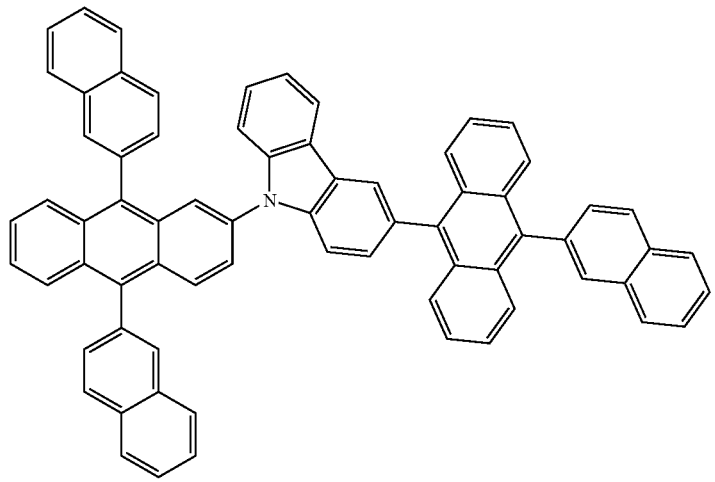
[Formula 1-212]
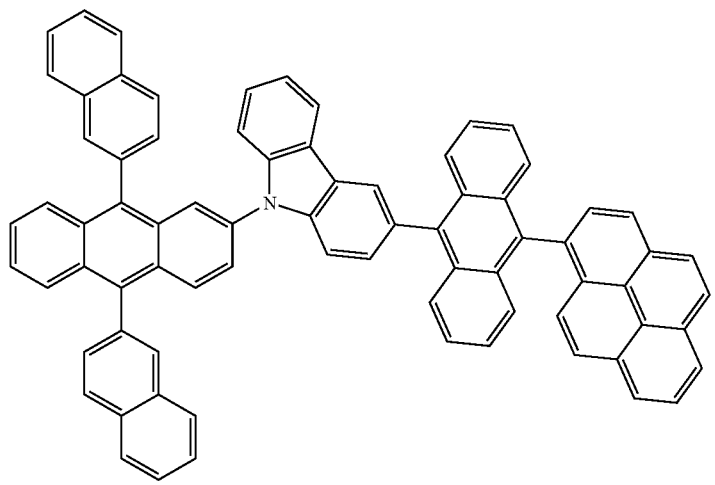
[Formula 1-213]
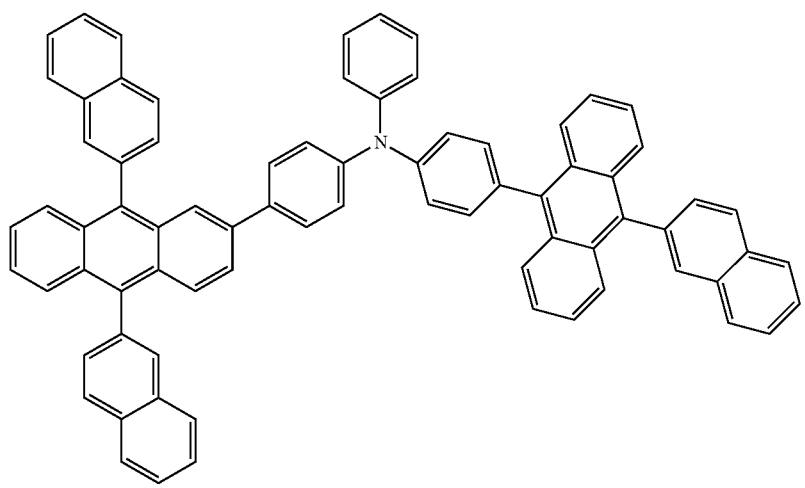

[Formula 1-214]
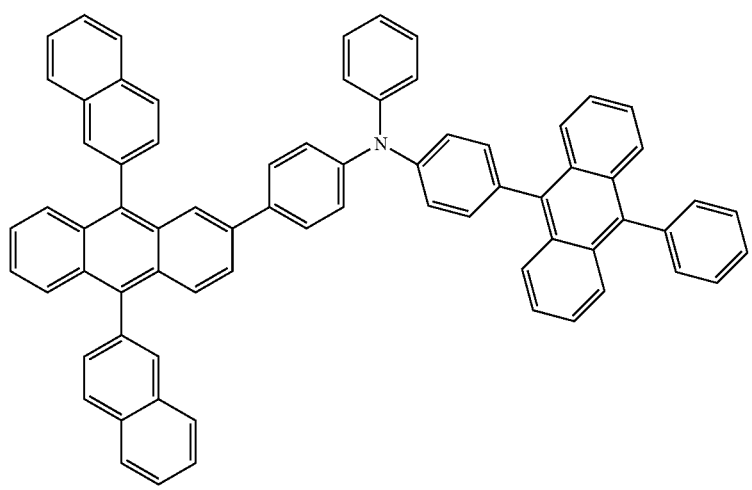
[Formula 1-215]
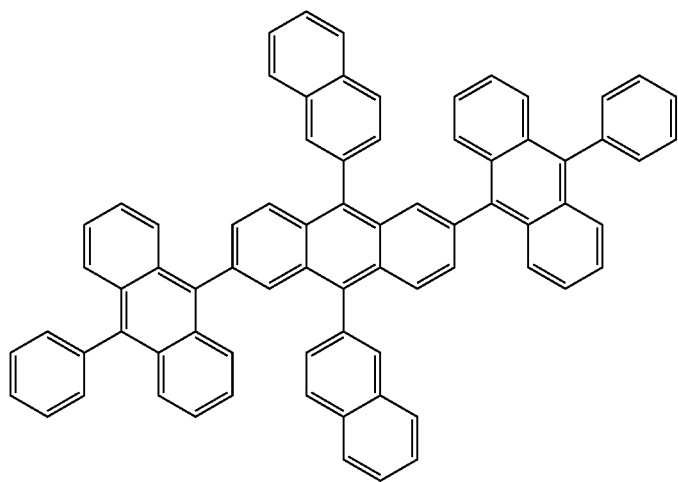
[Formula 1-216]
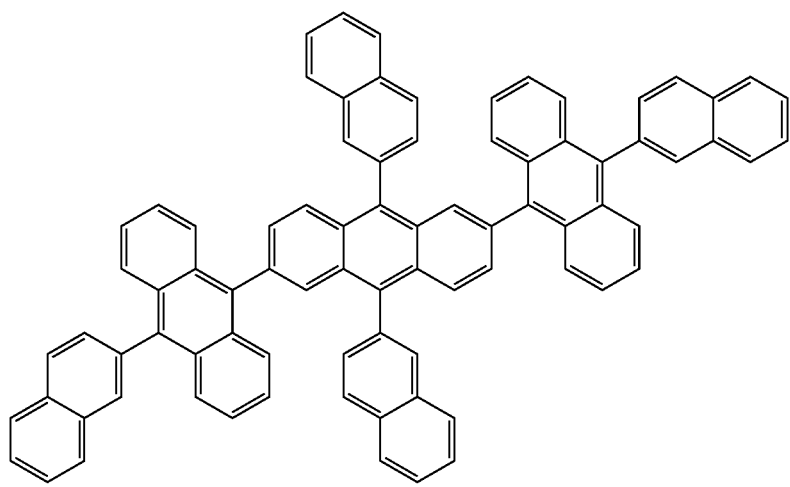

[Formula 1-217]
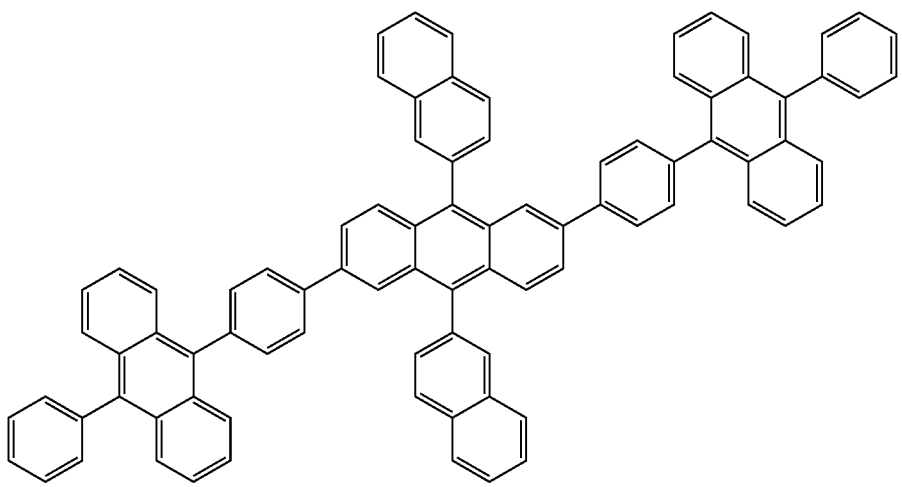
[Formula 1-218]
[Formula 1-219]

[Formula 1-220]
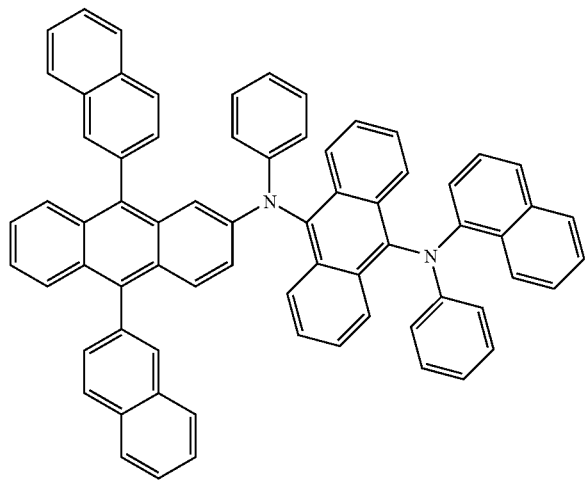
[Formula 1-221]
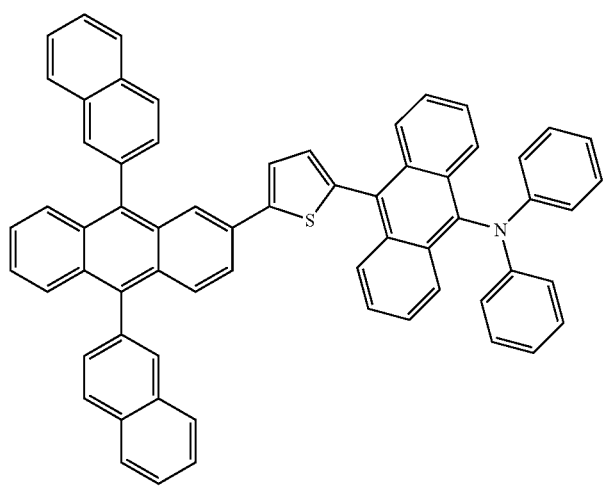
[Formula 1-222]
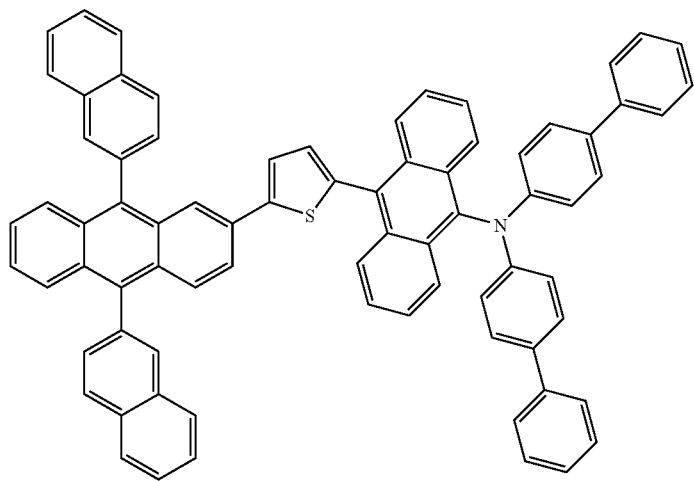

[Formula 1-223]
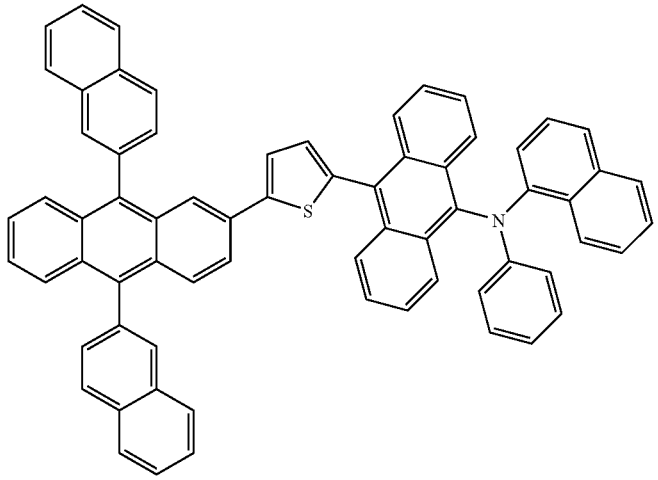
[Formula 1-224]
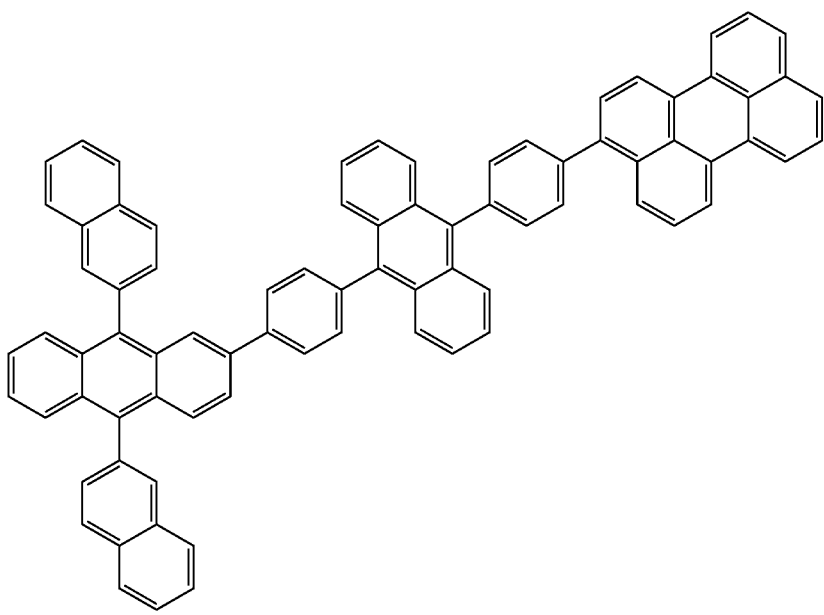
[Formula 1-225]
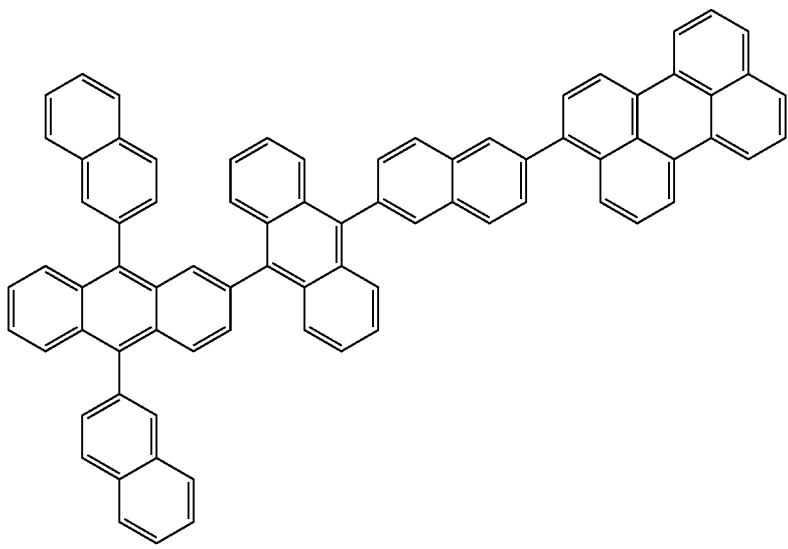

-continued

[Formula 1-226]

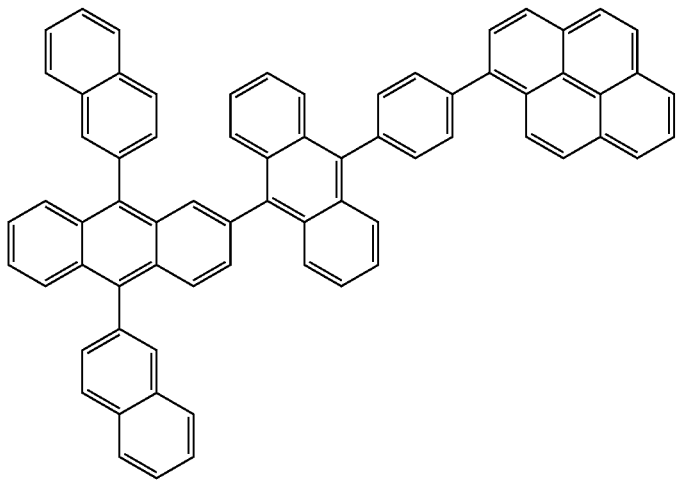

Hereinbelow, a method for preparing the compound of the formula 1 will be described.

The compound of the formula 1 can be prepared by introducing an aryl substituent to an anthracene derivative. Specifically, the compound of the formula 1 can be prepared by subjecting a 2-anthracene boronic acid or 2-anthracene boronic ester derivative having an aromatic substituent introduced to the positions 9 and 10, and an arylhalide derivative or heteroarylhalide derivative to a Suzuki coupling reaction in the presence of a Pd catalyst.

For the process used for preparation of the compound of the formula 1, other general processes known in the art can be used, in addition to the Suzuki coupling reaction.

Specifically, the compound of the formula 1 can be prepared by the method comprising the steps of:

1) preparing a R4-substituted anthraquinone derivative by subjecting a halogen-substituted anthraquinone derivative and a boronic acid or boronic ester compound having a R4 substituent to Suzuki coupling in the presence of a Pd catalyst, 2) preparing a dialcohol derivative from the anthraquinone derivative prepared in the step 1), and 3) preparing an anthracene derivative by reducing the dialcohol derivative prepared in the step 2). This preparation method can be represented by each of Reaction scheme 1.

[Reaction scheme 1]

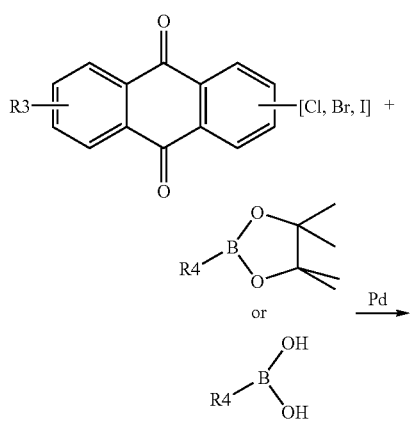

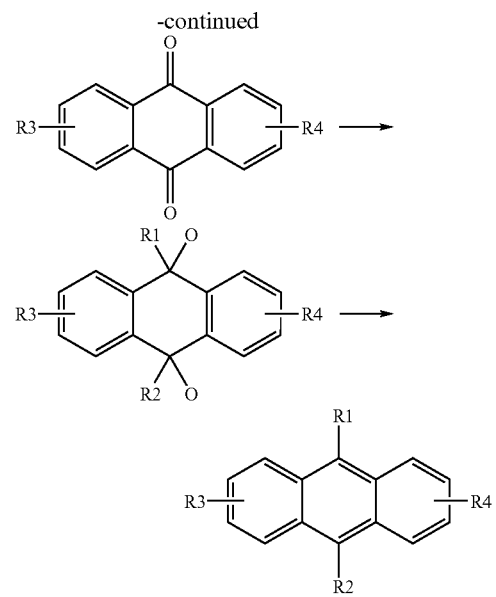

The compound of the formula 1 can be prepared by the method comprising the steps of:

1) preparing an anthraquinone derivative by introducing an arylamino group to a halogen-substituted anthraquinone derivative in the presence of a Pd catalyst, 2) preparing a dialcohol derivative from the anthraquinone derivative prepared in the step 1), and 3) preparing an anthracene derivative by reducing the dialcohol derivative prepared in the step 2).

Further, the compound of the formula 1 can be prepared by the method comprising the steps of:

1) preparing a dialcohol derivative from a halogen-substituted anthraquinone derivative, 2) preparing an anthracene derivative by reducing the dialcohol derivative prepared in the step 1), 3) preparing an anthracene boronic ester derivative from an anthracene derivative prepared in the step 2), and 4) preparing a R4-substituted compound of the formula 1 by subjecting the anthracene boronic ester derivative prepared in the step 3) and a halide of R4 to Suzuki coupling in the presence of a Pd catalyst. This preparation method can be represented by each of Reaction scheme 2.

[Reaction scheme 2]

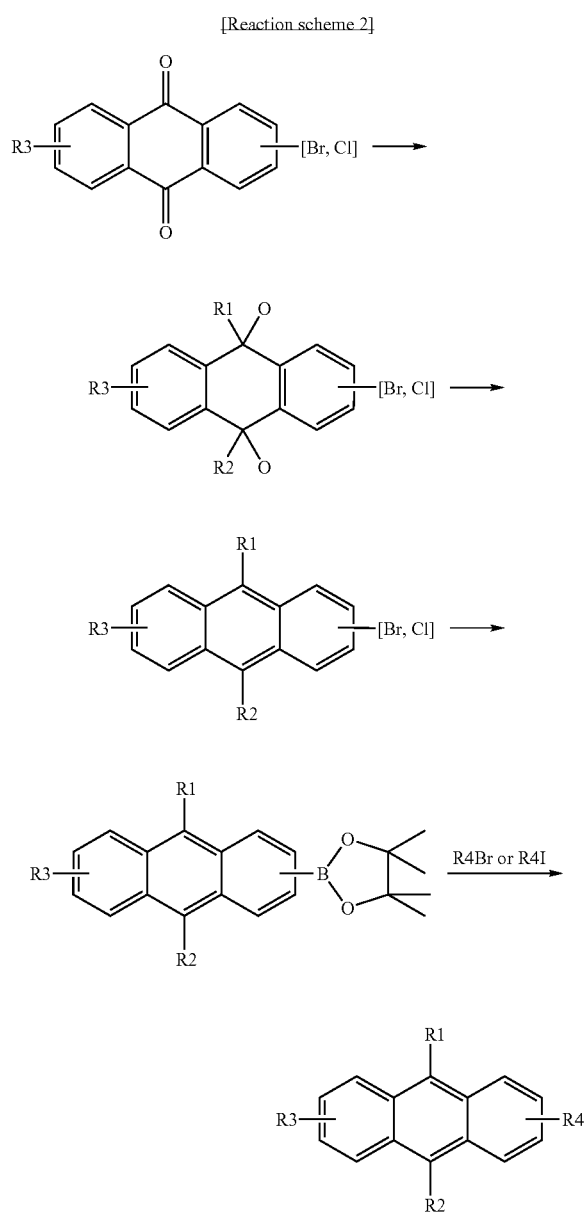

Further, the present invention provides an organic electronic device comprising a first electrode, a second electrode, and at least one organic material layer interposed between the first electrode and the second electrode, wherein at least one organic material layer comprises the compound of the formula 1.

The organic electronic device of the present invention can be prepared by usual methods and materials for preparing an organic electronic device, except that the above-described compounds are used to form at least one organic material layer.

Hereinbelow, the organic light emitting device will be exemplified.

In one embodiment of the present invention, the organic light emitting device can have a structure comprising a first electrode, a second electrode, and organic material layers interposed therebetween. The organic material layer in the organic light emitting device of the present invention may be a monolayer structure comprising a single layer, or a multilayer structure comprising two or more layers including a light emitting layer. If the organic material layer in the organic light emitting device of the present invention has a multilayer structure, it can has a structure in which a hole injecting layer, a hole transporting layer, a light emitting layer, an electron transporting layer, and the like are laminated. However, the structure of the organic light emitting device is not limited thereto, and it can further comprise a fewer number of organic materials layer. For example, the structure of the organic light emitting device of the present invention can be that as shown FIG. 1. In FIG. 1, the numeral reference 1 represents a substrate, 2 represents an anode, 3 represents a hole injecting layer, 4 represents a hole transporting layer, 5 represents an organic light emitting layer, 6 represents an electron transporting layer, and 7 represents a cathode. The organic light emitting device having the structure as shown in FIG. 1 is referred to as an organic light emitting device having a forward structure. The present invention is not limited thereto, and it also includes an organic light emitting device having a reverse structure. That is, the organic light emitting device of the present invention can have a structure in which a substrate, a cathode, an electron transporting layer, an organic light emitting layer, a hole transporting layer, a hole injecting layer, and an anode are sequentially laminated.

If the organic light emitting device according to the present invention has a multilayer structure of the organic material layers, the compound of the formula 1 can be contained in a light emitting layer, a hole transporting layer, a hole transporting and light emitting layer, a light emitting and electron transporting layer, an electron transporting layer, an electron transporting and/or injecting layer, and the like. In the present invention, the compound of the formula 1 is particularly preferably contained in an electron injecting and/or transporting layer, or a light emitting layer.

The organic light emitting device of the present invention can be prepared by usual methods and materials for preparing an organic light emitting device, except that the compound of the formula 1 is used to form at least one of the organic material layers. For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer, and an electron transporting layer on the anode; and depositing a material, which can be used as a cathode, thereon. Alternatively, an organic light emitting device can be prepared by sequentially depositing a cathode material, an organic material layer, and an anode material on a substrate, thus preparing the above-described organic light emitting device having a reverse structure.

Further, the organic material layer can be prepared to have a fewer number of layers, using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to the organic material layers. Specific examples of the anode material which can be used in the present invention include metals such as vanadium, chromium, copper, zinc, and gold, or an alloy thereof; metal oxides such as zinc oxide, indium oxide, indium-tin oxide (ITO), and indium zinc oxide (IZO); a combination of a metal and an oxide, such as ZnO:Al and SnO$_2$:Sb; conductive polymers such as poly(3-methylthiophene), poly[3,4-(ethylene-1,2-dioxy)thiophene] (PEDT), polypyrrole, and polyaniline, but are not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin, and lead, and an alloy thereof; and multilayered materials such as LiF/Al and $LiO_2$/Al, but are not limited thereto.

The hole injecting material is a material facilitating hole injection from an anode at low voltage. The HOMO (highest occupied molecular orbital) of the hole injecting material is preferably located between the work function of the anode materials and the HOMO level of its neighboring organic material layer. Specific examples of the hole injecting material include organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is a material having high hole mobility, which can transfer holes from the anode or the hole injecting layer toward the light emitting layer. Specific examples thereof include organic materials of arylamine series, conductive polymers, and block copolymers having both of the conjugated portions and the non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole, and benzimidazole series; polymers of poly(p-phenylenevinylene) (PPV) series; spiro compounds; and polyfluorene and rubrene compounds, but are not limited thereto.

The electron transporting material is suitably a material having high electron mobility, which can easily receive electrons from the cathode and then transfer them to the light emitting layer. Specific examples thereof include an Al complex of an 8-hydroxyquinoline; complexes including $Alq_3$; organic radical compounds; and hydroxyflavone-metal complexes, but are not limited thereto.

The organic light emitting device according to the present invention may be of a front-sided, back-sided, or double-sided light emission according to the materials used.

The compound according to the invention can also function in an organic electronic device including an organic solar cell, an organic photoconductor, and an organic transistor, according to a principle similar to that applied to the organic light emitting device.

Hereinafter, preferable Examples are provided for the purpose of making the present invention more understandable. As such, Examples are provided for illustrating the Examples, but the scope of the invention is not limited thereto.

MODE FOR INVENTION

Example

Preparative Example 1

1) Synthesis of Compound of the Following Formula 1-A

[Formula 1-A]

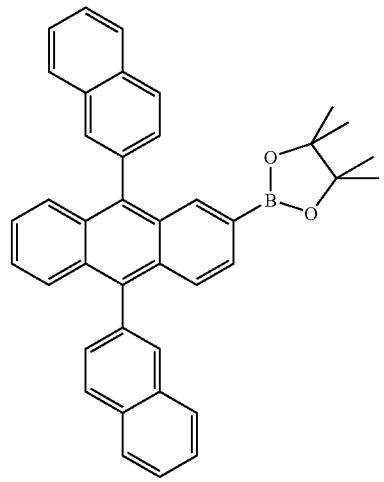

2-Bromo-9,10-dinaphthylanthracene (5.00 g, 9.81 mmol), bis(pinacolato)diboron (2.75 g, 10.8 mmol), and potassium acetate (2.89 g, 29.4 mmol) were suspended in dioxane (50 mL). To the suspension, was added palladium(diphenyl phosphinoferrocene)chloride (0.24 g, 0.3 mmol). The obtained mixture was stirred at 80 for about 6 hours, and then cooled to room temperature. The mixture was diluted with water (50 mL), and extracted from dichloromethane (3×50 mL). The organic extract was dried over magnesium sulfate, and concentrated in vacuo. The crude product washed with ethanol, and dried in vacuo to prepare a compound of the formula 1-A (4.46 g, yield 82%), which is 9,10-dinaphthylanthracenyl-2-boronate.

MS: $[M+H]^+=557$

2) Synthesis of Compound of the Following Formula 1-B

[Formula 1-B]

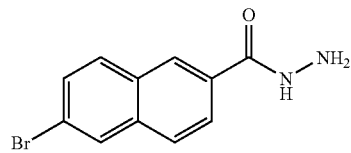

6-bromo-2-naphthoatemethylester compound (8.0 g, 30 mmol) and hydrazine monohydrate (6 mL, 120 mmol) were dissolved in 150 mL of methanol, and the solution was stirred at room temperature for 2 hours, and then stirred at 80 for 20 hours. The resultant was cooled to normal temperature, and the formed white solid was filtered, washed (with methanol), and then dried. Thus, a compound of the formula 1-B (7.5 g, yield 94%) was prepared.

MS: $[M+H]^+=265$

3) Synthesis of Compound of the Following Formula 1-C

[Formula 1-C]

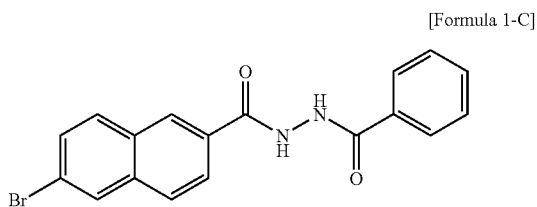

The compound of the formula 1-B (3.5 g, 13.2 mmol) and diisopropylethylamine (4.6 mL, 26.4 mmol) were 100 mL of xylene, and then benzoyl chloride (1.8 mL, 19.8 mmol) was added dropwise to the solution at 0. 20 minutes later, the solution was subject to reaction at 140. The solution was cooled to normal temperature to form a white solid, and the solid was filtered, washed, and then dried. Thus, the compound of the formula 1-C (3.5 g, yield 72%) was prepared.

MS: [M+H]$^+$=369

4) Synthesis of Compound of the Following Formula 1-D

[Formula 1-D]

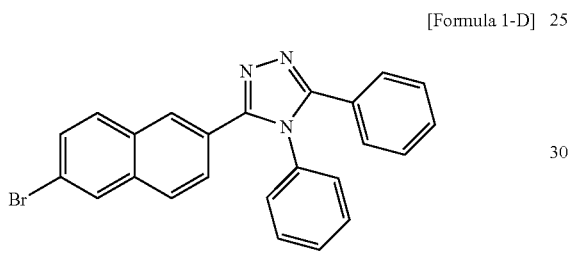

The compound of the formula 1-C (3.1 g, 8.5 mmol), and aniline (4.7 g, 51 mmol) were dispersed in 1,2-dichlorobenzene, and to the dispersion, POCl$_3$ (0.8 mL, 8.5 mmol) was added dropwise slowly. The dispersion was stirred at a reaction temperature of 180 for 4 hours, and then cooled to normal temperature to prepared a white solid. The solid obtained after filtration was dispersed in 2 M NaOH, and the dispersion was stirred under heating to 70. Again, the solid was filtered, sufficiently washed with water, and dried to prepare a compound of the formula 1-D (3.5 g, yield 72%).

MS: [M+H]$^+$=426

5) Synthesis of Compound of the Following Formula 1-E

[Formula 1-E]

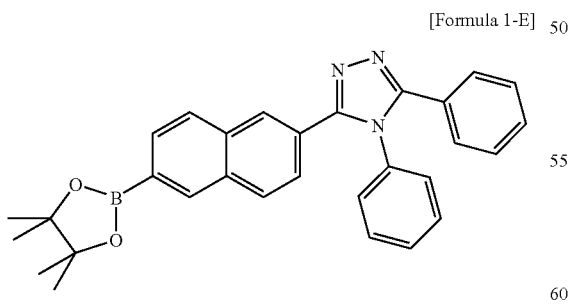

The compound of the formula 1-D (3.5 g, 8.2 mmol), bis(pinacolato)diboron (2.3 g, 9.1 mmol), and potassium acetate (2.4 g, 24.5 mmol) were suspended in dioxane (50 mL). To the suspension, palladium (diphenylphosphinoferrocene)chloride (0.12 g, 0.15 mmol) was added. The obtained mixture was stirred at 80 for about 6 hours, and cooled to room temperature. The mixture was diluted with water (50 mL), and extracted from dichloromethane (3×50 mL). The organic extract was dried over magnesium sulfate, and concentrated in vacuo. A crude product washed with ethanol, and dried in vacuo to prepare a compound of the formula 1-E (3.4 g, yield 89%) which is 9,10-dinaphthylanthracenyl-2-borate.

MS: [M+H]$^+$=474

6) Synthesis of Compound of the Following Formula 1-F

[Formula 1-F]

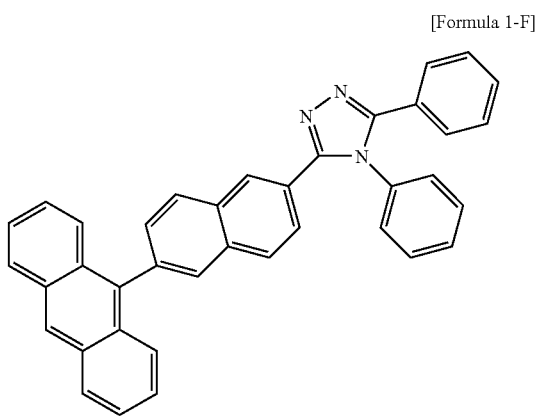

9-Bromoanthracene (1.9 g, 7.4 mmol) and the compound of the formula 1-E (3.5 g, 7.4 mmol) were completely dissolved in tetrahydrofuran (60 mL), and then a 2 M aqueous solution of potassium carbonate was added to the solution. To the resultant, tetra(bistriphenylphosphino)palladium (300 mg, 0.26 mmol) was added, and then the mixture was stirred under heating for 5 hours. The mixture was cooled to normal temperature, and the aqueous phase was removed. The resultant was dried over anhydrous magnesium sulfate, concentrated under reduced pressure and recrystallized from petrolether to prepare a compound of the formula 1-F (3.6 g, yield 93%).

MS: [M+H]$^+$=524

7) Synthesis of Compound of the Following Formula 1-G

[Formula 1-G]

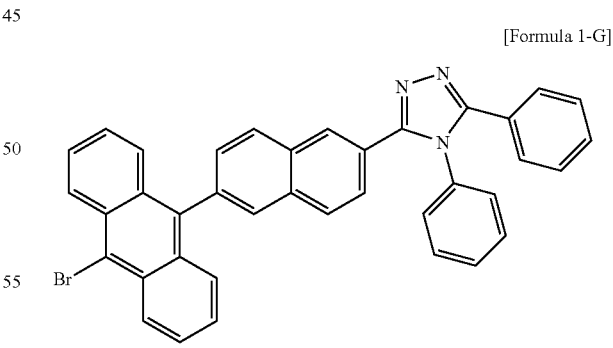

The compound of the formula 1-F (3.6 g, 6.87 mmol) was added to dimethylformamide (DMF, 50 mL), and the mixture was stirred for 30 minutes. Then, N-bromosuccinimide (NBS, 1.22 g, 6.87 mmol) was slowly added thereto, and the mixture was stirred for 3 hours. The resulting solid was filtered to prepare a compound of the formula 1-G (3.8 g, yield 92%).

MS: [M+H]$^+$=602

8) Synthesis of Compound of the Following Formula 1-63

[Formula 1-63]

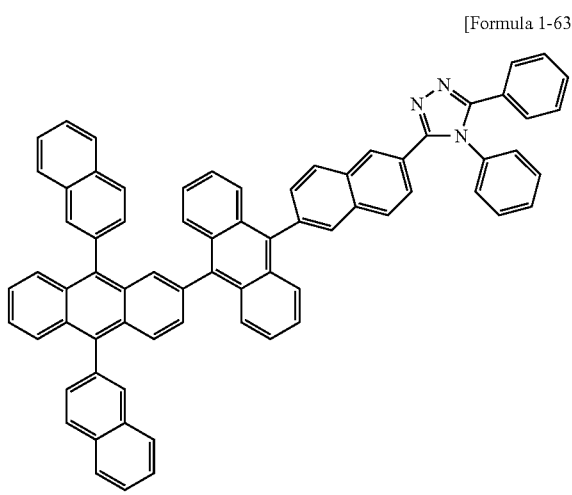

The compound of the formula 1-A (4.5 g, 8.0 mmol) and the compound of the formula 1-G (3.8 g, 6.3 mmol) were completely dissolved in tetrahydrofuran (100 mL), and then a 2 M aqueous solution of potassium carbonate was added to the solution. To the resultant, tetrakis(triphenylphosphino)palladium (155 mg, 0.013 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and purified by column chromatography using tetrahydrofuran:hexane=1:6 to prepare a compound of the formula 1-63 (3.6 g, yield 47%).

MS: [M+H]$^+$=952

Preparative Example 2

1) Synthesis of Compound of the Following Formula 2-A

[Formula 2-A]

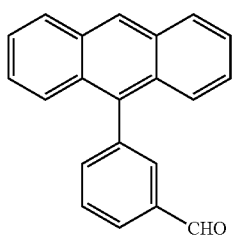

9-Bromoanthracene (10 g, 38.9 mmol) and 3-formylphenyl boronic acid (7.0 g, 46.7 mmol) were completely dissolved in tetrahydrofuran (100 mL), and then a 2 M aqueous solution of potassium carbonate was added to the solution. To the resultant, tetra(bistriphenylphosphino)palladium (900 mg, 0.78 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and recrystallized from petro-lether to prepare a compound of the formula 2-A (9 g, yield 82%).

MS: [M+H]$^+$=283

2) Synthesis of Compound of the Following Formula 2-B

[Formula 2-B]

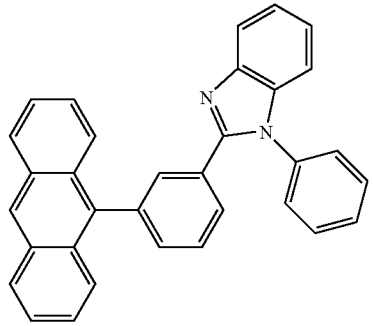

The compound of the formula 2-A (9 g, 31.9 mmol) and N-phenyl-1,2-diaminobenzene (5.87 g, 31.9 mmol) were added to dimethylacetamide (DMAC, 50 mL), and the mixture was stirred under heating for 24 hours. The mixture was cooled to normal temperature, and distilled water was added thereto to form a precipitate, which was filtered off. The filtered solid was purified by column chromatography using tetrahydrofuran:hexane=1:6 to prepare a compound of the formula 2-B (5 g, yield 35%).

MS: [M+H]$^+$=447

3) Synthesis of Compound of the Following Formula 2-C

[Formula 2-C]

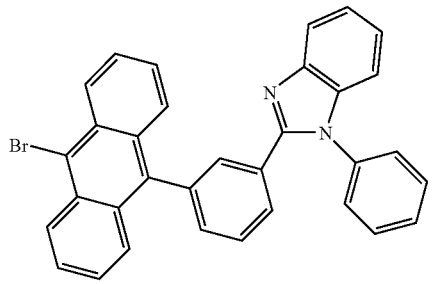

The compound of the formula 2-B (5 g, 11.2 mmol) was added to dimethylformamide (DMF, 50 mL), and the mixture was stirred for 30 minutes. Then, N-bromosuccinimide (NBS, 2 g, 11.2 mmol) was slowly added thereto, and the mixture was stirred for 3 hours. The resulting solid was filtered to prepare a compound of the formula 2-C (5.1 g, yield 87%).

MS: [M+H]$^+$=525

4) Synthesis of Compound of the Following Formula 1-11

[Formula 1-11]

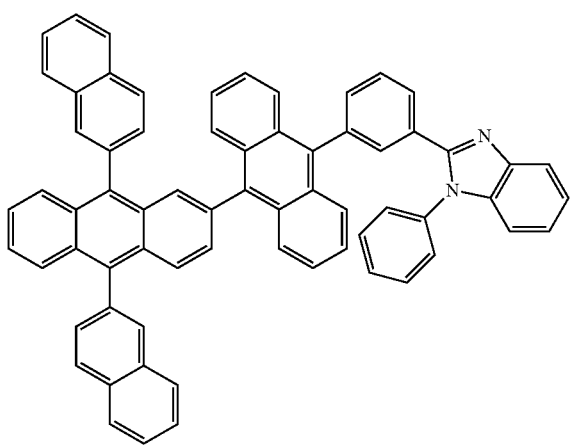

The compound of the formula 1-A (4.5 g, 8.1 mmol) and the compound of the formula 2-C (3.5 g, 6.7 mmol) were completely dissolved in tetrahydrofuran (100 mL), and then a 2 M aqueous solution of potassium carbonate was added to the solution. To the resultant, tetrakis(triphenylphosphino) palladium (155 mg, 0.013 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and purified by column chromatography using tetrahydrofuran:hexane=1:6 to prepare a compound of the formula 1-11 (3.7 g, yield 63%).

MS: [M+H]$^+$=875
UV (2×10$^{-5}$ M toluene solution): $\lambda_{max}$ 398, 376 nm
PL (2×10$^{-5}$ M toluene solution): $\lambda_{max}$ 454 nm Preparative Example 3

1) Synthesis of Compound of the Following Formula 3-A

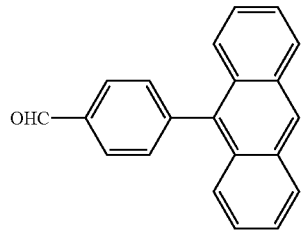

[Formula 3-A]

9-Bromoanthracene (10 g, 38.9 mmol) and 3-formylphenyl boronic acid (7.0 g, 46.7 mmol) were completely dissolved in tetrahydrofuran (100 mL), and then a 2 M aqueous solution of potassium carbonate was added to the solution. To the resultant, tetra(bistriphenylphosphino)palladium (900 mg, 0.78 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and recrystallized from petrolether to prepare a compound of the 3-A (7.6 g, yield 69%).

MS: [M+H]$^+$=283

2) Synthesis of Compound of the Following Formula 3-B

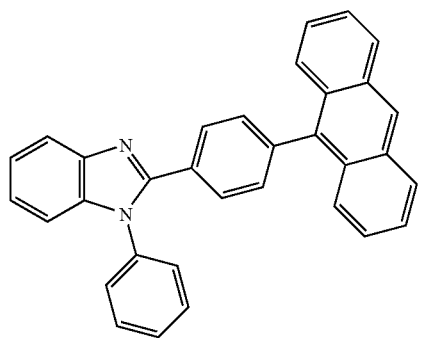

[Formula 3-B]

The compound of the formula 3-A (9 g, 31.9 mmol) and N-phenyl-1,2-diaminobenzene (5.9 g, 31.9 mmol) were added to dimethylacetamide (DMAC, 50 mL), and the mixture was stirred under heating for 24 hours. The mixture was cooled to normal temperature, and distilled water was added thereto to form a precipitate, which was filtered off. The filtered solid was purified by column chromatography using tetrahydrofuran:hexane=1:6 to prepare a compound of the formula 3-B (9.5 g, yield 67%).

MS: [M+H]$^+$=447

3) Synthesis of Compound of the Following Formula 3-C

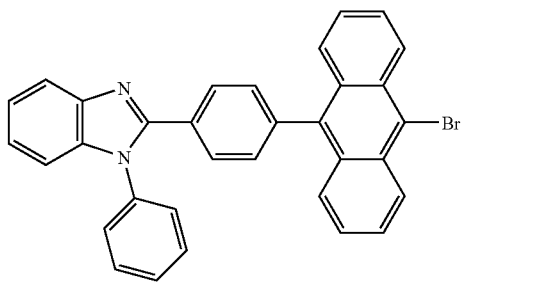

[Formula 3-C]

The compound of the formula 3-B (5 g, 11.2 mmol) was added to dimethylformamide (DMF, 50 mL), and the mixture was stirred for 30 minutes. Then, N-bromosuccinimide (NBS, 2 g, 11.2 mmol) was slowly added thereto, and the mixture was stirred for 3 hours. The resulting solid was filtered to prepare a compound of the formula 3-C (5.1 g, yield 87%).

MS: [M+H]$^+$=525

4) Synthesis of Compound of the Following Formula 1-10

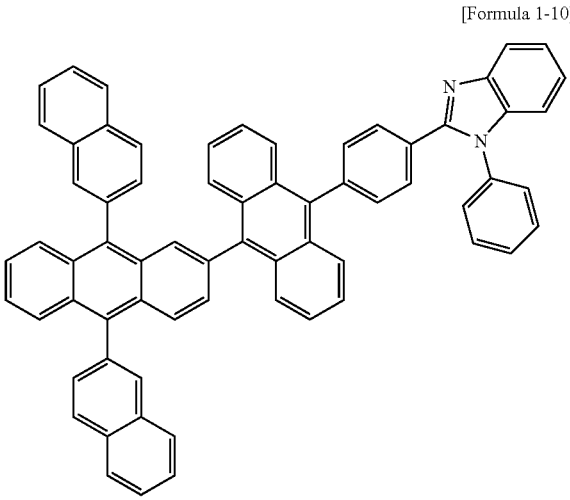

[Formula 1-10]

The compound of the formula 1-A (3.8 g, 6.8 mmol) as synthesized in Preparative Example 1 and the compound of the formula 3-C (2.9 g, 5.5 mmol) were completely dissolved in tetrahydrofuran (80 mL), and then a 2 M aqueous solution of potassium carbonate was added to the solution. To the resultant, tetra(bistriphenylphosphino)palladium (155 mg, 0.013 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and purified by column chromatography using tetrahydrofuran:hexane=1:6 to prepare a compound of the formula 1-10 (3.9 g, yield 81%).

MS: [M+H]$^+$=875
UV (2×10$^{-5}$ M toluene solution): $\lambda_{max}$ 398, 379 nm
PL (2×10$^{-5}$ M toluene solution): $\lambda_{max}$ 458 nm

Preparative Example 4

1) Synthesis of Compound of the Following Formula 4-A

[Formula 4-A]

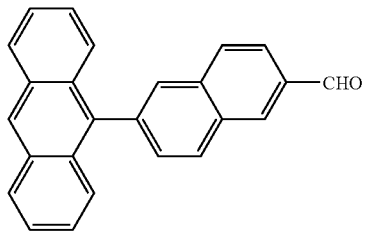

9-Bromoanthracene (10 g, 38.9 mmol) and 6-formyl-2-naphthyl boronic acid (8.56 g, 42.8 mmol) were completely dissolved in tetrahydrofuran (100 mL), and then a 2 M aqueous solution of potassium carbonate was added to the solution. To the resultant, tetra(bistriphenylphosphino)palladium (900 mg, 0.78 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and recrystallized from petrolether/ethyl ether to prepare a compound of the 4-A (5 g, yield 39%).

MS: $[M+H]^+$=333

2) Synthesis of Compound of the Following Formula 4-B

[Formula 4-B]

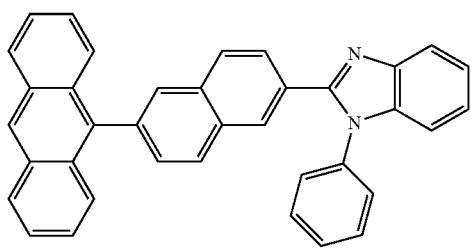

The compound of the formula 4-A (4.9 g, 14.7 mmol) and N-phenyl-1,2-diaminobenzene (3.2 g, 17.4 mmol) were added to dimethylacetamide (DMAC, 50 mL), and the mixture was stirred under heating for 24 hours. The mixture was cooled to normal temperature, and distilled water was added thereto to form a precipitate, which was filtered off. The resultant was recrystallized from ethanol to prepare a compound of the formula 4-B (3.2 g, yield 44%).

MS: $[M+H]^+$=497

3) Synthesis of Compound of the Following Formula 4-C

[Formula 4-C]

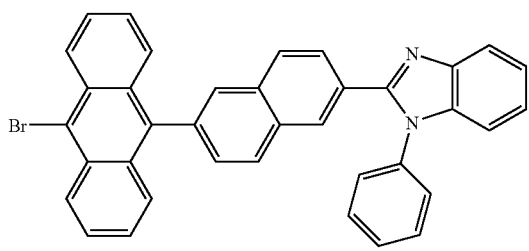

The compound of the 4-B (3.2 g, 6.4 mmol) was added to dimethylformamide (DMF, 50 mL), and the mixture was stirred for 30 minutes. Then, N-bromosuccinimide (NBS, 1.1 g, 6.4 mmol) was slowly added thereto, and the mixture was stirred for 2 hours. The resulting solid was filtered to prepare a compound of the formula 4-C (2.3 g, yield 62%).

MS: $[M+H]^+$=575

4) Synthesis of Compound of the Following Formula 1-12

[Formula 1-12]

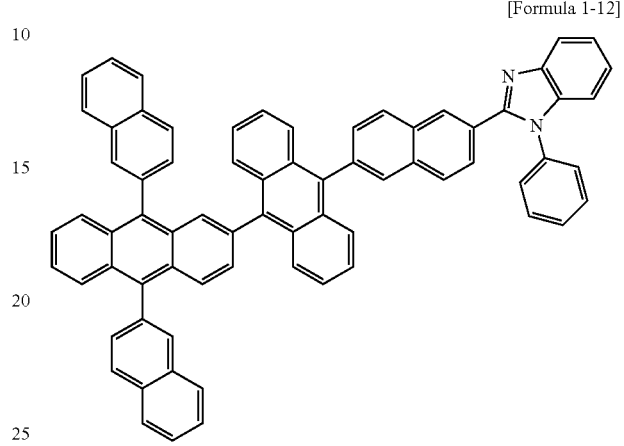

The compound of the formula 1-A (2.4 g, 4.4 mmol) as synthesized in Preparative Example 1 and the compound of the formula 4-C (2.3 g, 4.0 mmol) were completely dissolved in tetrahydrofuran (100 mL), and then a 2 M aqueous solution of potassium carbonate was added to the solution. To the resultant, tetra(bistriphenylphosphino)palladium (231 mg, 0.2 mmol) was added, and then the mixture was stirred under heating for 5 hours. The mixture was cooled to normal temperature, and the aqueous phase was removed. The resultant was dried over anhydrous magnesium sulfate, concentrated under reduced pressure, and purified by column chromatography using tetrahydrofuran:hexane=1:6 to prepare a compound of the formula 1-12 (1.5 g, yield 41%).

MS: $[M+H]^+$=925
UV ($2\times10^{-5}$M toluene solution): $\lambda_{max}$ 385, 548 nm
PL ($2\times10^{-5}$M toluene solution): $\lambda_{max}$ 360, 377, 399 nm

Preparative Example 5

1) Synthesis of Compound of the Following Formula 5-A

[Formula 5-A]

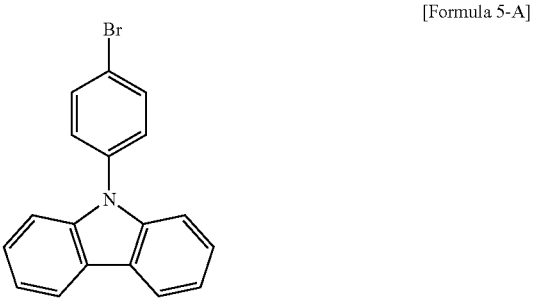

Carbazole (3.3 g, 20 mmol), 1-bromo-4-iodobenzene (3.0 mL, 24 mmol), potassium carbonate ($K_2CO_3$, 5.6 g, 41 mmol), copper iodide (CuI, 1.9 g, 1.0 mmol), and 50 mL of xylene were refluxed under nitrogen atmosphere. The resultant was cooled to normal temperature, and the product was extracted from ethyl acetate, the moisture was removed over anhydrous magnesium sulfate (MgSO₄), and the solvent was removed under reduced pressure. The resultant was passed through as silica gel column chromatography using a hexane solvent to obtain a compound, and the solvent was removed under reduced pressure. The resultant was dried in vacuo to prepare a white solid compound of the formula 5-A (1.6 g, yield 25%).

MS: [M+H]⁺=322

2) Synthesis of Compound of the Following Formula 5-B

[Formula 5-B]

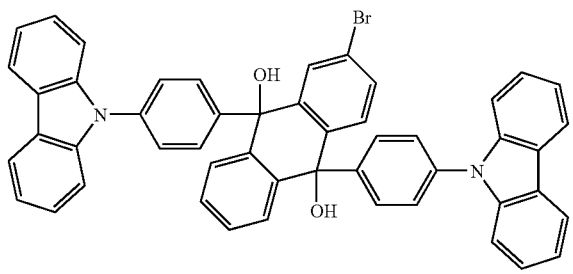

The compound of the formula 5-A (4.4 g, 13.7 mmol) was dissolved in anhydrous tetrahydrofuran (80 mL) under a nitrogen atmosphere. The solution was cooled to −78, n-butyl lithium (6.6 mL, 2.5 M hexane solution) was slowly added over 10 minutes to the cooled solution, and the solution was stirred at −78 for about 40 minutes. 2-bromoanthraquinone compound (1.6 g, 5.6 mmol) was added to the reaction mixture, and the mixture was further stirred at −78 for about 3 hours. The mixture was stirred at room temperature for about 1 hour. To the mixture, an aqueous ammonium chloride solution (50 mL) was added. The organic layer was separated, and the aqueous layer was extracted from diethyl ether (60 mL). The combined organic extract was dried over magnesium sulfate, and concentrated under reduced pressure. The obtained solid was suspended in diethyl ether, stirred about 1 hour, filtered, and then dried to obtain a compound of the formula 5-B (7.7 g, yield 73%), which is a dialcohol compound.

3) Synthesis of Compound of the Following Formula 5-C

[Formula 5-C]

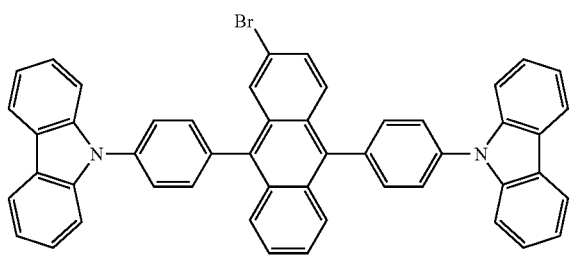

The compound of the formula 5-B (2.82 g, 3.65 mmol) was added to a dispersion of acetic acid (60 mL), potassium iodide (3.32 g, 20 mmol), and hydrous sodium hypophosphite (4.2 g, 40 mmol) were added to the suspension. The mixture was continuously stirred under reflux for about 3 hours, and then cooled to room temperature. The mixture was filtered, washed with water, and then dried in vacuo to prepare a compound of the formula 5-C (1.8 g, yield 67%).

MS: [M+H]⁺=739

4) Synthesis of Compound of the Following Formula 5-D

[Formula 5-D]

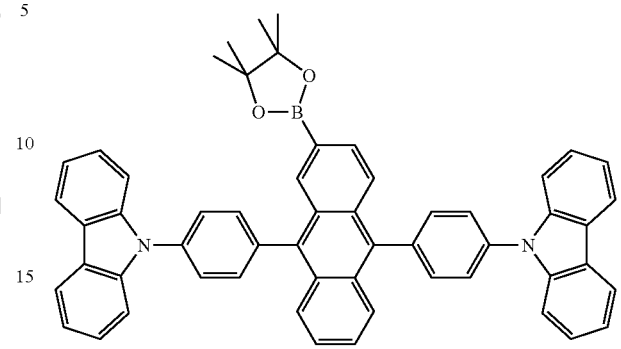

A compound of the formula 5-D was prepared in the same manner as in the method for preparation of the compound of the formula 1-A, except that a compound of the formula 5-C was used instead of 2-bromo-9,10-dinaphthylanthracene compound in the method for preparation of the compound of the formula 1-A of Preparative Example 1.

MS: [M+H]⁺=787

5) Synthesis of Compound of the Following Formula 1-40

[Formula 1-40]

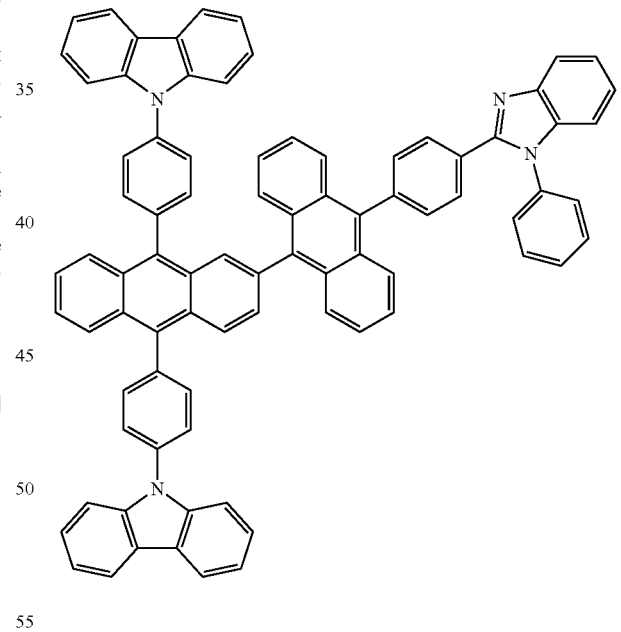

A compound of the formula 1-40 was prepared in the same manner as in the method for preparation of the compound of the formula 1-63 of Preparative Example 1, except that a compound of the formula 5-D was used instead of the compound of the formula 1-A, and a compound of the formula 3-C was used instead of the compound of the formula 1-G in the method for preparation of the compound of the formula 1-63 of Preparative Example 1.

MS: [M+H]⁺=1105

Preparative Example 6

Synthesis of Compound of the Following Formula 1-19

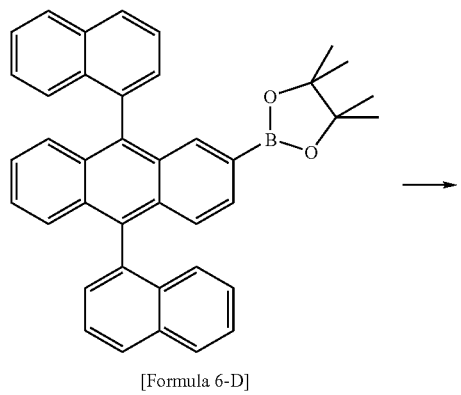

[Formula 6-D]

→

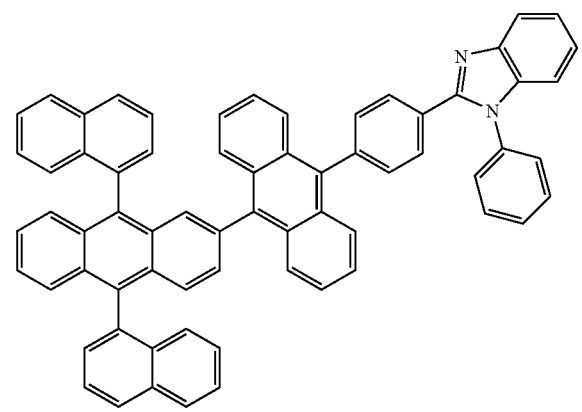

[Formula 1-19]

A compound of the formula 1-19 was prepared in the same manner as in the method for preparation of the compound of the formula 1-63 of Preparative Example 1, except that a compound of the formula 6-D was used instead of the compound of the formula 1-A, and a compound of the formula 3-C was used instead of the compound of the formula 1 G in the method for preparation of the compound of the formula 1-63 of Preparative Example 1.

MS: $[M+H]^+=875$

Preparative Example 7

Synthesis of Compound of the Following Formula 1-34

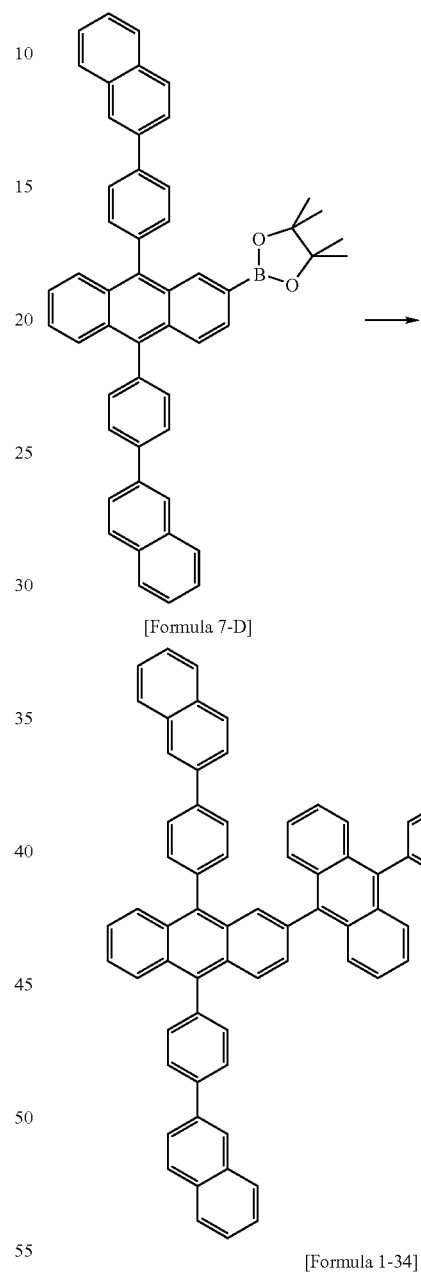

[Formula 7-D]

[Formula 1-34]

A compound of the formula 1-34 was prepared in the same manner as in the method for preparation of the compound of the formula 1-63 of Preparative Example 1, except that a compound of the formula 7-D was used instead of the compound of the formula 1-A, and a compound of the formula 3-C was used instead of the compound of the formula 1-G in the method for preparation of the compound of the formula 1-63 of Preparative Example 1.

MS: $[M+H]^+=1027$

Preparative Example 8

Synthesis of Compound of the Following Formula 1-155

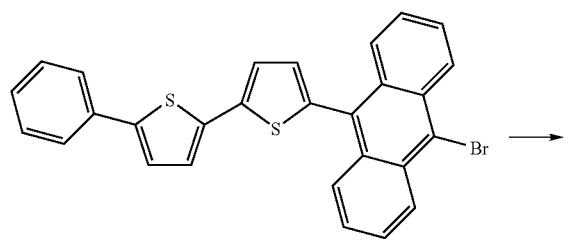

[Formula 8-D]

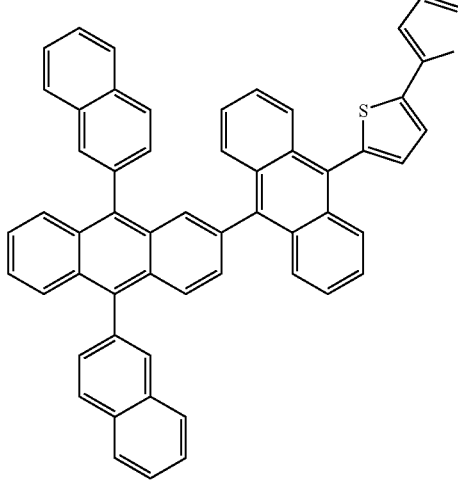

[Formula 1-155]

A compound of the formula 1-155 was prepared in the same manner as in the method for preparation of the compound of the formula 1-63 of Preparative Example 1, except that a compound of the formula 8-D was used instead of the compound of the formula 1-A and a compound of the formula 3-C in the method for preparation of the compound of the formula 1-63 of Preparative Example 1.

MS: $[M+H]^+=847$

Preparative Example 9

1) Synthesis of Compound of the Following Formula 9-A

[Formula 9-A]

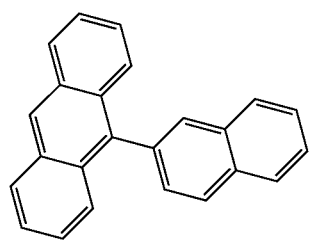

9-Bromoanthracene (5 g, 19.4 mmol) and 2-naphthylboronic acid (3.5 g, 20.3 mmol) were added to and dissolved in THF (200 mL), and then a 2 M aqueous solution of potassium carbonate (150 mL) and tetrakis(triphenylphosphino)palladium (450 mg, 0.39 mmol) was added to the solution, and then the mixture was stirred under heating for 4 hours. The mixture was cooled to normal temperature, the aqueous phase was removed. The resultant was dried over anhydrous magnesium sulfate and filtered. The residue obtained by removing the solvent was purified by column chromatography using hexane to prepare a compound of the formula 9-A (5 g, yield 85%).

MS: $[M+H]^+=305$

2) Synthesis of Compound of the Following Formula 9-B

[Formula 9-B]

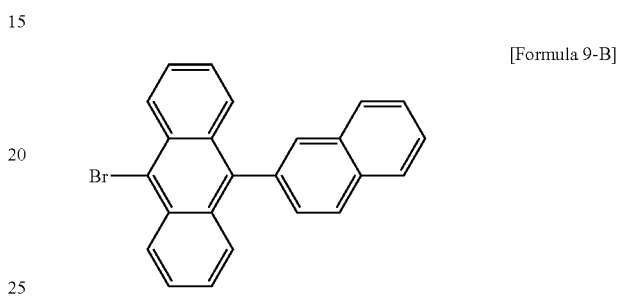

The compound of the formula 9-A (5 g, 16.4 mmol) was added to dimethylformamide (160 mL), and N-bromosuccinimide (2.9 g, 16.4 mmol) was slowly added thereto. The mixture was stirred for 1 hour at normal temperature. The resulting precipitate was filtered to prepare a compound of the formula 9-B (6 g, yield 95%).

MS: $[M+H]^+=383$

3) Synthesis of Compound of the Following Formula 1-112

[Formula 1-112]

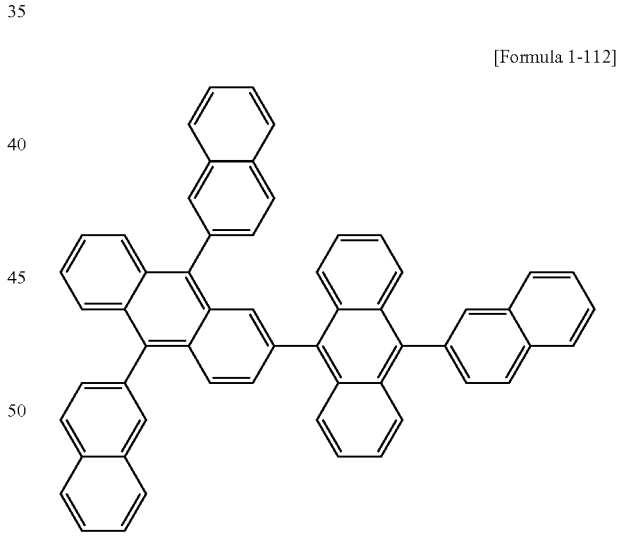

The compound of the formula 9-B (6 g, 15.7 mmol) and the compound of the formula 1-A (9.6 g, 17.2 mmol) were completely dissolved in tetrahydrofuran (150 mL), and then a 2 M aqueous solution of potassium carbonate (150 mL) was added to the solution. To the resultant, tetrakis(triphenylphosphino) palladium (398 mg, 0.34 mmol) was added, and then the mixture was stirred under heating for 5 hours. The mixture was cooled to normal temperature, and the resulting solid was filtered, dried, and recrystallized from THF/EtOH to prepare a compound of the formula 1-112 (8.1 g, yield 70%).

MS: $[M+H]^+=733$

UV ($2\times10^{-5}$M toluene solution): $\lambda_{max}$ 400, 382 nm

PL ($2\times10^{-5}$M toluene solution): $\lambda_{max}$ 462 nm

Preparative Example 10

1) Synthesis of Compound of the Following Formula 10-A

[Formula 10-A]

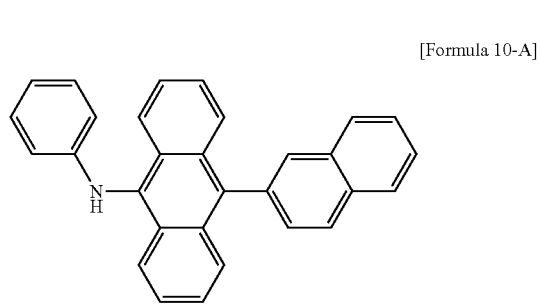

The compound of the formula 9-B (5 g, 13.0 mmol) and aniline (18 mL, 19.6 mmol) were completely dissolved in toluene (150 mL), Na(t-BuO) (3.1 g, 32.6 mmol) was added to the solution, and then bis(dibenzylidineacetone)palladium (Pd(dba)$_2$, 150 mg, 0.26 mmol) and tri(t-butyl)phosphine (P(t-Bu)$_3$ 50 wt % toluene solution, 0.12 mL, 0.26 mmol) were further added thereto. The mixture was stirred under heating for 5 hours. The mixture was cooled to normal temperature, and the aqueous phase was removed, and the resultant was dried over anhydrous magnesium sulfate, concentrated under reduced pressure, and purified by column chromatography using tetrahydrofuran:hexane=1:4 to prepare a compound of the formula 10-A (5.1 g, yield 99%).

MS: $[M]^+=395$

2) Synthesis of Compound of the Following Formula 1-164

[Formula 1-164]

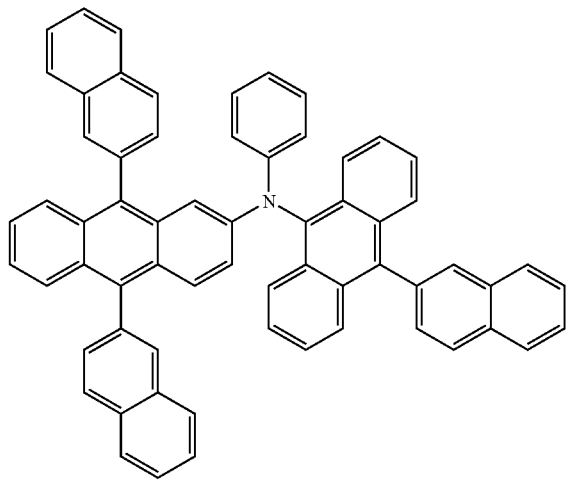

A compound 1-164 (4.3 g, yield 67%) was prepared in the same manner as in the method for preparation of the compound 10-A, using the compound 10-A (3.1 g, 7.8 mmol) and the 2-bromo-9,10-dinaphthylanthracene compound (4.1 g, 8.0 mmol).

MS: $[M]^+=823$

UV ($2\times10^{-5}$M toluene solution): $\lambda_{max}$ 438, 491 nm

PL ($2\times10^{-5}$M toluene solution): $\lambda_{max}$ 526 nm

Preparative Example 11

1) Synthesis of Compound of the Following Formula 11-A

[Formula 11-A]

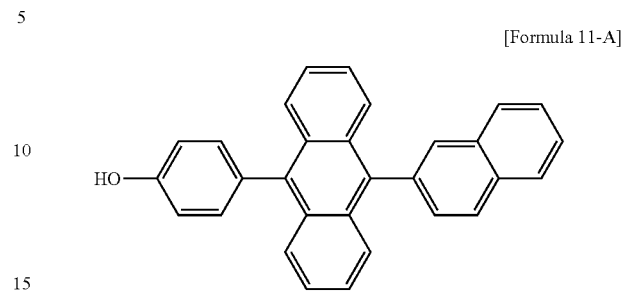

A compound 11-A (3.5 g, yield 88%) was prepared in the same manner as in the method for preparation of the compound 9-A of Preparative Example 9, except that a compound 9-B (3.8 g, 10 mmol) was used instead of 9-bromoanthracene, and 6-hydroxy-2-phenylboronic acid (1.5 g, 12 mmol) was used instead of 2-naphthylboronic acid in the method for preparation of the compound 9-A of Preparative Example 9.

MS: $[M+H]^+=397$

2) Synthesis of Compound of the Following Formula 11-B

[Formula 11-B]

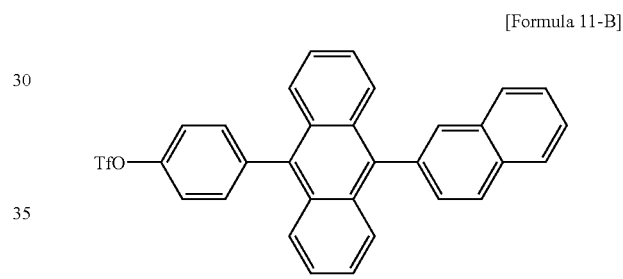

To the compound 11-A (3.5 g, 8.8 mmol), CH$_2$Cl$_2$ (60 mL) was added, and the mixture was stirred while slowly adding triethylamine (0.9 g, 8.8 mmol), and a trifluoroacetic acid anhydride (2.0 g, 9.7 mmol) dropwise. The mixture was stirred at normal temperature for 2 hours, and water and CH$_2$Cl$_2$ were added to separate the organic layer. The organic extract was dried over anhydrous magnesium sulfate, concentrated under reduced pressure, and purified using CH$_2$Cl$_2$/EtOH to prepare a compound 11-B (3.9 g, yield 90%).

MS: $[M+H]^+=493$

3) Synthesis of Compound of the Following Formula 1-109

[Formula 1-109]

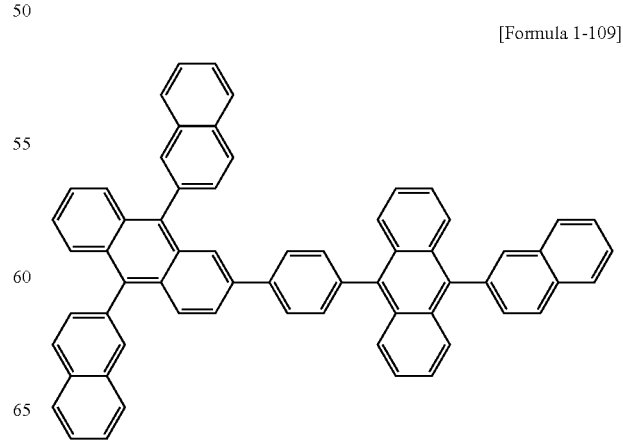

The compound of the formula 11-B (3.8 g, 7.7 mmol) and the compound of the formula 1-A (4.8 g, 8.6 mmol) were completely dissolved in tetrahydrofuran (150 mL), and then a 2 M aqueous solution of potassium carbonate (150 mL) was added to the solution. To the resultant, tetrakis(triphenylphosphino)palladium (180 mg, 0.16 mmol) was added, and then the mixture was stirred under heating for 5 hours. The mixture was cooled to normal temperature, and the resulting solid was filtered, and then dried to prepare a compound 1-109 (4.2 g, yield 67%).

MS: $[M+H]^+ = 809$

UV ($2 \times 10^{-5}$ M toluene solution): $\lambda_{max}$ 298, 389, 400 nm

Preparative Example 12

Synthesis of Compound of the Following Formula 1-110

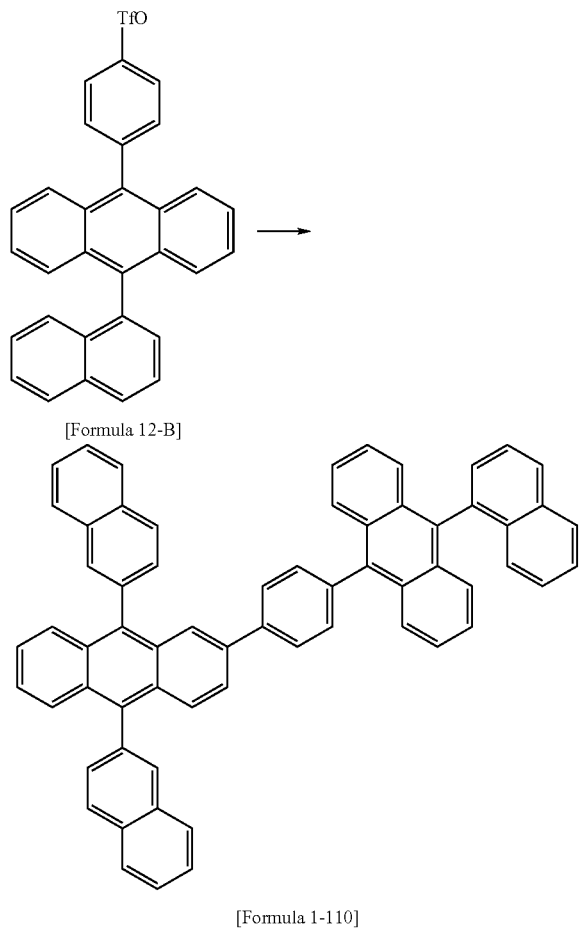

[Formula 12-B]

[Formula 1-110]

A compound 1-110 was prepared in the same manner as in the method for preparation of the compound of the formula 1-10 of Preparative Example 3, except that a compound of the formula 12-B was used instead of the compound of the formula 3-C for the compound of the formula 1-A in the method for preparation of the compound of the formula 1-10 of 4) Preparative Example 3.

MS: $[M+H]^+ = 809$

Preparative Example 13

Synthesis of Compound of the Following Formula 1-117

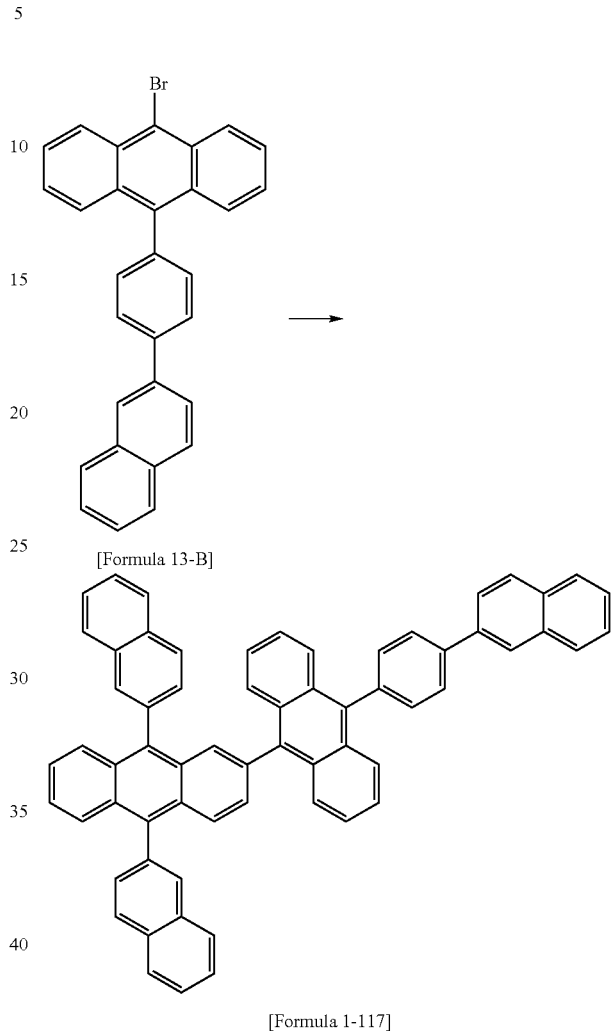

[Formula 13-B]

[Formula 1-117]

A compound 1-117 was prepared in the same manner as in the method for preparation of the compound of the formula 1-10 of Preparative Example 3, except that a compound of the formula 13-B was used instead of the compound of the formula 3-C for the compound of the formula 1-A in the method for preparation of the compound of the formula 1-10 of 4) Preparative Example 3.

MS: $[M+H]^+ = 809$

UV ($2 \times 10^{-5}$ M toluene solution): $\lambda_{max}$ 380, 400 nm

Example 1

A glass substrate on which a thin film of ITO (indium tin oxide) was coated to a thickness of 1,500 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone, and methanol. The resultant product was dried, and then transported to a plasma washing machine. Using an oxygen plasma, the substrate was washed for 5 minutes and then transported to a vacuum depositing machine.

On the ITO transparent electrode thus prepared, hexanitrile hexaazatriphenylene (HAT) of the following formula was coated to thicknesses of 500 Å by thermal vacuum deposition to form a hole injecting layer.

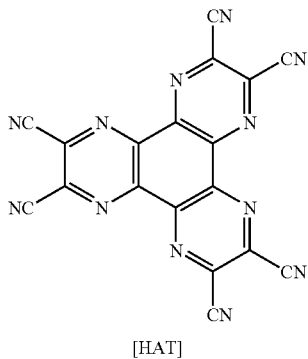

[HAT]

4,4'-Bis[N-(1-naphthyl)-N-phenylamino]biphenyl (NPB) (400 Å) of the following formula, which is a hole transporting material, was coated on the hole injecting layer by vacuum deposition, to form a hole transporting layer.

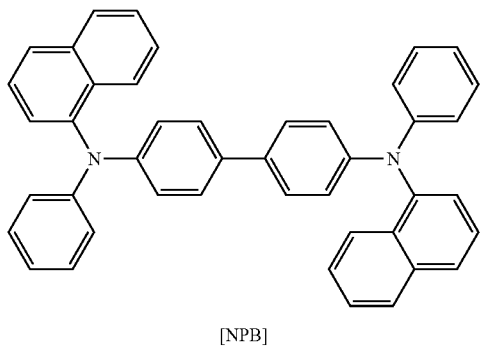

[NPB]

Then, $Alq_3$ (aluminum tris(8-hydroxyquinoline)) of the following formula was coated to a thickness of 300 Å on the hole transporting layer by vacuum deposition to form a light emitting layer.

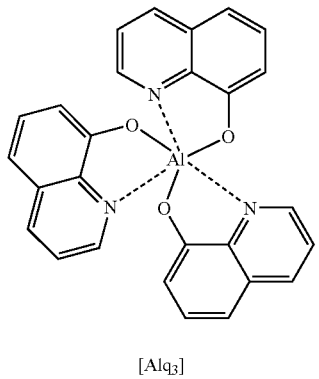

[Alq₃]

The compound of the formula 1-63 as prepared in Preparative Example 1 was coated to a thickness of 200 Å on the light emitting layer by vacuum deposition to form an electron injecting and transporting layer.

Lithium fluoride (LiF) and aluminum were sequentially deposited on the electron injecting and transporting layer to thicknesses of 12 Å and 2,000 Å respectively, to form a cathode.

In the above process, the deposition rate of the organic material was maintained at 0.4 to 0.7 Å/sec, and the deposition rate of lithium fluoride was maintained at 0.3 Å/sec, and the deposition rate of aluminum was maintained at 2 Å/sec, respectively. The degree of vacuum upon deposition was maintained at $2 \times 10^{-7}$ to $5 \times 10^{-8}$ torr.

When a forward electric field of 7.7 V was applied to the organic light emitting device as prepared above, green light emission was observed with x=0.29 and y=0.57 based on the 1931 CIE color coordinate at a current density of 50 mA/. When a forward electric field of 10.8 V was applied, green light emission of 5.83 cd/A was observed at a current density of 100 mA/.

Example 2

On the ITO electrode as prepared as in Example 1, hexanitrile hexaazatriphenylene (500 Å), 4,4'-bis[N-(1-naphthyl)-N-phenylamino]biphenyl (NPB) (400 Å), $Alq_3$ (300 Å), and the compound 1-10 (200 Å) were sequentially coated by thermal vacuum deposition, to form a hole injecting layer, a hole transporting layer, a light emitting layer, and an electron transporting layer in this order.

Lithium fluoride (LiF) and aluminum were sequentially deposited on the electron transporting layer to thicknesses of 12 Å and 2,000 Å respectively, to form a cathode, thereby preparing an organic light emitting device.

In the above process, the deposition rate of the organic material was maintained at 0.4 to 0.7 Å/sec, and the deposition rate of lithium fluoride was maintained at 0.3 Å/sec, and the deposition rate of aluminum was maintained at 2 Å/sec, respectively. The degree of vacuum upon deposition was maintained at $2 \times 10^{-7}$ to $5 \times 10^{-8}$ torr.

When a forward electric field of 6.2 V was applied to the organic light emitting device as prepared above, green light emission was observed with x=0.31 and y=0.55 based on the 1931 CIE color coordinate at a current density of 50 mA/. When a forward electric field of 8.6 V was applied, green light emission of 6.7 cd/A was observed at a current density of 100 mA/.

Example 3

On the ITO electrode as prepared as in Example 1, hexanitrile hexaazatriphenylene (500 Å), 4,4'-bis[N-(1-naphthyl)-N-phenylamino]biphenyl (NPB) (400 Å), and the compound 1-11 (400) were sequentially coated by thermal vacuum deposition, to form a hole injecting layer, a hole transporting layer, and a light emitting and electron transporting layer in this order.

Lithium fluoride (LiF) and aluminum were sequentially deposited on the light emitting and electron transporting layer to thicknesses of 12 Å and 2,000 Å respectively, to form a cathode, thereby preparing an organic light emitting device.

In the above process, the deposition rate of the organic material was maintained at 0.4 to 0.7 Å/sec, and the deposition rate of lithium fluoride was maintained at 0.3 Å/sec, and the deposition rate of aluminum was maintained at 2 Å/sec, respectively. The degree of vacuum upon deposition was maintained at $2 \times 10^{-7}$ to $5 \times 10^{-8}$ torr.

When a forward electric field of 6.5 V was applied to the organic light emitting device as prepared above, blue light emission was observed with x=0.15 and y=0.23 based on the 1931 CIE color coordinate at a current density of 50 mA/. When a forward electric field of 8.4 V was applied, blue light emission of 2.9 cd/A was observed at a current density of 100 mA/.

Example 4

On the ITO electrode as prepared as in Example 1, hexanitrile hexaazatriphenylene (500 Å), 4,4'-bis[N-(1-naphthyl)-N-phenylamino]biphenyl (NPB) (400 Å), the compound of the formula 1-112 (300 Å), Alq$_3$ (200 Å), lithium fluoride (LiF) (12 Å) were sequentially coated by thermal vacuum deposition, to form a hole injecting layer, a hole transporting layer, a light emitting layer, an electron transporting layer, and an electron injecting layer in this order. Aluminum was deposited thereon to a thickness of 2,000 Å to form a cathode, thereby preparing an organic light emitting device.

When a forward electric field of 6.7 V was applied to the organic light emitting device as prepared above, blue light emission was observed with x=0.14 and y=0.18 based on the 1931 CIE color coordinate at a current density of 50 mA/. When a forward electric field of 8.5 V was applied, blue light emission of 5.1 cd/A was observed at a current density of 100 mA/.

Example 5

On the ITO electrode as prepared as in Example 1, hexanitrile hexaazatriphenylene (500 Å), 4,4'-bis[N-(1-naphthyl)-N-phenylamino]biphenyl (NPB) (400 Å), the compound of the formula 1-109 (300 Å), Alq$_3$ (200 Å), lithium fluoride (LiF) (12) were sequentially coated by thermal vacuum deposition, to form a hole injecting layer, a hole transporting layer, a light emitting layer, an electron transporting layer, and an electron injecting layer in this order. Aluminum was deposited thereon to a thickness of 2,000 Å to form a cathode, thereby preparing an organic light emitting device.

When a forward electric field of 6.2 V was applied to the organic light emitting device as prepared above, blue light emission was observed with x=0.14 and y=0.21 based on the 1931 CIE color coordinate at a current density of 50 mA/. When a forward electric field of 8.3 V was applied, blue light emission of 4.2 cd/A was observed at a current density of 100 mA/.

What is claimed is:

1. A compound which is selected from the compounds of the following formulae:

[Formula 1-1]

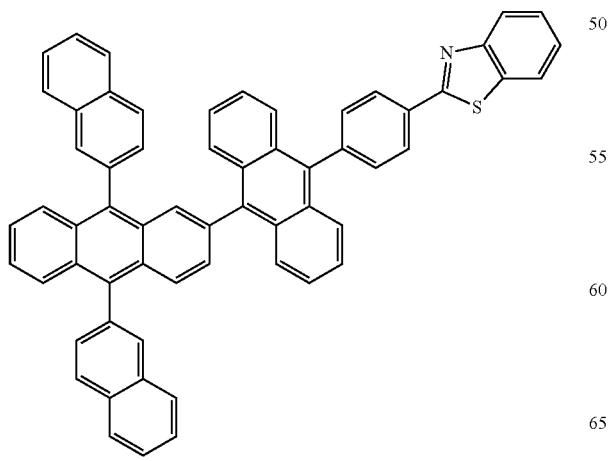

[Formula 1-2]

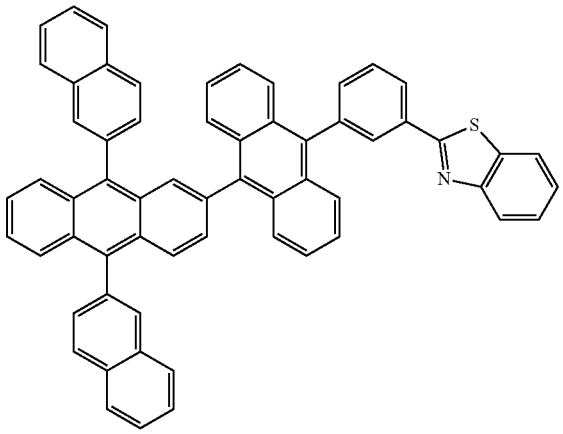

[Formula 1-3]

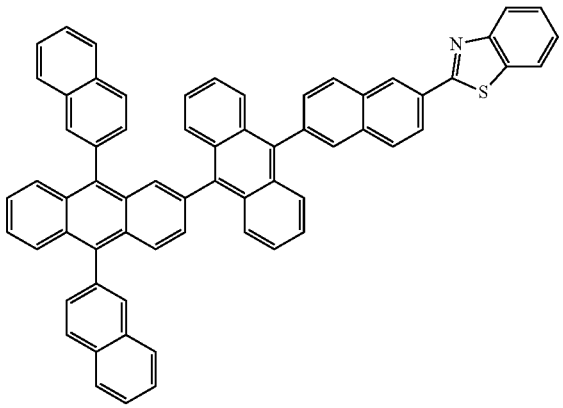

[Formula 1-4]

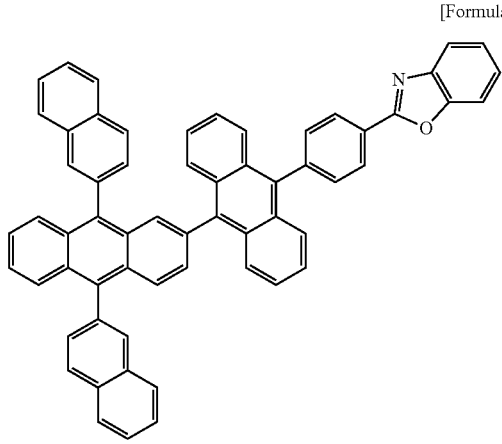

[Formula 1-5]
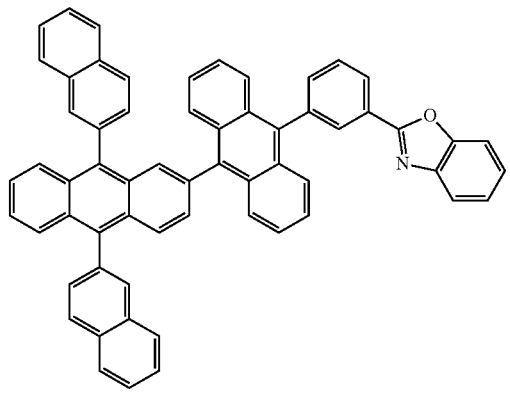
[Formula 1-6]
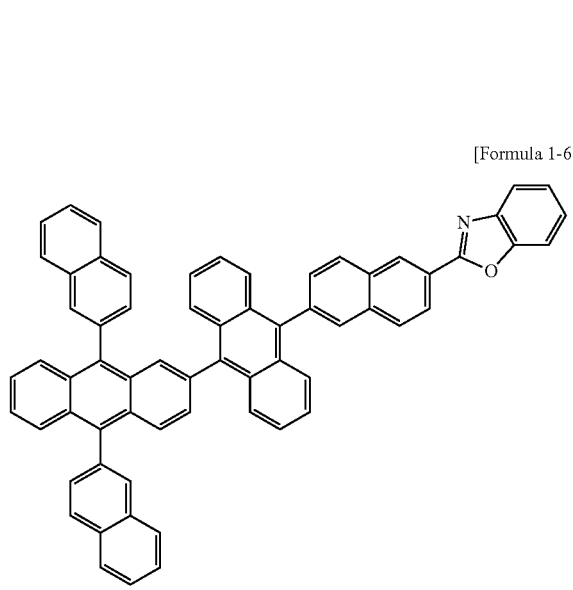
[Formula 1-7]
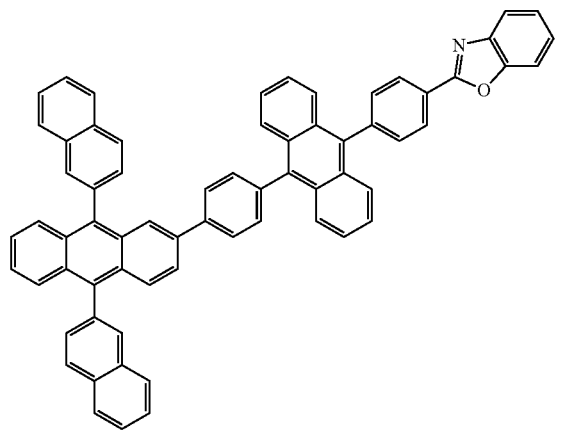
[Formula 1-8]
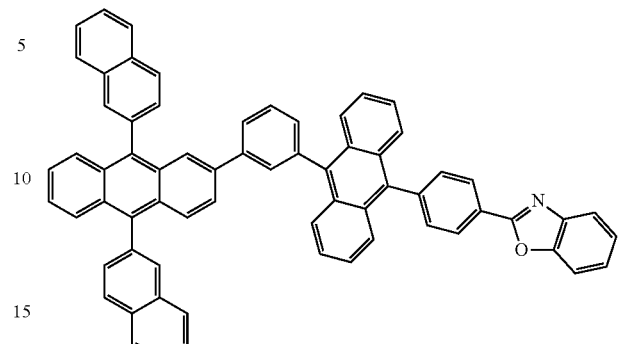
[Formula 1-9]
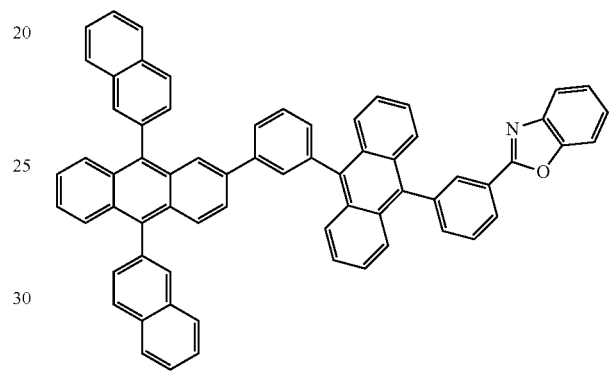
[Formula 1-10]
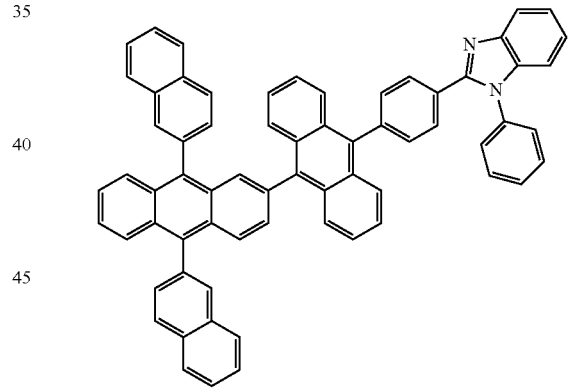
[Formula 1-11]
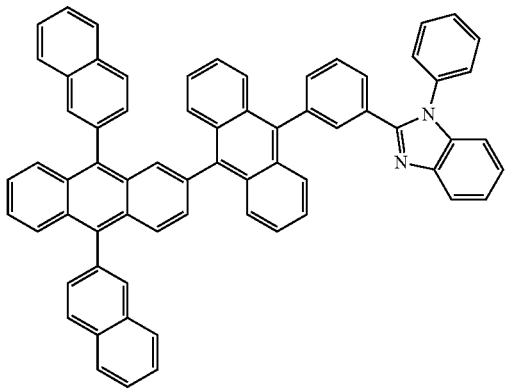

[Formula 1-12]
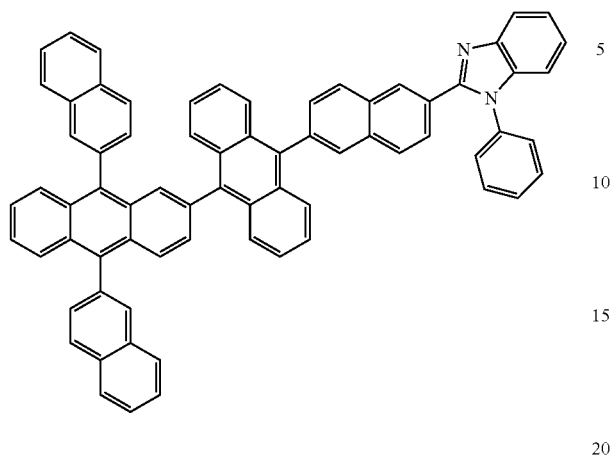
[Formula 1-15]
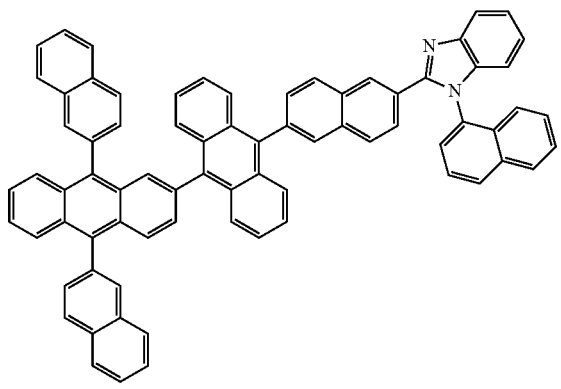
[Formula 1-13]
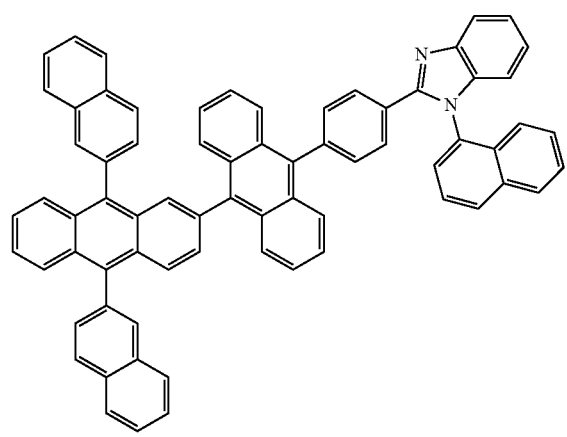
[Formula 1-16]
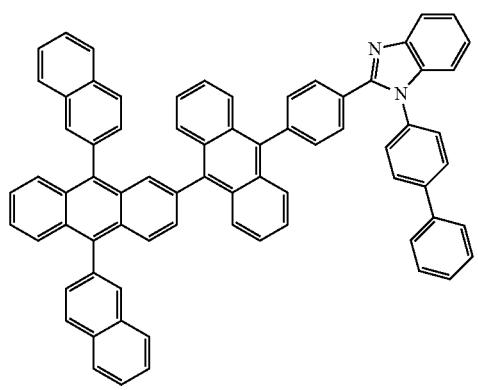
[Formula 1-14]
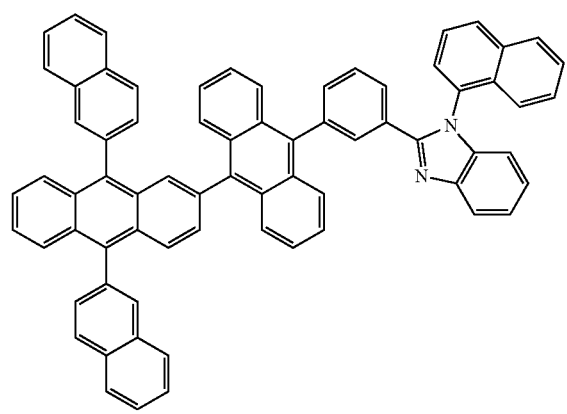
[Formula 1-17]
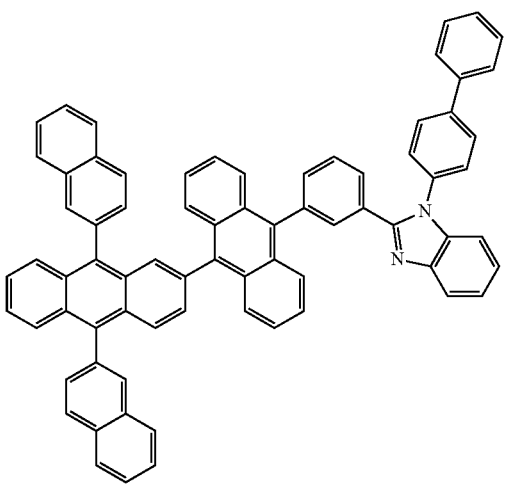

[Formula 1-18]
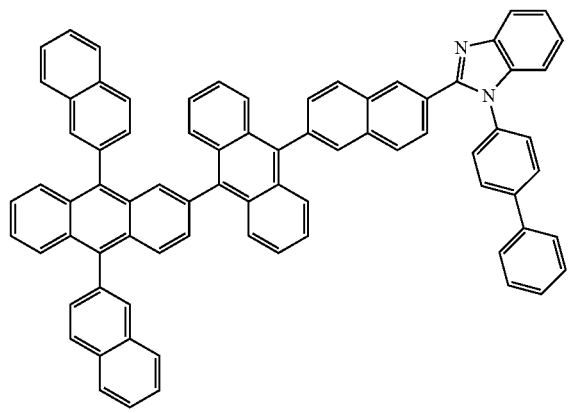
[Formula 1-19]
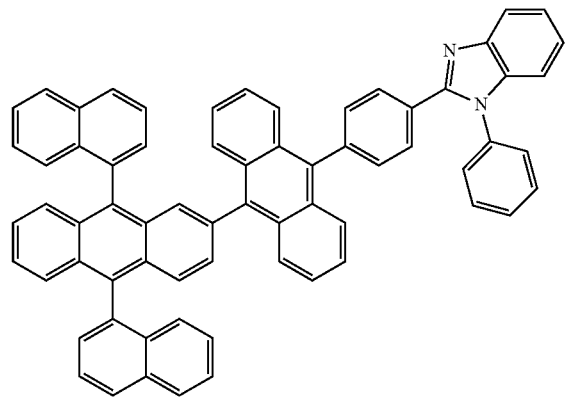
[Formula 1-20]
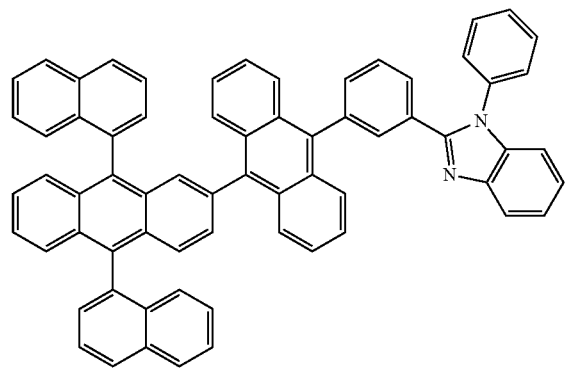
[Formula 1-21]
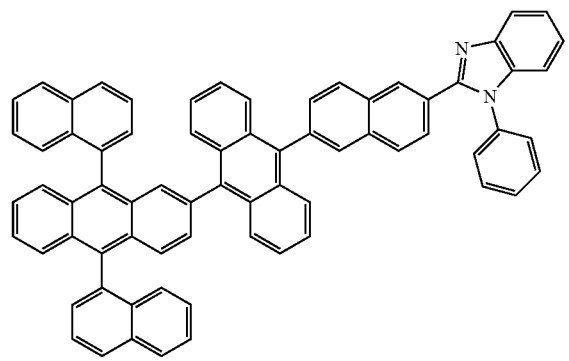
[Formula 1-22]
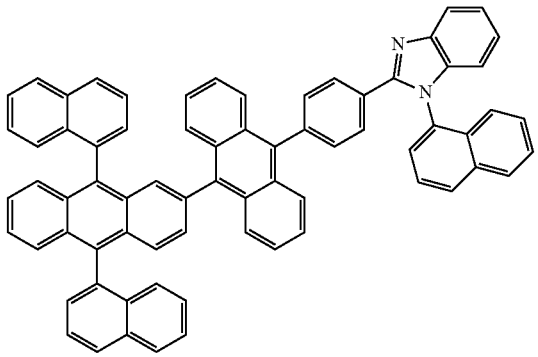
[Formula 1-23]
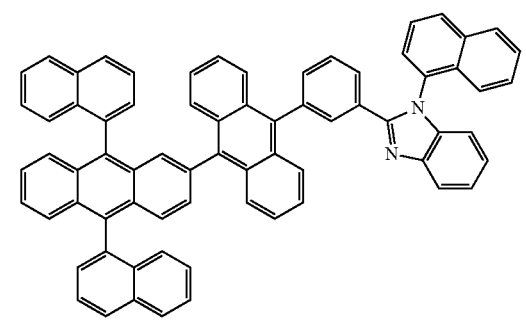
[Formula 1-24]
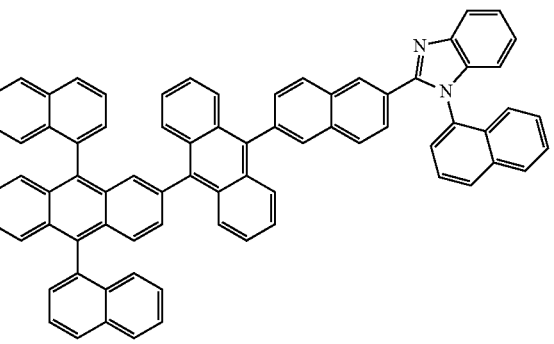
[Formula 1-25]
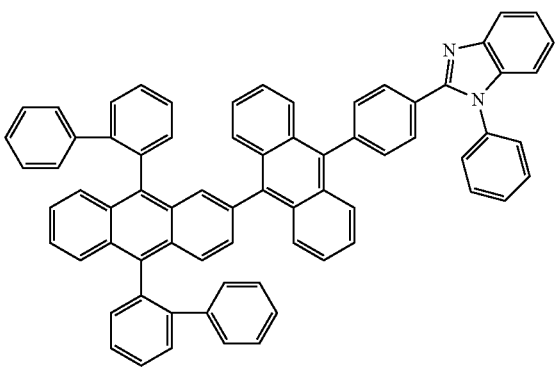

[Formula 1-26]
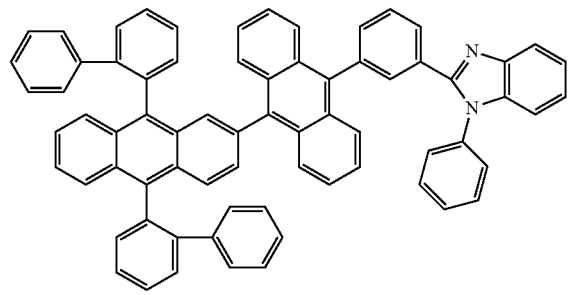
[Formula 1-27]
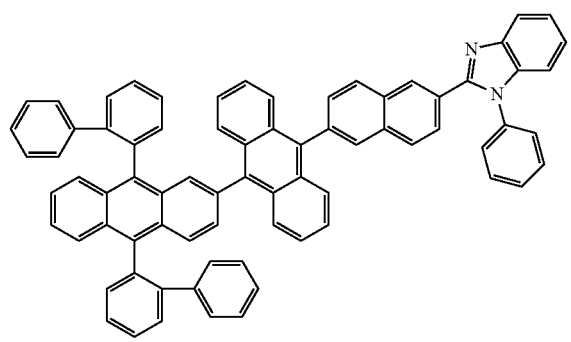
[Formula 1-28]
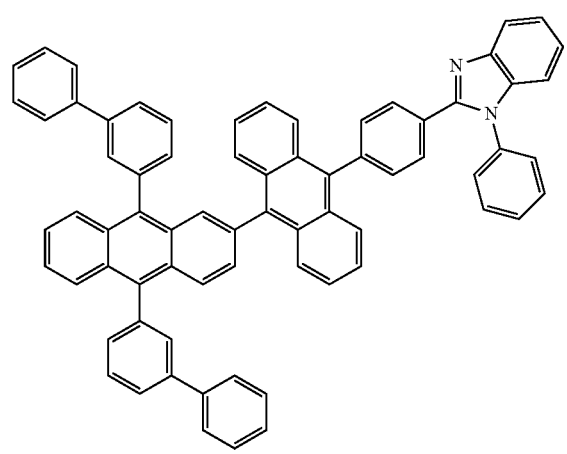
[Formula 1-29]
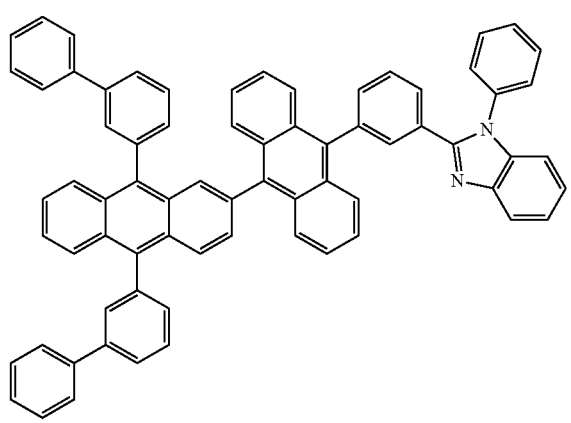
[Formula 1-30]
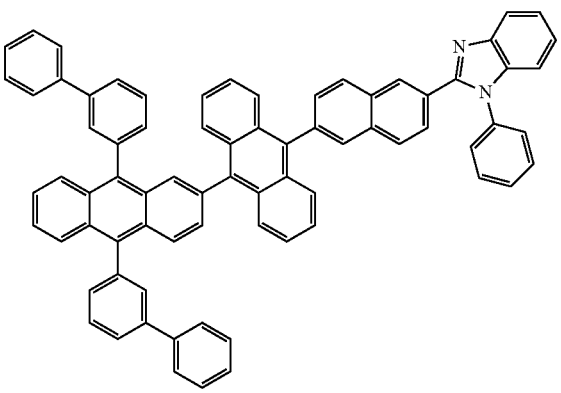
[Formula 1-31]
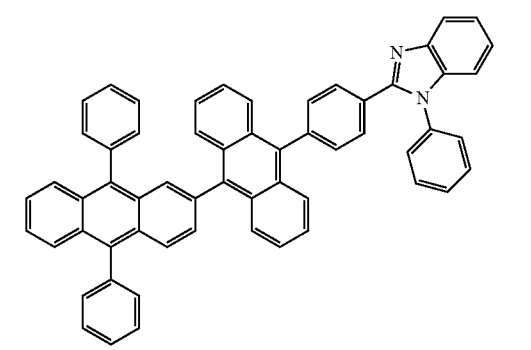
[Formula 1-32]
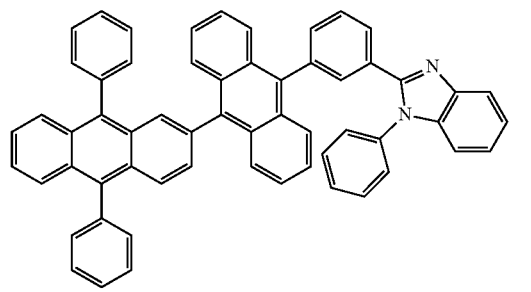
[Formula 1-33]
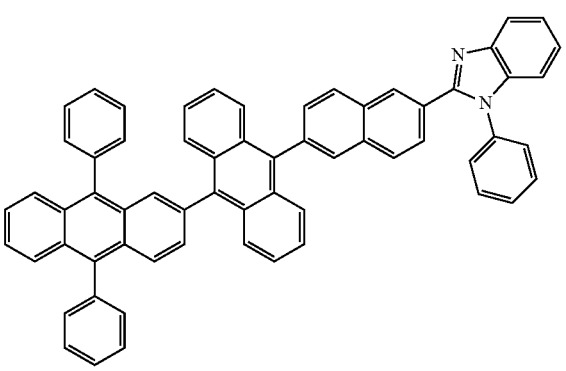

[Formula 1-34]
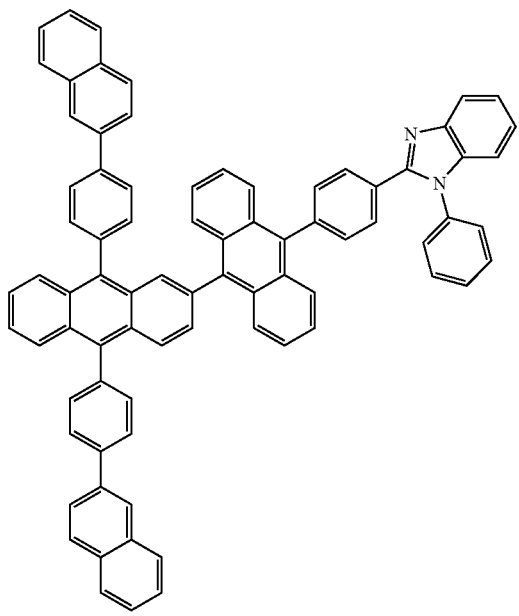
[Formula 1-36]
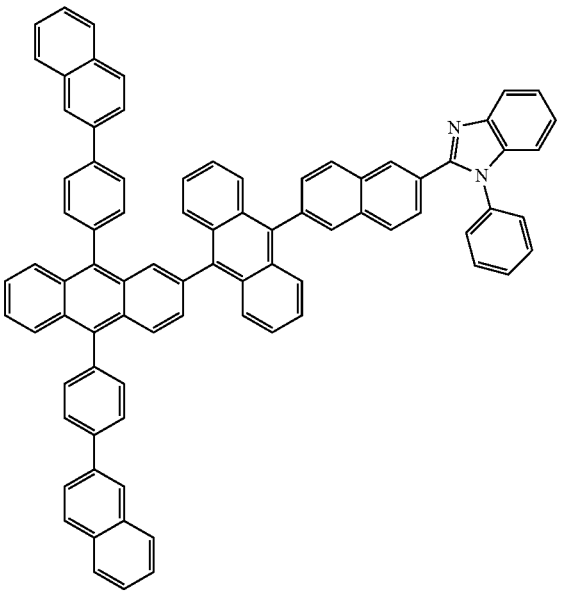
[Formula 1-35]
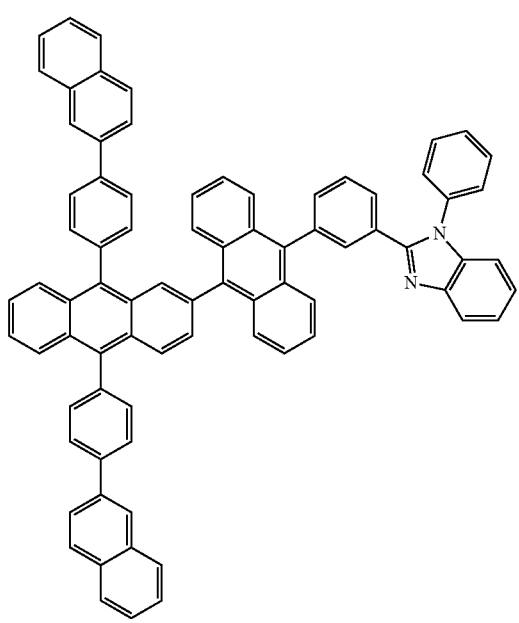
[Formula 1-37]
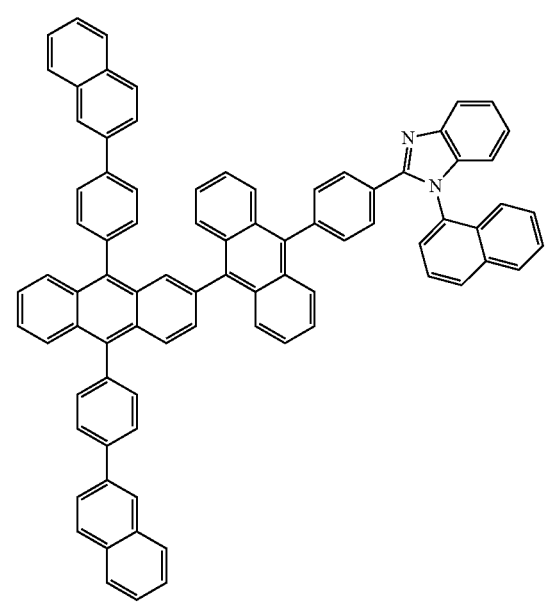

[Formula 1-38]
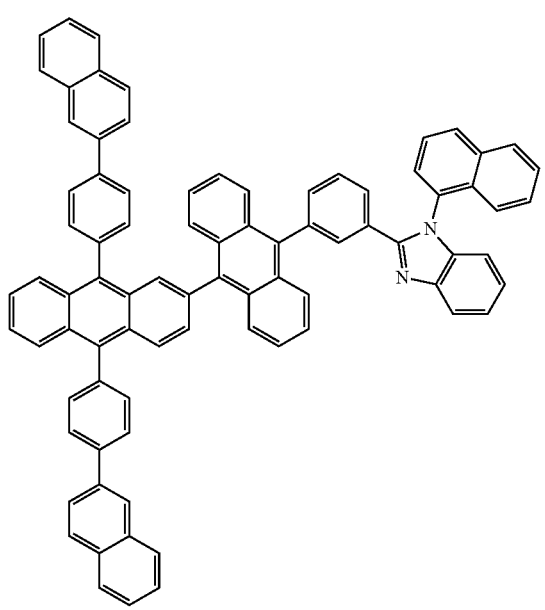
[Formula 1-39]
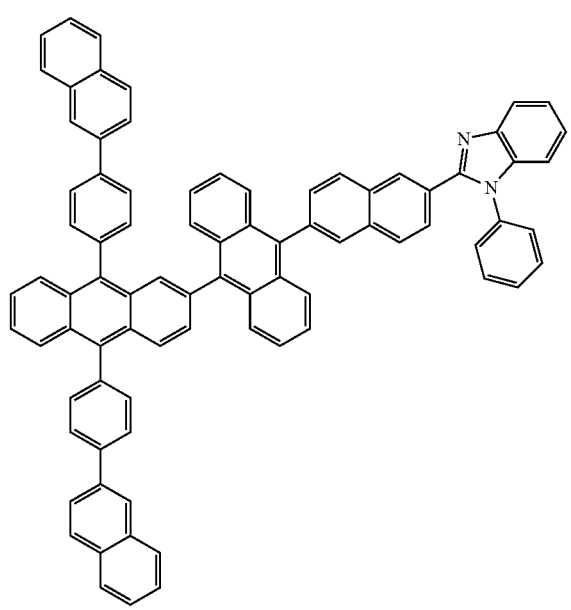
[Formula 1-40]
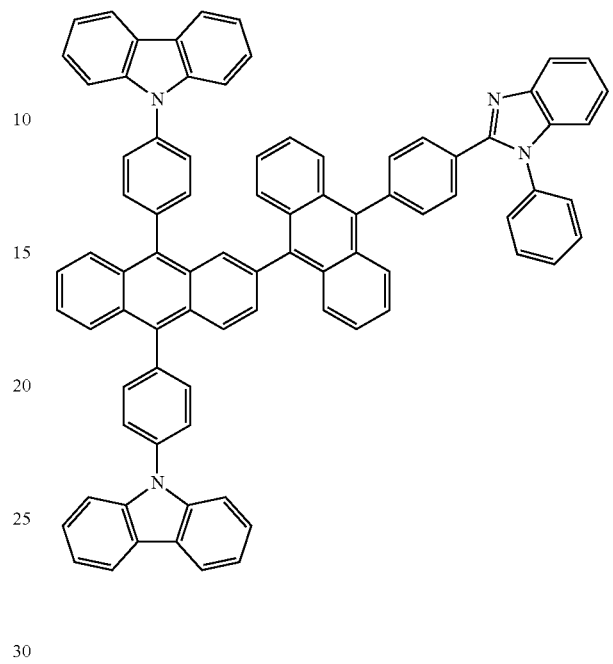
[Formula 1-41]

-continued
[Formula 1-42]
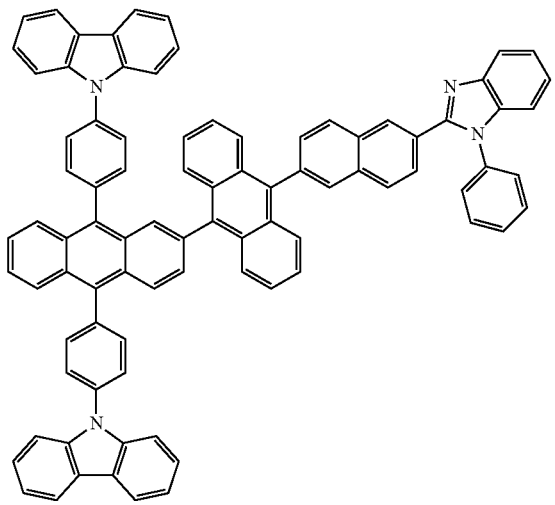
[Formula 1-43]
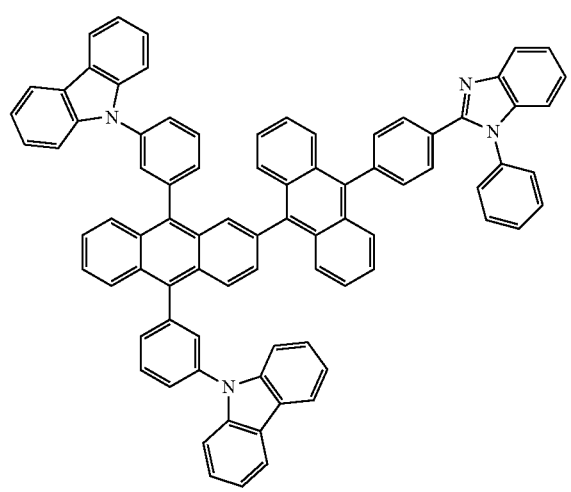
[Formula 1-44]
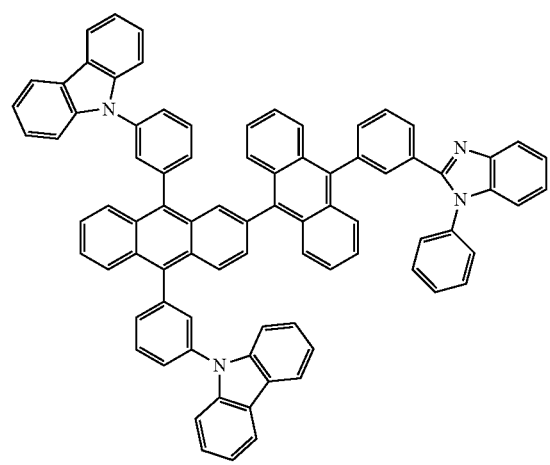
-continued
[Formula 1-45]
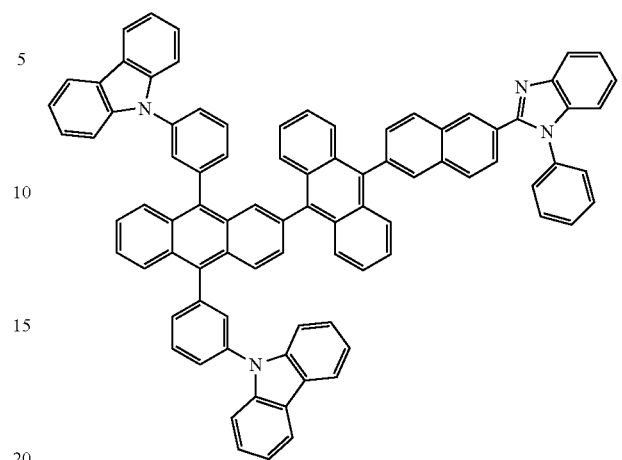
[Formula 1-46]
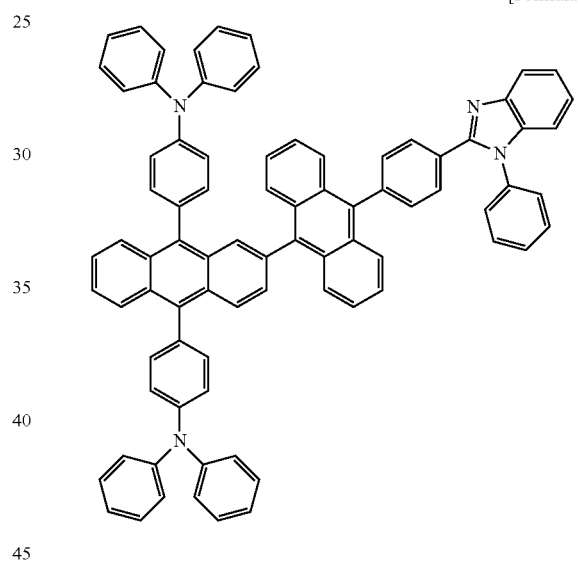
[Formula 1-47]
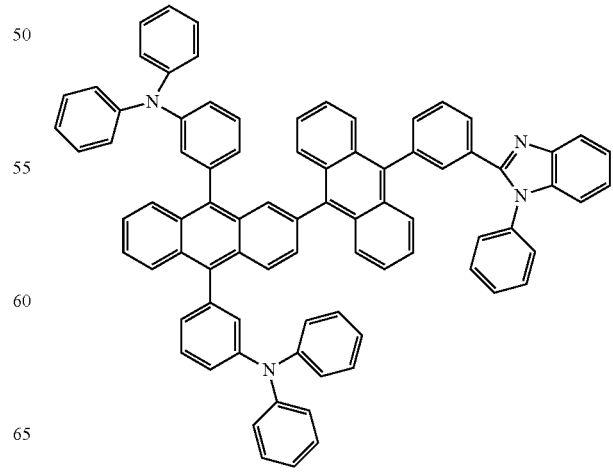

-continued
[Formula 1-48]
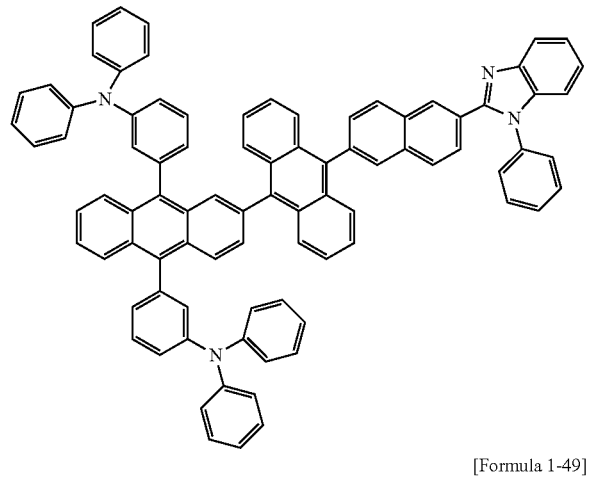
[Formula 1-49]
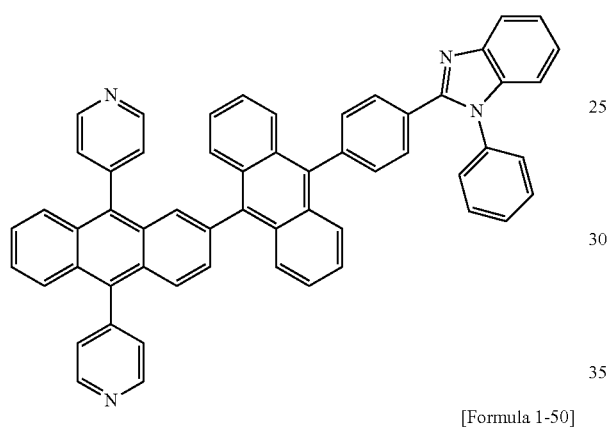
[Formula 1-50]
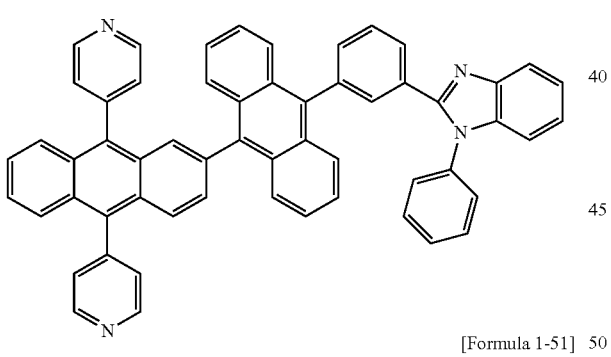
[Formula 1-51]
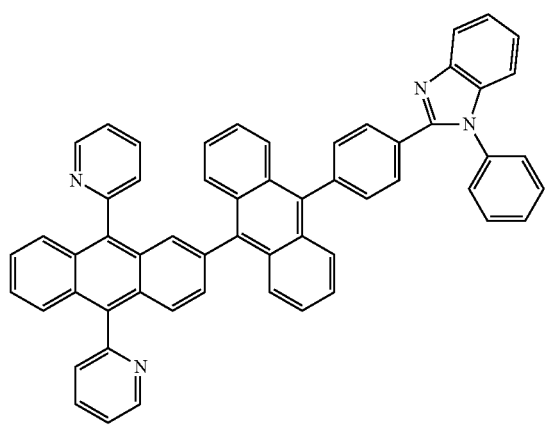
-continued
[Formula 1-52]
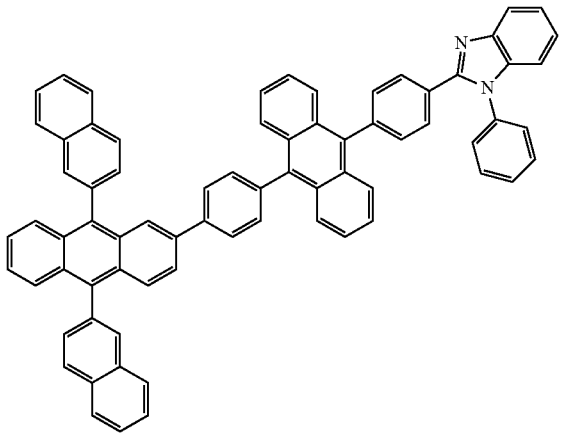
[Formula 1-53]
[Formula 1-54]
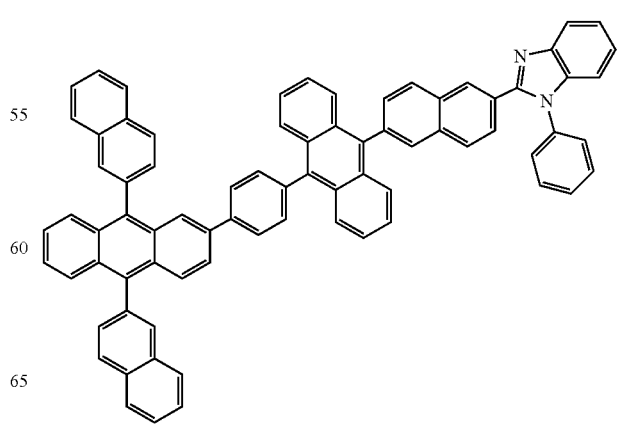

[Formula 1-55]
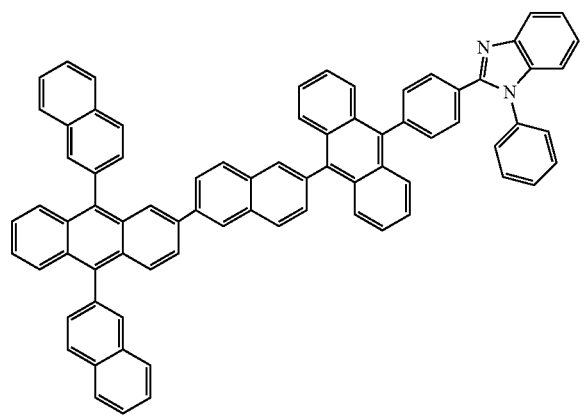
[Formula 1-58]
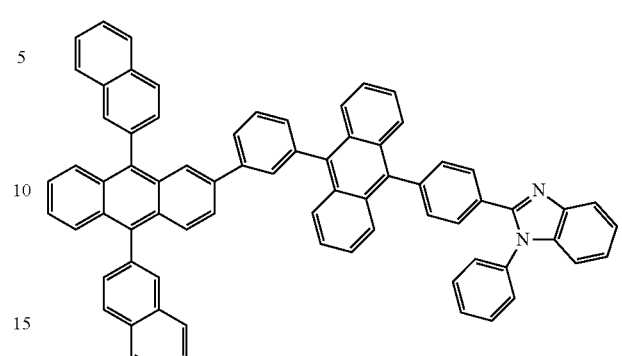
[Formula 1-56]
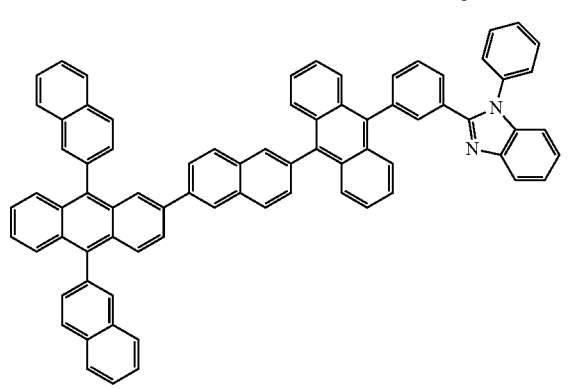
[Formula 1-59]
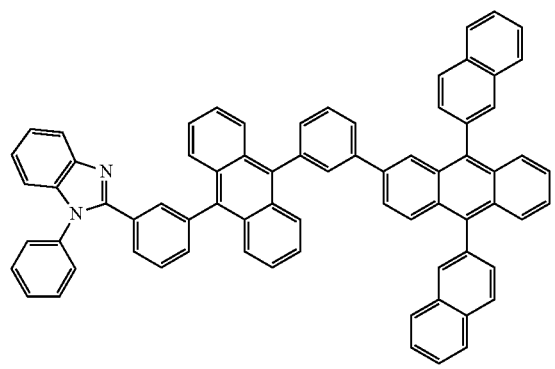
[Formula 1-57]
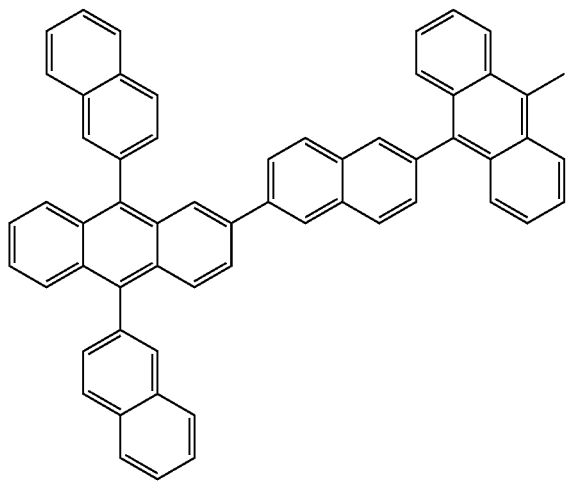
[Formula 1-60]
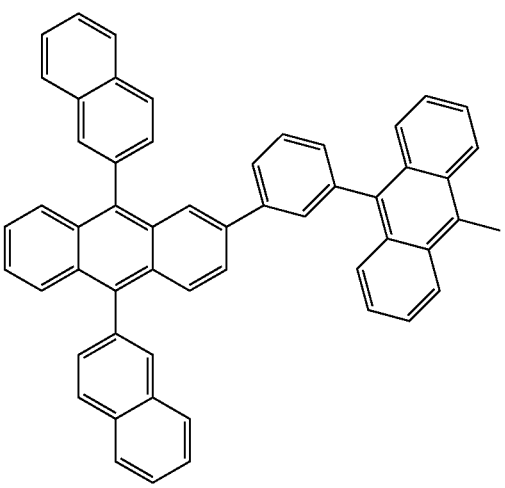
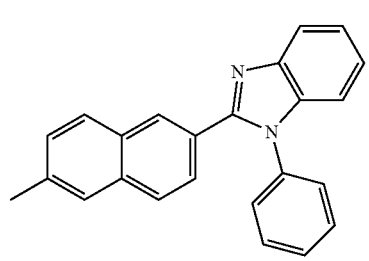
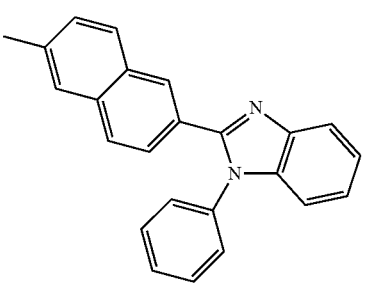

207
-continued
[Formula 1-61]
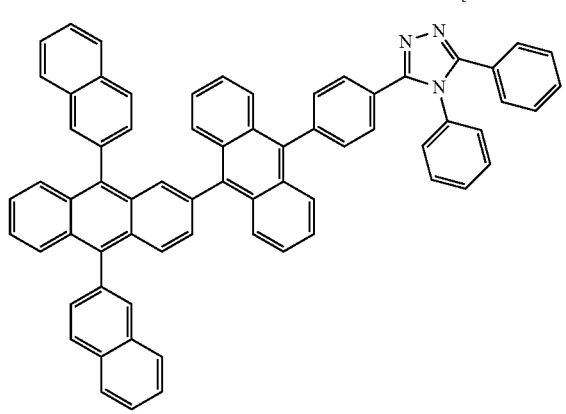
[Formula 1-62]
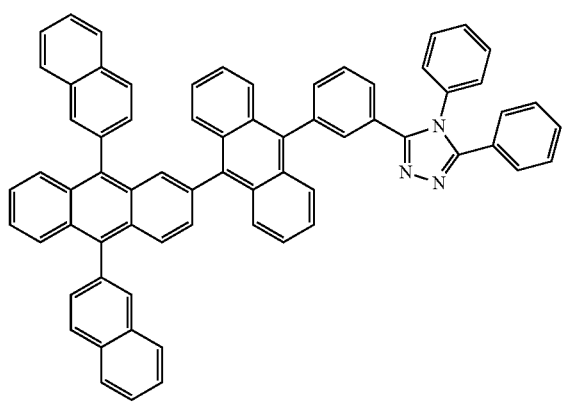
[Formula 1-63]
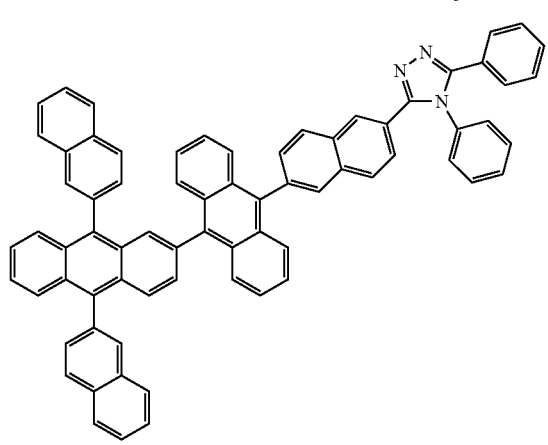
208
-continued
[Formula 1-64]
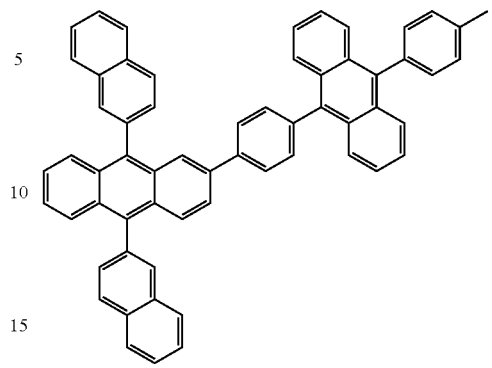
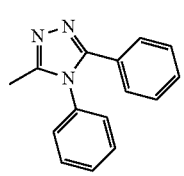
[Formula 1-65]
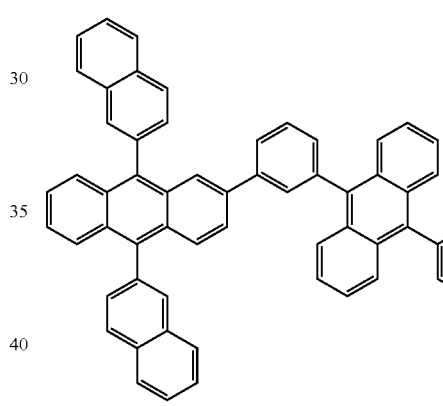
[Formula 1-66]
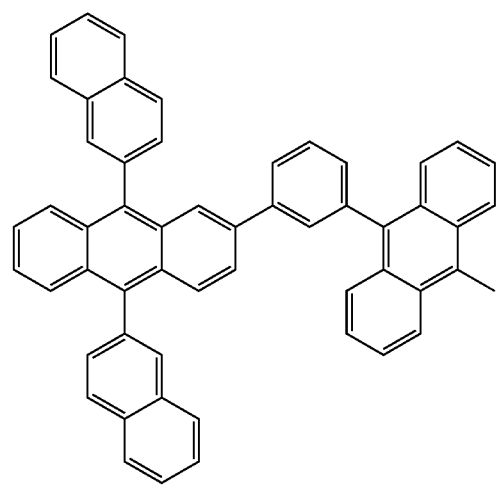

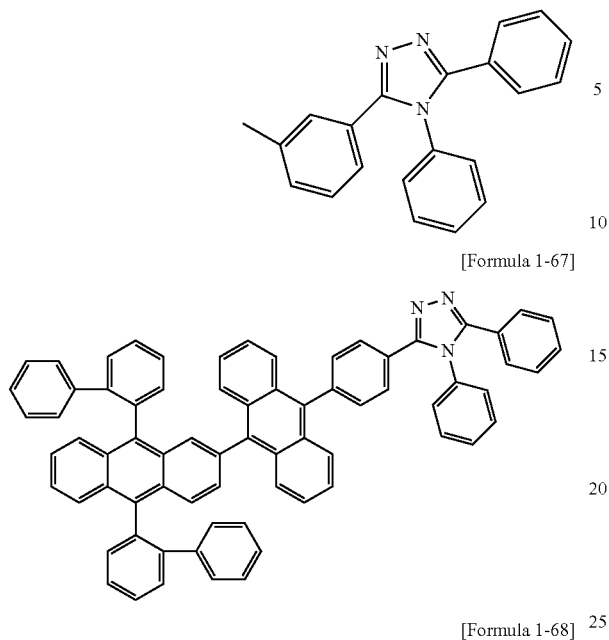
[Formula 1-67]
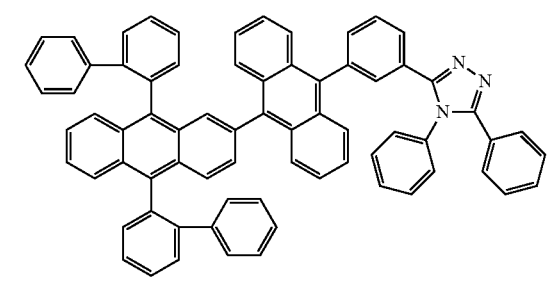
[Formula 1-68]
[Formula 1-69]
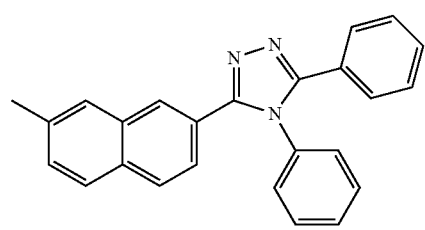
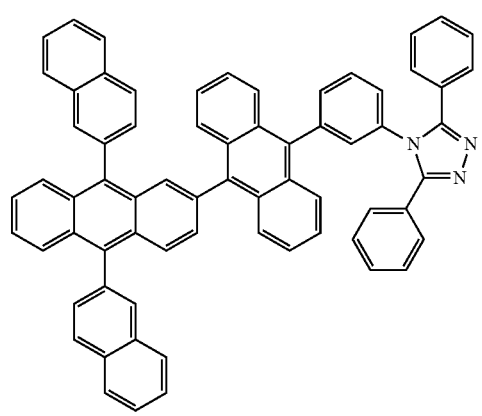
[Formula 1-70]
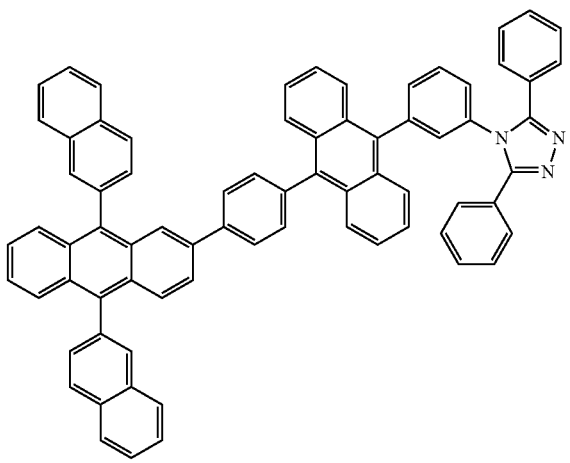
[Formula 1-71]
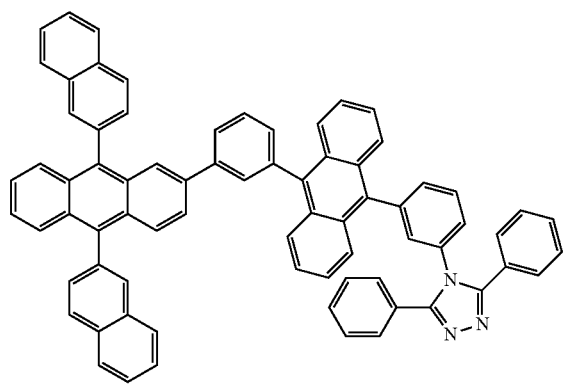
[Formula 1-72]

[Formula 1-73]
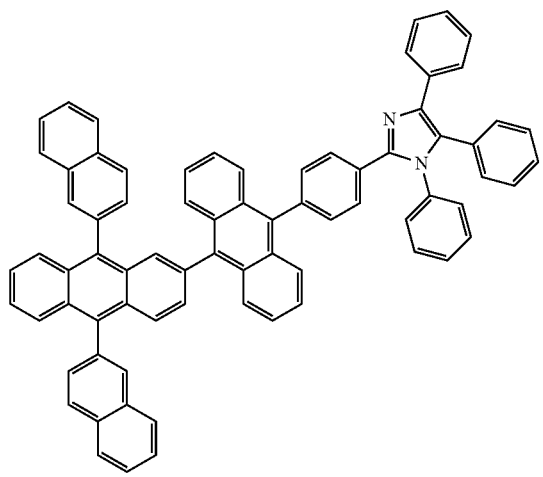
[Formula 1-74]
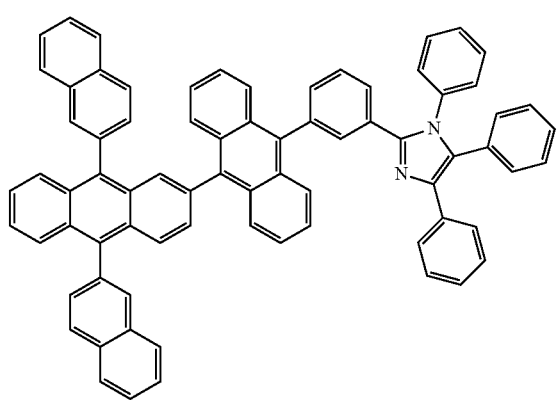
[Formula 1-75]
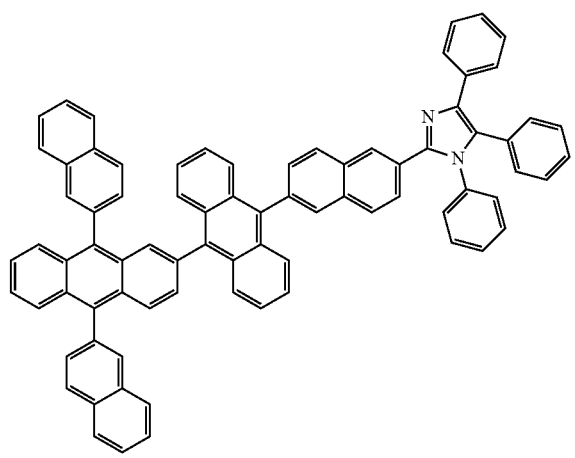
[Formula 1-76]
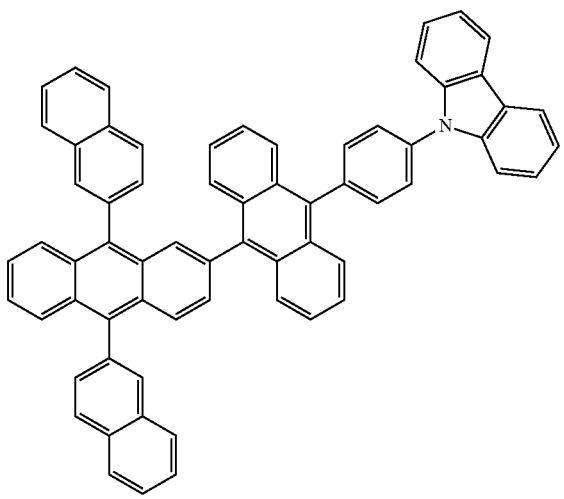
[Formula 1-77]
[Formula 1-78]
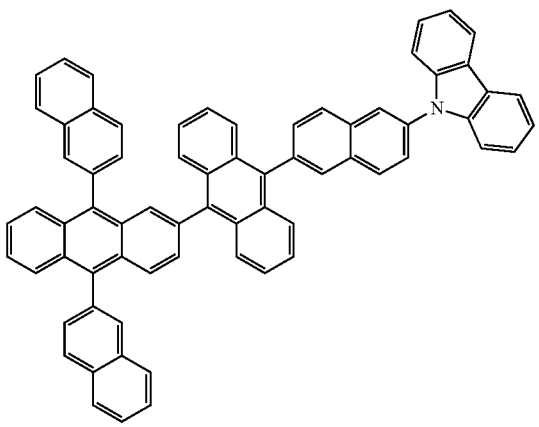

[Formula 1-79]
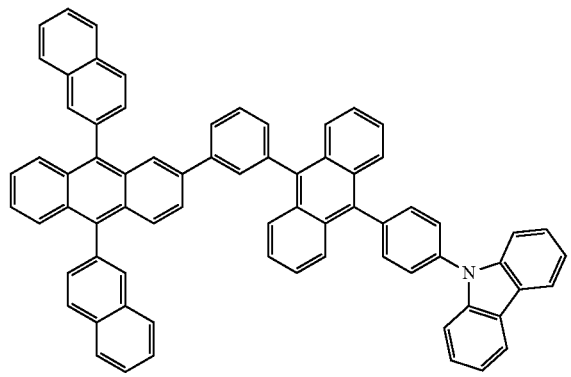
[Formula 1-80]
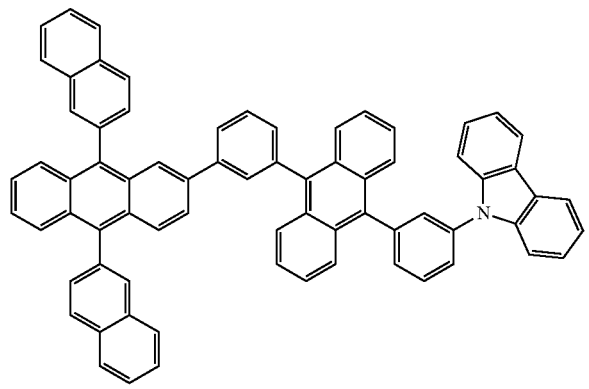
[Formula 1-81]
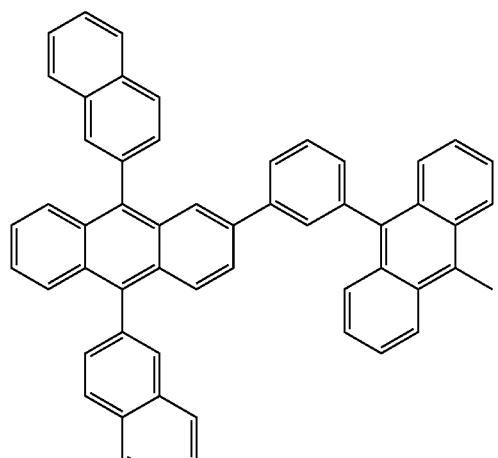
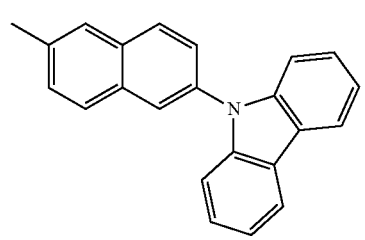
[Formula 1-82]
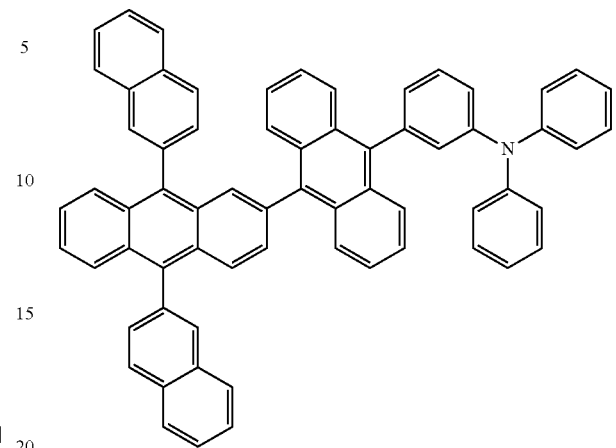
[Formula 1-83]
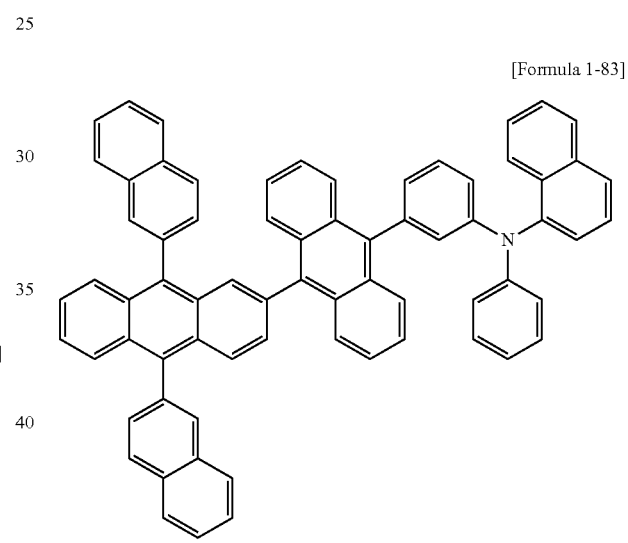
[Formula 1-84]
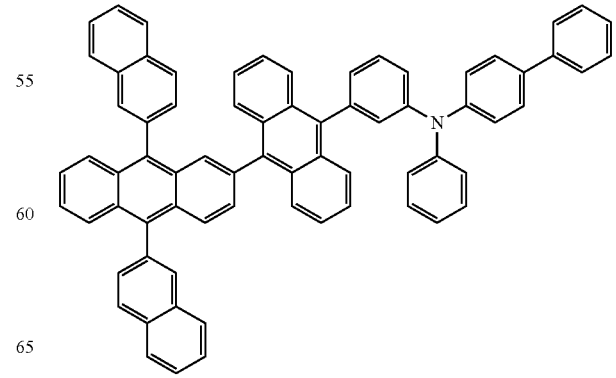

[Formula 1-85]
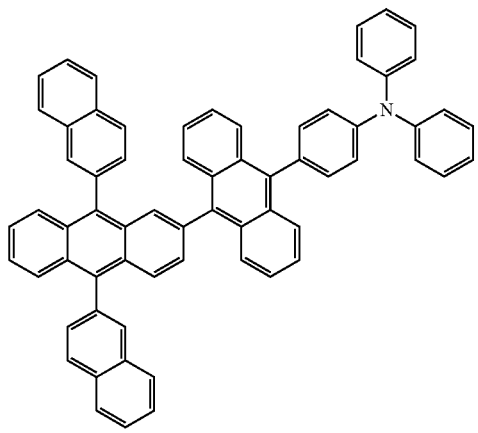
[Formula 1-86]
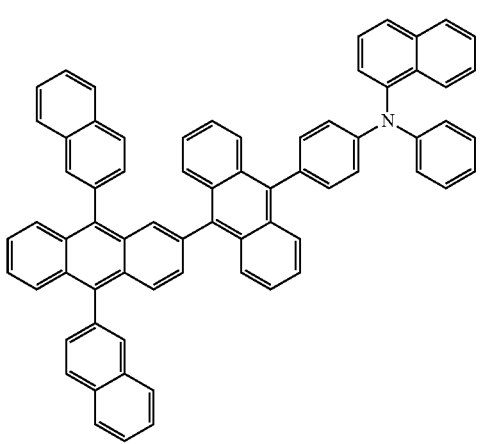
[Formula 1-87]
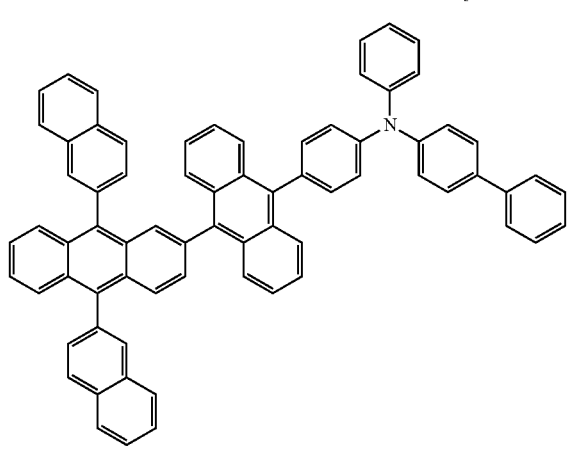
[Formula 1-88]
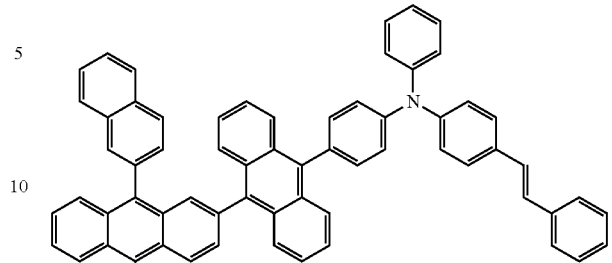
[Formula 1-89]
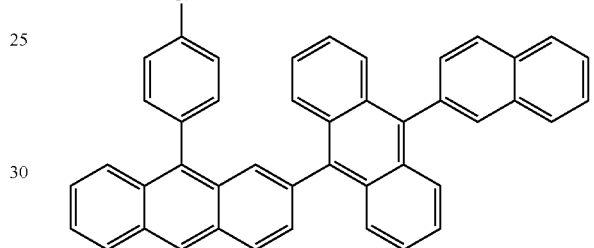
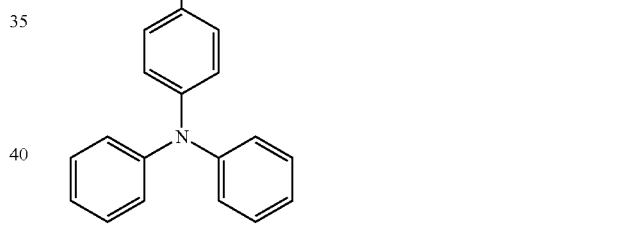
[Formula 1-90]
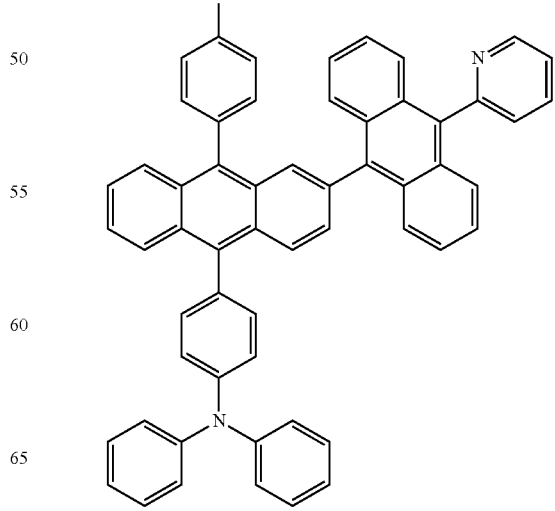

[Formula 1-91]
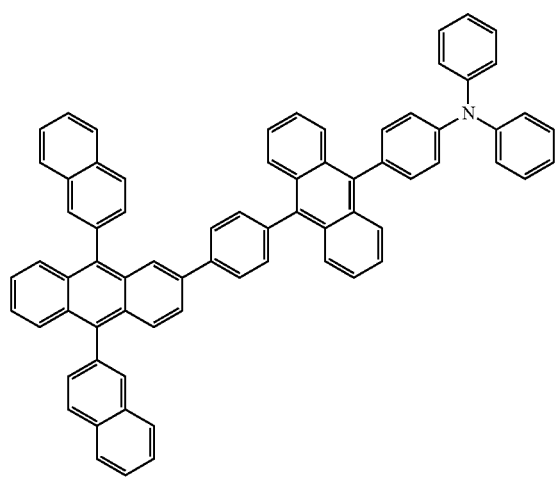
[Formula 1-92]
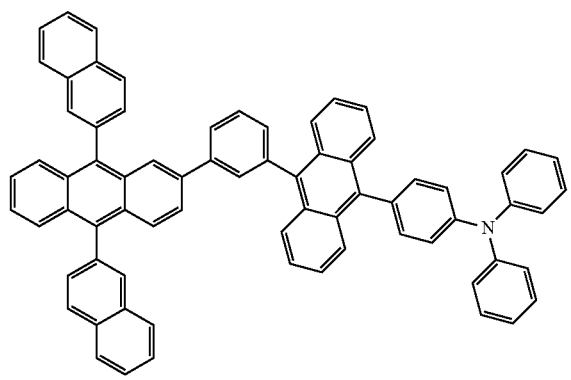
[Formula 1-93]
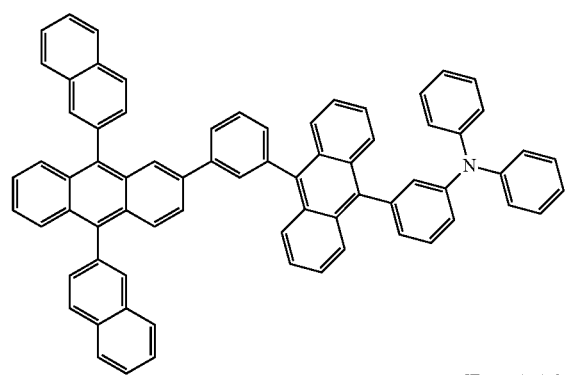
[Formula 1-94]
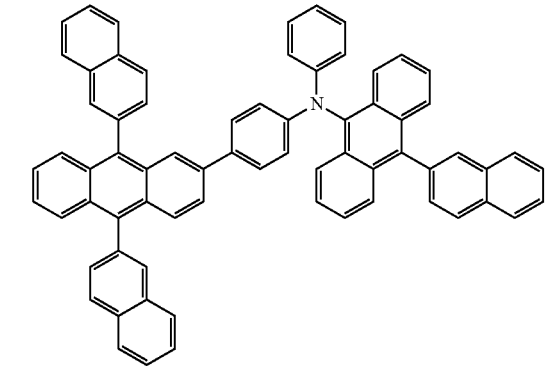
[Formula 1-95]
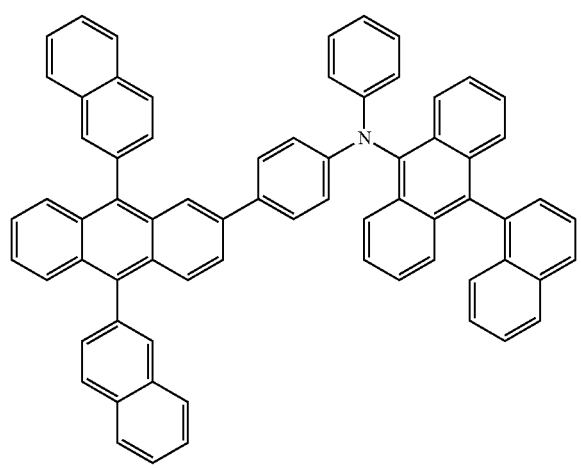
[Formula 1-97]
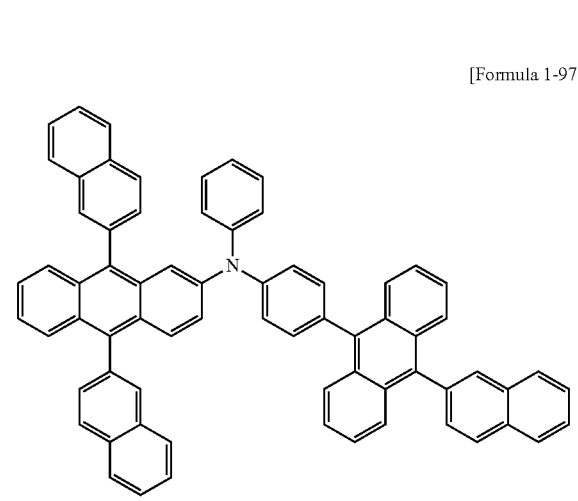
[Formula 1-98]
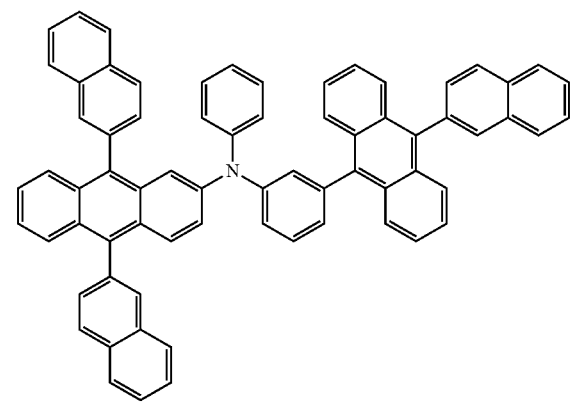

[Formula 1-99]
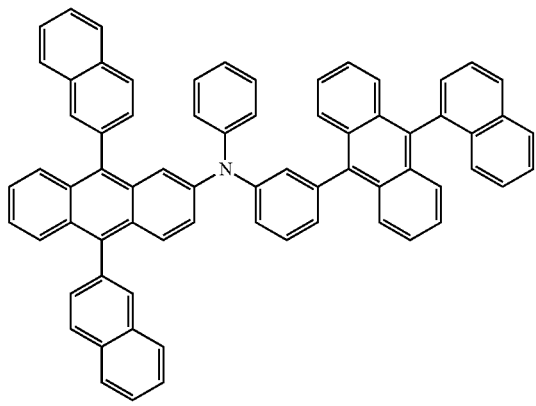
[Formula 1-100]
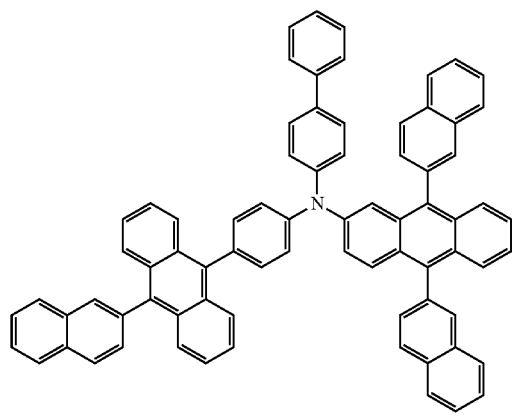
[Formula 1-101]
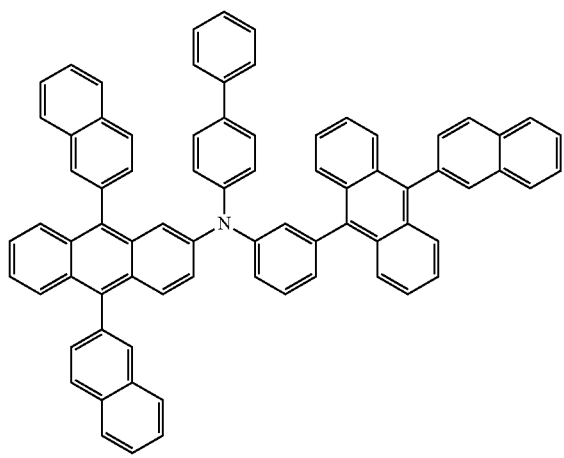
[Formula 1-102]
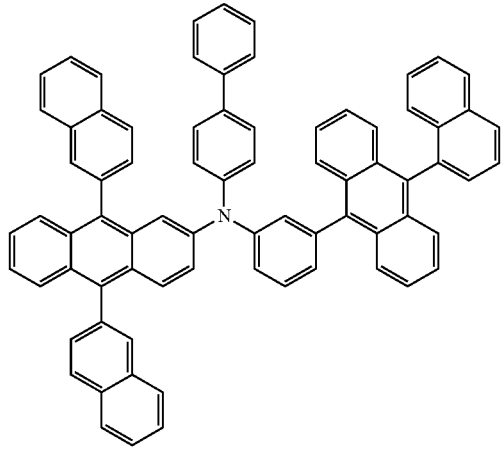
[Formula 1-103]
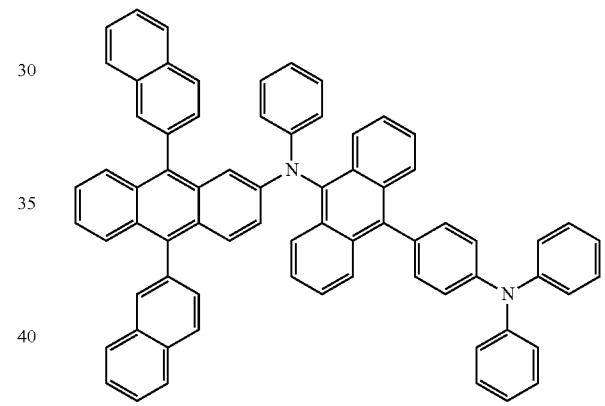
[Formula 1-104]
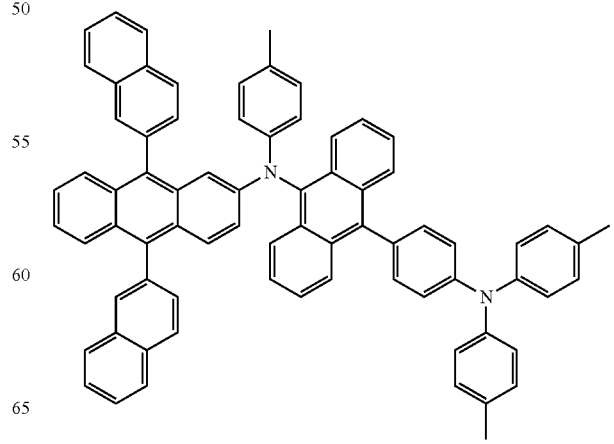

[Formula 1-105]
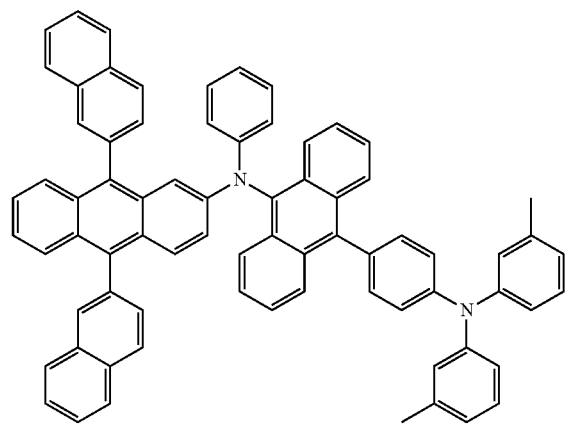
[Formula 1-106]
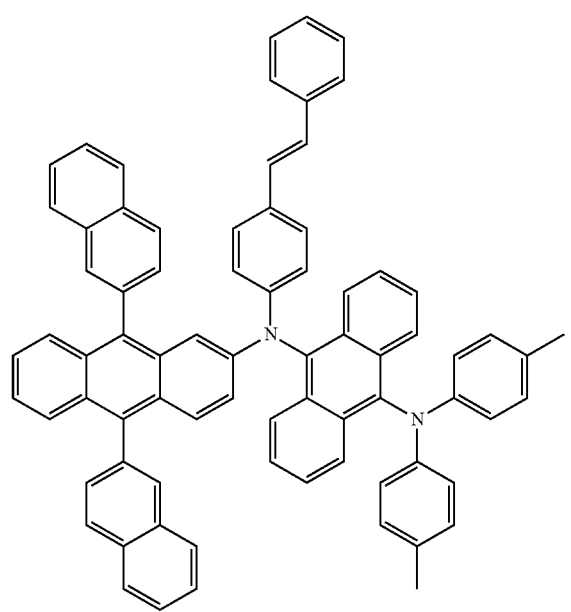
[Formula 1-107]
[Formula 1-108]
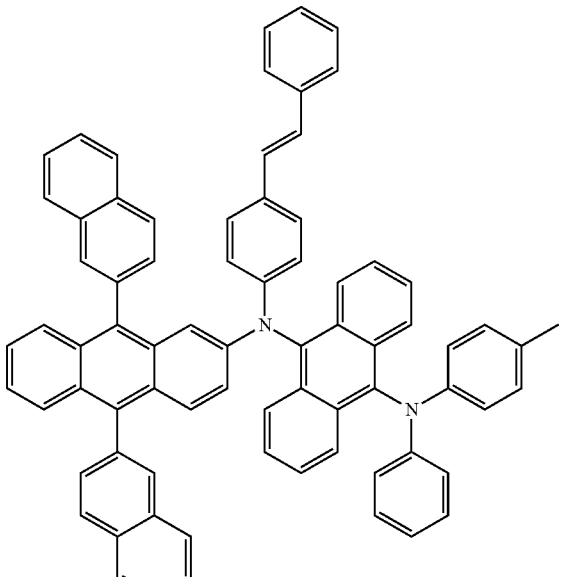
[Formula 1-109]
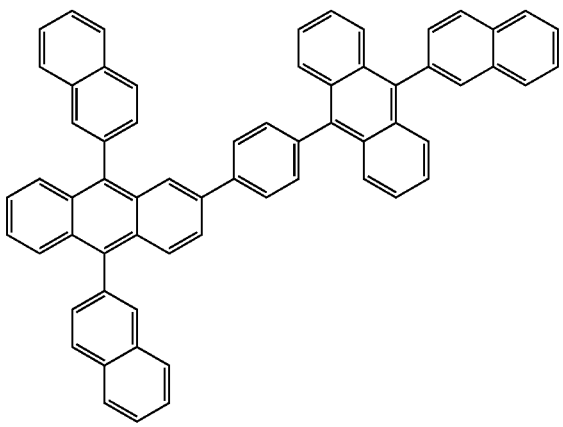
[Formula 1-110]
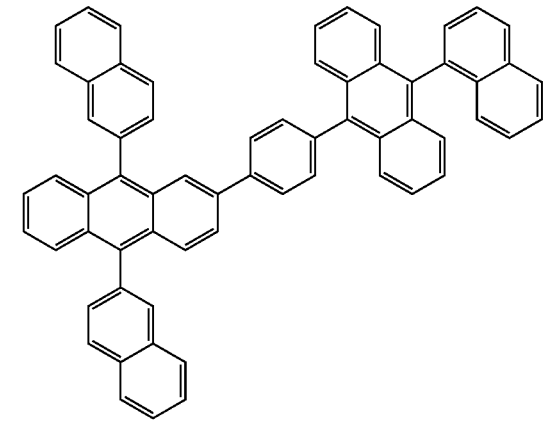

[Formula 1-112]
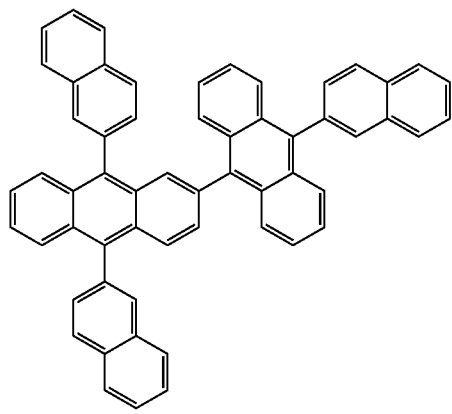
[Formula 1-113]
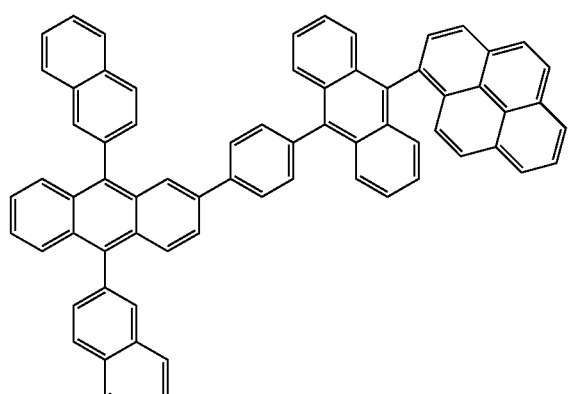
[Formula 1-114]
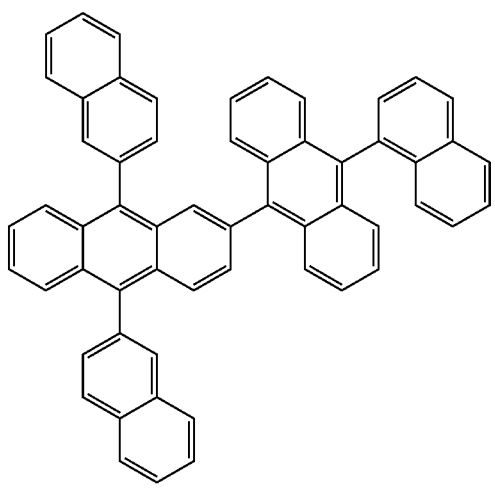
[Formula 1-115]
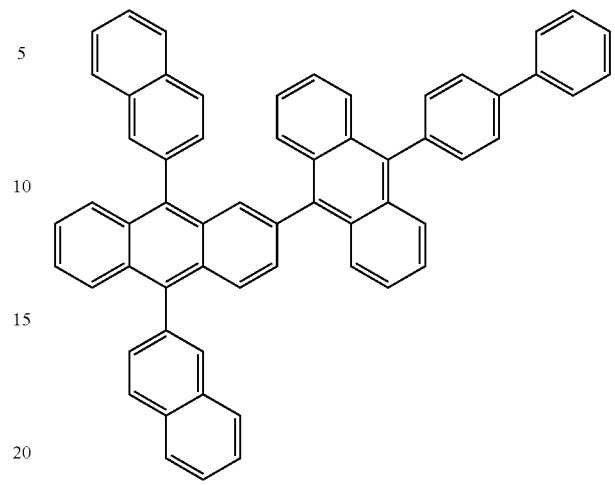
[Formula 1-116]
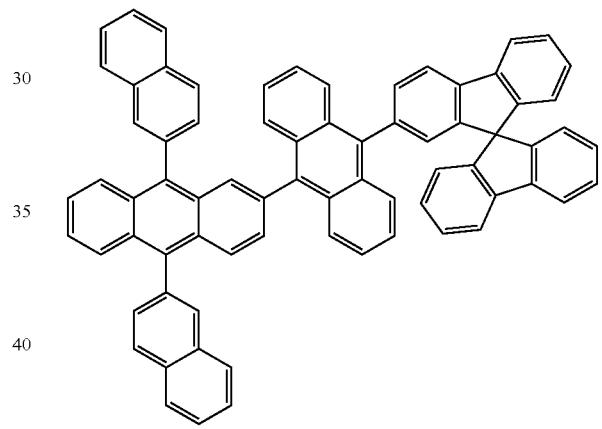
[Formula 1-117]
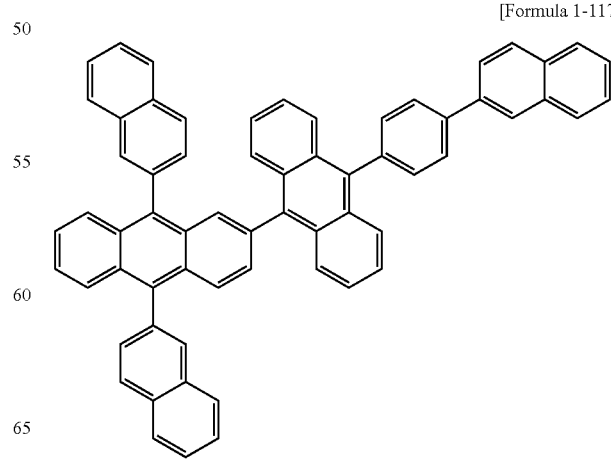

[Formula 1-118]
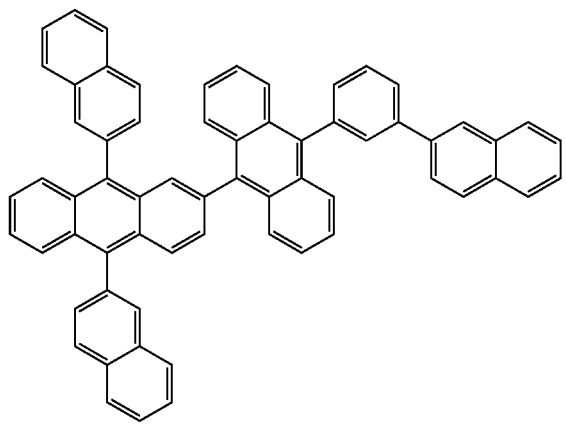
[Formula 1-119]
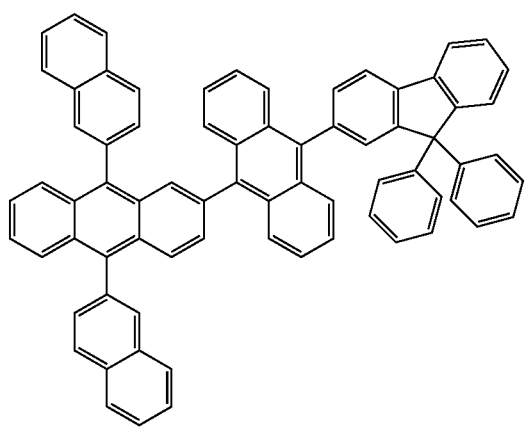
[Formula 1-120]
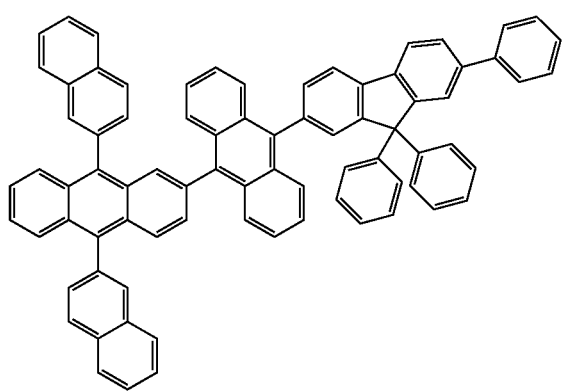
[Formula 1-121]
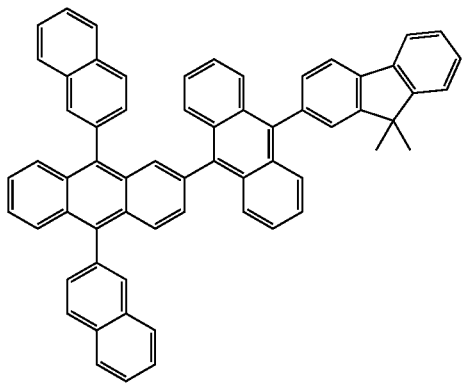
[Formula 1-131]
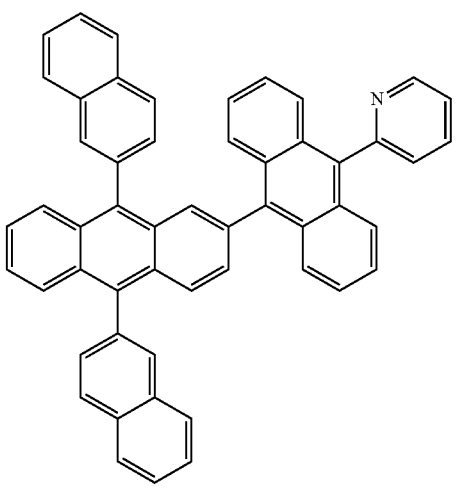
[Formula 1-132]
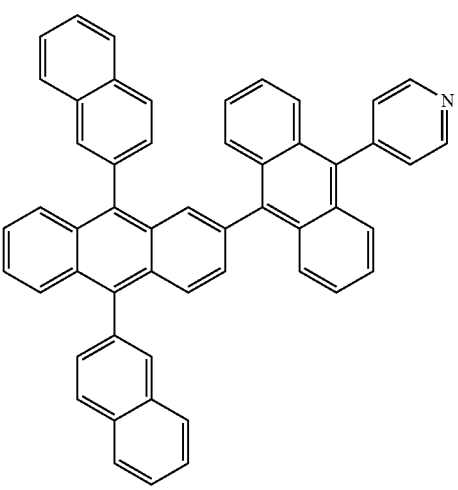

[Formula 1-133]
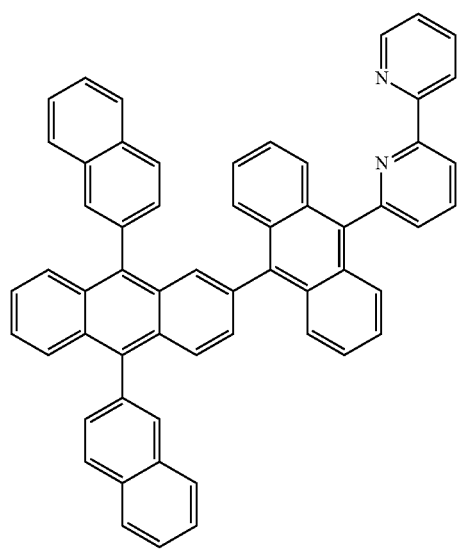
[Formula 1-134]
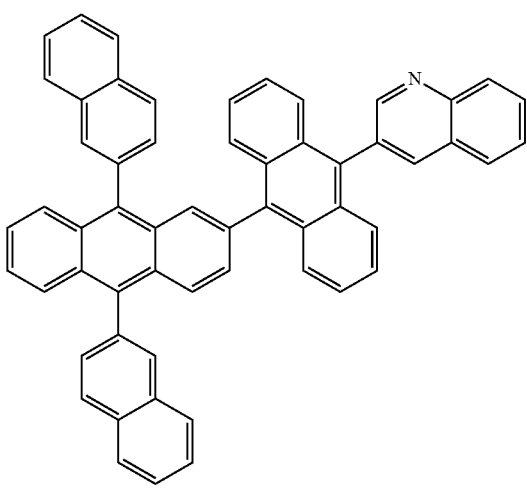
[Formula 1-135]
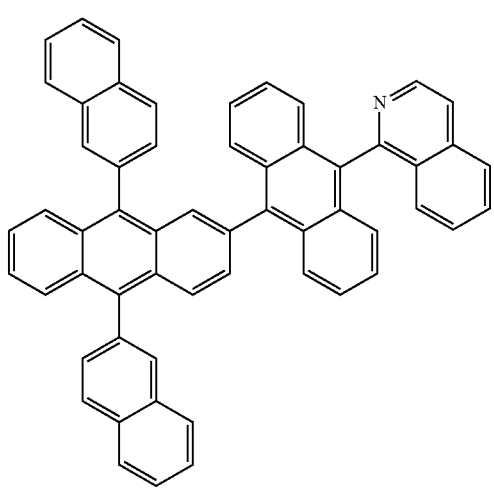
[Formula 1-136]
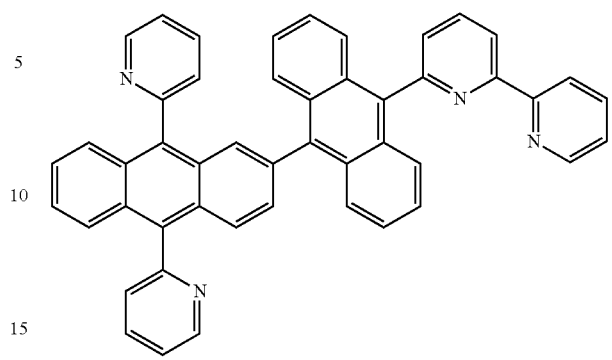
[Formula 1-137]
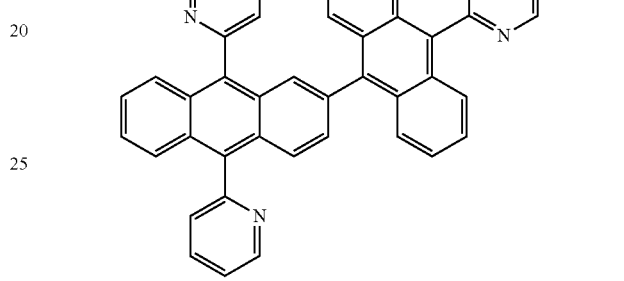
[Formula 1-138]
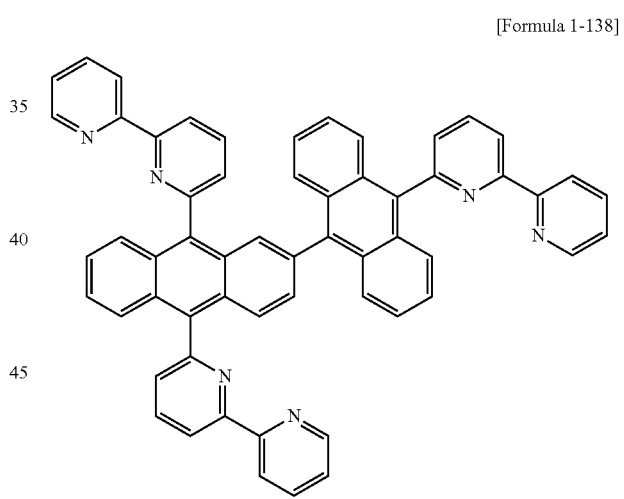
[Formula 1-139]
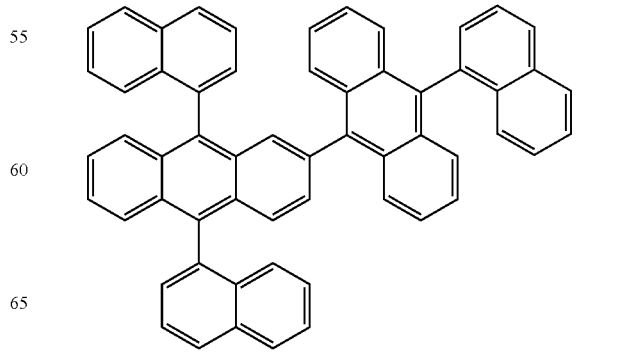

229
230
-continued
-continued
[Formula 1-140]
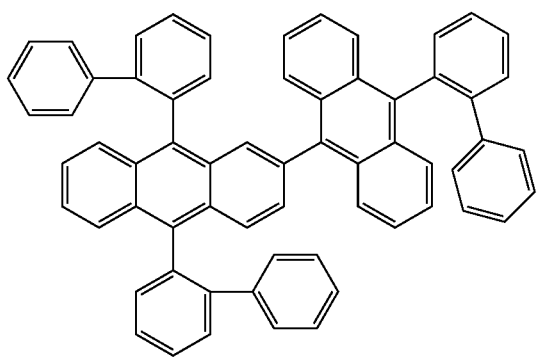
[Formula 1-149]
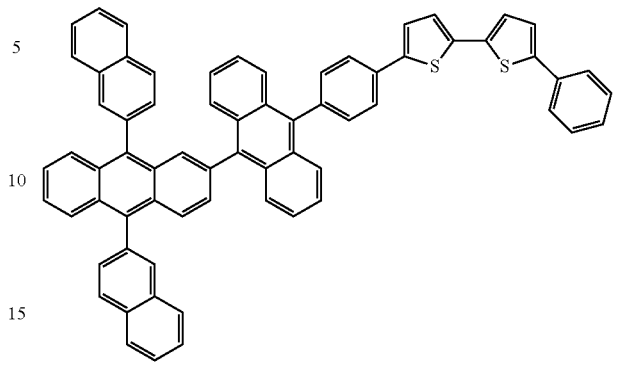
[Formula 1-141]
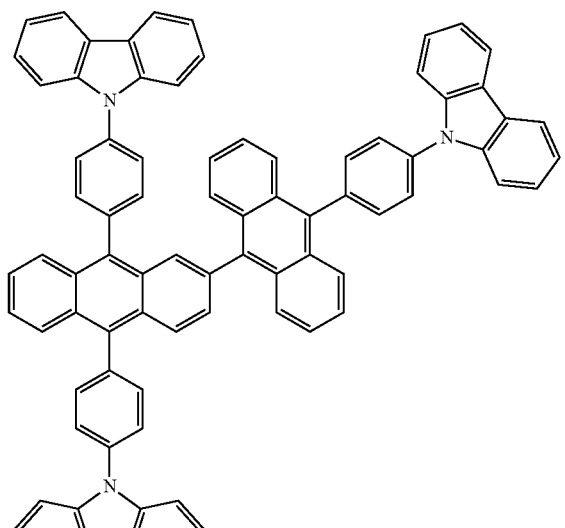
[Formula 1-150]
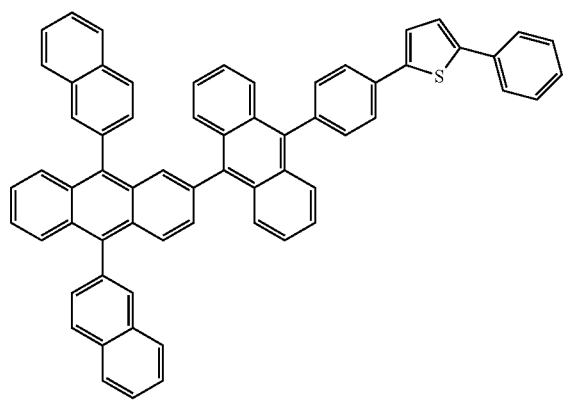
[Formula 1-151]
[Formula 1-142]
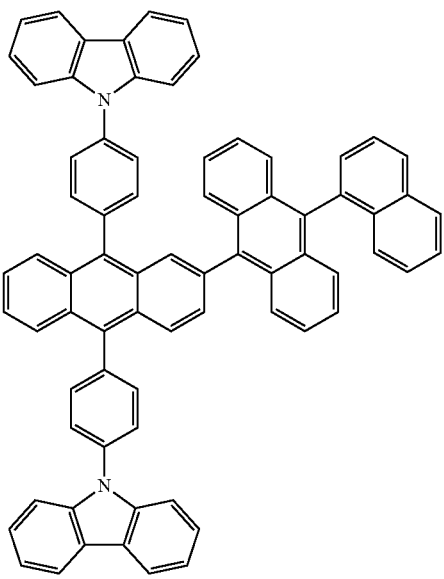
[Formula 1-152]

-continued
[Formula 1-153]
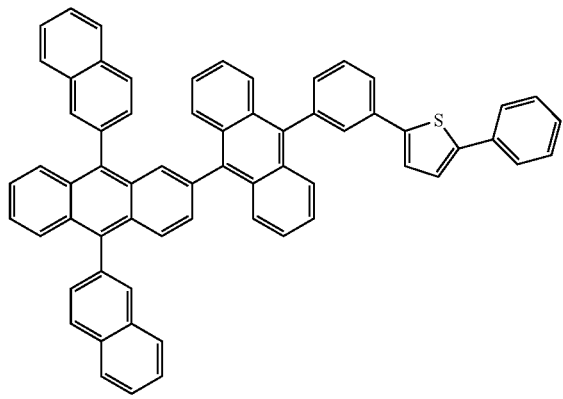
[Formula 1-154]
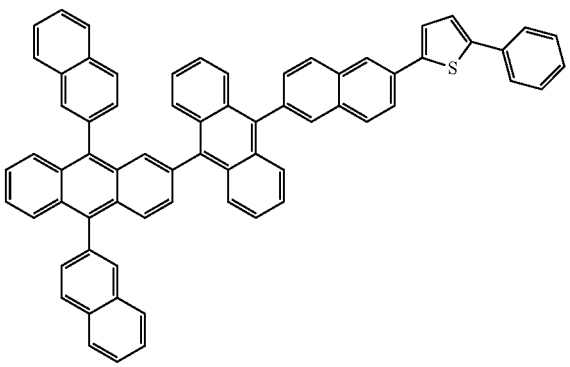
[Formula 1-155]
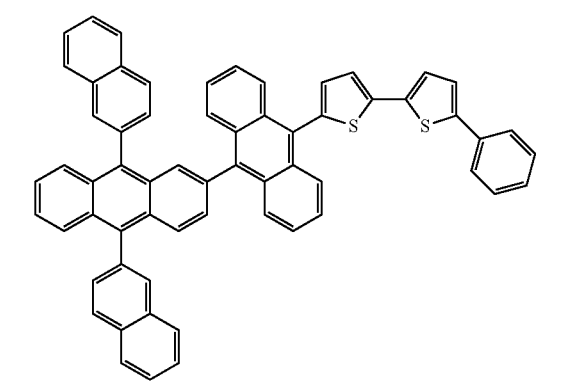
[Formula 1-156]
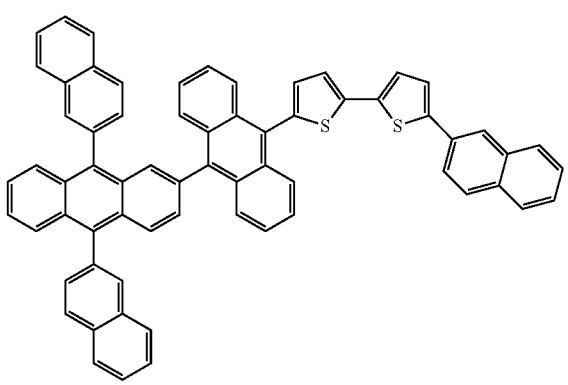
-continued
[Formula 1-157]
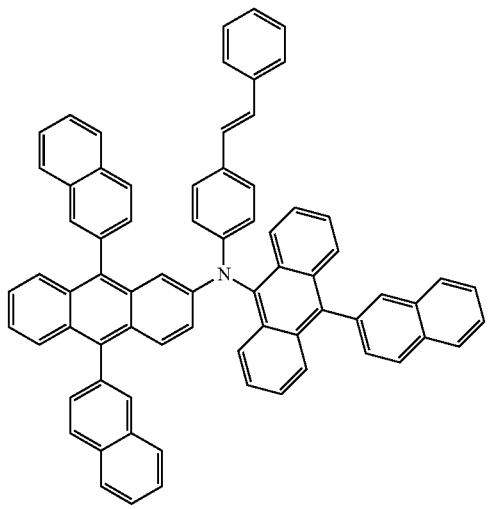
[Formula 1-163]
[Formula 1-164]
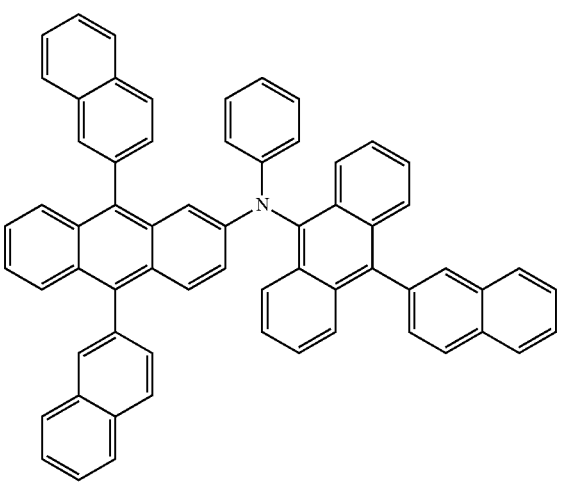

[Formula 1-165]
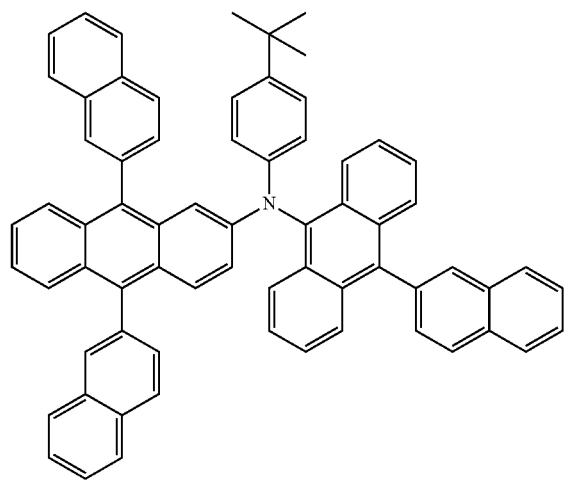
[Formula 1-166]
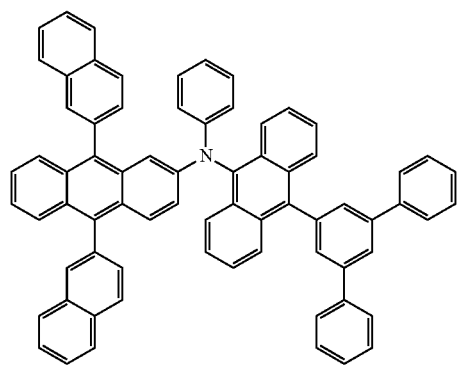
[Formula 1-170]
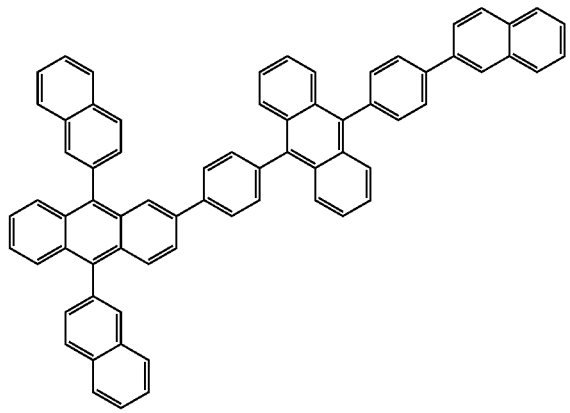
[Formula 1-171]
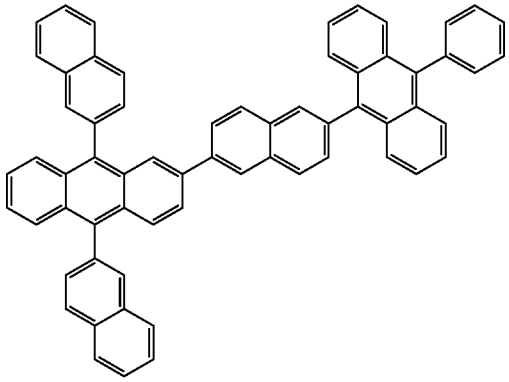
[Formula 1-172]
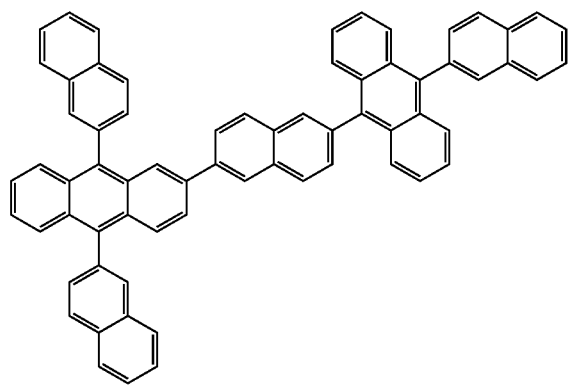
[Formula 1-173]
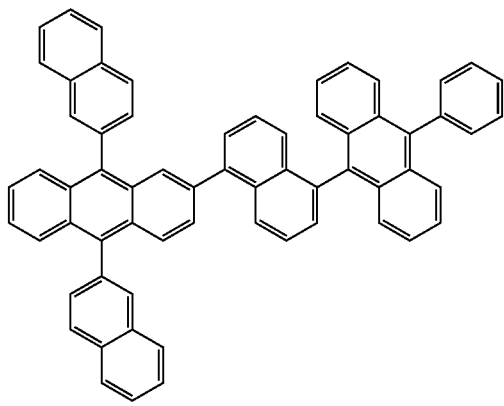
[Formula 1-174]
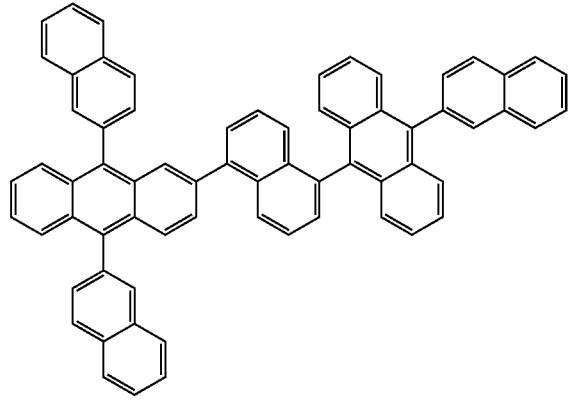

[Formula 1-175]
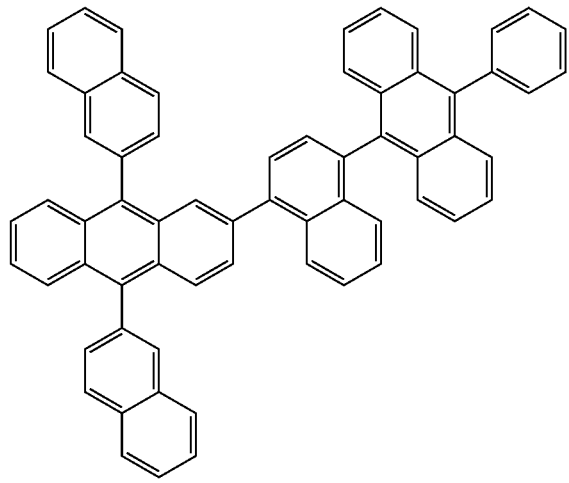
[Formula 1-176]
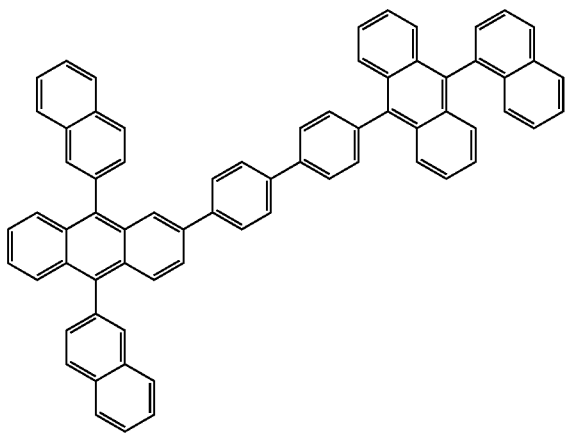
[Formula 1-177]
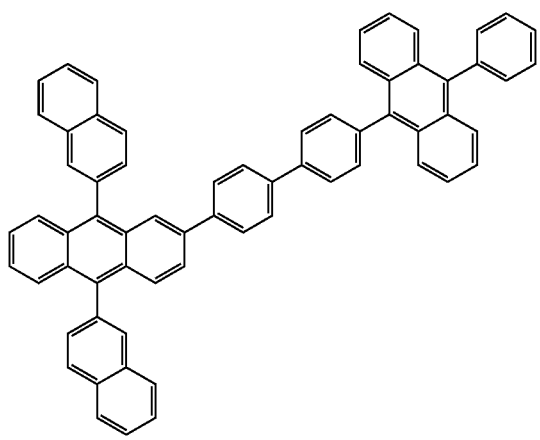
[Formula 1-178]
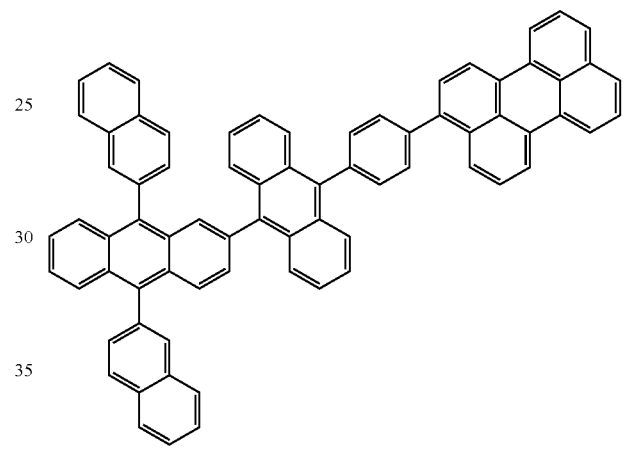
[Formula 1-179]
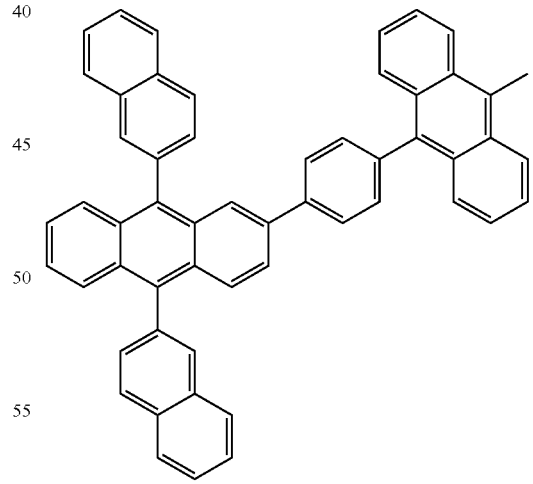
[Formula 1-180]
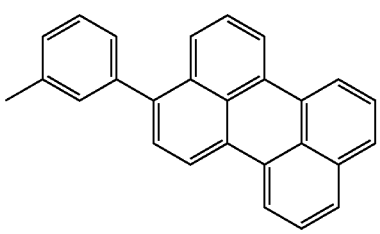

[Formula 1-181]
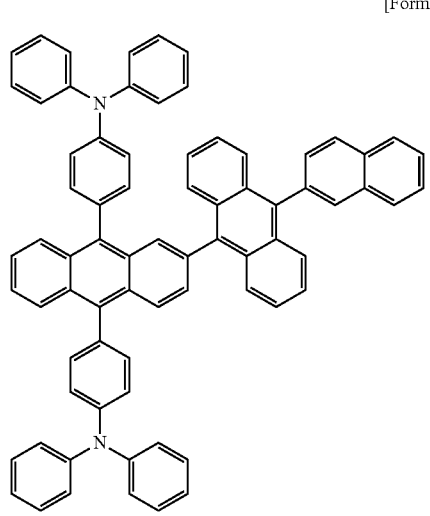
[Formula 1-183]
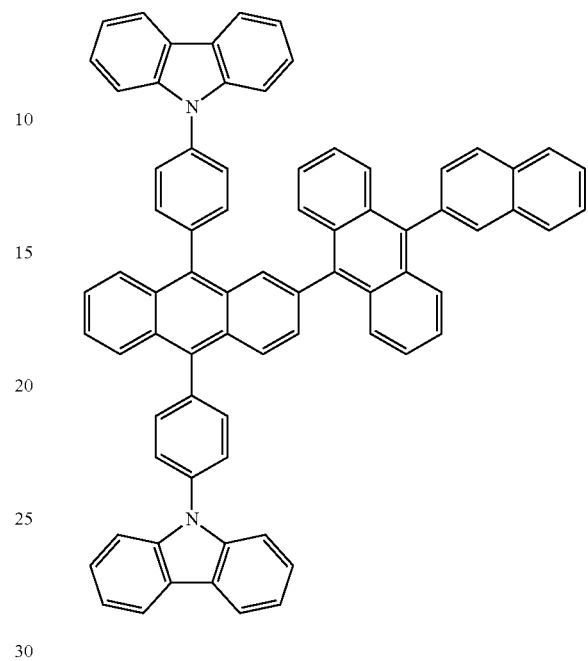
[Formula 1-182]
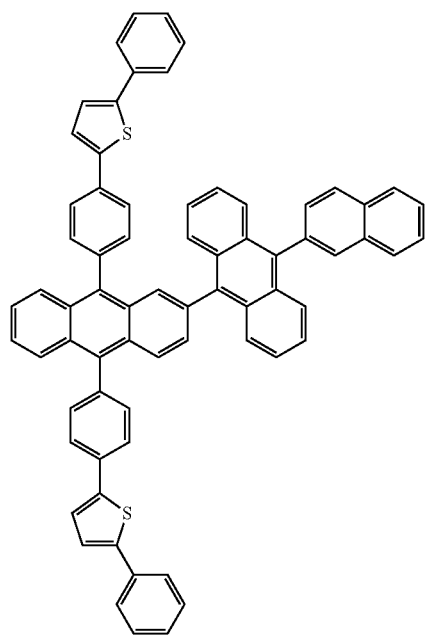
[Formula 1-184]
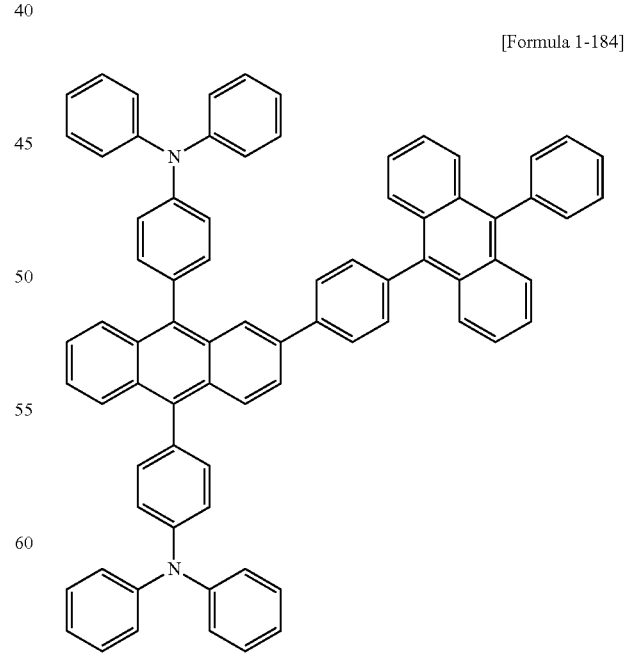

[Formula 1-185]
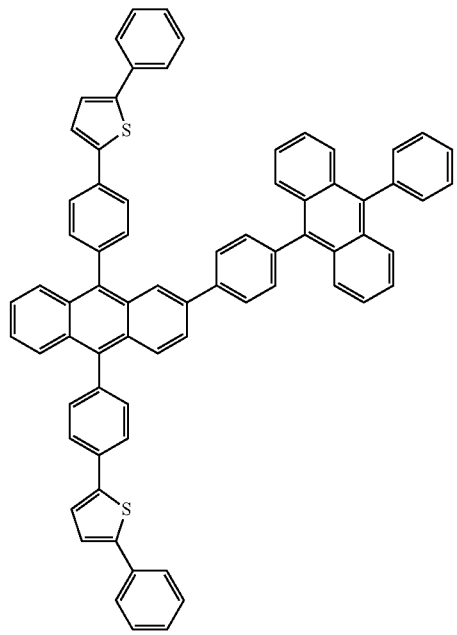
[Formula 1-186]
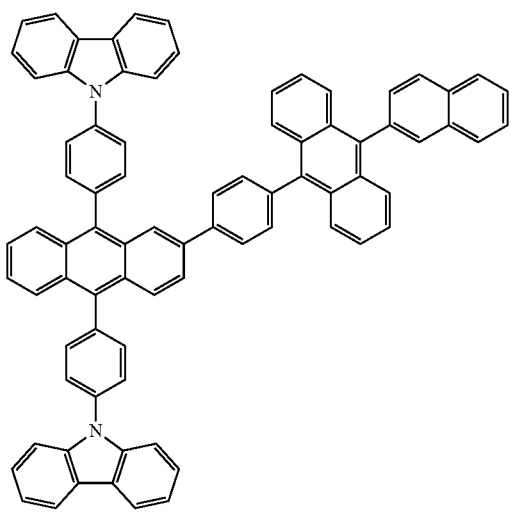
[Formula 1-187]
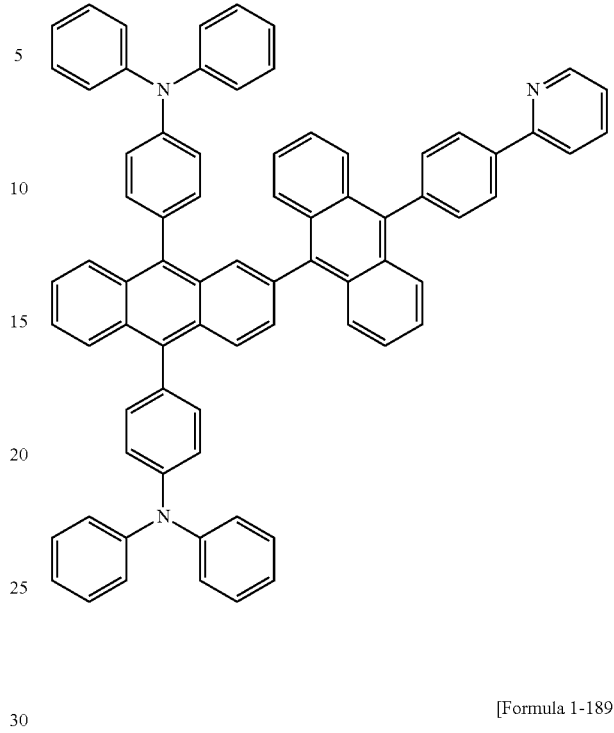
[Formula 1-189]
[Formula 1-190]
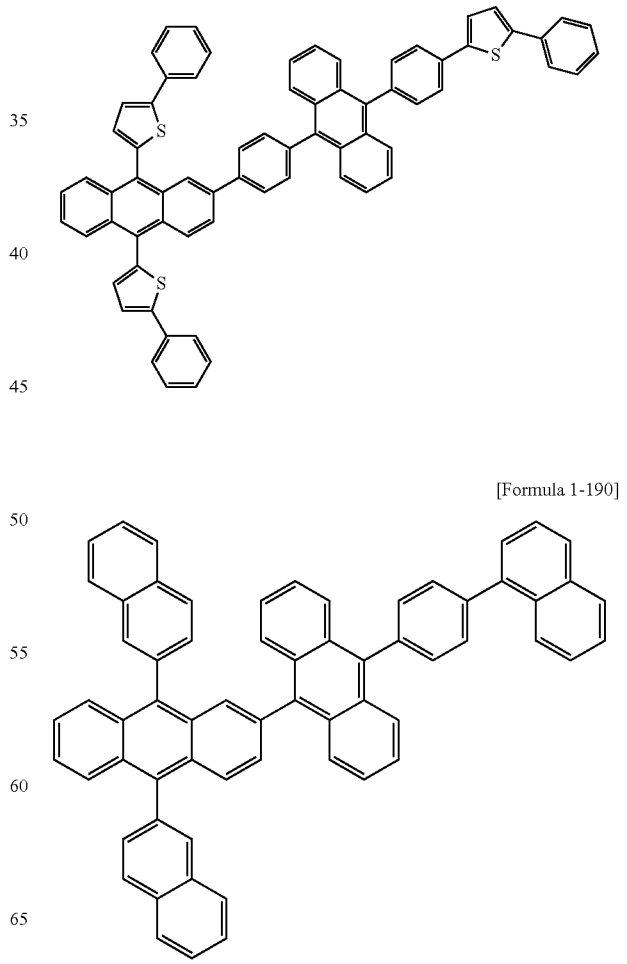

[Formula 1-197]
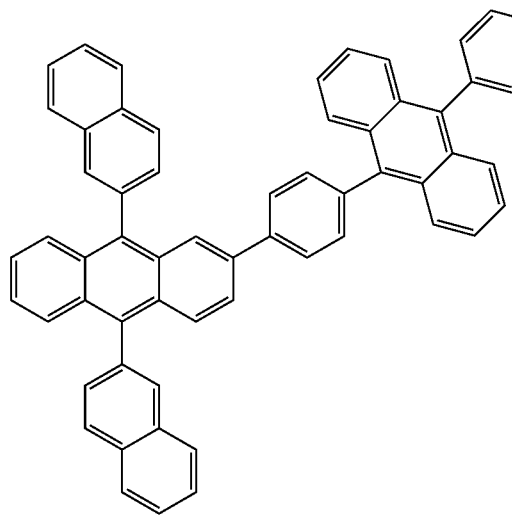
[Formula 1-200]
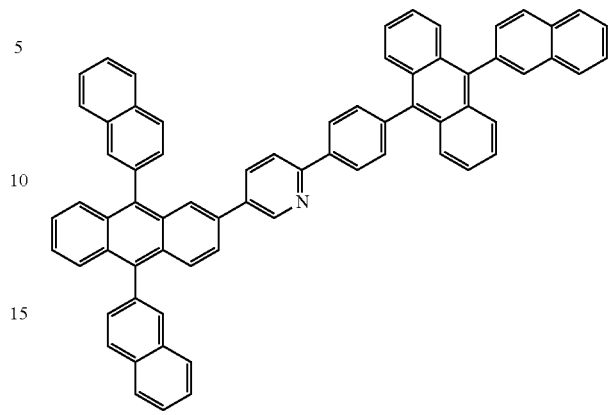
[Formula 1-198]
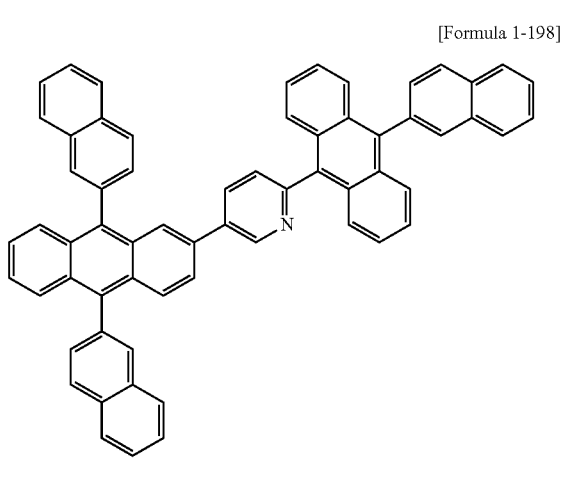
[Formula 1-201]
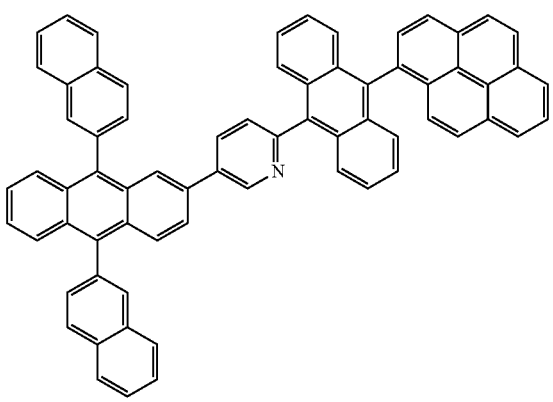
[Formula 1-199]
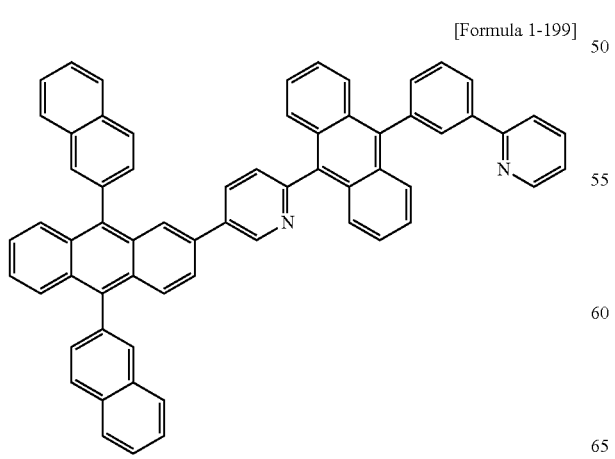
[Formula 1-202]
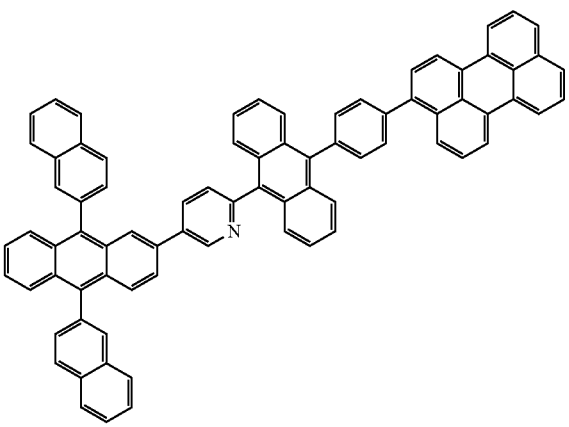

[Formula 1-203]
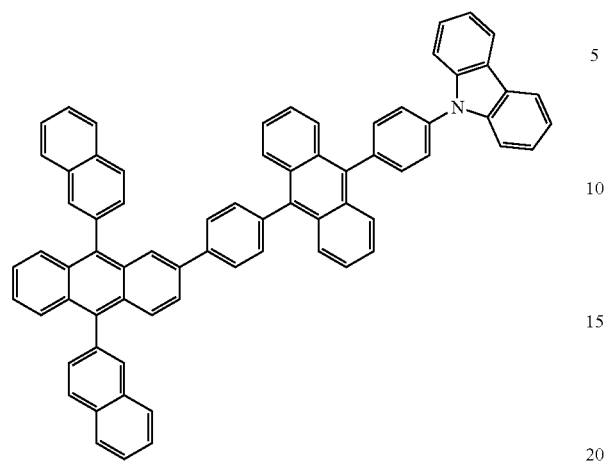
[Formula 1-204]
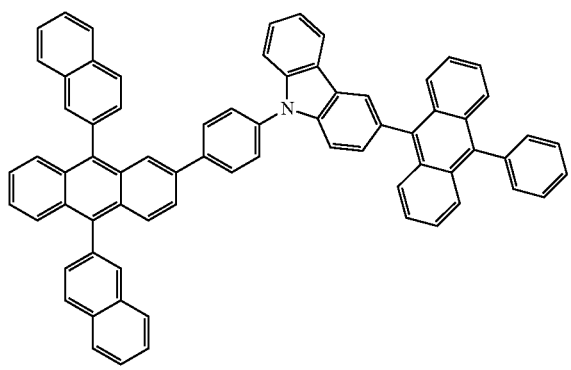
[Formula 1-209]
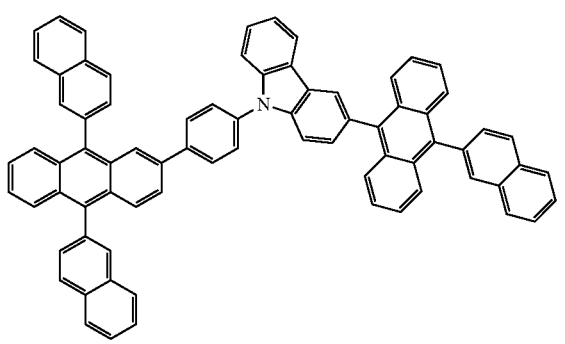
[Formula 1-210]
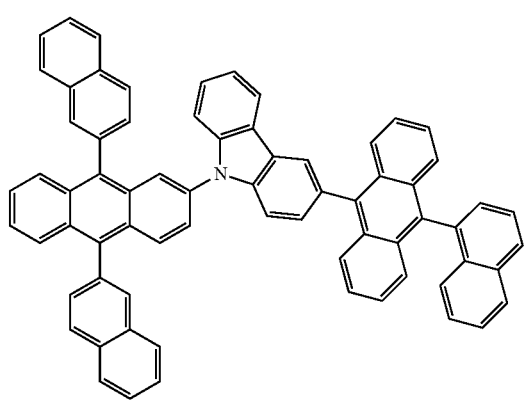
[Formula 1-211]
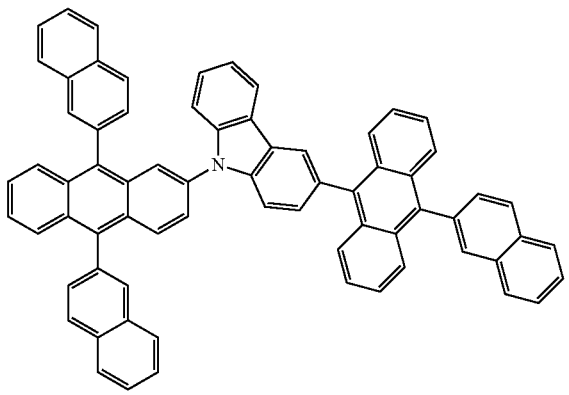
[Formula 1-212]
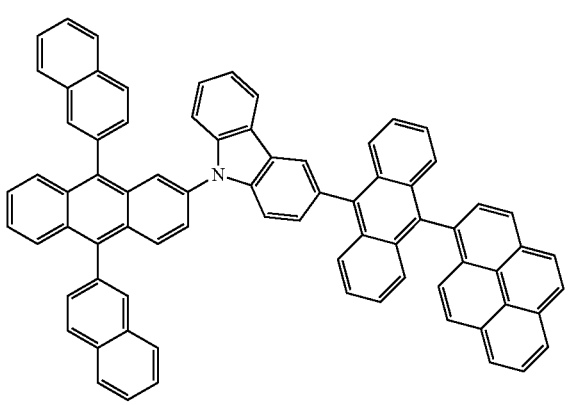
[Formula 1-213]
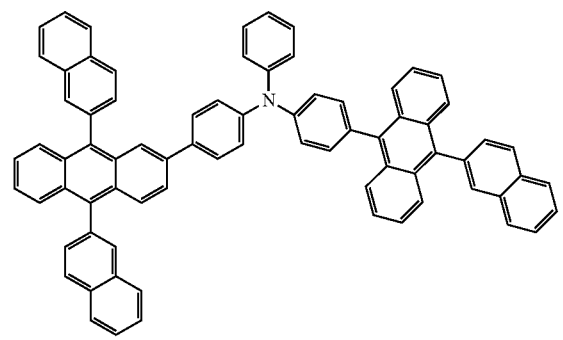

[Formula 1-214]
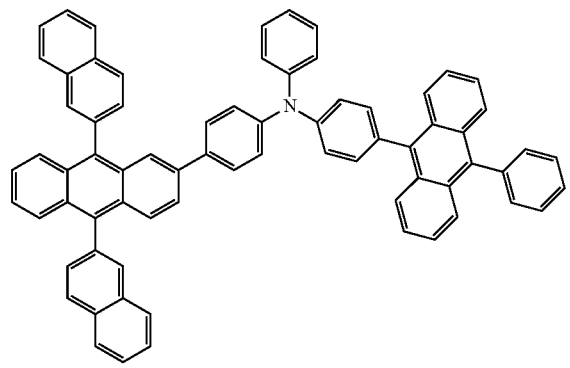
[Formula 1-215]
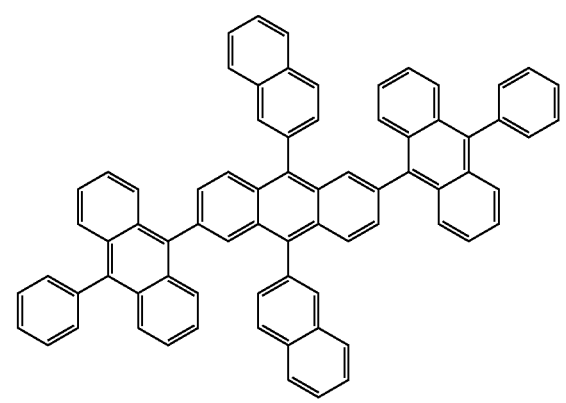
[Formula 1-216]
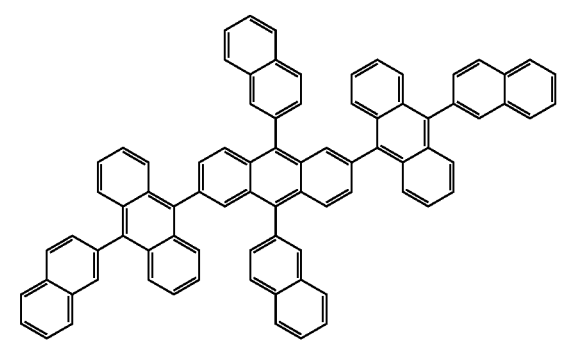
[Formula 1-217]
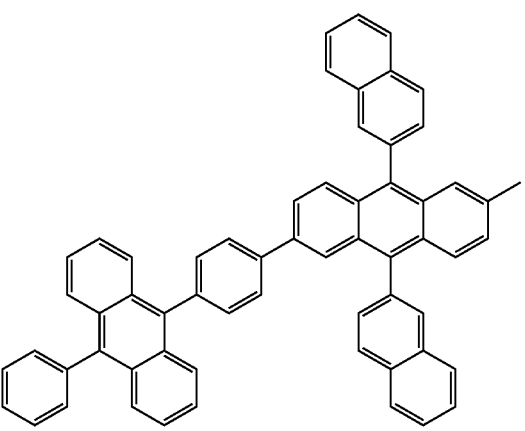
[Formula 1-218]
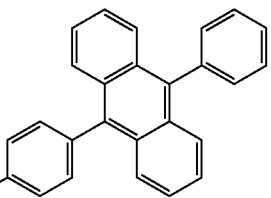
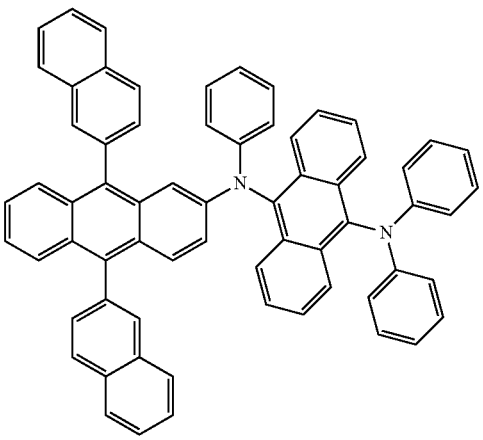
[Formula 1-219]
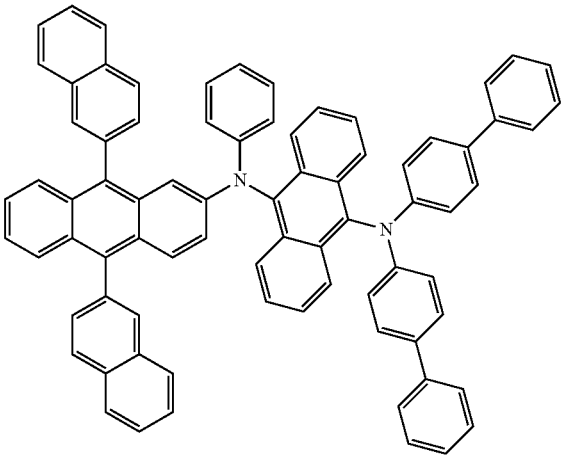
[Formula 1-220]
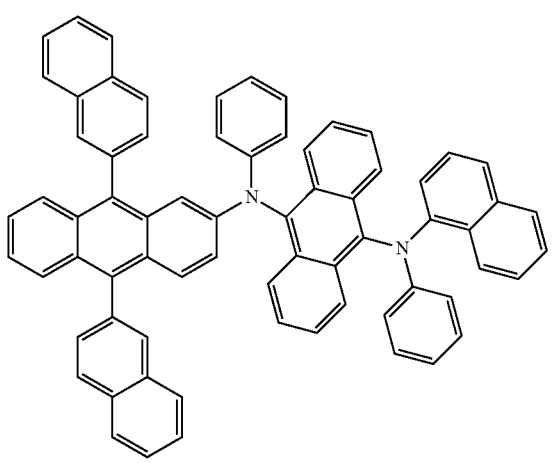

[Formula 1-224]

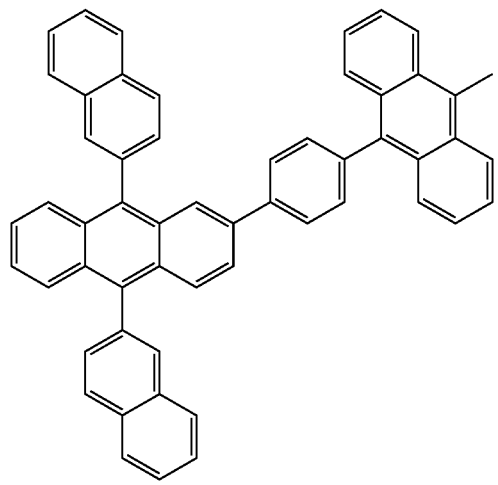

[Formula 1-225]

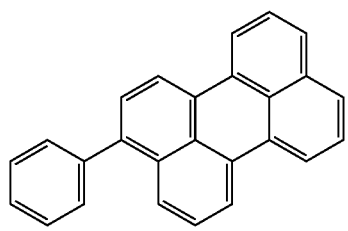

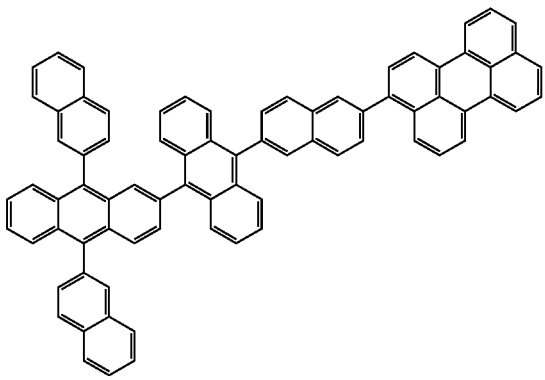

[Formula 1-226]

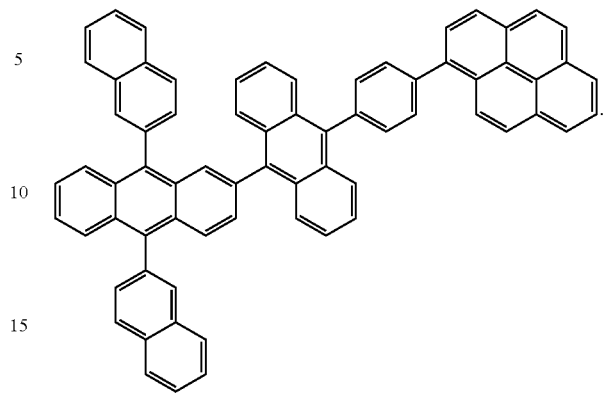

2. An organic electronic device comprising a first electrode, a second electrode, and at least one organic material layer interposed between the first electrode and the second electrode, wherein at least one of the organic material layers comprises the compound according to claim 1.

3. The organic electronic device according to claim 2, wherein the organic electronic device is selected from the group consisting of an organic light emitting device, an organic solar cell, an organic photoconductor (OPC) drum, and an organic transistor.

4. The organic electronic device according to claim 2, wherein the organic electronic device is an organic light emitting device.

5. The organic electronic device according to claim 4, wherein the organic light emitting device has a forward structure in which an anode, at least one organic material layer, and a cathode are sequentially laminated on a substrate.

6. The organic electronic device according to claim 4, wherein the organic light emitting device has a reverse structure in which a cathode, at least one organic material layer, and an anode are sequentially laminated on a substrate.

7. The organic electronic device according to claim 4, wherein the organic material layer of the organic light emitting device comprises a hole injecting layer, a hole transporting layer, a light emitting layer, and an electron injecting and transporting layer.

8. The organic electronic device according to claim 4, wherein the organic material layer of the organic light emitting device comprises a light emitting layer, and the light emitting layer comprises the compound.

9. The organic electronic device according to claim 4, wherein the organic material layer of the organic light emitting device comprises an electron transporting and/or injecting layer, and this layer comprises the compound.

* * * * *